United States Patent [19]

Warren et al.

[11] Patent Number: 5,888,801
[45] Date of Patent: Mar. 30, 1999

[54] PESTICIDAL STRAINS OF BACILLUS

[75] Inventors: Gregory W. Warren, Cary; Martha A. Mullins, Raleigh; Annick J. de Framond, Pittsboro, all of N.C.

[73] Assignee: Novartis Finance Corporation, New York, N.Y.

[21] Appl. No.: 467,506

[22] Filed: Jun. 6, 1995

Related U.S. Application Data

[60] Division of Ser. No. 463,483, Jun. 5, 1995, which is a continuation-in-part of Ser. No. 314,594, Sep. 28, 1994, abandoned, which is a continuation-in-part of Ser. No. 218,018, Mar. 23, 1994, abandoned, Continuation of Ser. No. 37,057, Mar. 25, 1993, abandoned.

[51] Int. Cl.$^6$ .............................. C12N 1/20; A01N 63/00
[52] U.S. Cl. ...................................... 435/252.5; 424/93.41
[58] Field of Search ....................... 435/252.5; 424/93.46

[56] References Cited

U.S. PATENT DOCUMENTS

| | | | |
|---|---|---|---|
| 3,632,747 | 1/1972 | Satohiro et al. | 424/93 |
| 3,651,215 | 3/1972 | Satohiro et al. | 424/93 |
| 4,996,155 | 2/1991 | Sick et al. | 435/252.3 |
| 4,996,156 | 2/1991 | Zaehner | 435/252.5 |
| 5,262,323 | 11/1993 | Baird et al. | 435/252.5 |

FOREIGN PATENT DOCUMENTS

| | | |
|---|---|---|
| 0498537A2 | 1/1992 | European Pat. Off. . |
| 0501650A2 | 2/1992 | European Pat. Off. . |
| WO88/08880 | 11/1988 | WIPO . |
| WO90/13651 | 11/1990 | WIPO . |
| WO91/16432 | 10/1991 | WIPO . |
| WO91/16434 | 10/1991 | WIPO . |
| US94/03131 | 7/1994 | WIPO . |
| WO94/21795 | 9/1994 | WIPO . |

OTHER PUBLICATIONS

European International Search Report dated May 3, 1996.
Bernier et al., "*Bacillus thuringiensis* Strains A20 and A29 and Insecticidal Compounds Therefrom, And Compositions Containing These Compounds", Abstract No. 227249, *New Zealand Patent Office Journal*, 80(6):798, (1988).
Jellis et al., "*Bacillus thuringiensis* δ–Endotoxin Variants and Insecticidal Compositions", Abstract No. 228108, *New Zealand Patent Office Journal*, 81(3):359, (1992).
Schurter et al., "Genetic Manifpulation of *B.thuringiensis* And *B.cereus* Vectors And Insecticidal Composition", Abstract No. 229191, *New Zealand Patent Office Journal*, 81(3):363, 1992.
Tayabali et al., "Semiautomated Quantification of Cytotoxic Damage Induced in Cultured Insect Cells Exposed to Commercial *Bacillus thuringiensis* Biopesticides", *Journal of Applied Toxicology*, 15(5): 365–373 (1995).
Thanabalu et al., "Cytotoxicity and ADP–Ribosylating Activity of the Mosquitocidal Toxin from *Bacillus sphaericus* SSII–1: Possible Roles of the 27–and 70–Kilodalton Peptides", *Journal of Bacteriology*, 175(8): 2314–2320 (1993).

Vaithlingam et al., "Anti–Coleopteran Toxin and Gene", Abstract No. 226442, *New Zealand Patent Office Journal*, 80(7):931, (1991).
Wahisaka et al., "*Bacillus thuringiensis* Mutant and Bacterial Insecticide", Abstract No. 199725, *New Zealand Patent Office Journal*, (1982).
Walther et al., "Analysis of Mosquito Larvicidal Potential Exhibited by Vegetative Cells of *Bacillus thuringiensis* subsp. israelensis", *Applied and Environmental Microbiology*, 52(4): 650–653 (1986).
Ward et al., "*Bacillus thuringiensis* var. israelensis δ–Endotoxin Cloning and Expression of the Toxin in Sporogenic and Asporogenic Strains of *Bacillus subtilis*", *Journal of Molecular Biology*, 191(1): 13–22 (1986).
Arellano, A., et al., "Evidence of a New *Bacillus thuriengiensis* Toxin Active Against the Australian Sheep Blowfly *Lucilla cuprina* ", *Proceedings and Abstracts of the 5th International Colloquium on Invertebrate Pathology and Microbial Control*, Adelaide, Austrailia, 20–24 Aug., 1990, p. 291.
Beecher, Douglas J., et al., "A Novel Bicomponent Hemolysin from *Bacillus cereus* ", *Inspection and Immunity*, 58(7):2220–2227 (1990).
Faust, R.M., "Bacterial Diseases", In: *Insect Diseases*, G. Cantwell, ed., Marcel Dekker, NY 1974, pp. 90–102.
Faust, R.M., et al., "Bacteria and Their Toxins as Insecticides", In: *Microbial and Viral Pesticides*, E. Kurstak, Ed., Marcel Dekker, NY, 1982, pp. 84–89, 108–120.
Gilmore, Michael S., et al., "A *Bacillus cereus* Cytolytic Determinant, Cereolysin AB, Which Comprises the Phospholipase C and Sphingomyelinase Genes: Nucleotide Sequence and Genetic Linkage", *Journal of Bacteriology*, 171(2):744–753 (1989).
Heimpel, A.M., "The pH in the Gut and Blood of the Larch Sawfly, *Pristiphora erichsonii* (HTG.), and Other Insects with Reference to the Pathogenicity of *Bacillus cereus* FR. and FR.", *Can. J. Zool.*, 33:99–106 (1955).
Heimpel, A.M., "Investigations of the Mode of Action of Strains of *Bacillus cereus* FR. and FR. Pathogenic for the Larch Sawfly, *Pristiphora erichsonii* (HTG.)", *Can. J. Zool.*, 33:311–326 (1995).
Hofte, H., et al., "Insecticidal Crystal Proteins of *Bacillus thuringiensis*", *Microbiological Reviews*, 53(2):242–255 (1989).
Koziel, M.G., "Field Performance of Elite Tansgenic Maize Plants Expressing an Insecticidal Protein Derived from *Bacillus thuringiens*", *Bio/Technology*, 11:194–200 (1993).

(List continued on next page.)

*Primary Examiner*—Irene Marx
*Attorney, Agent, or Firm*—J. Timothy Meigs; Gary M. Pace

[57] ABSTRACT

The present invention is drawn to pesticidal strains and proteins. Bacillus strains which are capable of producing pesticidal proteins and auxiliary proteins during vegetative growth are provided. Also provided are the purified proteins, nucleotide sequences encoding the proteins and methods for using the strains, proteins and genes for controlling pests.

12 Claims, No Drawings

OTHER PUBLICATIONS

Krieg, A., "Thuricin, a Bacteriocin Produced by *Bacillus thuringiensis*", *J. Invert. Path.*, 15:291 (1970).

Krieg, A., "Concerning Alpha–exotoxin Produced by Vegetative Cells of *Bacillus thuringiensis* and *Bacillus cereus*", *J. Invert. Path.*, 17:134–135 (1971).

Kushner, D.J., et al., "Lecithinase Production by Strains of *Bacillus cereus* FR. and FR. Pathogenic for the Larch Sawfly, *Pristiphora erichsonii* (HTG.)", *Can. J. Microbiol.*, 3:547–551 (1957).

Luthy, P., et al., "*Bacillus thuringiensis* as a Bacterial Insecticide: Basic Consideration and Application", In: *Microbial and Viral Pesticides*, E. Kurstak, Ed., Marcel Dekker, NY 1982, pp. 37–39, 54–56.

Myers, P.S., et al., "Localization of a Mosquito–Larval Toxin of *Bacillus sphaericus* 1593", *Appl. Environ. Microbiol.*, 39(1):1205–1211 (1980).

Porter, A.G., et al., "Mosquitocidal Toxins of Bacilli and Their Genetic Manipulation for Effective Biological Control of Mosquitoes", *Microbiological Reviews*, 57(4):838–861 (1993).

Sekar, V., "The Insecticidal Crystal Protein Gene is Expressed in Vegetative Cells of *Bacillus thuringiensis* var. temebropmos", *Current Microbiology*, 17:347–349.

Shivakumar, A.G., et al., Abstract, :Cloned Crystal Protein Genes Express Vegetatively in *Bacillus subtilis*, *Plasmid*, 16(3):230 (1986).

Thanabalu, T., et al., "Proteolytic Processing of the Mosquitocidal Toxin from *Bacillus sphaericus* SSII–1", *J. Bacteriol.*, 174(15):5051–5056 (1992).

Yoshisue, H., et al., "Effects of *Bacillus thuringiensis* var. israelensis 20 kDa Protein on Production of the Bti 130–kDa Crystal Protein in *Escherichia coli*", *Bioscience, Biotechnology, and Biochemistry*, 56(9):1429–1433 (1992).

MeHus et al., Appl. Environ. Microbiol., 1990, pp. 1128–1134, vol. 56.

Luthy et al, Can. J. Microbiol., vol. 16, 1970 pp. 905–906.

Turnbull et al, Am. J. Clinical Natr., 1979, vol. 32, pp. 219–228.

PESTICIDAL STRAINS OF BACILLUS

This is a divisional application of Ser. No. 08/463,483, filed Jun. 5, 1995 which is a continuation-in-part of Ser. No. 08/314,594 filed Sep. 28, 1994, now abandoned, which is a continuation-in-part of Ser. No. 08/218,018, filed Mar. 23, 1994, now abandoned, which is a continuation-in-part of Ser. No. 08/037,057, filed Mar. 25, 1993, now abandoned.

FIELD OF THE INVENTION

The present invention is drawn to methods and compositions for controlling plant and non-plant pests.

BACKGROUND OF THE INVENTION

Insect pests are a major factor in the loss of the world's commercially important agricultural crops. Broad spectrum chemical pesticides have been used extensively to control or eradicate pests of agricultural importance. There is, however, substantial interest in developing effective alternative pesticides.

Microbial pesticides have played an important role as alternatives to chemical pest control. The most extensively used microbial product is based on the bacterium *Bacillus thuringiensis* (*Bt*). *Bt* is a gram-positive spore forming Bacillus which produces an insecticidal crystal protein (ICP) during sporulation.

Numerous varieties of *Bt* are known that produce more than 25 different but related ICP's. The majority of ICP's made by *Bt* are toxic to larvae of certain insects in the orders Lepidoptera, Diptera and Coleoptera. In general, when an ICP is ingested by a susceptible insect the crystal is solubilized and transformed into a toxic moiety by the insect gut proteases. None of the ICP's active against coleopteran larvae such as Colorado potato beetle (*Leptinotarsa decemlineata*) or Yellow mealworm (*Tenebrio molitor*) have demonstrated significant effects on members of the genus Diabrotica particularly *Diabrotica virgifera virgifera*, the western corn rootworm (WCRW) or *Diabrotica longicornis barberi*, the northern corn rootworm.

*Bacillus cereus* (*Bc*) is closely related to *Bt*. A major distinguishing characteristic is the absence of a parasporal crystal in *Bc*. *Bc* is a widely distributed bacterium that is commonly found in soil and has been isolated from a variety of foods and drugs. The organism has been implicated in the spoilage of food.

Although *Bt* has been very useful in controlling insect pests, there is a need to expand the number of potential biological control agents.

SUMMARY OF THE INVENTION

The present invention is drawn to compositions and methods for controlling plant and non-plant pests. Particularly, new pesticidal proteins are disclosed which are isolatable from the vegetative growth stage of Bacillus. Bacillus strains, proteins, and genes encoding the proteins are provided.

The methods and compositions of the invention may be used in a variety of systems for controlling plant and non-plant pests.

DETAILED DESCRIPTION OF THE INVENTION

Compositions and methods for controlling plant pests are provided. In particular, novel pesticidal proteins are provided which are produced during vegetative growth of Bacillus strains. The proteins are useful as pesticidal agents.

The present invention recognizes that pesticidal proteins are produced during vegetative growth of Bacillus strains. To date, all of the identified pesticidal proteins of the invention are secreted from the cell. Prior to the present invention, there was no recognition in the art that a class or classes of pesticidal proteins are produced during vegetative growth of Bacillus. The only report was of a single mosquitocidal toxin from *Bacillus sphaericus* SSII-1 by Myers and Yousten in *Infect. Immun.*, 19:1047–1053 (1978). Having recognized that such a class exists, the present invention embraces all vegetative insecticidal proteins, hereinafter referred to as VIPs, except for the mosquitocidal toxin from *B. sphaericus*.

The present VIPs are not abundant after sporulation and are particularly expressed during log phase growth before stationary phase. For the purpose of the present invention vegetative growth is defined as that period of time before the onset of sporulation. Genes encoding such VIPs can be isolated, cloned and transformed into various delivery vehicles for use in pest management programs.

For purposes of the present invention, pests include but are not limited to insects, fungi, bacteria, nematodes, mites, ticks, protozoan pathogens, animal-parasitic liver flukes, and the like. Insect pests include insects selected from the orders Coleoptera, Diptera, Hymenoptera, Lepidoptera, Mallophaga, Homoptera, Hemiptera, Orthroptera, Thysanoptera, Dermaptera, Isoptera, Anoplura, Siphonaptera, Trichoptera, etc., particularly Coleoptera and Lepidoptera.

Tables 1–10 gives a list of pests associated with major crop plants and pests of human and veterinary importance. Such pests are included within the scope of the present invention.

TABLE 1

| Lepidoptera (Butterflies and Moths) | |
|---|---|
| Maize | Sunflower |
| *Ostrinia nubilalis*, European corn borer | *Suleima helianthana*, sunflower bud moth |
| *Agrotis ipsilon*, black cutworm | *Homoeosoma electellum*, sunflower moth |
| *Helicoverpa zea*, corn earworm | |
| *Spodoptera frugiperda*, fall armyworm | Cotton |
|  | *Heliothis virescens*, cotton boll worm |
| *Diatraea grandiosella*, southwestern corn borer | *Helicoverpa zea*, cotton bollworm |
| *Elasmopalpus lignosellus*, lesser cornstalk borer | *Spodoptera exigua*, beet armyworm |
| *Diatraea saccharalis*, sugarcane borer | *Pectinophora gossypiella*, pink bollworm |
| Sorghum | Rice |
| *Chilo partellus*, sorghum borer | *Diatraea saccharalis*, sugarcane borer |
| *Spodoptera frugiperda*, fall armyworm | *Spodoptera frugiperda*, fall armyworm |
| *Helicoverpa zea*, corn earworm | *Helicoverpa zea*, corn earworm |
| *Elasmopalpus lignosellus*, lesser cornstalk borer | Soybean |
| *Feltia subterranea*, granulate cutworm | *Pseudoplusia includens*, soybean looper |
| Wheat | *Anticarsia gemmatalis*, velvetbean caterpillar |
| *Pseudaletia unipunctata*, army worm | |
| *Spodoptera frugiperda*, fall armyworm | *Plathypena scabra*, green cloverworm |
| *Elasmopalpus lignosellus*, lesser | *Ostrinia nubilalis*, European corn |

TABLE 1-continued

Lepidoptera (Butterflies and Moths)

| | |
|---|---|
| cornstalk borer | borer |
| *Agrotis orthogonia*, pale western cutworm | *Agrotis ipsilon*, black cutworm |
| | *Spodoptera exigua*, beet armyworm |
| *Elasmopalpus lignosellus*, lesser cornstalk borer | *Heliothis virescens*, cotton boll worm |
| | *Helicoverpa zea*, cotton bollworm |
| | Barley |
| | |
| | *Ostrinia nubilalis*, European corn borer |
| | *Agrotis ipsilon*, black cutworm |

TABLE 2

Coleoptera (Beetles)

Maize

*Diabrotica virgifera virgifera*, western corn rootworm
*Diabrotica longicornis barberi*, northern corn rootworm
*Diabrotica undecimpunctata howardi*, southern corn rootworm
*Melanotus spp.*, wireworms
*Cyclocephala borealis*, northern masked chafer (white grub)
*Cyclocephala immaculata*, southern masked chafer (white grub)
*Popillia japonica*, Japanese beetle
*Chaetocnema pulicaria*, corn flea beetle
*Sphenophorus maidis*, maize billbug
Sorghum

*Phyllophaga crinita*, white grub
*Eleodes, Conoderus,* and *Aeolus spp.*, wireworms
*Oulema melanopus*, cereal leaf beetle
*Chaetocnema pulicaria*, corn flea beetle
*Sphenophorus maidis*, maize billbug
Wheat

*Oulema melanopus*, cereal leaf beetle
*Hypera punctata*, clover leaf weevil
*Diabrotica undecimpunctata howardi*, southern corn rootworm
Sunflower

*Zygogramma exclamationis*, sunflower beetle
*Bothyrus gibbosus*, carrot beetle
Cotton

*Anthonomus grandis*, boll weevil
Rice

*Colaspis brunnea*, grape colaspis
*Lissorhoptrus oryzophilus*, rice water weevil
*Sitophilus oryzae*, rice weevil
Soybean

*Epilachna varivestis*, Mexican bean beetle

TABLE 3

Homoptera (Whiteflies, Aphids etc.)

Maize

*Rhopalosiphum maidis*, corn leaf aphid
*Anuraphis maidiradicis*, corn root aphid
Sorghum

*Rhopalosiphum maidis*, corn leaf aphid
*Sipha flava*, yellow sugarcane aphid
Wheat Russian wheat aphid
*Schizaphis graminum*, greenbug

TABLE 3-continued

Homoptera (Whiteflies, Aphids etc.)

*Macrosiphum avenae*, English grain aphid
Cotton

*Aphis gossypii*, cotton aphid
*Pseudatomoscelis seriatus*, cotton fleahopper
*Trialeurodes abutilonea*, bandedwinged whitefly
Rice

*Nephotettix nigropictus*, rice leafhopper
Soybean

*Myzus persicae*, green peach aphid
*Empoasca fabae*, potato leafhopper
Barley

*Schizaphis graminum*, greenbug
Oil Seed Rape

*Brevicoryne brassicae*, cabbage aphid

TABLE 4

Hemiptera (Bugs)

Maize

*Blissus leucopterus leucopterus*, chinch bug
Sorghum

*Blissus leucopterus leucopterus*, chinch bug
Cotton

*Lygus lineolaris*, tarnished plant bug
Rice

*Blissus leucopterus leucopterus*, chinch bug
*Acrosternum hilare*, green stink bug
Soybean

*Acrosternum hilare*, green stink bug
Barley

*Blissus leucopterus leucopterus*, chinch bug
*Acrosternum hilare*, green stink bug
*Euschistus servus*, brown stink bug

TABLE 5

Orthoptera (Grasshoppers, Crickets, and Cockroaches)

Maize

*Melanoplus femurrubrum*, redlegged grasshopper
*Melanoplus sanguinipes*, migratory grasshopper
Wheat

*Melanoplus femurrubrum*, redlegged grasshopper
*Melanoplus differentialis*, differential grasshopper
*Melanoplus sanguinipes*, migratory grasshopper
Cotton

*Melanoplus femurrubrum*, redlegged grasshopper
*Melanoplus differentialis*, differential grasshopper
Soybean

*Melanoplus femurrubrum*, redlegged grasshopper
*Melanoplus differentialis*, differential grasshopper
Structural/Household

*Periplaneta americana*, American cockroach

TABLE 5-continued

| Orthoptera (Grasshoppers, Crickets, and Cockroaches) |
|---|
| *Blattella germanica*, German cockroach |
| *Blatta orientalis*, oriental cockroach |

TABLE 6

| Diptera (Flies and Mosquitoes) |
|---|
| Maize |
| *Hylemya platura*, seedcorn maggot |
| *Agromyza parvicornis*, corn blotch leafminer |
| Sorghum |
| *Contarinia sorghicola*, sorghum midge |
| Wheat |
| *Mayetiola destructor*, Hessian fly |
| *Sitodiplosis mosellana*, wheat midge |
| *Meromyza americana*, wheat stem maggot |
| *Hylemya coarctata*, wheat bulb fly |
| Sunflower |
| *Neolasioptera murtfeldtiana*, sunflower seed midge |
| Soybean |
| *Hylemya platura*, seedcorn maggot |
| Barley |
| *Hylemya platura*, seedcorn maggot |
| *Mayetiola destructor*, Hessian fly |
| Insects attacking humans and animals and disease carriers |
| *Aedes aegypti*, yellowfever mosquito |
| *Aedes albopictus*, forest day mosquito |
| *Phlebotomus papatasii*, sand fly |
| *Musca domestica*, house fly |
| *Tabanus atratus*, black horse fly |
| *Cochliomyia hominivorax*, screwworm fly |

TABLE 7

| Thysanoptera (Thrips) |
|---|
| Maize |
| *Anaphothrips obscurus*, grass thrips |
| Wheat |
| *Frankliniella fusca*, tobacco thrips |
| Cotton |
| *Thrips tabaci*, onion thrips |
| *Frankliniella fusca*, tobacco thrips |
| Soybean |
| *Sericothrips variabilis*, soybean thrips |
| *Thrips tabaci*, onion thrips |

TABLE 8

| Hymenoptera (Sawflies, Ants, Wasps, etc.) |
|---|
| Maize |
| *Solenopsis milesta*, thief ant |
| Wheat |
| *Cephus cinctus*, wheat stem sawfly |

TABLE 9

| Other Orders and Representative Species |
|---|
| Dermaptera (Earwigs) |
| *Forficula auricularia*, European earwig |
| Isoptera (Termites) |
| *Reticulitermes flavipes*, eastern subterranean termite |
| Mallophaga (Chewing Lice) |
| *Cuclotogaster heterographa*, chicken head louse |
| *Bovicola bovis*, cattle biting louse |
| Anoplura (Sucking Lice) |
| *Pediculus humanus*, head and body louse |
| Siphonaptera (Fleas) |
| *Ctenocephalides felis*, cat flea |

TABLE 10

| Acari (Mites and Ticks) |
|---|
| Maize |
| *Tetranychus urticae*, twospotted spider mite |
| Sorghum |
| *Tetranychus cinnabarinus*, carmine spider mite |
| *Tetranychus urticae*, twospotted spider mite |
| Wheat |
| *Aceria tulipae*, wheat curl mite |
| Cotton |
| *Tetranychus cinnabarinus*, carmine spider mite |
| *Tetranychus urticae*, twospotted spider mite |
| Soybean |
| *Tetranychus turkestani*, strawberry spider mite |
| *Tetranychus urticae*, twospotted spider mite |
| Barley |
| *Petrobia latens*, brown wheat mite |
| Important human and animal Acari |
| *Demacentor variabilis*, American dog tick |
| *Argas persicus*, fowl tick |
| *Dermatophagoides farinae*, American house dust mite |
| *Dermatophagoides pteronyssinus*, European house dust mite |

Now that it has been recognized that pesticidal proteins can be isolated from the vegetative growth phase of Bacillus, other strains can be isolated by standard techniques and tested for activity against particular plant and non-plant pests. Generally Bacillus strains can be isolated from any environmental sample, including soil, plant, insect, grain elevator dust, and other sample material, etc., by methods known in the art. See, for example, Travers et al. (1987) Appl. Environ. Microbiol. 53:1263–1266; Saleh et al. (1969) Can J. Microbiol. 15:1101–1104; DeLucca et al. (1981) Can. J. Microbiol. 27:865–870; and Norris, et al. (1981) "The genera Bacillus and Sporolactobacillus," In Starr et al. (eds.), The Prokaryotes: A Handbook on Habitats, Isolation, and Identification of Bacteria, Vol. II, Springer-Verlog Berlin Heidelberg. After isolation, strains can be tested for pesticidal activity during vegetative growth. In this manner, new pesticidal proteins and strains can be identified.

Such Bacillus microorganisms which find use in the invention include *Bacillus cereus* and *Bacillus thuringiensis*, as well as those Bacillus species listed in Table 11.

TABLE 11

List of Bacillus species

| Morphological Group 1 | Unassigned Strains |
|---|---|
| B. megaterium | Subgroup A |
| B. cereus* | B. apiarus* |
| B. cereus var. mycoides | B. filicolonicus |
| B. thuringiensis* | B. thiaminolyticus |
| B. licheniformis | B. alcalophilus |
| B. subtilis* | Subgroup B |
| B. pumilus | B. cirroflagellosus |
| B. firmus* | B. chitinosporus |
| B. coagulans | B lentus |
| Morphological Group 2 | Subgroup C |
| B. polymyxa | B. badius |
| B. macerans | B. aneurinolyticus |
| B. circulans | B. macroides |
| B. stearothermophilus | B. freundenreichii |
| B. alvei* | Subgroup D |
| B. laterosporus* | B. pantothenticus |
| B. brevis | B. epiphytus |
| B. pulvifaciens | Subgroup E1 |
| B. popilliae* | B. aminovorans |
| B. lentimorbus* | B. globisporus |
| B. larvae* | B. insolitus |
| Morphological Group 3 | B. psychrophilus |
| B. sphaericus * | Subgroup E2 |
| B. pasteurii | B. psychrosaccharolyticus |
| | B. macquariensis |

\* = Those Bacillus strains that have been previously found associated with insects
Grouping according to Parry, J.M. et al. (1983) Color Atlas of Bacillus species, Wolfe Medical Publications, London.

In accordance with the present invention, the pesticidal proteins produced during vegetative growth can be isolated from Bacillus. In one embodiment, insecticidal proteins produced during vegetative growth, can be isolated. Methods for protein isolation are known in the art. Generally, proteins can be purified by conventional chromatography, including gel-filtration, ion-exchange, and immunoaffinity chromatography, by high-performance liquid chromatography, such as reversed-phase high-performance liquid chromatography, ion-exchange high-performance liquid chromatography, size-exclusion high-performance liquid chromatography, high-performance chromatofocusing and hydrophobic interaction chromatography, etc., by electrophoretic separation, such as one-dimensional gel electrophoresis, two-dimensional gel electrophoresis, etc. Such methods are known in the art. See for example Current Protocols in Molecular Biology, Vols. 1 and 2, Ausubel et al. (eds.), John Wiley & Sons, N.Y. (1988). Additionally, antibodies can be prepared against substantially pure preparations of the protein. See, for example, Radka et al. (1983) J. Immunol. 128:2804; and Radka et al. (1984) Immunogenetics 19:63. Any combination of methods may be utilized to purify protein having pesticidal properties. As the protocol is being formulated, pesticidal activity is determined after each purification step.

Such purification steps will result in a substantially purified protein fraction. By "substantially purified" or "substantially pure" is intended protein which is substantially free of any compound normally associated with the protein in its natural state. "Substantially pure" preparations of protein can be assessed by the absence of other detectable protein bands following SDS-PAGE as determined visually or by densitometry scanning. Alternatively, the absence of other amino-terminal sequences or N-terminal residues in a purified preparation can indicate the level of purity. Purity can be verified by rechromatography of "pure" preparations showing the absence of other peaks by ion exchange, reverse phase or capillary electrophoresis. The terms "substantially pure" or "substantially purified" are not meant to exclude artificial or synthetic mixtures of the proteins with other compounds. The terms are also not meant to exclude the presence of minor impurities which do not interfere with the biological activity of the protein, and which may be present, for example, due to incomplete purification.

Once purified protein is isolated, the protein, or the polypeptides of which it is comprised, can be characterized and sequenced by standard methods known in the art. For example, the purified protein, or the polypeptides of which it is comprised, may be fragmented as with cyanogen bromide, or with proteases such as papain, chymotrypsin, trypsin, lysyl-C endopeptidase, etc. (Oike et al. (1982) J. Biol. Chem. 257:9751–9758; Liu et al. (1983) Int. J. Pept. Protein Res. 21:209–215). The resulting peptides are separated, preferably by HPLC, or by resolution of gels and electroblotting onto PVDF membranes, and subjected to amino acid sequencing. To accomplish this task, the peptides are preferably analyzed by automated sequenators. It is recognized that N-terminal, C-terminal, or internal amino acid sequences can be determined. From the amino acid sequence of the purified protein, a nucleotide sequence can be synthesized which can be used as a probe to aid in the isolation of the gene encoding the pesticidal protein.

It is recognized that the pesticidal proteins may be oligomeric and will vary in molecular weight, number of protomers, component peptides, activity against particular pests, and in other characteristics. However, by the methods set forth herein, proteins active against a variety of pests may be isolated and characterized.

Once the purified protein has been isolated and characterized it is recognized that it may be altered in various ways including amino acid substitutions, deletions, truncations, and insertions. Methods for such manipulations are generally known in the art. For example, amino acid sequence variants of the pesticidal proteins can be prepared by mutations in the DNA. Such variants will possess the desired pesticidal activity. Obviously, the mutations that will be made in the DNA encoding the variant must not place the sequence out of reading frame and preferably will not create complementary regions that could produce secondary mRNA structure. See, EP Patent Application Publication No. 75,444.

In this manner, the present invention encompasses the pesticidal proteins as well as components and fragments thereof. That is, it is recognized that component protomers, polypeptides or fragments of the proteins may be produced which retain pesticidal activity. These fragments include truncated sequences, as well as N-terminal, C-terminal, internal and internally deleted amino acid sequences of the proteins.

Most deletions, insertions, and substitutions of the protein sequence are not expected to produce radical changes in the characteristics of the pesticidal protein. However, when it is difficult to predict the exact effect of the substitution, deletion, or insertion in advance of doing so, one skilled in the art will appreciate that the effect will be evaluated by routine screening assays.

The proteins or other component polypeptides described herein may be used alone or in combination. That is, several proteins may be used to control different insect pests.

Some proteins are single polypeptide chains while many proteins consist of more than one polypeptide chain, i.e., they are oligomeric. Additionally, some VIPs are pesticidally active as oligomers. In these instances, additional protomers are utilized to enhance the pesticidal activity or to activate pesticidal proteins. Those protomers which enhance or activate are referred to as auxiliary proteins. Auxiliary proteins activate or enhance a pesticidal protein by interacting with the pesticidal protein to form an oligomeric protein having increased pesticidal activity compared to that observed in the absence of the auxiliary protein.

Auxiliary proteins activate or increase the activity of pesticidal proteins such as the VIP1 protein from AB78. Such auxiliary proteins are exemplified by, but not limited to, the VIP2 protein from AB78. As demonstrated in the Experimental section of the application, auxiliary proteins can activate a number of pesticidal proteins. Thus, in one embodiment of the invention, a plant, Parent 1, can be transformed with an auxiliary protein. This Parent 1 can be crossed with a number of Parent 2 plants transformed with one or more pesticidal proteins whose pesticidal activities are activated by the auxiliary protein.

The pesticidal proteins of the invention can be used in combination with Bt endotoxins or other insecticidal proteins to increase insect target range. Furthermore, the use of the VIPs of the present invention in combination with Bt δ-endotoxins or other insecticidal principles of a distinct nature has particular utility for the prevention and/or management of insect resistance. Other insecticidal principles include protease inhibitors (both serine and cysteine types), lectins, α-amylase and peroxidase. In one preferred embodiment, expression of VIPs in a transgenic plant is accompanied by the expression of one or more Bt δ-endotoxins. This co-expression of more than one insecticidal principle in the same transgenic plant can be achieved by genetically engineering a plant to contain and express all the genes necessary. Alternatively, a plant, Parent 1, can be genetically engineered for the expression of VIPs. A second plant, Parent 2, can be genetically engineered for the expression of Bt δ-endotoxin. By crossing Parent 1 with Parent 2, progeny plants are obtained which express all the genes introduced into Parents 1 and 2. Particularly preferred Bt δ-endotoxins are those disclosed in U.S. application Ser. No. 07/951,715, herein incorporated by reference.

A substantial number of cytotoxic proteins, though not all, are binary in action. Binary toxins typically consist of two protein domains, one called the A domain and the other called the B domain (see *Sourcebook of Bacterial Protein Toxins*, J. E. Alouf and J. H. Freer eds.(1991) Academic Press). The A domain possesses a potent cytotoxic activity. The B domain binds an external cell surface receptor before being internalized. Typically, the cytotoxic A domain must be escorted to the cytoplasm by a translocation domain. Often the A and B domains are separate polypeptides or protomers, which are associated by a protein-protein interaction or a di-sulfide bond. However, the toxin can be a single polypeptide which is proteolytically processed within the cell into two domains as in the case for Pseudomonas exotoxin A. In summary binary toxins typically have three important domains, a cytotoxic A domain, a receptor binding B domain and a translocation domain. The A and B domain are often associated by protein-protein interacting domains.

The receptor binding domains of the present invention are useful for delivering any protein, toxin, enzyme, transcription factor, nucleic acid, chemical or any other factor into target insects having a receptor recognized by the receptor binding domain of the binary toxins described in this patent. Similarly, since binary toxins have translocation domains which penetrate phospholipid bilayer membranes and escort cytotoxins across those membranes, such translocation domains may be useful in escorting any protein, toxin, enzyme, transcription factor, nucleic acid, chemical or any other factor across a phospholipid bilayer such as the plasma membrane or a vesicle membrane. The translocation domain may itself perforate membranes, thus having toxic or insecticidal properties. Further, all binary toxins have cytotoxic domains; such a cytotoxic domain may be useful as a lethal protein, either alone or when delivered into any target cell(s) by any means.

Finally, since binary toxins comprised of two polypeptides often form a complex, it is likely that there are protein-protein interacting regions within the components of the binary toxins of the invention. These protein-protein interacting domains may be useful in forming associations between any combination of toxins, enzymes, transcription factors, nucleic acids, antibodies, cell binding moieties, or any other chemicals, factors, proteins or protein domains.

Toxins, enzymes, transcription factors, antibodies, cell binding moieties or other protein domains can be fused to pesticidal or auxiliary proteins by producing in frame genetic fusions which, when translated by ribosomes, would produce a fusion protein with the combined attributes of the VIP and the other component used in the fusion. Furthermore, if the protein domain fused to the VIP has an affinity for another protein, nucleic acid, carbohydrate, lipid, or other chemical or factor, then a three-component complex can be formed. This complex will have the attributes of all of its components. A similar rationale can be used for producing four or more component complexes. These complexes are useful as insecticidal toxins, pharmaceuticals, laboratory reagents, and diagnostic reagents, etc. Examples where such complexes are currently used are fusion toxins for potential cancer therapies, reagents in ELISA assays and immunoblot analysis.

One strategy of altering pesticidal or auxiliary proteins is to fuse a 15-amino-acid "S-tag" to the protein without destroying the insect cell binding domain(s), translocation domains or protein-protein interacting domains of the proteins. The S-tag has a high affinity ($K_d=10^{-9}M$) for a ribonuclease S-protein, which, when bound to the S-tag, forms an active ribonuclease (See F. M. Richards and H. W. Wyckoff (1971) in "The Enzymes", Vol. IV (Boyer, P. D. ed.). pp. 647–806. Academic Press, New York). The fusion can be made in such a way as to destroy or remove the cytotoxic activity of the pesticidal or auxiliary protein, thereby replacing the VIP cytotoxic activity with a new cytotoxic ribonuclease activity. The final toxin would be comprised of the S-protein, a pesticidal protein and an auxiliary protein, where either the pesticidal protein or the auxiliary protein is produced as translational fusions with the S-tag. Similar strategies can be used to fuse other potential cytotoxins to pesticidal or auxiliary proteins including (but not limited to) ribosome inactivating proteins, insect hormones, hormone receptors, transcription factors, proteases, phosphatases, Pseudomonas exotoxin A, or any other protein or chemical factor that is lethal when delivered into cells. Similarly, proteins can be delivered into cells which are not lethal, but might alter cellular biochemistry or physiology.

The spectrum of toxicity toward different species can be altered by fusing domains to pesticidal or auxiliary proteins which recognize cell surface receptors from other species. Such domains might include (but are not limited to) antibodies, transferrin, hormones, or peptide sequences isolated from phage displayed affinity selectable libraries. Also, peptide sequences which are bound to nutrients, vitamins, hormones, or other chemicals that are transported into cells could be used to alter the spectrum of toxicity. Similarly, any other protein or chemical which binds a cell surface receptor or the membrane and could be internalized might be used to alter the spectrum of activity of VIP1 and VIP2.

The pesticidal proteins of the present invention are those proteins which confer a specific pesticidal property. Such proteins may vary in molecular weight, having component polypeptides at least a molecular weight of 30 kDa or greater, preferably about 50 kDa or greater.

The auxiliary proteins of the invention may vary in molecular weight, having at least a molecular weight of about 15 kDa or greater, preferably about 20 kDa or greater; more preferably, about 30 kDa or greater. The auxiliary proteins themselves may have component polypeptides.

It is possible that the pesticidal protein and the auxiliary protein may be components of a multimeric, pesticidal protein. Such a pesticidal protein which includes the auxiliary proteins as one or more of its component polypeptides may vary in molecular weight, having at least a molecular weight of 50 kDa up to at least 200 kDa, preferably about 100 kDa to 150 kDa.

An auxiliary protein may be used in combination with the pesticidal proteins of the invention to enhance activity or to activate the pesticidal protein. To determine whether the auxiliary protein will affect activity, the pesticidal protein can be expressed alone and in combination with the auxiliary protein and the respective activities compared in feeding assays for pesticidal activity.

It may be beneficial to screen strains for potential pesticidal activity by testing activity of the strain alone and in combination with the auxiliary protein. In some instances an auxiliary protein in combination with the native proteins of the strains yields pesticidal activity where none is seen in the absence of an auxiliary protein.

The auxiliary protein can be modified, as described above, by various methods known in the art. Therefore, for purposes of the invention, the term "Vegetative Insecticidal Protein" (VIP) encompasses those proteins produced during vegetative growth which alone or in combination can be used for pesticidal activity. This includes pesticidal proteins, auxiliary proteins and those proteins which demonstrate activity only in the presence of the auxiliary protein or the polypeptide components of these proteins.

It is recognized that there are alternative methods available to obtain the nucleotide and amino acid sequences of the present proteins. For example, to obtain the nucleotide sequence encoding the pesticidal protein, cosmid clones, which express the pesticidal protein, can be isolated from a genomic library. From larger active cosmid clones, smaller subclones can be made and tested for activity. In this manner, clones which express an active pesticidal protein can be sequenced to determine the nucleotide sequence of the gene. Then, an amino acid sequence can be deduced for the protein. For general molecular methods, see, for example, Molecular Cloning, A Laboratory Manual, Second Edition, Vols. 1–3, Sambrook et al. (eds.) Cold Spring Harbor Laboratory Press, Cold Spring Harbor, N.Y. (1989), and the references cited therein.

The present invention also encompasses nucleotide sequences from organisms other than Bacillus, where the nucleotide sequences are isolatable by hybridization with the Bacillus nucleotide sequences of the invention. Proteins encoded by such nucleotide sequences can be tested for pesticidal activity. The invention also encompasses the proteins encoded by the nucleotide sequences. Furthermore, the invention encompasses proteins obtained from organisms other than Bacillus wherein the protein cross-reacts with antibodies raised against the proteins of the invention. Again the isolated proteins can be assayed for pesticidal activity by the methods disclosed herein or others well-known in the art.

Once the nucleotide sequences encoding the pesticidal proteins of the invention have been isolated, they can be manipulated and used to express the protein in a variety of hosts including other organisms, including microorganisms and plants.

The pesticidal genes of the invention can be optimized for enhanced expression in plants. See, for example U.S. application Ser. No. 07/951,715; EPA 0359472; EPA 0385962; WO 91/16432; Perlak et al. (1991) Proc. Natl. Acad. Sci. USA 88:3324–3328; and Murray et al. (1989) Nucleic Acids Research 17:477–498. In this manner, the genes can be synthesized utilizing plant preferred codons. That is the preferred codon for a particular host is the single codon which most frequently encodes that amino acid in that host. The maize preferred codon, for example, for a particular amino acid may be derived from known gene sequences from maize. Maize codon usage for 28 genes from maize plants is found in Murray et al. (1989), Nucleic Acids Research 17:477–498, the disclosure of which is incorporated herein by reference. Synthetic genes can also be made based on the distribution of codons a particular host uses for a particular amino acid.

In this manner, the nucleotide sequences can be optimized for expression in any plant. It is recognized that all or any part of the gene sequence may be optimized or synthetic. That is, synthetic or partially optimized sequences may also be used.

In like manner, the nucleotide sequences can be optimized for expression in any microorganism. For Bacillus preferred codon usage, see, for example U.S. Pat. No. 5,024,837 and Johansen et al. (1988) Gene 65:293–304.

Methodologies for the construction of plant expression cassettes as well as the introduction of foreign DNA into plants are described in the art. Such expression cassettes may include promoters, terminators, enhancers, leader sequences, introns and other regulatory sequences operably linked to the pesticidal protein coding sequence. It is further recognized that promoters or terminators of the VIP genes can be used in expression cassettes.

Generally, for the introduction of foreign DNA into plants Ti plasmid vectors have been utilized for the delivery of foreign DNA as well as direct DNA uptake, liposomes, electroporation, micro-injection, and the use of microprojectiles. Such methods had been published in the art. See, for example, Guerche et al., (1987) Plant Science 52:111–116; Neuhause et al., (1987) Theor. Appl. Genet. 75:30–36; Klein et al., (1987) Nature 327:70–73; Howell et al., (1980) Science 208:1265; Horsch et al., (1985) Science 227:1229–1231; DeBlock et al., (1 989) Plant Physiology 91:694–701; Methods for Plant Molecular Biology (Weissbach and Weissbach, eds.) Academic Press, Inc. (1988); and Methods in Plant Molecular Biology (Schuler and Zielinski, eds.) Academic Press, Inc. (1989). See also U.S. patent application Ser. No. 08/008,374 herein incorporated by reference. See also, EPA 0193259 and EPA 0451878A1. It is understood that the method of transformation will depend upon the plant cell to be transformed.

It is further recognized that the components of the expression cassette may be modified to increase expression. For example, truncated sequences, nucleotide substitutions or other modifications may be employed. See, for example Perlak et al. (1991) *Proc. Natl. Acad. Sci. USA* 88:3324–3328; Murray et al., (1989) *Nucleic Acids Research* 17:477–498; and WO 91/16432.

The construct may also include any other necessary regulators such as terminators, (Guerineau et al., (1991), *Mol. Gen. Genet.*, 226:141–144; Proudfoot, (1991), *Cell,* 64:671–674; Sanfacon et al., (1991), *Genes Dev.,* 5:141–149; Mogen et al., (1990), *Plant Cell,* 2:1261–1272; Munroe et al., (1990), *Gene,* 91:151–158; Ballas et al et al., (1989), *Nucleic Acids Res.,* 17:7891–7903; Joshi et al., (1987), *Nucleic Acid Res.,* 15:9627–9639); plant translational consensus sequences (Joshi, C. P., (1987), *Nucleic Acids Research,* 15:6643–6653), introns (Luehrsen and Walbot, (1991), *Mol. Gen. Genet.*, 225:81–93) and the like, operably linked to the nucleotide sequence. It may be beneficial to include 5' leader sequences in the expression cassette construct. Such leader sequences can act to enhance translation. Translational leaders are known in the art and include:

Picornavirus leaders, for example, EMCV leader (encephalomyocarditis 5' noncoding region) (Elroy-Stein, O., Fuerst, T. R., and Moss, B. (1989) *PNAS USA* 86:6126–6130);

Potyvirus leaders, for example, TEV leader (Tobacco Etch Virus) (Allison et al., (1986); MDMV leader (Maize Dwarf Mosaic Virus); *Virology,* 154:9–20), and Human immunoglobulin heavy-chain binding protein (BiP), (Macejak, D. G., and Sarnow, P., (1991), *Nature,* 353:90–94;

Untranslated leader from the coat protein mRNA of alfalfa mosaic virus (AMV RNA 4), (Jobling, S. A., and Gehrke, L., (1987), *Nature,* 325:622–625;

Tobacco mosaic virus leader (TMV), (Gallie, D. R. et al., (1989), *Molecular Biology of RNA,* pages 237–256; and Maize Chlorotic Mottle Virus leader (MCMV) (Lommel, S. A. et al., (1991), *Virology, 81:382–385*. See also, Della-Cioppa et al., (1987), *Plant Physiology,* 84:965–968.

A plant terminator may be utilized in the expression cassette. See, Rosenberg et al., (1987), *Gene,* 56:125; Guerineau et al., (1991), *Mol. Gen. Genet.,* 226:141–144; Proudfoot, (1991), *Cell,* 64:671–674; Sanfacon et al., (1991), *Genes Dev.,* 5:141–149; Mogen et al., (1990), *Plant Cell,* 2:1261–1272; Munroe et al., (1990), *Gene,* 91:151–158; Ballas et al., (1989), *Nucleic Acids Res.,* 17:7891–7903; Joshi et al., (1987), *Nucleic Acid Res.,* 15:9627–9639.

For tissue specific expression, the nucleotide sequences of the invention can be operably linked to tissue specific promoters. See, for example, U.S. application Ser. No. 07/951,715 herein incorporated by reference.

It is recognized that the genes encoding the pesticidal proteins can be used to transform insect pathogenic organisms. Such organisms include Baculoviruses, fungi, protozoa, bacteria and nematodes.

The Bacillus strains of the invention may be used for protecting agricultural crops and products from pests. Alternatively, a gene encoding the pesticide may be introduced via a suitable vector into a microbial host, and said host applied to the environment or plants or animals. Microorganism hosts may be selected which are known to occupy the "phytosphere" (phylloplane, phyllosphere, rhizosphere, and/or rhizoplana) of one or more crops of interest. These microorganisms are selected so as to be capable of successfully competing in the particular environment with the wild-type microorganisms, provide for stable maintenance and expression of the gene expressing the polypeptide pesticide, and, desirably, provide for improved protection of the pesticide from environmental degradation and inactivation.

Such microorganisms include bacteria, algae, and fungi. Of particular interest are microorganisms, such as bacteria, e.g., Pseudomonas, Erwinia, Serratia, Klebsiella, Xanthomonas, Streptomyces, Rhizobium, Rhodopseudomonas, Methylius, Agrobacterium, Acetobacter, Lactobacillus, Arthrobacter, Azotobacter, Leuconostoc, and Alcaligenes; fungi, particularly yeast, e.g., Saccharomyces, Cryptococcus, Kluyveromyces, Sporobolomyces, Rhodotorula, and Aureobasidium. Of particular interest are such phytosphere bacterial species as *Pseudomonas syringae, Pseudomonas fluorescens, Serratia marcescens, Acetobacter xylinum*, Agrobacteria, *Rhodopseudomonas spheroides, Xanthomonas campestris, Rhizobium melioti, Alcaligenes entrophus, Clavibacter xyli and Azotobacter vinlandii*; and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces rosues, S. odorus, Kluyveromyces veronae, and Aureobasidium pollulans*. Of particular interest are the pigmented microorganisms.

A number of ways are available for introducing a gene expressing the pesticidal protein into the microorganism host under conditions which allow for stable maintenance and expression of the gene. For example, expression cassettes can be constructed which include the DNA constructs of interest operably linked with the transcriptional and translational regulatory signals for expression of the DNA constructs, and a DNA sequence homologous with a sequence in the host organism, whereby integration will occur, and/or a replication system which is functional in the host, whereby integration or stable maintenance will occur.

Transcriptional and translational regulatory signals include but are not limited to promoter, transcriptional initiation start site, operators, activators, enhancers, other regulatory elements, ribosomal binding sites, an initiation codon, termination signals, and the like. See, for example, U.S. Pat. No. 5,039,523; U.S. Pat. No. 4,853,331; EPO 0480762A2; Sambrook et al. supra; Molecular Cloning, a Laboratory Manual, Maniatis et al. (eds) Cold Spring Harbor Laboratory, Cold Spring Harbor, N.Y. (1982); Advanced Bacterial Genetics, Davis et al. (eds.) Cold Spring Harbor Laboratory, Cold Spring Harbor, N.Y. (1980); and the references cited therein.

Suitable host cells, where the pesticide-containing cells will be treated to prolong the activity of the toxin in the cell when the then treated cell is applied to the environment of the target pest(s), may include either prokaryotes or eukaryotes, normally being limited to those cells which do not produce substances toxic to higher organisms, such as mammals. However, organisms which produce substances toxic to higher organisms could be used, where the toxin is unstable or the level of application sufficiently low as to avoid any possibility of toxicity to a mammalian host. As hosts, of particular interest will be the prokaryotes and the lower eukaryotes, such as fungi. Illustrative prokaryotes, both Gram-negative and -positive, include Enterobacteriaceae, such as Escherichia, Erwinia, Shigella, Salmonella, and Proteus; Bacillaceae; Rhizobiceae, such as Rhizobium; Spirillaceae, such as photobacterium, Zymomonas, Serratia, Aeromonas, Vibrio, Desulfovibrio, Spirillum; Lactobacillaceae; Pseudomonadaceae, such as Pseudomonas and Acetobacter; Azotobacteraceae and Nitrobacteraceae. Among eukaryotes are fungi, such as Phycomycetes and Ascomycetes, which includes yeast, such a Saccharomyces and Schizosaccharmomyces; and Basidiomycetes yeast, such as Rhodotorula, Aureobasidium, Sporobolomyces, and the like.

Characteristics of particular interest in selecting a host cell for purposes of production include ease of introducing the protein gene into the host, availability of expression systems, efficiency of expression, stability of the protein in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; leaf affinity; lack of mammalian toxicity; attractiveness to pests for ingestion; ease of killing and fixing without damage to the toxin; and the like. Other considerations include ease of formulation and handling, economics, storage stability, and the like.

Host organisms of particular interest include yeast, such as Rhodotorula sp., Aureobasidium sp., Saccharomyces sp., and Sporobolomyces sp.; phylloplane organisms such as Pseudomonas sp., Erwinia sp. and Flavobacterium sp.; or such other organisms as Escherichia, LactoBacillus sp., Bacillus sp., and the like. Specific organisms include *Pseudomonas aeurginosa, Pseudomonas fluorescens, Saccharomyces cerevisiae, Bacillus thuringiensis, Escherichia coli, Bacillus subtilis*, and the like.

VIP genes can be introduced into micro-organisms that multiply on plants (epiphytes) to deliver VIP proteins to potential target pests. Epiphytes can be gram-positive or gram-negative bacteria for example.

Root colonizing bacteria, for example, can be isolated from the plant of interest by methods known in the art. Specifically, a *Bacillus cereus* strain which colonizes roots could be isolated from roots of a plant (for example see J. Handelsman, S. Raffel, E. Mester, L. Wunderlich and C. Grau, *Appl. Environ. Microbiol.* 56:713–718, (1990)). VIP1 and/or VIP2 could be introduced into a root colonizing *Bacillus cereus* by standard methods known in the art.

Specifically, VIP1 and/or VIP2 derived from *Bacillus cereus* strain AB78 can be introduced into a root colonizing *Bacillus cereus* by means of conjugation using standard methods (J. Gonzalez, B. Brown and B. Carlton, *Proc. Natl. Acad. Sci.* 79:6951–6955, (1982)).

Also, VIP1 and/or VIP2 or other VIPs of the invention can be introduced into the root colonizing Bacillus by means of electro-transformation. Specifically, VIPs can be cloned into a shuttle vector, for example, pHT3101 (D. Lereclus et al., *FEMS Microbiol. Letts.*, 60:211–218 (1989)) as described in Example 10. The shuttle vector pHT3101 containing the coding sequence for the particular VIP can then be transformed into the root colonizing Bacillus by means of electroporation (D. Lereclus et al. 1989, *FEMS Microbiol. Letts.* 60:211–218).

Expression systems can be designed so that VIP proteins are secreted outside the cytoplasm of gram negative bacteria, *E. coli*, for example. Advantages of having VIP proteins secreted are (1) it avoids potential toxic effects of VIP proteins expressed within the cytoplasm and (2) it can increase the level of VIP protein expressed and (3) can aid in efficient purification of VIP protein.

VIP proteins can be made to be secreted in *E. coli*, for example, by fusing an appropriate *E. coli* signal peptide to the amino-terminal end of the VIP signal peptide or replacing the VIP signal peptide with the *E. coli* signal peptide. Signal peptides recognized by *E. coli* can be found in proteins already known to be secreted in *E. coli*, for example the OmpA protein (J. Ghrayeb, H. Kimura, M. Takahara, Y. Masui and M. Inouye, *EMBO J.*, 3:2437–2442 (1984)). OmpA is a major protein of the *E. coli* outer membrane and thus its signal peptide is thought to be efficient in the translocation process. Also, the OmpA signal peptide does not need to be modified before processing as may be the case for other signal peptides, for example lipoprotein signal peptide (G. Duffaud, P. March and M. Inouye, *Methods in Enzymology.* 153:492 (1987)).

Specifically, unique BamHI restriction sites can be introduced at the amino-terminal and carboxy-terminal ends of the VIP coding sequences using standard methods known in the art. These BamHI fragments can be cloned, in frame, into the vector pIN-III-ompA1, A2 or A3 (J. Ghrayeb, H. Kimura, M. Takahara, H. Hsiung, Y. Masui and M. Inouye, *EMBO J.*, 3:2437–2442 (1984)) thereby creating ompA:VIP fusion gene which is secreted into the periplasmic space. The other restriction sites in the polylinker of pIN-III-ompA can be eliminated by standard methods known in the art so that the VIP amino-terminal amino acid coding sequence is directly after the ompA signal peptide cleavage site. Thus, the secreted VIP sequence in *E. coli* would then be identical to the native VIP sequence.

When the VIP native signal peptide is not needed for proper folding of the mature protein, such signal sequences can be removed and replaced with the ompA signal sequence. Unique BamHI restriction sites can be introduced at the amino-termini of the proprotein coding sequences directly after the signal peptide coding sequences of VIP and at the carboxy-termini of VIP coding sequence. These BamHI fragments can then be cloned into the pIN-III-ompA vectors as described above.

General methods for employing the strains of the invention in pesticide control or in engineering other organisms as pesticidal agents are known in the art. See, for example U.S. Pat. No. 5,039,523 and EP 0480762A2.

VIPs can be fermented in a bacterial host and the resulting bacteria processed and used as a microbial spray in the same manner that *Bacillus thuringiensis* strains have been used as insecticidal sprays. In the case of a VIP(s) which is secreted from Bacillus, the secretion signal is removed or mutated using procedures known in the art. Such mutations and/or deletions prevent secretion of the VIP protein(s) into the growth medium during the fermentation process. The VIPs are retained within the cell and the cells are then processed to yield the encapsulated VIPs. Any suitable microorganism can be used for this purpose. Psuedomonas has been used to express *Bacillus thuringiensis* endotoxins as encapsulated proteins and the resulting cells processed and sprayed as an insecticide. (H. Gaertner et al. 1993, In Advanced Engineered Pesticides, L. Kim ed.)

Various strains of *Bacillus thuringiensis* are used in this manner. Such *Bt* strains produce endotoxin protein(s) as well as VIPs. Alternatively, such strains can produce only VIPs. A sporulation deficient strain of *Bacillus subtilis* has been shown to produce high levels of the CryIIIA endotoxin from *Bacillus thuringiensis* (Agaisse, H. and Lereclus, D., "Expression in *Bacillus subtilis* of the *Bacillus thuringiensis* CryIIIA toxin gene is not dependent on a sporulation-specific sigma factor and is increased in a spoOA mutant", *J. Bacteriol.*, 176:4734–4741 (1994)). A similar spoOA mutant can be prepared in *Bacillus thuringiensis* and used to produce encapsulated VIPs which are not secreted into the medium but are retained within the cell.

To have VIPs maintained within the Bacillus cell the signal peptide can be disarmed so that it no longer functions as a secretion signal. Specifically, the putative signal peptide for VIP1 encompasses the first 31 amino acids of the protein with the putative consensus cleavage site, Ala-X-Ala, at the C-terminal portion of this sequence (G. von Heijne, *J. Mol. Biol.* 184:99–105 (1989)) and the putative signal peptide for VIP2 encompasses the first 40 amino acids of the protein with the putative cleavage site after Ala40. The cleavage sites in either VIP1 or VIP2 can be mutated with methods known in the art to replace the cleavage site consensus sequence with alternative amino acids that are not recognized by the signal peptidases.

Alternatively, the signal peptides of VIP1, VIP2 and/or other VIPs of the invention can be eliminated from the sequence thereby making them unrecognizable as secretion proteins in Bacillus. Specifically, a methionine start site can be engineered in front of the proprotein sequence in VIP1, starting at Asp32, or the proprotein sequence in VIP2, starting at Glu41 using methods known in the art.

VIP genes can be introduced into micro-organisms that multiply on plants (epiphytes) to deliver VIP proteins to potential target pests. Epiphytes can be gram-positive or gram-negative bacteria for example.

The Bacillus strains of the invention or the microorganisms which have been genetically altered to contain the pesticidal gene and protein may be used for protecting agricultural crops and products from pests. In one aspect of the invention, whole, i.e., unlysed, cells of a toxin (pesticide)-producing organism are treated with reagents that prolong the activity of the toxin produced in the cell when the cell is applied to the environment of target pest(s).

Alternatively, the pesticides are produced by introducing a heterologous gene into a cellular host. Expression of the heterologous gene results, directly or indirectly, in the intracellular production and maintenance of the pesticide. These cells are then treated under conditions that prolong the activity of the toxin produced in the cell when the cell is applied to the environment of target pest(s). The resulting product retains the toxicity of the toxin. These naturally encapsulated pesticides may then be formulated in accordance with conventional techniques for application to the environment hosting a target pest, e.g., soil, water, and foliage of plants. See, for example EPA 0192319, and the references cited therein.

The active ingredients of the present invention are normally applied in the form of compositions and can be applied to the crop area or plant to be treated, simultaneously or in succession, with other compounds. These compounds can be both fertilizers or micronutrient donors or other preparations that influence plant growth. They can also be selective herbicides, insecticides, fungicides, bactericides, nematicides, mollusicides or mixtures of several of these preparations, if desired, together with further agriculturally acceptable carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers.

Preferred methods of applying an active ingredient of the present invention or an agrochemical composition of the present invention which contains at least one of the pesticidal proteins produced by the bacterial strains of the present invention are leaf application, seed coating and soil application. The number of applications and the rate of application depend on the intensity of infestation by the corresponding pest.

In one embodiment of the invention a *Bacillus cereus* microorganism has been isolated which is capable of killing *Diabrotica virgifera virgifera*, and *Diabrotica longicornis barber*. The novel *B. cereus* strain AB78 has been deposited in the Agricultural Research Service, Patent Culture Collection (NRRL), Northern Regional Research Center, 1815 North University Street, Peoria, Ill. 61604, USA and given Accession No. NRRL B-21058.

A fraction protein has been substantially purified from the *B. cereus* strain. This purification of the protein has been verified by SDS-PAGE and biological activity. The protein has a molecular weight of about 60 to about 100 kDa, particularly about 70 to about 90 kDa, more particularly about 80 kDa, hereinafter VIP.

Amino-terminal sequencing has revealed the N-terminal amino-acid sequence to be: $NH_2$-Lys-Arg-Glu-Ile-Asp-Glu-Asp-Thr-Asp-Thr-Asx-Gly-Asp-Ser-Ile-Pro- (SEQ ID NO:8) where Asx represents either Asp or Asn. The entire amino acid sequence is given in SEQ ID NO:7. The DNA sequence which encodes the amino acid sequence of SEQ ID NO:7 is disclosed in SEQ ID NO:6.

An oligonucleotide probe for the region of the gene encoding amino acids 3–9 of the $NH_2$-terminus has been generated. The probe was synthesized based on the codon usage of a *Bacillus thuringiensis* (*Bt*) δ-endotoxin gene. The nucleotide sequence of the oligonucleotide probe used for Southern hybridizations was as follows:

5'-GAA ATT GAT CAA GAT ACN GAT -3' (SEQ ID NO:9)

where N represents any base.

In addition, the DNA probe for the Bc AB78 VIP1 gene described herein, permits the screening of any Bacillus strain or other organisms to determine whether the VIP1 gene (or related gene) is naturally present or whether a particular transformed organism includes the VIP1 gene.

The invention now being generally described, the same will be better understood by reference to the following detailed examples that are provided for the purpose of illustration and are not to be considered limiting of the invention unless so specified.

A standard nomenclature has been developed based on the sequence identity of the proteins encompassed by the present invention. The gene and protein names for the detailed examples which follow and their relationship to the names used in the parent application are shown below.

| Gene/Protein Name under Standard Nomenclature | Gene/Protein Name in Parent | Desription of Protein |
|---|---|---|
| VIP1A(a) | VIP1 | VIP1 from strain AB78 as disclosed in SEQ ID NO:5. |
| VIP2A(a) | VIP2 | VIP2 from strain AB78 as disclosed in SEQ ID NO:2. |
| VIP1A(b) | VIP1 homolog | VIP1 from *Bacillus thuringiensis var. tenebrionis* as disclosed in SEQ ID NO:21. |

-continued

| Gene/Protein Name under Standard Nomenclature | Gene/Protein Name in Parent | Desription of Protein |
|---|---|---|
| VIP2A(b) | VIP2 homolog | VIP2 from *Bacillus thuringiensis var. tenebrionis* as disclosed in SEQ ID NO:20. |
| VIP3A(a) | — | VIP from strain AB88 as disclosed in SEQ ID NO:28 of the present application |
| VIP3A(b) | — | VIP from strain AB424 as disclosed in SEQ ID NO:31 of the present application |

Experimental

EXAMPLE 1
AB78 ISOLATION AND CHARACTERIZATION

*Bacillus cereus* strain AB78 was isolated as a plate contaminant in the laboratory on T3 media (per liter: 3 g tryptone, 2 g tryptose, 1.5 g yeast extract, 0.05M sodium phosphate (pH 6.8), and 0.005 g $MnCl_2$; Travers, R. S. 1983). During log phase growth, AB78 gave significant activity against western corn rootworm. Antibiotic activity against gram-positive Bacillus spp. was also demonstrated (Table 12).

TABLE 12

Antibiotic activity of AB78 culture supernatant

| Bacteria tested | Zone of inhibition (cm) | |
|---|---|---|
| | AB78 | Streptomycin |
| *E. coli* | 0.0 | 3.0 |
| *B. megaterium* | 1.1 | 2.2 |
| *B. mycoides* | 1.3 | 2.1 |
| *B. cereus* CB | 1.0 | 2.0 |
| *B. cereus* 11950 | 1.3 | 2.1 |
| *B. cereus* 14579 | 1.0 | 2.4 |
| *B. cereus* AB78 | 0.0 | 2.2 |
| Bt var. *israelensis* | 1.1 | 2.2 |
| Bt var. *tenebrionis* | 0.9 | 2.3 |

Morphological characteristics of AB78 are as follows: Vegetative rods straight, 3.1–5.0 mm long and 0.5–2.0 mm wide. Cells with rounded ends, single in short chains. Single subterminal, cylindrical-oval, endospore formed per cell. No parasporal crystal formed. Colonies opaque, erose, lobate and flat. No pigments produced. Cells motile. Flagella present.

Growth characteristics of AB78 are as follows:

Facultative anaerobe with optimum growth temperature of 21°–30° C. Will grow at 15°, 20°, 25°, 30° and 37° C. Will not grow above 40° C. Grows in 5–7% NaCl.

Table 13 provides the biochemical profile of AB78.

TABLE 13

Biochemical characteristics of *B. cereus* strain AB78.

| | |
|---|---|
| Acid from L-arabinose | − |
| Gas from L-arabinose | − |
| Acid from D-xylose | − |
| Gas from D-xylose | − |
| Acid from D-glucose | + |
| Gas from D-glucose | − |
| Acid from lactose | − |
| Gas from lactose | − |
| Acid from sucrose | − |
| Gas from sucrose | − |
| Acid from D-mannitol | − |

TABLE 13-continued

Biochemical characteristics of *B. cereus* strain AB78.

| | |
|---|---|
| Gas from D-mannitol | − |
| Proprionate utilization | + |
| Citrate utilization | + |
| Hippurate hydrolysis | w |
| Methylene blue reduced | + |
| Methyleneblue reoxidized | + |
| Nitrate reduced | + |
| $NO_3$ reduced to $NO_2$ | + |
| VP | + |
| $H_2O_2$ decomposed | + |
| Indole | − |
| Tyrosine decomposed | + |
| Dihydroxiacetone | − |
| Litmus milk acid | − |
| Litmus milk coagulated | − |
| Litmus milk alkaline | − |
| Litmus milk peptonized | − |
| Litmus miik reduced | − |
| Casein hydrolyzed | + |
| Starch hydrolyzed | + |
| Gelatin liquidified | + |
| Lecithinase produced | w | w = weak reaction

EXAMPLE 2
BACTERIAL CULTURE

A subculture of *Bc* strain AB78 was used to inoculate the following medium, known as TB broth:

| | |
|---|---|
| Tryptone | 12 g/l |
| Yeast Extract | 24 g/l |
| Glycerol | 4 ml/l |
| $KH_2PO_4$ | 2.1 g/l |
| $K_2HPO_4$ | 14.7 g/l |
| pH 7.4 | |

The potassium phosphate was added to the autoclaved broth after cooling. Flasks were incubated at 30° C. on a rotary shaker at 250 rpm for 24 h.–36 h, which represents an early to mid-log growth phase.

The above procedure can be readily scaled up to large fermentors by procedures well known in the art.

During vegetative growth, usually 24–36 h. after starting the culture, which represents an early to mid-log growth phase, AB78 bacteria were centrifuged from the culture supernatant. The culture supernatant containing the active protein was used in bioassays.

EXAMPLE 3
INSECT BIOASSAYS

*B. cereus* strain AB78 was tested against various insects as described below.

Western, Northern and Southern corn rootworm, *Diabrotica virgifera virgifera, D. longcornis barberi* and *D.* undecempunctata howardi, respectively: dilutions were made of AB78 culture supernatant grown 24–36 h., mixed with molten artificial diet (Marrone et al. (1985) *J. of Economic Entomology* 78:290–293) and allowed to solidify. Solidified diet was cut and placed in dishes. Neonate larvae were placed on the diet and held at 30° C. Mortality was recorded after 6 days.

E. coli clone bioassay: *E. coli* cells were grown overnight in broth containing 100 μg/ml ampicillin at 37° C. Ten ml culture was sonicated 3x for 20 sec each. 500 μl of sonicated culture was added to molten western corn rootworm diet.

Colorado potato beetle, *Leptinotarsa decemlineata:* dilutions in Triton X-100 (to give final concentration of 0.1% TX-100) were made of AB78 culture supernatant grown 24–36 h. Five $cm^2$ potato leaf pieces were dipped into these dilutions, air dried, and placed on moistened filter paper in plastic dishes. Neonate larvae were placed on the leaf pieces and held at 30° C. Mortality was recorded after 3–5 days.

Yellow mealworm, *Tenebrio molitor:* dilutions were made of AB78 culture supernatant grown 24–36 h., mixed with molten artificial diet (Bioserv #F9240) and allowed to solidify. Solidified diet was cut and placed in plastic dishes. Neonate larvae were placed on the diet and held at 30° C. Mortality was recorded after 6–8 days.

European corn borer, black cutworm, tobacco budworm, tobacco hornworm and beet armyworm; *Ostrinia nubilalis, Agrotis ipsilon, Heliothis virescens, Manduca sexta* and *Spodoptera exigua,* respectively: dilutions, in TX- 100 (to give final concentration of 0.1 % TX-100), were made of AB78 culture supernatant grown 24–36 hrs. 100 μl was pipetted onto the surface of 18 $cm^2$ of solidified artificial diet (Bioserv #F9240) and allowed to air dry. Neonate larvae were then placed onto the surface of the diet and held at 30° C. Mortality was recorded after 3–6 days.

Northern house mosquito, *Culex pipiens*:-dilutions were made of AB78 culture supernatant grown 24–36 h. 100 μl was pipetted into 10 ml water in a 30 ml plastic cup. Third instar larvae were added to the water and held at room temperature. Mortality was recorded after 24–48 hours. The spectrum of entomocidal activity of AB78 is given in Table 14.

TABLE 14

Activity of AB78 culture supernatant against various insect species

| Insect species tested to date | Order | Activity |
|---|---|---|
| Western corn rootworm (*Diabrotica virgifera virgifera*) | Col | +++ |
| Northern orn rootworm (*Diabrotica longacornis barberi*) | Col | +++ |
| Southern corn rootworm (*Diabrotica undecimpunctata howardi*) | Col | – |
| Colorado potato beetle (*Lepinotarsa decemlineata*) | Col | – |
| Yellow mealworm (*Tenebrio molitor*) | Col | – |
| European corn borer (*Ostrinia nubilalis*) | Lep | – |
| Tobacco budworm (*Manduca sexta*) | Lep | – |
| Beet armyworm (*Spodoptera exigua*) | Lep | – |
| Black cutworm (*Agrotis ipsilon*) | Lep | – |

TABLE 14-continued

Activity of AB78 culture supernatant against various insect species

| Insect species tested to date | Order | Activity |
|---|---|---|
| Northern house mosquito (*Culex pipiens*) | Dip | – |

The newly discovered *B. cereus* strain AB78 showed a significantly different spectrum of insecticidal activity as compared to known coleopteran active δ-endotoxins from *Bt*. In particular, AB78 showed more selective activity against beetles than known coleopteran-active *Bt* strains in that it was specifically active against Diabrotica spp. More specifically, it was most active against *D. virgifera virgifera* and *D. longicornis barberi* but not *D. undecimpunctata howardi.*

A number of Bacillus strains were bioassayed for activity during vegetative growth (Table 15) against western corn rootworm. The results demonstrate that AB78 is unique in that activity against western corn rootworm is not a general phenomenon.

TABLE 15

Activity of culture supernatants from various *Bacillus spp.* against western corn rootworm

| Bacillus strain | Percent WCRW mortality |
|---|---|
| *B. cereus* AB78 (Bat.1) | 100 |
| *B. cereus* AB78 (Bat.2) | 100 |
| *B. cereus* (Carolina Bio.) | 12 |
| *B. cereus* ATCC 11950 | 12 |
| *B. cereus* ATCC 14579 | 8 |
| *B. mycoides* (Carolina Bio.) | 30 |
| *B. popilliae* | 28 |
| *B. thuringiensis* HD135 | 41 |
| *B. thuringiensis* HD191 | 9 |
| *B. thuringiensis* GC91 | 4 |
| *B. thuringiensis isrealensis* | 24 |
| Water Control | 4 |

Specific activity of AB78 against western corn rootworm is provided in Table 16.

TABLE 16

Activity of AB78 culture supernatant against neonate western corn rootworm

| Culture supernatant concentration (μl/ml) | Percent WCRW mortality |
|---|---|
| 100 | 100 |
| 25 | 87 |
| 10 | 80 |
| 5 | 40 |
| 2.5 | 20 |
| 1 | 6 |
| 0 | 0 |

The $LC_{50}$ was calculated to be 6.2 μl of culture supernatant per ml of western corn rootworm diet.

The cell pellet was also bioassayed and had no activity against WCRW. Thus, the presence of activity only in the supernatant indicates that this VIP is an exotoxin.

EXAMPLE 4
ISOLATION AND PURIFICATION OF CORN ROOTWORM ACTIVE PROTEINS FROM AB78

Culture media free of cells and debris was made to 70% saturation by the addition of solid ammonium sulfate (472 g/L). Dissolution was at room temperature followed by cooling in an ice bath and centrifugation at 10,000×g for thirty minutes to pellet the precipitated proteins. The supernatant was discarded and the pellet was dissolved in 1/10 the original volume of 20 mM TRIS-HCl at pH 7.5. The dissolved pellet was desalted either by dialysis in 20 mM TRIS-HCl pH 7.5, or passing through a desalting column.

The desalted material was titrated to pH 3.5 using 20 mM sodium citrate pH 2.5. Following a thirty minute room temperature incubation the solution was centrifuged at 3000×g for ten minutes. The supernatant at this stage contained the greatest amount of active protein.

Following neutralization of the pH to 7.0 the supernatant was applied to a Mono-Q, anion exchange, column equilibrated with 20 mM TRIS pH 7.5 at a flow rate of 300 mL/min. The column was developed with a stepwise and linear gradient employing 400 mM NaCl in 20 mM TRIS pH 7.5.

Bioassay of the column fractions and SDS-PAGE analysis were used to confirm the active fractions. SDS-PAGE analysis identified the biologically active protein as having components of a molecular weight in the range of about 80 kDa and 50 kDa.

EXAMPLE 5

SEQUENCE ANALYSIS OF THE CORN ROOTWORM ACTIVE PROTEIN

The 80 kDa component isolated by SDS-PAGE was transferred to PVDF membrane and was subjected to amino-terminal sequencing as performed by repetitive Edman cycles on an ABI 470 pulsed-liquid sequencer. Transfer was carried out in 10 mM CAPS buffer with 10% methanol pH 11.0 as follows:

Incubation of the gel following electrophoresis was done in transfer buffer for five minutes. ProBlott PVDF membrane was wetted with 100% MeOH briefly then equilibrated in transfer buffer. The sandwich was arranged between foam sponges and filter paper squares with the configuration of cathode-gel-membrane-anode.

Transfer was performed at 70 V constant voltage for 1 hour.

Following transfer, the membrane was rinsed with water and stained for two minutes with 0.25% Coomassie Blue R-250 in 50% MeOH.

Destaining was done with several rinses with 50% MeOH 40% water 10% acetic acid.

Following destaining the membrane was air dried prior to excision of the bands for sequence analysis. A BlottCartridge and appropriate cycles were utilized to achieve maximum efficiency and yield. Data analysis was performed using model 610 Sequence Analysis software for identifying and quantifying the PTH-amino acid derivatives for each sequential cycle.

The N-terminal sequence was determined to be:

NH2-Lys-Arg-Glu-Ile-Asp-Glu-Asp-Thr-Asp-Thr-Asx-Gly-Asp-Ser-Ile-Pro (SEQ ID NO:8)

where Asx represents Asp or Asn. The complete amino acid sequence for the 80 kDa component is disclosed in SEQ ID NO:7. The DNA sequence which encodes SEQ ID NO:7 is disclosed in SEQ ID NO:6.

EXAMPLE 6

CONSTRUCTION OF DNA PROBE

An oligonucleotide probe for the region of the gene encoding amino acids 3–9 of the N-terminal sequence (Example 5) was generated. The probe was synthesized based on the codon usage of a *Bacillus thuringiensis* (*Bt*) δ-endotoxin gene. The nucleotide sequence

5'-GAA ATT GAT CAA GAT ACN GAT -3' (SEQ ID NO:9)

was used as a probe in Southern hybridizations. The oligonucleotide was synthesized using standard procedures and equipment.

EXAMPLE 7

ISOELECTRIC POINT DETERMINATION OF THE CORN ROOTWORM ACTIVE PROTEIN

Purified protein from step 5 of the purification process was analyzed on a 3–9 pI isoelectric focusing gel using the Phastgel electrophoresis system (Pharmacia). Standard operating procedures for the unit were followed for both the separation and silver staining development procedures. The pI was approximated at about 4.9.

EXAMPLE 8

PCR DATA ON AB78

PCR analysis (See, for example U.S. patent application Ser. No. 08/008,006; and, Carozzi et al. (1991) *Appl. Environ. Microbiol.* 57(11):3057–3061, herein incorporated by reference.) was used to verify that the *B. cereus* strain AB78 did not contain any insecticidal crystal protein genes of *B. thuringiensis* or *B. sphaericus* (Table 17).

TABLE 17

Bacillus insecticidal crystal protein gene primers tested by PCR against AB7S DNA.

| Primers Tested | Product Produced |
|---|---|
| 2 sets specific for CryIIIA | Negative |
| CryIIIB | Negative |
| 2 sets specific for CryIA | Negative |
| CryIA(a) | Negative |
| CryIA(b) specific | Negative |
| CryIB | Negative |
| CryIC specific | Negative |
| CryIE specific | Negative |
| 2 sets specific for *B. sphaericus* | Negative |
| 2 sets specific for CryIV | Negative |
| Bacillus Control (PI-PLC) | Positive |

EXAMPLE 9

COSMID CLONING OF TOTAL DNA FROM *B. CEREUS* STRAIN AB78

The VIP1A(a) gene was cloned from total DNA prepared from strain AB78 as follows:

Isolation of AB78 DNA was as follows

1. Grow bacteria in 10 ml L-broth overnight. (Use 50 ml sterile centrifuge tube)
2. Add 25 ml of fresh L-broth and ampicillin (30 μg/ml).
3. Grow cells 2–6 h. at 30° C. with shaking.
4. Spin cells in a 50 ml polypropylene orange cap tube in IEC benchtop clinical centrifuge at ¾ speed.
5. Resuspend cell pellet in 10 ml TES (TES=50 mM TRIS pH 8.0, 100 mM EDTA, 15 mM NaCl).
6. Add 30 mg lysozyme and incubate 2 hrs at 37° C.
7. Add 200 μl 20% SDS and 400 μl Proteinase K stock (20 mg/ml). Incubate at 37° C.
8. Add 200 μl fresh Proteinase K. Incubate 1 hr. at 55° C. Add 5 ml TES to make 15 ml final volume.
9. Phenol extract twice (10 ml phenol, spin at room temperature at ¾ speed in an IEC benchtop clinical centrifuge). Transfer supernatant (upper phase) to a clean tube using a wide bore pipette.

10. Extract once with 1:1 vol. phenol:chloroform/isoamyl alcohol (24:1 ratio).
11. Precipitate DNA with an equal volume of cold isopropanol; Centrifuge to pellet DNA.
12. Resuspend pellet in 5 ml TE.
13. Precipitate DNA with 0.5 ml 3M NaOAc pH 5.2 and 11 ml 95% ethanol. Place at −20° C. for 2 h. 14. "Hook" DNA from tube with a plastic loop, transfer to a microfuge tube, spin, pipette off excess ethanol, dry in vacuo.
15. Resuspend in 0.5 ml TE. Incubate 90 min. at 65° C. to help get DNA back into solution.
16. Determine concentration using standard procedures.

Cosmid Cloning of AB78

All procedures, unless indicated otherwise, were performed according to Stratagene Protocol, Supercos 1 Instruction Manual, Cat. No. 251301.

Generally, the steps were as follows:

A. Sau 3A partial digestion of the AB78 DNA.
B. Preparation of vector DNA
C. Ligation and packaging of DNA
D. Tittering the cosmid library
   1. Start a culture of HB101 cells by placing 50 ml of an overnight culture in 5 mls of TB with 0.2% maltose. Incubate 3.5 hrs. at 37° C.
   2. Spin out cells and resuspend in 0.5 ml 10 mM MgSO$_4$.
   3. Add together:
      100 μl cells
      100 μl diluted packaging mixture
      100 μl 10 mM MgSO$_4$
      30 μl TB
   4. Adsorb at room temperature for 30 minutes with no shaking.
   5. Add 1 ml TB and mix gently. Incubate 30 minutes at 37° C.
   6. Plate 200 μl onto L-amp plates. Incubate at 37° C. overnight.

At least 400 cosmid clones were selected at random and screened for activity against western corn rootworm as described in Example 3. DNA from 5 active clones and 5 non-active clones were used in Southern hybridizations. Results demonstrated that hybridization using the above described oligonucleotide probe correlated with western corn rootworm activity (Table 18).

Cosmid clones P3-12 and P5-4 have been deposited with the Agricultural Research Service Patent Culture Collection (NRRL) and given Accession Nos. NRRL B-21061 and NRRL B-21059 respectively.

TABLE 18

Activity of AB78 cosmid clones against western cornrootworm.

| Clone | Mean percent mortality (n = 4) |
|---|---|
| Clones which hybridize with probe | |
| P1-73 | 47 |
| P1-83 | 64 |
| P2-2 | 69 |
| P3-12 | 85 |
| P5-4 | 97 |
| Clones which do not hybridize with probe | |
| P1-2 | 5 |
| P3-8 | 4 |

TABLE 18-continued

Activity of AB78 cosmid clones against western cornrootworm.

| Clone | Mean percent mortality (n = 4) |
|---|---|
| P3-9 | 12 |
| P3-18 | 0 |
| P4-6 | 9 |

EXAMPLE 10

IDENTIFICATION OF A 6 KB REGION ACTIVE AGAINST WESTERN CORN ROOTWORM

DNA from P3-12 was partially digested with restriction enzyme Sau 3A, and ligated into the E. coli vector pUC19 and transformed into E. coli. A DNA probe specific for the 80 kDa VIP1A(a) protein was synthesized by PCR amplification of a portion of P3-12 DNA. Oligonucleotides MK113 and MK117, which hybridize to portions of VIP1A (a), were synthesized using the partial amino acid sequence of the 80 kDa protein. Plasmid subclones were identified by colony hybridization to the PCR-generated probe, and tested for activity against western corn rootworm. One such clone, PL2, hybridized to the PCR-generated fragment, and was active against western corn rootworm in the assay previously described.

A 6 kb Cla I restriction fragment from pL2 was cloned into the Sma I site of the E. coli-Bacillus shuttle vector pHT 3101 (Lereclus, D. et al., FEMS Microbiology Letters 60:211–218 (1989)) to yield pCIB6201. This construct confers anti-western corn rootworm activity upon both Bacillus and E.coli strains, in either orientation. pCIB6022 contains this same 6 kb Cla I fragment in pbluescript SK(+) (Stratagene), produces equivalent VIP1A(a) protein (by western blot), and is also active against western corn rootworm.

The nucleotide sequence of pCIB6022 was determined by the dideoxy termination method of Sanger et al., Proc. Natl. Acad. Sci. USA, 74:5463–5467 (1977), using PRISM Ready Reaction Dye Deoxy Terminator Cycle Sequencing Kits and PRISM Sequenase® Terminator Double-Stranded DNA Sequencing Kit and analyzed on an ABI 373 automatic sequencer. The sequence is given in SEQ ID NO:1. The 6 kb fragment encodes both VIP1A(a) and VIP2A(a), as indicated by the open reading frames described in SEQ ID NO:1. The sequence encoding VIP1A(a) is further disclosed in SEQ ID NO:4. The relationship between VIP1A(a) and VIP2A(a) within the 6 kb fragment found in pCIB6022 is depicted in Table 19. pCIB6022 was deposited with the Agricultural Research Service, Patent Culture Collection, (NRRL), Northern Regional Research Center, 1815 North University Street, Peoria, Ill. 61604, USA, and given the Accession No. NRRL B-21222.

EXAMPLE 11

FUNCTIONAL DISSECTION OF THE VIP1A(a) DNA REGION

To confirm that the VIP1A(a) open reading frame (ORF) is necessary for insecticidal activity a translational frameshift mutation was created in the gene. The restriction enzyme Bgl II recognizes a unique site located 857 bp into the coding region of VIP1A(a). pCIB6201 was digested with Bgl II, and the single-stranded ends filled-in with DNA polymerase (Klenow fragment) and dNTPS. The plasmid was re-ligated and transformed into E. coli. The resulting plasmid, pCIB6203, contains a four nucleotide insertion in the coding region of VIP1A(a). pCIB6203 does not confer WCRW insecticidal activity, confirming that VIP1A(a) is an essential component of western corn rootworm activity.

To further define the region necessary to encode VIP1A (a), subclones of the VIP1A(a) and VIP2A(a) (auxiliary protein) region were constructed and tested for their ability to complement the mutation in pCIB6203. pCIB6023 contains the 3.7 kb Xba I-EcoRV fragment in pBluescript SK(+) (Stratagene). Western blot analysis indicates that pCIB6023 produces VIP1A(a) protein of equal size and quantity as clones PL2 and pCIB6022. pCIB6023 contains the entire gene encoding the 80 kD protein. pCIB6023 was deposited with the Agricultural Research Service, Patent Culture Collection, (NRRL), Northern Regional Research Center, 1815 North University Street, Peoria, Ill. 61604, USA, and given the Accession No. NRRL B-21223N. pCIB6206 contains the 4.3 kb Xba I-Cla I fragment from pCIB6022 in pBluescript SK(+) (Stratagene). pCIB6206 was also deposited with the Agricultural Research Service, Patent Culture Collection, (NRRL), Northern Regional Research Center, 1815 North University Street, Peoria, Ill. 61604, USA, and given the Accession No. NRRL B-21321.

pCIB6023, pCIB6206, and pCIB6203 do not produce detectable western corn rootworm activity when tested individually. However, a mixture of cells containing pCIB6203 (VIP1 A(a)-mutated, plus VIP2A(a)) and cells containing pCIB6023 (only VIP1A(a)) shows high activity against western corn rootworm. Similarly, a mixture of cells containing pCIB6206 and cells containing pCIB6203 shows high activity against western corn rootworm.

To further define the limits of VIP2A(a), we constructed pCIB6024, which contains the entirety of VIP2A(a), but lacks most of the VIP1A(a) coding region. pCIB6024 was constructed by gel purifying the 2.2 kb Cla I-Sca I restriction fragment from pCIB6022, filling in the single-stranded ends with DNA polymerase (Klenow fragment) and dNTPs, and ligating this fragment into pBluescript SK(+) vector (Stratagene) digested with the enzyme Eco RV. Cells containing pCIB6024 exhibit no activity against western corn rootworm. However, a mixture of cells containing pCIB6024 and cells containing pCIB6023 shows high activity against western corn rootworm. (See Table 19).

Thus, pCIB6023 and pCIB6206 must produce a functional VIP1A(a) gene product, while pCIB6203 and pCIB6024 must produce a functional VIP2A(a) gene product. These results suggest a requirement for a gene product (s) from the VIP2A(a) region, in combination with VIP1A (a), to confer maximal western corn rootworm activity. (See Table 19.)

TABLE 19

| | Activity vs. WCRW |
|---|---|
| Characterization of pCIB6022 | |
| pCIB6022 | +++ |
| pCIB6203 | − |
| pCIB6023 | − |
| pCIB6206 | − |
| pCIB6024 | − |
| Functional Complementation of VIP Clones | |
| pCIB6203 pCIB6023 | +++ |
| pCIB6203 pCIB6206 | +++ |

TABLE 19-continued

| | | Activity vs. WCRW |
|---|---|---|
| ▶▨▨▨━▬▭┘ | pCIB6023 | +++ |
| └━▨▨▨▨━▬ | pCIB6024 | |

Boxed regions represent the extent of VIP1A(a) and YIP2A(a). White box represents the portion of VIP1 encoding the 80 kDa peptide observed in Bacillus. Dark box represents the N-terminal 'propeptide' of VIP1A(a) predicted by DNA sequence analysis. Stippled box represents the VIP2A(a) coding region. Large 'X' represents the location of the frameshift mutation introduced into VIP1A(a). Arrows represent constructs transcribed by the beta-galactosidase promoter. Restriction Sites: C-Cla I; X-Xba I; S-Sca I; RI-Eco RI; B-Bgl II; RV-Eco RV.

EXAMPLE 12
AB78 ANTIBODY PRODUCTION

Antibody production was initiated in 2 Lewis rats to allow for both the possibility of moving to production of hybridoma cell lines and also to produce enough serum for limited screening of genomic DNA library. Another factor was the very limited amount of antigen available and the fact that it could only be produced to purity by PAGE and subsequent electrotransfer to nitrocellulose.

Due to the limited availability of antigen on nitrocellulose, the nitrocellulose was emulsified in DMSO and injected into the hind footpads of the animals to elicit B-cell production in the popliteal lymph nodes just upstream. A strong reacting serum was produced as judged by western blot analysis with the first production bleed. Several subsequent injections and bleeds produced enough serum to accomplish all of the screening required.

Hybridoma production with one of the rats was then initiated. The popliteal lymph node was excised, macerated, and the resulting cells fused with mouse myeloma P3×63Ag8.653. Subsequent cell screening was accomplished as described below. Four initial wells were selected which gave the highest emulsified antigen reaction to be moved to limited dilution cloning. An additional 10 wells were chosen for expansion and cryoperservation.

Procedure to Emulsify AB78 on nitrocellulose in DMSO for ELISA screening:

After electrotransfer of AB78 samples run on PAGE to nitrocellulose, the reversible strain Ponceau S is used to visualize all protein transferred. The band corresponding to AB78 toxin, previously identified and N-terminal sequenced, was identified and excised from nitrocellulose. Each band is approximately 1 mm×5 mm in size to minimize the amount of nitrocellulose emulsified. A single band is placed in a microfuge tube with 250 μl of DMSO and macerated using a plastic pestle (Kontes, Vineland, N.J.). To aid in emulsification, the DMSO mixture is heated for 2–3 minutes at 37° C.–45° C. Some further maceration might be necessary following heating; however, all of the nitrocellulose should be emulsified. Once the AB78 sample is emulsified, it is placed on ice. In preparation for microtiter plate coating with the emulsified antigen, the sample must be diluted in borate buffered saline as follows: 1:5, 1:10, 1:15, 1:20, 1:30, 1:50, 1:100, and 0. The coating antigen must be prepared fresh immediately prior to use.

ELISA protocol:
1. Coat with AB78/DMSO in BBS. Incubate overnight at 4° C.
2. Wash plate 3× with 1× ELISA wash buffer.
3. Block (1% BSA & 0.05% Tween 20 in PBS) for 30 minutes at Room Temperature.
4. Wash plate 3× with 1× ELISA wash buffer.
5. Add rat serum. Incubate 1.5 hours at 37° C.
6. Wash plate 3× with 1× ELISA wash buffer.
7. Add goat anti-rat at a concentration of 2 μg/ml in ELISA diluent. Incubate 1 hr. at 37° C.
8. Wash plate 3× with 1× ELISA wash buffer.
9. Add rabbit anti-goat alkaline phosphatase at 2 μg/ml in ELISA diluent. Incubate 1 hr. at 37° C.
10. Wash 3× with 1× ELISA wash buffer.
11. Add Substrate. Incubate 30 minutes at room temperature.
12. Stop with 3N NaOH after 30 minutes.

Preparation of VIP2A(a) Antisera

A partially purified AB78 culture supernatant was separated by discontinuous SDS PAGE (Novex) following manufacturer's instructions. Separated proteins were electrophoresed to nitrocellulose (S&S #21640) as described by Towbin et al., (1979). The nitrocellulose was stained with Ponceau S and the VIP2A(a) band identified. The VIP2A(a) band was excised and emulsified in DMSO immediately prior to injection. A rabbit was initially immunized with emulsified VIP2A(a) mixed approximately 1:1 with Freund's Complete adjuvant by intramuscular injection at four different sites. Subsequent immunizations occurred at four week intervals and were identical to the first, except for the use of Freund' Incomplete adjuvant. The first serum harvested following immunization reacted with VIP2A(a) protein. Western blot analysis of AB78 culture supernatant using this antisera identifies predominately full length VIP2A(a) protein.

EXAMPLE 13

ACTIVATION OF INSECTICIDAL ACTIVITY OF NON-ACTIVE BT STRAINS WITH AB78 VIP CLONES

Adding pCIB6203 together with a 24 h culture (early to mid-log phase) supernatant from Bt strain GC91 produces 100% mortality in Diabrotica virgifera virgifera. Neither pCIB6203 nor GC91 is active on Diabrotica virgifera virgifera by itself. Data are shown below:

| Test material | Percent Diabrotica mortality |
|---|---|
| pCIB6203 | 0 |
| GC91 | 16 |
| pCIB6233 + GC91 | 100 |
| Control | 0 |

EXAMPLE 14
ISOLATION AND BIOLOGICAL ACTIVITY OF B. CEREUS AB81

A second *B. cereus* strain, designated AB81, was isolated from grain bin dust samples by standard methodologies. A subculture of AB81 was grown and prepared for bioassay as described in Example 2. Biological activity was evaluated as described in Example 3. The results are as follows:

| Insect species tested | Percent Mortality |
| --- | --- |
| Ostrinia nubilalis | 0 |
| Agrotis ipsilon | 0 |
| Diabrotica virgifera virgifera | 55 |

EXAMPLE 15
ISOLATION AND BIOLOGICAL ACTIVITY OF B. THURINGIENSIS AB6

A *B. thuringiensis* strain, designated AB6, was isolated from grain bin dust samples by standard methods known in the art. A subculture of AB6 was grown and prepared for bioassay as described in Example 2. Half of the sample was autoclaved 15 minutes to test for the presence of β-exotoxin.

Biological activity was evaluated as described in Example 3. The results are as follows:

| Insect species tested | Percent Mortality |
| --- | --- |
| Ostrinia nubilalis | 0 |
| Agrotis ipsilon | 100 |
| Agrotis ipsilon (autoclaved sample) | 0 |
| Diabrotica virgifera virgifera | 0 |

The reduction of insecticidal activity of the culture supernatant to insignificant levels by autoclaving indicates that the active principle is not β-exotoxin.

Strain AB6 has been deposited in the Agricultural Research Service, Patent Culture Collection (NRRL), Northern Regional Research Center, 1815 North University Street, Peoria, Ill. 61604, USA, and given Accession No. NRRL B-21060.

EXAMPLE 16
ISOLATION AND BIOLOGICAL CHARACTERIZATION OF B. THURINGIENSIS AB88

A *Bt* strain, designated AB88, was isolated from grain bin dust samples by standard methodologies. A subculture of AB88 was grown and prepared for bioassay as described in Example 2. Half of the sample was autoclaved 15 minutes to test for the presence of β-exotoxin. Biological activity was evaluated against a number of insect species as described in Example 3. The results are as follows:

| Insect species tested | Order | Percent mortality of culture supernatant | |
| --- | --- | --- | --- |
| | | Non-autoclaved | Autoclaved |
| Agrotis ipsilon | Lepidoptera | 100 | 5 |
| Ostrinia nubilalis | Lepidoptera | 100 | 0 |
| Spodoptera frugiperda | Lepidoptera | 100 | 4 |
| Helicoverpa zea | Lepidoptera | 100 | 12 |
| Heliothis virescens | Lepidoptera | 100 | 12 |
| Leptinotarsa decemlineata | Coleoptera | 0 | 0 |
| Diabrotica virgifera virifera | Coleoptera | 0 | 5 |

The reduction of insecticidal activity of the culture supernatant to insignificant levels by autoclaving indicates that the active principle is not β-exotoxin.

Delta-endotoxin crystals were purified from strain AB88 by standard methodologies. No activity from pure crystals was observed when bioassayed against *Agrotis epsilon*.

EXAMPLE 17
PURIFICATION OF VIPS FROM STRAIN AB88

Bacterial liquid culture was grown overnight at 30° C. in TB media. Cells were spun out and the supernatant retained. Proteins were precipitated with ammonium sulfate (70% saturation), centrifuged and the pellet retained. The pellet was resuspended in the original volume of 20 mM Tris pH 7.5 and dialyzed against the same buffer. AB88 dialysate was more turbid than comparable material from AB78. AB88 proteins have been separated by several different methods following clarification including isoelectric focusing (Rotofor, BioRad, Hercules, Calif.), precipitation at pH 4.5, ion-exchange chromatography, size exclusion chromatography and ultrafiltration.

European corn borer (ECB)-active protein remained in the pellet obtained by pH 4.5 precipitation of dialysate. When preparative IEF was done on the dialysate using pH 3–10 ampholytes, ECB insecticidal activity was found in all fractions with pH of 7 or greater. SDS-PAGE analysis of these fractions showed protein bands of MW ~60 kDa and ~80 kDa. The 60 kDa and 80 kDa bands were separated by anion exchange HPLC on a Poros-Q column (PerSeptive Biosystems, Cambridge, Mass.). N-terminal sequence was obtained from two fractions containing proteins of slightly differing MW, but both of approximately 60 kDa in size. The sequences obtained were similar to each other and to some δ-endotoxins.

anion exchange fraction 23 (smaller): xEPFVSAxxxQxxx (SEQ ID NO:10)

anion exchange fraction 28 (larger): xEYENVEPFVSAx (SEQ ID NO:11)

When the ECB-active pH 4.5 pellet was further separated by anion exchange on a Poros-Q column, activity was found only in fractions containing a major band of ~60 kDa.

Black cutworm-active protein also remained in the pellet when AB88 dialysate was brought down to pH 4.5. In preparative IEF using pH 3–10 ampholytes, activity was not found in the ECB-active IEF fractions; instead, it was highest in a fraction of pH 4.5–5.0. Its major components have molecular weights of ~35 and ~80 kDa.

The pH 4.5 pellet was separated by anion exchange HPLC to yield fractions containing only the 35 kDa material and fractions containing both 35 kDa and 80 kDa bands.

EXAMPLE 18
CHARACTERIZATION OF AB88 VIP

Fractions containing the various lepidopteran active vegetative proteins were generated as described in Example 17. Biological analysis of fractions demonstrated that different VIPs were responsible for the different lepidopteran species activity.

The *Agrotis ipsilon* activity is due to an 80 kDa and/or a 35 kDa protein, either delivered singly or in combination. These proteins are not related to any δ-endotoxins from *Bt* as proteins are not found in the AB88 δ-endotoxin crystal. N-terminal sequences of the major δ-endotoxin proteins were compared with the N-terminal sequences of the 80 kDa and 35 kDa VIP and revealed no sequence homology. A summary of the results follows:

| Agrotis VIP N-terminal sequences | N-terminal sequence of major δ-endotoxin proteins |
|---|---|
| | 130 kDa |
| | MDNNPNINE (SEQ ID NO:14) |
| 80 kDa | 80 kDa |
| MNKNNTKLPTRALP (SEQ ID NO:12) | MDNNPNINE (SEQ ID NO:15) |
| | 60 kDa |
| | MNVLNSGRTTI (SEQ ID NO:16) |
| 35 kDa | |
| ALSENTGKDGGYIVP (SEQ ID NO:13) | |

The *Ostrinia nubilalis* activity is due to a 60 kDa VIP and the *Spodoptera frugiperda* activity is due to a VIP of unknown size.

*Bacillus thuringiensis* strain AB88 has been deposited in the Agricultural Research Service, Patent Culture Collection (NRRL), Northern Regional Research Center, 1815 North University Street, Peoria, Ill. 61604, USA and given the Accession No. NRRL B-21225.

EXAMPLE 18A
ISOLATION AND BIOLOGICAL ACTIVITY OF *B THURINGIENSIS* AB424

A *B. thuringiensis* strain, designated AB424, was isolated from a moss covered pine cone sample by standard methods known in the art. A subculture of AB424 was grown and prepared for bioassay as described in Example 2.

Biological activity was evaluated as described in Example 3. The results are as follows:

| Insect species tested | Percent mortality |
|---|---|
| Ostrinia nubilalis | 100 |
| Agrotis ipsilon | 100 |
| Diabrotica virgifera virgifera | 0 |

Strain AB424 has been deposited in the Agricultural Research Service, Patent Culture Collection (NRRL), Northern Regional Research Center, 1815 North University Street, Peoria, Ill. 61604, USA, and given Accession No. NRRL B-21439.

EXAMPLE 18B
CLONING OF THE VIP3A(a) and VIP3A(b) GENES WHICH ENCODE PROTEINS ACTIVE AGAINST BLACK CUTWORM DNA from isolates AB88 and AB424 was digested with the restriction enzymes XbaI and EcoRI respectively, ligated into pBluescript vector previously linearized with the same enzymes and dephosphorylated, and transformed into *E. coli* DH5α strain. Recombinant clones were blotted onto nitrocellulose filters which were subsequently probed with a 33-bases long oligonucleotide corresponding to the 11-N terminal amino acids of the 80 kDa protein active against *Agrotis ipsilon* (black cutworm). Four out of 400 recombinant clones were positive. Insect bioassays of the positive recombinants exhibited toxicity to black cutworm larvae comparable to that of AB88 or AB424 supernatants.

The nucleotide sequence of pCIB7104, a positive recombinant clone from AB88, and of pCIB7107, a positive recombinant clone from AB424, was determined by the dideoxy termination method of Sanger et al., *Proc. Natl. Acad. Sci.* USA, 74:5463–5467 (1977), using PRISM Ready Reaction Dye Deoxy Terminator Cycle Sequencing Kits and PRISM Sequenase® Terminator Double-Stranded DNA Sequencing Kit and analysed on an ABI 373 automatic sequencer.

The clone pCIB7104 contains the VIP3A(a) gene whose coding region is disclosed in SEQ ID NO:28 and the encoded protein sequence is disclosed in SEQ ID NO:29. A synthetic version of the coding region designed to be highly expressed in maize is given in SEQ ID NO:30. Any number of synthetic genes can be designed based on the amino acid sequence given in SEQ ID NO:29.

The clone pCIB7107 contains the VIP3A(b) gene whose coding region is disclosed in SEQ ID NO:31 and the encoded protein is disclosed in SEQ ID NO:32. Both pCIB7104 and pCIB7107 have been deposited with the Agricultural Research Service Patent Culture Collection (NRRL) and given Accession Nos. NRRL B-21422 and B-21423, respectively.

EXAMPLE 18C
IDENTIFICATION OF NOVEL VIP3-LIKE GENES BY HYBRIDIZATION

To identify Bacillus containing genes related to the VIP3A(a) from isolate AB88, a collection of Bacillus isolates was screened by hybridization. Cultures of 463 Bacillus strains were grown in microtiter wells until sporulation. A 96-pin colony stampel was used to transfer the cultures to 150 mm plates containing L-agar. Inoculated plates were kept at 30° C. for 10 hours, then at 4° C. overnight. Colonies were blotted onto nylon filters and probed with a 1.2 Kb HindIII VIP3A(a) derived fragment. Hybridization was performed overnight at 62° C. using hybridization conditions of Maniatis et al. *Molecular Cloning: A Laboratory Manual* (1982). Filters were washed with 2×SSC/0.1% SDS at 62° C. and exposed to X-ray film.

Of the 463 Bacillus strains screened, 60 contain VIP3-like genes that could detected by hybridization.

EXAMPLE 18D
CHARACTERIZATION OF A *B. thuringiensis* STRAIN M2194 CONTAINING A CRYPTIC VIP3-LIKE GENE A *B. thuringiensis* strain, designated M2194, was shown to contain VIP3-like gene(s) by colony hybridization as described in Example 18C. The M2194 VIP3 like gene is considered cryptic since no expression can be detected throughout the bacterial growth phases either by immunoblot analysis using polyclonal antibodies raised against the VIP3A(a) protein isolated from AB88 or by bioassay as described in Example 3.

The M2194 VIP3-like gene was cloned into pKS by following the protocol described in Example 9, which created pCIB7108. *E. coli* containing pCIB7108 which comprises the M2194 VIP3 gene were active against black cutworm demonstrating that the gene encodes a functional protein with insecticidal activity. The plasmid pCIB7108 has been deposited with the Agricultural Research Service Patent Culture Collection (NRRL) and given Accession No. NRRL B-21438.

EXAMPLE 19
ISOLATION AND BIOLOGICAL ACTIVITY OF OTHER BACILLUS SP

Other Bacillus species have been isolated which produce proteins with insecticidal activity during vegetative growth. These strains were isolated from environmental samples by standard methodologies. Isolates were prepared for bioassay and assayed as described in Examples 2 and 3 respectively. Isolates which produced insecticidal proteins during vegetative growth with activity against *Agrotis ipsilon* in the bioassay are tabulated below. No correlation was observed between the presence of a δ-endotoxin crystal and vegetative insecticidal protein production.

| Bacillus isolate | Presence of δ-endotoxin crystal | Percent mortality |
|---|---|---|
| AB6 | + | 100 |
| AB53 | − | 80 |
| AB88 | + | 100 |
| AB195 | − | 60 |
| AB211 | − | 70 |
| AB217 | − | 83 |
| AB272 | − | 80 |
| AB279 | − | 70 |
| AB289 | + | 100 |
| AB292 | + | 80 |
| AB294 | − | 100 |
| AB300 | − | 80 |
| AB359 | − | 100 |

Isolates AB289, AB294 and AB359 have been deposited in the Agricultural Research Service, Patent Culture Collection (NRRL), Northern Regional Research Center, 1815 North University Street, Peoria Ill. 61604, USA and given the Accession Numbers NRRL B-21227, NRRL B-21229, and NRRL B-21226 respectively.

Bacillus isolates which produce insecticidal proteins during vegetative growth with activity against *Diabrotica virgifera virgifera* are tabulated below.

| Bacillus isolate | Presence of δ-endotoxin crystal | Percent mortality |
|---|---|---|
| AB52 | − | 50 |
| AB59 | − | 71 |
| AB68 | + | 60 |
| AB78 | − | 100 |
| AB122 | − | 57 |
| AB218 | − | 64 |
| AB256 | − | 64 |

Isolates AB59 and AB256 have been deposited in the Agricultural Research Service, Patent Culture Collection (NRRL), Northern Regional Research Center, 1815 North University Street, Peoria Ill. 61604, USA, and given the Accession Numbers NRRL B-21228 and NRRL B-21230, respectively.

EXAMPLE 20
IDENTIFICATION OF NOVEL VIP1/VIP2 LIKE GENES BY HYBRIDIZATION

To identify strains containing genes related to those found in the VIP1A(a)/VIP2A(a) region of AB78, a collection of Bacillus strains was screened by hybridization. Independent cultures of 463 Bacillus strains were grown in wells of 96 well microtiter dishes (five plates total) until the cultures sporulated. Of the strains tested, 288 were categorized as *Bacillus thuringiensis*, and 175 were categorized as other Bacillus species based on the presence or absence of δ-endotoxin crystals. For each microtiter dish, a 96-pin colony stamper was used to transfer approximately 10 µl of spore culture to two 150 mm plates containing L-agar. Inoculated plates were grown 4–8 hours at 30° C., then chilled to 4° C. Colonies were transferred to nylon filters, and the cells lysed by standard methods known in the art. The filters were hybridized to a DNA probe generated from DNA fragments containing both VIP1A(a) and VIP2A(a) DNA sequences. Hybridization was performed overnight at 65° C. using the hybridization conditions of Church and Gilbert (Church, G. M., and W. Gilbert, PNAS, 81:1991–1995 (1984)). Filters were washed with 2×SSC containing 0.1% SDS at 65° C. and exposed to X-Ray film.

Of the 463 Bacillus strains screened, 55 strains were identified that hybridized to the VIP1A(a)/VIP2A(a) probe. DNA was isolated from 22 of these strains, and analyzed using a Southern blot with VIP1A(a)/VIP2A(a) DNA as probes. These strains were grouped into 8 classes based on their Southern blot pattern. Each class differed in Southern blot pattern from AB78. One class had a pattern identical to that of the VIP1A(a)/VIP2A(a) homologs from *Bacillus thuringiensis* var *tenebrionis* (see below). Each of the 22 strains was tested for activity against western corn rootworm (WCRW). Three strains, AB433, AB434, and AB435 were found to be active on WCRW. Western blot analysis using VIP2A(a) antisera revealed that strains AB6, AB433, AB434, AB435, AB444, and AB445 produce a protein(s) of equivalent size to VIP2A(a).

Notable among the strains identified was *Bacillus thuringiensis* strain AB6, (NRRL B-21060) which produced a VIP active against black cutworm (*Agrotis ipsilon*) as described in Example 15. Western blot analysis with polyclonal antisera to VIP2A(a) and polyclonal antisera to VIP1A(a) suggests that AB6 produces proteins similar to VIP2A(a) and VIP1A(a). Thus, AB6 may contain VIPs similar to VIP1A(a) and VIP2A(a), but with a different spectrum of insecticidal activity.

EXAMPLE 21
CLONING OF A VIP1A(a)/VIP2A(a) HOMOLOG FROM *BACILLUS THURINGIENSIS* VAR. *TENEBRIONIS*

Several previously characterized Bacillus strains were tested for presence of DNA similar to VIP1A(a)/VIP2A(a) by Southern blot analysis. DNA from Bacillus strains AB78, AB88, GC91, HD-1 and ATCC 10876 was analyzed for presence of VIP1A(a)/VIP2A(a) like sequences. DNA from *Bt* strains GC91 and HD-1, and the Bc strain ATCC 10876 did not hybridize to VIP2A(a)/VIP1A(a) DNA, indicating they lack DNA sequences similar to VIP1A(a)/VIP2A(a) genes. Similarly, DNA from the insecticidal strain AB88 (Example 16) did not hybridize to VIP1A(a)/VIP2A(a) DNA region, suggesting that the VIP activity produced by this strain does not result from VIP1A(a)/VIP2A(a) homologs. In contrast, *Bacillus thuringiensis* var. *tenebrionis* (*Btt*) contained sequences that hybridized to the VIP1A(a)/VIP2A (a) region. Further analysis confirmed that *Btt* contains VIP1A(a)/VIP2A(a) like sequences.

To characterize the *Btt* homologs of VIP2A(a) and VIP1A (a), the genes encoding these proteins were cloned. Southern blot analysis identified a 9.5 kb Eco RI restriction fragment likely to contain the coding regions for the homologs. Genomic DNA was digested with Eco RI, and DNA fragments of approximately 9.5 kb in length were gel-purified. This DNA was ligated into pBluescript SK(+) digested with Eco RI, and transformed into *E. coli* to generate a plasmid library. Approximately 10,000 colonies were screened by colony hybridization for the presence of VIP2A(a) homologous sequences. Twenty eight positive colonies were identified. All twenty eight clones are identical, and contain VIP1A(a)/VIP2A(a) homologs. Clone pCIB7100 has been deposited in the Agricultural Research Service, Patent Culture Collection (NRRL), Northern Regional Research Center, 1815 North University Street, Peoria Ill. 61604, USA, and given the Accession Number B-21322. Several subclones were constructed from pCIB7100. A 3.8 kb Xba I fragment from pCIB7100 was cloned into pBluescript SK(+) to yield pCIB7101. A 1.8 kb Hind III fragment and a 1.4 kb Hind III fragment from pCIB7100 were cloned into pbluescript SK(+) to yield pCIB7102 and pCIB7103, respectively. Subclones pCIB7101, pCIB7102 and pCIB7103 have been deposited in the Agricultural Research Service, Patent Culture Collection (NRRL), Northern Regional Research Center, 1815 North University Street, Peoria Ill. 61604, USA, and given the Accession Numbers B-21323, B-21324 and B-21325 respectively.

The DNA sequence of the region of pCIB7100 containing the VIP2A(a)/VIP1A(a) homologs was determined by the dideoxy chain termination method (Sanger et al., 1977, Proc. Natl. Acad. Sci. USA 74:5463–5467). Reactions were performed using PRISM Ready Reaction Dye Deoxy Terminator Cycle Sequencing Kits and PRISM Sequenase® Terminator Double-Stranded DNA Sequencing Kits, and analyzed on an ABI model 373 automated sequencer. Custom oligonucleotides were used as primers to determine the DNA sequence in certain regions. The DNA sequence of this region is shown in SEQ ID NO: 19.

The 4 kb region shown in SEQ ID NO: 19 contains two open readings frames (ORFs), which encode proteins with a high degree of similarity to VIP1A(a) and VIP2A(a) proteins from strain AB78. The amino acid sequence of the VIP2A(a) homolog, designated as VIP2A(b) using the standardized nomenclature, is found at SEQ ID NO:20 and the amino acid sequence of the VIP1A(a) homolog, designated as VIP1A(b) using the standardized nomenclature, is disclosed at SEQ ID NO:21. The VIP2A(b) protein exhibits 91% amino acid identity to VIP2A(a) from AB78. An alignment of the amino acid sequences of the two VIP2 proteins is provided in Table 20. The VIP1A(b) protein exhibits 77% amino acid identity to VIP1A(a) from AB78. An alignment of these two VIP1 proteins is provided in Table 21. The alignment shown in Table 21 discloses the similarity between VIP1A(b) and VIP1A(a) from AB78. This alignment reveals that the amino terminal regions of the two VIP1 proteins share higher amino acid identity in the amino-terminal region than in the carboxy terminal region. In fact, the amino terminal two thirds (up to aa 618 of the VIP1A(b) sequence shown in Table 21) of the two proteins exhibit 91% identity, while the carboxy-terminal third (from aa 619–833 of VIP1A(b)) exhibit only 35% identity.

Western blot analysis indicated that *Bacillus thuringiensis* var. *tenebrionis* (*Btt*) produces both VIP1A(a) like and VIP2A(a) like proteins. However, these proteins do not appear to have activity against western corn rootworm. Bioassay for activity against western corn rootworm was performed using either a 24 h culture supernatant from *Btt* or *E. Coli* clone pCIB7100 (which contains the entire region of the VIP1A(a)/VIP2A(a) homologs). No activity against western corn rootworm was detected in either case.

Given the similarity between the VIP2 proteins from *Btt* and AB78, the ability of VIP2A(b) from *Btt* to substitute for VIP2A(a) from AB78 was tested. Cells containing pCIB6206 (which produces AB78 VIP1A(a) but not VIP2A (a) protein) were mixed with *Btt* culture supernatant, and tested for activity against western corn rootworm. While neither *Btt* culture supernatant nor cells containing pCIB6206 had activity on WCRW, the mixture of *Btt* and pCIB6206 gave high activity against WCRW. Furthermore, additional bioassay showed that the *Btt* clone pCIB7100, which contains the *Btt* VIP1A(b)/VIP2A(b) genes in *E. coli*, also confers activity against WCRW when mixed with pCIB6206. Thus, the VIP2A(b) protein produced by *Btt* is functionally equivalent to the VIP2A(a) protein produced by AB78.

Thus, the ability to identify new strains with insecticidal activity by using VIP DNA as hybridization probes has been demonstrated. Furthermore, Bacillus strains that contain VIP1A(a)/VIP2A(a) like sequences, produce VIP1A(a)/ VIP2A(a) like protein, yet demonstrate toxicity toward different insect pests. Similar methods can identify many more members of the VIP1/VIP2 family. Furthermore, use of similar methods can identify homologs of other varieties of VIPs (for example, the VIPs from AB88).

TABLE 20

Alignment of VIP2 Amino Acid Sequences from *Bacillus thuringiensis* var. *tenebrionis*
(VIP2A(b)) vs. AB78 (VIP2A(a))

```
Btt    1  MQ R ME GKL F VVS KT L Q VVT RT VLL S T VYS I TLL NNV VI KAD QL NI NS QS K  50  SEQ ID NO: 20
          | . | | | | | | | : | | | . | | | | | : | | | | | | | | : | | . | | | |   | | | | : | | | | | | | |
AB78   1  MK R ME GKL F MVS KK L Q VVT KT VLL S T VFS I SLL NNE VI KAE QL NI NS QS K  50  SEQ ID NO: 2

51  YT NL QNL KI P DNAE DF KE DKG KAKE WG KE KGE E WR P P ATE KGE MNNF LDN  100
          | | | | | | | | . | . . | | | | | | | | : | | | | | | | | | | : . | | :   . | | | | | . | | | | | | |
      51  YT NL QNL KI T DKVE DF KE DKE KAKE WG KE KE KE WKL T ATE KG KMNNF LDN  100

101  KND I KT NYKE I TF S MAGS CE DE I KDLE E I DKI F DKANL SSS I I TYKNVE P  150
          | | | |   | | | | | | | | | | | | | |   | | | | | | | . | | | | : | | | . | | | . | | | | | | | | |
     101  KND I XT NYKE I TF S MAGS FE DE I KDL KE I DKMF DKT NLS NS I I TYKNVE P  150

151  AT I GF NKS LTE GNT I NS DAMAQF KE QF LGKD MKF DS YL DT HL T AQQ VS S K  200
          . | | | | | | | | | | | | | | | | | | | | | | | : : | : | : | | | | | | | | | | | | | | | |
     151  TT I GF NKS LTE GNT I NS DAMAQF KE QF LDRD I KF DS YL DT HL T AQQ VS S K  200

201  KR VI LKVT VP S GKGS TTP T KAGVI LNNNE YKML I DNGY VL HVDKVS KVVK  250
          . | | | | | | | | | | | | | | | | | | | | | | | | | | . | | | | | | | | | : : | | | | | | | | | |
     201  ER VI LKVT VP S GKGS TTP T KAGVI LNNSE YKML I DNGY MV HVDKVS KVVK  250
```

TABLE 20-continued

Alignment of VIP2 Amino Acid Sequences from *Bacillus thuringiensis* var. *tenebrionis* (VIP2A(b)) vs. AB78 (VIP2A(a))

```
251 K G ME C L Q V E G T L K K S L D F K N D I N A E A H S WG M K I Y E D WA K N L T A S Q R E A L D 300
    | | : | | | | : | | | | | | | | | | | | | | | | | | | | | | | | | | | | | : | | | : | | . | | | | | | | |
251 K G V E C L Q I E G T L K K S L D F K N D I N A E A H S WG M K N Y E E WA K D L T D S Q R E A L D 300

301 G Y A R Q D Y K E I N N Y L R N Q G G S G N E K L D A Q L K N I S D A L G K K P I P E N I T V Y R W 350
    | | | | | | | | | | | | | | | | | | | | | | | | | | | | : | | | | | | | | | | | | | | | | | | | | |
301 G Y A R Q D Y K E I N N Y L R N Q G G S G N E K L D A Q I K N I S D A L G K K P I P E N I T V Y R W 350

351 C G MP E F G Y Q I S D P L P S L K D F E E Q F L N T I K E D K G Y M S T S L S S E R L A A F G S R 400
    | | | | | | | | | | | | | | | | | | | | | | | | | | | | | | | | | | | | | | | | | | | | | | | | | |
351 C G MP E F G Y Q I S D P L P S L K D F E E Q F L N T I K E D K G Y M S T S L S S E R L A A F G S R 400

401 K I I L R L Q V P K G S T G A Y L S A I G G F A S E K E I L L D K D S K Y H I D K A T E V I I K G V 450
    | | | | | | | | | | | | | | | | | | | | | | | | | | | | | | | | | | | | | | | | . | | | | | | | |
401 K I I L R L Q V P K G S T G A Y L S A I G G F A S E K E I L L D K D S K Y H I D K V T E V I I K G V 450

451 K R Y V V D A T L L T N 462
    | | | | | | | | | | | |
451 K R Y V V D A T L L T N 462
```

TABLE 21

Alignment of VIP1 Amino Acid Sequences from *Bacillus thuringiensis* var. *tenebrionis* (VIP1A(b)) vs. AB78(VIP1A(a))

```
Btt    1 M K N M K K K L A S V V T C M L L A P M F L N G N V N A V N A D S K I N Q I S T T Q E N Q Q K E M D 50   SEQ ID NO: 21
         | | | | | | | | | | | | | | | | | | | | | | | | | | | | | . | | | | | | | | | | | | | | | | | | | |
Ab78   1 M K N M K K K L A S V V T C T L L A P M F L N G N V N A V Y A D S K T N Q I S T T Q K N Q Q K E M D 50   SEQ ID NO: 5

51 R K G L L G Y Y F K G K D F N N L T M F A P T R D N T L M Y D Q Q T A N A L L D K K Q Q E Y Q S I R 100
         | | | | | | | | | | | | | | . | | | | | | | | | | | | | | : | | | | | | | | | | | | | | | | | | | |
      51 R K G L L G Y Y F K G K D F S N L T M F A P T R D S T L I Y D Q Q T A N K L L D K K Q Q E Y Q S I R 100

101 W I G L I Q R K E T G D F T F N L S K D E Q A I I E I D G K I I S N K G K E K Q V V H L E K E K L V 150
         | | | | | | . | | | | | | | | | | | | . | | | | | | | | : | | | | | | | | | | | | | | | | | : | | |
     101 W I G L I Q S K E T G D F T F N L S E D E Q A I I E I N G K I I S N K G K E K Q V V H L E K G K L V 150

151 P I K I E Y Q S D T K F N I D S K T F K E L K L F K I D S Q N Q S Q Q V Q . . . L R N P E F N K K E 197
         | | | | | | | | | | | | | | | | | | | | | | | | | | | | | | | | | | . | | | |   | | | | | | | | |
     151 P I K I E Y Q S D T K F N I D S K T F K E L K L F K I D S Q N Q P Q Q V Q Q D E L R N P E F N K K E 200

198 S Q E F L A K A S K T N L F K Q M K R D I D E D T D T D G D S I P D L W E E N G Y T I Q N K V A V 247
         | | | | | | | : | | . | | | . | | | | | : | | | | | | | | | | | | | | | | | | | | | | | | | : : | |
     201 S Q E F L A K P S K I N L F T Q K M K R E I D E D T D T D G D S I P D L W E E N G Y T I Q N R I A V 250

248 K W D D S L A S K G Y T K F V S N P L D S H T V G D P Y T D Y E K A A R D L D L S N A K E T F N P L 297
         | | | | | | | | | | | | | | | | | : | | | | | | | | | | | | | | | | | | | | | | | | | | | | | | |
     251 K W D D S L A S K G Y T K F V S N P L E S H T V G D P Y T D Y E K A A R D L D L S N A K E T F N P L 300

298 V A A F P S V N V S M E K V I L S P N E N L S N S V E S H S S T N W S Y T N T E G A S I E A G G G P 347
         | | | | | | | | | | | | | | | | | | | | | | | | | | | | | | | | | | | | | | | | | : | | | | | |
     301 V A A F P S V N V S M E K V I L S P N E N L S N S V E S H S S T N W S Y T N T E G A S V E A G I G P 350

348 L G L S F G V S V T Y Q H S E T V A Q E W G T S T G N T S Q F N T A S A G Y L N A N V R Y N N V G T 397
         | : | | | | | | . | | | | | | | | | | | | | | | | | | | | | | | | | | | | | | | | | | | | | | | |
     351 K G I S F G V S V N Y Q H S E T V A Q E W G T S T G N T S Q F N T A S A G Y L N A N V R Y N N V G T 400

398 G A I Y D V K P T T S F V L N N N T I A T I T A K S N S T A L R I S P G D S Y P E I G E N A I A I T 447
         | | | | | | | | | | | | | | : | | | | | | | | | | | | | | | . | | | | : | | | . | | : | : | | | |
     401 G A I Y D V K P T T S F V L N N D T I A T I T A K S N S T A L N I S P G E S Y P K K G Q N G I A I T 450

448 S M D D F N S H P I T L N K Q Q V N Q L I N N K P I M L E T D Q T D G V Y K I R D T H G N I V T G G 497
         | | | | | | | | | | | | | | | . | | : . | : | | | | | : | | | | | | | | | | | | | | : | | | | | | |
     451 S M D D F N S H P I T L N K K Q V D N L L N N K P M M L E T N Q T D G V Y K I K D T H G N I V T G G 500

498 E W N G V T Q Q I K A K T A S I I V D D G K Q V A E K R V A A K D Y G H P E D K T P P L T L K D T L 547
         | | | | | . | | | | | | | | | | | | | | | . . | | | | | | | | | | | | : : | | | | | | . | | | | | . |
     501 E W N G V I Q Q I K A K T A S I I V D D G E R V A E K R V A A K D Y E N P E D K T P S L T L K D A L 550
```

TABLE 21-continued

Alignment of VIP1 Amino Acid Sequences from *Bacillus thuringiensis* var. *tenebrionis* (VIP1A(b)) vs. AB78(VIP1A(a))

```
      548  K L S YP DE I KE TNGL L Y YDDKP I YE S S VMT YL DE NT AKE VKKQ I NDT T GKF  597
           | | | | | | | | | | . : | | | | | . : | | | | | | | | | | | | | | | | | | | . | | : | | | | | | |
      551  K L S YP DE I KE I EGL L Y YKNKP I YE S S VMT YL DE NT AKE VT KQL NDT T GKF  600

Btt   598  KD VNHL YD VKL TP KMNF T I KMAS L YDG AE NNHNS L GT WYL T YNVAGGNT G       647  SEQ ID NO: 21
           | | | . | | | | | | | | | | | | . | | | : . | | | . | | . | . | | : | . |    | | . | | | . |
Ab78  601  KD VS HL YD VKL TP KMNVT I KLS I L YDNAE S NDNS I GKWT NT NI VS GGNNG      650  SEQ ID NO: 5

648  KR Q YR S AHS C AHVAL S S E AKKKL NQNANY YL S MYMKAD S T T E P T I E VAGE  697
           | : | | . | . : . | : : . | . . : | . . | | | . |  : | | : | : | | | . : . . | : . . | . : . | |
      651  KKQ YS S NNP DANL T L NT DAQE KL NKNR D Y Y I S L YMKS E KNT QCE I T I DGE  700

698  KS A I T S KKVKL NNQNYQR VD I L VKNS E RNP MDK I Y I RGNGT T NVYGDDVT     747
           : | | . | . | . : | . : | | . | : | | : . . |    . . | | : . . . : . | : . | : . . . . : :    | | : .
      701  I YP I T T KT VNVNKDNYKR LD I I AHN I KS NP I S S LH I KT NDE I T L FWDD I S  750

748  I P E VS A I NP AS L S DE E I QE I F KDS T I E YGNP S F VADAVT F K . . . . . . . . . . 788
           | . . : | . . | . | . . | . | . | | . . : | : .     . | . . . : : . .    : : . .  . . . : .
      751  I T DVAS I KP E NL T DS E I KQ I YS R YG I KL E DG I L I DKKGG I HYGE F I NE AS  800

789  . N I KP LQNYVKE YE I YHK . . . . . . . S HR YE KKT VF D I MGVHYE YS I ARE Q     830
           | | . | | | | | | . . | : . . .      | . . | . . . . : : .    . : . : : : .    . . .
      801  F N I E P LQNYVT KYKVT YS S E L GQNVS DT L E S DK I YKDGT I KF DF T KYS KN    850

831  K K A   833
           . . :
      851  E Q G   853
```

EXAMPLE 22
FUSION OF VIP PROTEINS TO MAKE A SINGLE POLYPEPTIDE

VIP proteins may occur in nature as single polypeptides, or as two or more interacting polypeptides. When an active VIP is comprised of two or more interacting protein chains, these protein chains can be produced as a single polypeptide chain from a gene resulting from the fusion of the two (or more) VIP coding regions. The genes encoding the two chains are fused by merging the coding regions of the genes to produce a single open reading frame encoding both VIP polypeptides. The composite polypeptides can be fused to produce the smaller polypeptide as the NH$_2$ terminus of the fusion protein, or they can be fused to produce the larger of the polypeptides as the NH$_2$ terminus of the fusion protein. A linker region can optionally be used between the two polypeptide domains. Such linkers are known in the art. This linker can optionally be designed to contain protease cleavage sites such that once the single fused polypeptide is ingested by the target insect it is cleaved in the linker region to liberate the two polypeptide components of the active VIP molecule.

VIP1A(a) and VIP2A(a) from *B. cereus* strain AB78 are fused to make a single polypeptide by fusing their coding regions. The resulting DNA has the sequence given in SEQ ID NO:22 with the encoded protein given in SEQ ID NO:23. In like manner, other fusion proteins may be produced.

The fusion of the genes encoding VIP1A(a) and VIP2A(a) is accomplished using standard techniques of molecular biology. The nucleotides deleted between the VIP1A(a) and VIP2A(a) coding regions are deleted using known mutagenesis techniques or, alternatively, the coding regions are fused using PCR techniques.

The fused VIP polypeptides can be expressed in other organisms using a synthetic gene, or partially synthetic gene, optimized for expression in the alternative host. For instance, to express the fused VIP polypeptide from above in maize, one makes a synthetic gene using the maize preferred codons for each amino acid, see for example patent application U.S. Ser. No. 07/951,715 herein incorporated by reference. Synthetic DNA sequences created according to these methods are disclosed in SEQ ID NO:17 (maize optimized version of the 100 kDa VIP1A(a) coding sequence), SEQ ID NO:18 (maize optimized version of the 80 kDa VIP1A(a) coding sequence) and SEQ ID NO:24 (maize optimized version of the VIP2A(a) coding sequence).

Synthetic VIP1 and VIP2 genes optimized for expression in maize can be fused using PCR techniques, or the synthetic genes can be designed to be fused at a common restriction site. Alternatively, the synthetic fusion gene can be designed to encode a single polypeptide comprised of both VIP1 and VIP2 domains.

Addition of a peptide linker between the VIP1 and VIP2 domains of the fusion protein can be accomplished by PCR mutagenesis, use of a synthetic DNA linker encoding the linker peptide, or other methods known in the art.

The fused VIP polypeptides can be comprised of one or more binding domains. If more than one binding domain is used in the fusion, multiple target pests are controlled using such a fusion. The other binding domains can be obtained by using all or part of other VIPs; *Bacillus thuringiensis* endotoxins, or parts thereof; or other proteins capable of binding to the target pest or appropriate biding domains derived from such binding proteins.

One example of a fusion construction comprising a maize optimized DNA sequence encoding a single polypeptide chain fusion having VIP2A(a) at VIP1A(a) at the N-terminal end and VIP1A(a) at the C-terminal end is provided by pCIB5531. A DNA sequence encoding a linker with the peptide sequence PSTPPTPSPSTPPTPS (SEQ ID NO:47) has been inserted between the two coding regions. The sequence encoding this linker and relevant cloning sites is 5'-<u>CCCGGG</u> CCT TCT ACT CCC CCA ACT CCC TCT CCT AGC ACG CCT CCG ACA CCT AGC <u>GAT ATC GGA TC</u> C-3' (SEQ ID NO:48). Oligonucleotides were synthesized to represent both the upper and lower strands and cloned into a pUC vector following hybridization and phosphorylation using standard procedures. The stop codon in VIP2A(a) was removed using PCR and replaced by the BglII restriction site with a SmaI site. A translation fusion was made by ligating the Bam HI/PstI fragment of the VIP2A(a) gene from pCIB5522 (see Example 24), a PCR fragment containing the PstI-end fragment of the VIP2A(a) gene (identical to that used to construct pCIB5522), a synthetic linker having ends that would ligate with a blunt site at the 5' end and with BamHI at the 3' end and the modified synthetic VIP1A(a) gene from pCIB5526 described below (See SEQ ID NO:35). The fusion was obtained by a four way ligation that resulted in a plasmid containing the VIP2A(a) gene without a translation stop codon, with a linker and the VIP1A(a) coding region without the Bacillus secretion signal. The DNA sequence for this construction is disclosed in SEQ ID NO:49, which encodes the fusion protein disclosed in SEQ ID NO:50. A single polypeptide fusion where VIP1A(a) is at the N-terminal end and VIP2A(a) is at the C-terminal end can be made in a similar fashion. Furthermore, either one or both genes can be linked in a translation fusion with or without a linker at either the 5' or the 3' end to other molecules like toxin encoding genes or reporter genes.

EXAMPLE 23
TARGETING OF VIP2 TO PLANT ORGANELLES

Various mechanisms for targeting gene products are known to exist in plants and the sequences controlling the functioning of these mechanisms have been characterized in some detail. For example, the targeting of gene products to the chloroplast is controlled by a signal sequence found at the amino-terminal end of various proteins. This signal is cleaved during chloroplast import, yielding the mature protein (e.g. Comai et al. J. Biol. Chem. 263:15104–15109 (1988)). These signal sequences can be fused to heterologous gene products such as VIP2 to effect the import of those products into the chloroplast (van den Broeck et al. Nature 313:358–363 (1985)). DNA encoding for appropriate signal sequences can be isolated from the 5' end of the cDNAs encoding the RUBISCO protein, the CAB protein, the EPSP synthase enzyme, the GS2 protein and many other proteins which are known to be chloroplast localized.

Other gene products are localized to other organelles such as the mitochondrion and the peroxisome (e.g. Unger et al. Plant Molec. Biol. 13:411–418 (1989)). The cDNAs encoding these products can also be manipulated to effect the targeting of heterologous gene products such as VIP2 to these organelles. Examples of such sequences are the nuclear-encoded ATPases and specific aspartate amino transferase isoforms for mitochondria. Similarly, targeting to cellular protein bodies has been described by Rogers et al. (Proc. Natl. Acad. Sci. USA 82:6512–6516 (1985)).

By the fusion of the appropriate targeting sequences described above to coding sequences of interest such as VIP2 it is possible to direct the transgene product to any organelle or cell compartment. For chloroplast targeting, for example, the chloroplast signal sequence from the RUBISCO gene, the CAB gene, the EPSP synthase gene, or the GS2 gene is fused in frame to the amino-terminal ATG of the transgene. The signal sequence selected should include the known cleavage site and the fusion constructed should take into account any amino acids after the cleavage site which are required for cleavage. In some cases this requirement may be fulfilled by the addition of a small number of amino acids between the cleavage site and the start codon ATG, or alternatively replacement of some amino acids within the coding sequence. Fusions constructed for chloroplast import can be tested for efficacy of chloroplast uptake by in vitro translation of in vitro transcribed constructions followed by in vitro chloroplast uptake using techniques described by (Bartlett et al. In: Edelmann et al. (Eds.) Methods in Chloroplast Molecular Biology, Elsevier. pp 1081–1091 (1982); Wasmann et al. Mol. Gen. Genet. 205:446–453 (1986)). These construction techniques are well known in the art and are equally applicable to mitochondria and peroxisomes.

The above described mechanisms for cellular targeting can be utilized not only in conjunction with their cognate promoters, but also in conjunction with heterologous promoters so as to effect a specific cell targeting goal under the transcriptional regulation of a promoter which has an expression pattern different to that of the promoter from which the targeting signal derives.

A DNA sequence encoding a secretion signal is present in the native Bacillus VIP2 gene. This signal is not present in the mature protein which has the N-terminal sequence of LKITDKVEDF (amino acid residues 57 to 66 of SEQ ID NO:2). It is possible to engineer VIP2 to be secreted out of the plant cell or to be targeted to subcellular organelles such as the endoplasmic reticulum, vacuole, mitochondria or plastids including chloroplasts. Hybrid proteins made by fusion of a secretion signal peptide to a marker gene have been successfully targeted into the secretion pathway. (Itirriaga G. et al., *The Plant Cell,* 1:381–390 (1989), Denecke et al., *The Plant Cell,* 2:51–59 (1990). Amino-terminal sequences have been identified that are responsible for targeting to the ER, the apoplast, and extracellular secretion from aleurone cells (Koehler & Ho, Plant Cell 2:769–783 (1990)).

The presence of additional signals are required for the protein to be retained in the endoplasmic reticulum or the vacuole. The peptide sequence KDEL/HDEL at the carboxy-terminal of a protein is required for its retention in the endoplasmic reticulum (reviewed by Pelham, *Annual Review Cell Biol.,* 5:1–23 (1989). The signals for retention of proteins in the vacuole have also been characterized. Vacuolar targeting signals may be present either at the amino-terminal portion, (Holwerda et al., *The Plant Cell,* 4:307–318 (1992), Nakamura et al., *Plant Physiol.,* 101:1–5 (1993)), carboxy-terminal portion, or in the internal sequence of the targeted protein. (Tague et al., *The Plant Cell,* 4:307–318 (1992), Saalbach et al., *The Plant Cell,* 3:695–708 (1991)). Additionally, amino-terminal sequences in conjunction with carboxy-terminal sequences are responsible for vacuolar targeting of gene products (Shinshi et al. Plant Molec. Biol. 14:357–368 (1990)). Similarly, proteins may be targeted to the mitochondria or plastids using specific carboxy terminal signal peptide fusions (Heijne et al., *Eur. J. Biochem.,* 180:535–545 (1989), Archer and Keegstra, *Plant Molecular Biology,* 23:1105–1115 (1993)).

In order to target VIP2, either for secretion or to the various subcellular organelles, a maize optimized DNA sequence encoding a known signal peptide(s) may be designed to be at the 5' or the 3' end of the gene as required. To secrete VIP2 out of the cell, a DNA sequence encoding the eukaryotic secretion signal peptide MGWSWIFLFLLS-GAAGVHCL (SEQ ID NO:25) from U.S. patent application Ser. No. 08/267,641 or any other described in the literature (Itirriaga et al., *The Plant Cell,* 1:381–390 (1989), Denecke, et al., *The Plant Cell,* 2:51–59 (1990)) may be added to the 5' end of either the complete VIP2 gene sequence or to the sequence truncated to encode the mature protein or the gene truncated to nucleotide 286 or encoding a protein to start at amino acid residue 94 (methionine). To target VIP2 to be retained in the endoplasmic reticulum, a DNA sequence encoding the ER signal peptide KDEL/HDEL, in addition to the secretion signal, can be added to the 3' end of the gene. For vacuolar targeting a DNA sequence encoding the signal peptide SSSSFADSNPIRVTDRAAST (SEQ ID NO:3; Holwerda et al., *The Plant Cell*, 4:307–318 (1992)) can be designed to be adjacent to the secretion signal or a sequence encoding a carboxyl signal peptide as described by Dombrowski et al., *The Plant Cell*, 5:587–596 (1993) or a functional variation may be inserted at the 3' end of the gene. Similarly, VIP2 can be designed to be targeted to either the mitochondria or the plastids, including the chloroplasts, by inserting sequences in the VIP2 sequence described that would encode the required targeting signals. The bacterial secretion signal present in VIP2 may be retained or removed from the final construction.

One example of a construction which incorporates a eukaryotic secretion signal fused to a coding sequence for a VIP is provided by pCIB5528. Oligonucleotides corresponding to both the upper and lower strand of sequences encoding the secretion signal peptide of SEQ ID NO:25 was synthesized and has the sequence 5'-GGATCCACC ATG GGC TGG AGC TGG ATC TTC CTG TTC CTG CTG AGC GGC GCC GCG GGC GTG CAC TGC CTGCAG-3' (SEQ ID NO:41). When hybridized, the 5' end of the secretion signal resembled "sticky-ends" corresponding to restriction sites BamHI and PstI. The oligonucleotide was hybridized and phosphorylated and ligated into pCIB5527 (construction described in Example 23A) which had been digested with BamHI/PstI using standard procedures. The resulting maize optimized coding sequence is disclosed in SEQ ID NO:42 which encodes the protein disclosed in SEQ ID NO:43. This encoded protein comprises the eukaryotic secretion signal in place of the Bacillus secretion signal.

One example of a construction which incorporates a vacuolar targetting signal fused to a coding sequence for a VIP is provided by pCIB5533. Oligonucleotides corresponding to both the upper and lower strand of sequences encoding the vacuolar targetting peptide of SEQ ID NO:3 was synthesized and has the sequence 5'-CCG CGG GCG TGC ACT GCC TCA GCA GCA GCA GCT TCG CCG ACA GCA ACC CCA TCC GCG TGA CCG ACC GCG CCG CCA GCA CCC TGC AG-3' (SEQ ID NO:44). When hybridized, the 5' end of the vacuolar targetting signal resembled "sticky-ends" corresponding to restriction sites SacII and PstI. The oligonucleotide was hybridized and phosphorylated and ligated into pCIB5528 (construction described above) which had been digested with SacII/PstI using standard procedures. The resulting maize optimized coding sequence is disclosed in SEQ ID NO:45 which encodes the protein disclosed in SEQ ID NO:46. This encoded protein comprises the vacuolar targetting peptide in addition to the eukaryotic secretion signal.

The VIP1 gene can also be designed to be secreted or targeted to subcellular organelles by similar procedures.

EXAMPLE 23A

REMOVAL OF BACILLUS SECRETION SIGNAL FROM VIP1A(a) AND VIP2A(a)

VIP1A(a) and VIP2A(a) are secreted during the growth of strain AB78. The nature of peptide sequences that act as secretion signals has been described in the literature (Simonen and Palva, Microbiological reviews, pg. 109–137 (1993)). Following the information in the above publication, the putative secretion signal was identified in both genes. In VIP1A(a) this signal is composed of amino acids 1–33 (See SEQ ID NO:5). Processing of the secretion signal probably occurs after the serine at amino acid 33. The secretion signal in VIP2A(a) was identified as amino acids 1–49 (See SEQ ID NO:2). N-terminal peptide analysis of the secreted mature VIP2A(a) protein revealed the N-terminal sequence LKITDKVEDFKEDK. This sequence is found beginning at amino acid 57 in SEQ ID NO:2. The genes encoding these proteins have been modified by removal of the Bacillus secretion signals.

A maize optimized VIP1A(a) coding region was constructed which had the sequences encoding the first 33 amino acids, i.e., the secretion signal, removed from its 5' end. This modification was obtained by PCR using an forward primer that contained the sequence 5'-GGA TCC ACC ATG AAG ACC AAC CAG ATC AGC-3' (SEQ ID NO:33), which hybridizes with the maize optimized gene (SEQ ID NO:26) at nucleotide position 100, and added a BamHI restriction site and a eukaryotic translation start site consensus including a start codon. The reverse primer that contained the sequence 5'-AAG CTT CAG CTC CTT G-3' (SEQ ID NO:34) hybridizes on the complementary strand at nucleotide position 507. A 527 bp amplification product was obtained containing the restriction sites BamHI at the 5' end and HindIII site at the 3' end. The amplification product was cloned into a T- vector (described in Example 24, below) and sequenced to ensure the correct DNA sequence. The BamHI/HindIII fragment was then obtained by restriction digest and used to replace the BamHI/HindIII fragment of the maize optimized VIP1A(a) gene cloned in the root-preferred promoter cassette. The construct obtained was designated pCIB5526. The maize optimized coding region for VIP1A(a) with the Bacillus secretion signal removed is disclosed as SEQ ID NO:35 and the encoded protein is disclosed as SEQ ID NO:36.

The gene encoding the processed form of VIP2A(a), i.e., a coding region with the secretion signal removed, was constructed by a procedure similar to that described for that used to construct the processed form of VIP1A(a), above. The modification was obtained by PCR using the forward primer 5'-GGA TCC ACC ATG CTG CAG AAC CTG AAG ATC AC -3' (SEQ ID NO:37). This primer hybridizes at nucleotide position 150 of the maize optimized VIP2A(a) gene (SEQ ID NO:27). A silent mutation has been inserted at nucleotide position 15 of this primer to obtain a PstI restriction site. The reverse primer has the sequence 5'-AAG CTT CCA CTC CTT CTC-3' (SEQ ID NO:38). A 259 bp product was obtained with HindIII restriction site at the 3' end. The amplification product was cloned into a T- vector, sequenced and ligated to a BamHI/HindIII digested root-preferred promoter cassette containing the maize optimized VIP2A(a). The construct obtained was designated pCIB5527. The maize optimized coding region for VIP2A(a) with the Bacillus secretion signal removed is disclosed as SEQ ID NO:39 and the encoded protein is disclosed as SEQ ID NO:40.

EXAMPLE 24

CONSTRUCTION AND CLONING OF THE VIP1A(a) AND VIP2A(a) MAIZE OPTIMIZED GENES

Design: The maize optimized genes were designed by reverse translation of the native VIP1A(a) and VIP2A(a) protein sequences using codons that are used most often in maize (Murray et al., *Nucleic Acid Research,* 17:477–498 (1989)). To facilitate cloning, the DNA sequence was further modified to incorporate unique restriction sites at intervals of every 200–360 nucleotides. VIP1A(a) was designed to be cloned in 11 such fragments and VIP2A(a) was cloned in 5 fragments. Following cloning of the individual fragments, adjacent fragments were joined using the restriction sites common to both fragments, to obtain the complete gene. To clone each fragment, oligonucleotides (50–85 nucleotides) were designed to represent both the upper and the lower strand of the DNA. The upper oligo of the first oligo pair was designed to have a 15 bp single stranded region at the 3' end which was homologous to a similar single stranded region of the lower strand of the next oligo pair to direct the orientation and sequence of the various oligo pairs within a given fragment. The oligos are also designed such that when the all the oligos representing a fragment are hybridized, the ends have single stranded regions corresponding to the particular restriction site to be formed. The structure of each oligomer was examined for stable secondary structures such as hairpin loops using the OLIGO program from NBI Inc. Whenever necessary, nucleotides were changed to decrease the stability of the secondary structure without changing the amino acid sequence of the protein. A plant ribosomal binding site consensus sequence, TAAACAATG (Joshi et al., *Nucleic Acid Res.,* 15:6643–6653 (1987)) or eukaryotic ribosomal binding site concensus sequence CCACCATG (Kozak, *Nucleic Acid Research,* 12:857–872 (1984)) was inserted at the translational start codon of the gene.

Cloning: Oligos were synthesized by IDT Inc., and were supplied as lyophilized powders. They were resuspended at a concentration of 200 μM. To 30 μl of each oligo formamide was added a final concentration of 25–50% and the sample was boiled for two minutes before separation on a premade 10% polyacryamide/urea gel obtained from Novex. After electrophoresis, the oligo was detected by UV shadowing by placing the gel on a TLC plate containing a fluorescent indicator and exposing it to UV light. The region containing DNA of the correct size was excised and extracted from the polyacryamide by an overnight incubation of the minced gel fragment in a buffer containing 0.4M LiCl, 0.1 mM EDTA. The DNA was separated from the gel residue by centrifugation through a Millipore UFMC filter. The extracted DNA was ethanol precipitated by the addition of 2 volumes of absolute alcohol. After centrifugation, the precipitate was resuspended in $dH_2O$ at a concentration of 2.5 μM. Fragments were cloned either by hybridization of the oligos and ligation with the appropriate vector or by amplification of the hybridized fragment using a equimolar mixture of all the oligos for a particular fragment as a template and end-specific PCR primers.

Cloning by hybridization and ligation: Homologous double stranded oligo pairs were obtained by mixing 5 μl of the upper and of the lower oligo for each oligo pair with buffer containing 1×polynucleotide kinase (PNK) buffer (70 mM Tris-HCl (pH 7.6), 10 mM $MgCl_2$ 5 mM dithiothreitol (DTT)), 50 mM KCl, and 5% formamide in a final volume of 50 μl. The oligos were boiled for 10 minutes and slow cooled to 37° C. or room temperature. 10 μl was removed for analysis on a 4% agarose in a TAE buffer system (Metaphore®; FMC). Each hybridized oligo pair was kinased by the addition of ATP at a final concentration of 1 mM, BSA at a final concentration of 100 μg per ml and 200 units of polynucleotide kinase and 1 μl of 10×PNK buffer in a volume of 10 μl. Following hybridization and phosphorylation, the reaction was incubated at 37° C. for 2 hours to overnight. 10 μl of each of the oligo pairs for a particular fragment, were mixed in a final volume of 50 μl. The oligo pairs were hybridized by heating at 80° C. for 10 minutes and slow cooling to 37° C. 2 μl of oligos was mixed with about 100 ng of an appropriate vector and ligated using a buffer containing 50 mM Tris-HCl (pH 7.8), 10 mM $MgCl_2$, 10 mM DTT, 1 mM ATP. The reaction was incubated at room temp. for 2 hours to overnight and transformed into DH5α strain of *E.coli*, plated on L-plates containing ampicillin at a concentration of 100 μg/ml using standard procedures. Positive clones were further characterized and confirmed by PCR miniscreen described in detail in U.S. patent application Ser. No. 07/951,715 using the universal primers "Reverse" and M13 "–20 " as primers. Positive clones were identified by digestion of DNA with appropriate enzymes followed by sequencing. Recombinants that had the expected DNA sequence were then selected for further work.

PCR Amplification and cloning into T-vector:

PCR amplification was carried out by using a mixture of all the oligomers that represented the upper and the lower strand of a particular fragment (final concentration 5 mM each) as template, specific end primers for the particular fragment (final concentration 2 μM) 200 μM of each dATP, dTTP, dCTP and dGTP, 10 mM Tris-HCl (pH 8.3), 50 mM KCl, 1.5 mM $MgCl_2$, 0.0 1% gelatin and 5 units of Taq polymerase in a final reaction volume of 50 μl. The amplification reaction was carried out in a Perkin Elmer thermocycler 9600 by incubation at 95° C. for 1 min (1 cycle), followed by 20 cycles of 95° C. for 45 sec., 50° C. for 45 sec., 72° C. for 30 sec. Finally the reaction was incubated for 5 min at 72° C. before analyzing the product. 10 μl of the reaction was analyzed on a 2.5% Nusieve (FMC) agarose gel in a TAE buffer system. The correct size fragment was gel purified and used for cloning into a PCR cloning vector or T-vector. T-vector construction was as described by Marchuk et al., *Nucleic Acid Research,* 19:1154 (1991). pBluescriptsk+(Stratagene®, Ca.) was used as the parent vector. Transformation and identification of the correct clone was carried out as described above.

Fragments 1, 3, 4, 5, 6, 8, and 9 of VIP1A(a) and fragments 2 and 4 of VIP2A(a) were obtained by cloning of PCR amplification products; whereas, fragments 2, 7, 10 and 11 of VIP1A(a) and fragments 1, 3, and 5 of VIP2A(a) were obtained by hybridization/ligation.

Once fragments with the desired sequence were obtained, the complete gene was assembled by cloning together adjacent fragments. The complete gene was resequenced and tested for activity against WCRW before moving it into plant expression vectors containing the root preferred promoter (disclosed in U.S. patent application Ser. No. 08/017,209, herein incorporated by reference) and the rice actin promoter.

One such plant expression vector is pCIB5521. The maize optimized VIP1A(a) coding region (SEQ ID NO:26) was cloned in a plant expression vector containing the root preferred promoter at the 5' of the gene with the PEP Carboxylase intron #9 followed by the 35S terminator at the 3' end. The plasmid also contains sequences for ampicillin resistance from the plasmid pUC19. Another plant expression vector is pCIB5522, which contains the maize optimized VIP2A(a) coding region (SEQ ID NO:27) fused to the root preferred promoter at the 5' of the gene with the PEP Carboxylase intron #9 followed by the 35S terminator at the 3' end.

EXAMPLE 25

NAD AFFINITY CHROMATOGRAPHY

A purification strategy was used based on the affinity of VIP2 for the substrate NAD. The supernatant from the pH 3.5 sodium citrate buffer treatment described in Example 4 was dialyzed in 20 mM TRIS pH 7.5 overnight. The neutralized supernatant was added to an equal volume of washed NAD agarose and incubated with gentle rocking at 4° C. overnight. The resin and protein solution were added to a 10 ml disposable polypropylene column and the protein solution allowed to flow out. The column was washed with 5 column volumes of 20 mM TRIS pH 7.5 then washed with 2–5 column volumes of 20 mM TRIS pH 7.5, 100 mM NaCl, followed by 2–5 column volumes of 20 mM TRIS 7.5. The VIP proteins were eluted in 20 mM TRIS pH 7.5 supplemented with 5 mM NAD. Approximately 3 column volumes of the effluent were collected and concentrated in a Centricon-10. Yield is typically about 7–15 μg of protein per ml of resin.

When the purified proteins were analyzed by SDS-PAGE followed by silver staining, two polypeptides were visible, one with Mr of approximately 80,000 and one with Mr of approximately 45,000. N-terminal sequencing revealed that the Mr 80,000 protein corresponded to a proteolytically processed form of VIP1A(A) and the Mr 45,000 form corresponded to a proteolytically processed form of VIP2A (a). The co-purification of VIP1A(a) with VIP2A(a) indicates that the two proteins probably form a complex and have protein-protein interacting regions. VIP1A(a) and VIP2A(a) proteins purified in this manner were biologically active against western corn rootworm.

EXAMPLE 26
EXPRESSION OF MAIZE OPTIMIZED VIP1A(a) AND VIP2A(a)

E. coli strains containing different plasmids comprising VIP genes were assayed for expression of VIPs. E. coli strains harboring the individual plasmids were grown overnight in L-broth and expressed protein was extracted from the culture as described in Example 3, above. Protein expression was assayed by Western Blot analysis using antibodies developed using standard methods known in the art, similar to those described in Example 12, above. Also, insecticidal activity of the expressed proteins were tested against Western corn rootworm according to the method in Example 3, above. The results of the E. coli expression assays are described below.

Expression of VIPs in E. coli

| Extract of E. coli Strain Harboring Indicated Plasmid | Assay No. 1 % Mortality | Assay No. 2 % Mortality | Protein Detected |
|---|---|---|---|
| Control | 0 | 0 | no |
| pCIB5521 (maize optimized VIP1A(a)) | 47 | 27 | yes |
| pCIB5522 (maize optimized VIP2A(a)) | 7 | 7 | yes |
| pCIB6024 (native VIP2A(a)) | 13 | 13 | yes |
| pCIB6206 (native VIP1A(a)) | 27 | 40 | yes |
| Extracts pCIB5521 + pCIB5522 combined | 87 | 47 | |
| Extracts pCIB5521 + pCIB6024 combined | 93 | 100 | |
| Extracts pCIB5522 + pCIB6206 combined | 100 | 100 | |
| Extracts pCIB6024 + pCIB6206 combined | 100 | 100 | |

The DNA from these plasmids was used to transiently express the VIPs in a maize protoplast expression system. Protoplasts were isolated from maize 2717 Line 6 suspension cultures by digestion of the cell walls using Cellulase RS and Macerase R10 in appropriate buffer. Protoplasts were recovered by sieving and centrifugation. Protoplasts were transformed by a standard direct gene transfer method using approximately 75 μg plasmid DNA and PEG40. Treated protoplasts were incubated overnight in the dark at room temperature. Analysis of VIP expression was accomplished on protoplast explants by Western blot analysis and insecticidal activity against Western corn rootworm as described above for the expression in E. coli. The results of the maize protoplast expression assays are described below.

Expression of VIPs in Plant Protoplasts

| Extract Tested | Assay No. 1 % Mortality | Assay No. 2 % Mortality | Protein Detected |
|---|---|---|---|
| No DNA control | 27 | 10 | no |
| pCIB5521 (p)(maize optimized vIP1A(a)) | 20 (0) | 30 | yes |
| pCIB5522 (p) (maize optmizied VIP2A(a)) | 20 (0) | 20 | yes |
| Extracts pCIB5521 (p) + pCIB5522 (p) combined | 87 (82) | 90 | |
| Extracts pCIB5521 (p) + pCIB5522 (e) combined | 100 | — | |
| Extracts pCIB5522 (p) + pCIB5521 (e) combined | 53 (36) | — | |
| Extracts pCIB5521 (p) + pCIB6024 (e) combined | 100 | — | |
| Extracts pCIB5522 (p) + pCIB6206 (e) combined | 100 | — | |
| pCIB6024(e) (native VIP2A(a)) | 0 | — | yes |
| pCIB6206(e) (native VIP1A(a)) | 20 | — | yes |
| pCIB5521 + pCIB 5522 (plasmids delivered by cotransformation) | 100 | 100 | yes |

(p) = extract of protoplast culture transformed with indicated plasmid
(e) = extract of E. Coli strain harboring indicated plasmid The expression data obtained with both E. coli and maize protoplasts show that the maize optimized VIP1A(a) and VIP2A(a) genes make the same protein as the native VIP1A (a) and VIP2A(a) genes, respectively, and that the proteins encoded by the maize optimized genes are functionally equivalent to the proteins encoded by the native genes.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The following deposits have been made at Agricultural Research Service, Patent Culture Collection (NRRL), Northern Regional Research Center, 1815 North University Street, Peoria, Ill. 61604, USA:

1. E. coli PL2 Accession No. NRRL B-21221N
2. E. coli pCIB6022 Accession No. NRRL B-21222
3. E. coli pCIB6023 Accession No. NRRL B-21223N
4. Bacillus thuringiensis HD73–78VIP Accession No. NRRL B-21224
5. Bacillus thuringiensis AB88 Accession No. NRRL B-21225
6. Bacillus thuringiensis AB359 Accession No. NRRL B-21226
7. Bacillus thuringiensis AB289 Accession No. NRRL B-21227
8. Bacillus sp. AB59 Accession No. NRRL B-21228
9. Bacillus sp. AB294 Accession No. NRRL B-21229
10. Bacillus sp. AB256 Accession No. NRRL B-21230
11. E. coli P5–4 Accession No. NRRL B-21059
12. E. coli P3-12 Accession No. NRRL B-21061
13. Bacillus cereus AB78 Accession No. NRRL B-21058
14. Bacillus thuringiensis AB6 Accession No. NRRL B-21060
15. E. coli pCIB6202 Accession No. NRRL B-21321

16. *E. coli* pCIB7100 Accession No. NRRL B-21322
17. *E. coli* pCIB7101 Accession No. NRRL B-21323
18. *E. coli* pCIB7102 Accession No. NRRL B-21324
19. *E. coli* pCIB7102 Accession No. NRRL B-21325
20. *E. coli* pCIB7104 Accession No. NRRL B-21422
21. *E. coli* pCIB7107 Accession No. NRRL B-21423
22. *E. coli* pCIB7108 Accession No. NRRL B-21438
23. *Bacillus thuringiensis* AB424 Accession No. NRRL B-21439

Although the foregoing invention has been described in some detail by way of illustration and example for purposes of clarity of understanding, it will be obvious that certain changes and modifications may be practiced within the scope of the appended claims.

SEQUENCE LISTING ( 1 ) GENERAL INFORMATION:

( i i i ) NUMBER OF SEQUENCES: 50

( 2 ) INFORMATION FOR SEQ ID NO:1:

( i ) SEQUENCE CHARACTERISTICS:
        ( A ) LENGTH: 6049 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Bacillus cereus
        ( B ) STRAIN: AB78
        ( C ) INDIVIDUAL ISOLATE: NRRL B- 21058

( i x ) FEATURE:
        ( A ) NAME/KEY: CDS
        ( B ) LOCATION: 1082..2467
        ( D ) OTHER INFORMATION: /product="VIP2A(a)"

( i x ) FEATURE:
        ( A ) NAME/KEY: misc_feature
        ( B ) LOCATION: 2475..5126
        ( D ) OTHER INFORMATION: /note= "Coding sequence for the 100
            kd VIP1A(a) protein. This coding sequence is repeated in
            SEQ ID NO:4 and translated separately."

( x i ) SEQUENCE DESCRIPTION: SEQ ID NO:1:

```
ATCGATACAA  TGTTGTTTTA  CTTAGACCGG  TAGTCTCTGT  AATTTGTTTA  ATGCTATATT      60
CTTTACTTTG  ATACATTTTA  ATAGCCATTT  CAACCTTATC  AGTATGTTTT  TGTGGTCTTC     120
CTCCTTTTTT  TCCACGAGCT  CTAGCTGCGT  TTAATCCTGT  TTTGGTACGT  TCGCTAATAA     180
TATCTCTTTC  TAATTCTGCA  ATACTTGCCA  TCATTCGAAA  GAAGAATTTC  CCCATAGCAT     240
TAGAGGTATC  AATGTTGTCA  TGAATAGAAA  TAAAATCTAC  ACCTAGCTCT  TTGAATTTTT     300
CACTTAACTC  AATTAGGTGT  TTTGTAGAGC  GAGAAATTCG  ATCAAGTTTG  TAAACAACTA     360
TCTTATCGCC  TTTACGTAAT  ACTTTTAGCA  ACTCTTCGAG  TTGAGGGCGC  TCTTTTTTA     420
TTCCTGTTAT  TTTCTCCTGA  TATAGCCTTT  CTACACCATA  TTGTTGCAAA  GCATCTATTT     480
GCATATCGAG  ATTTTGTTCT  TCTGTGCTGA  CACGAGCATA  ACCAAAAATC  AAATTGGTTT     540
CACTTCCTAT  CTAAATATAT  CTATTAAAAT  AGCACCAAAA  ACCTTATTAA  ATTAAAATAA     600
GGAACTTTGT  TTTTGGATAT  GGATTTTGGT  ACTCAATATG  GATGAGTTTT  TAACGCTTTT     660
GTTAAAAAAC  AAACAAGTGC  CATAAACGGT  CGTTTTTGGG  ATGACATAAT  AAATAATCTG     720
TTTGATTAAC  CTAACCTTGT  ATCCTTACAG  CCCAGTTTTA  TTTGTACTTC  AACTGACTGA     780
ATATGAAAAC  AACATGAAGG  TTTCATAAAA  TTTATATATT  TTCCATAACG  GATGCTCTAT     840
CTTTAGGTTA  TAGTTAAATT  ATAAGAAAAA  AACAAACGGA  GGGAGTGAAA  AAAAGCATCT     900
TCTCTATAAT  TTTACAGGCT  CTTTAATAAG  AAGGGGGGAG  ATTAGATAAT  AAATATGAAT     960
ATCTATCTAT  AATTGTTTGC  TTCTACAATA  ACTTATCTAA  CTTTCATATA  CAACAACAAA    1020
```

-continued

```
ACAGACTAAA TCCAGATTGT ATATTCATTT TCAGTTGTTC CTTTATAAAA TAATTTCATA         1080

A ATG AAA AGA ATG GAG GGA AAG TTG TTT ATG GTG TCA AAA AAA TTA             1126
  Met Lys Arg Met Glu Gly Lys Leu Phe Met Val Ser Lys Lys Leu
   1           5                  10                  15

CAA GTA GTT ACT AAA ACT GTA TTG CTT AGT ACA GTT TTC TCT ATA TCT           1174
Gln Val Val Thr Lys Thr Val Leu Leu Ser Thr Val Phe Ser Ile Ser
             20                  25                  30

TTA TTA AAT AAT GAA GTG ATA AAA GCT GAA CAA TTA AAT ATA AAT TCT           1222
Leu Leu Asn Asn Glu Val Ile Lys Ala Glu Gln Leu Asn Ile Asn Ser
             35                  40                  45

CAA AGT AAA TAT ACT AAC TTG CAA AAT CTA AAA ATC ACT GAC AAG GTA           1270
Gln Ser Lys Tyr Thr Asn Leu Gln Asn Leu Lys Ile Thr Asp Lys Val
         50                  55                  60

GAG GAT TTT AAA GAA GAT AAG GAA AAA GCG AAA GAA TGG GGG AAA GAA           1318
Glu Asp Phe Lys Glu Asp Lys Glu Lys Ala Lys Glu Trp Gly Lys Glu
         65                  70                  75

AAA GAA AAA GAG TGG AAA CTA ACT GCT ACT GAA AAA GGA AAA ATG AAT           1366
Lys Glu Lys Glu Trp Lys Leu Thr Ala Thr Glu Lys Gly Lys Met Asn
 80              85                  90                  95

AAT TTT TTA GAT AAT AAA AAT GAT ATA AAG ACA AAT TAT AAA GAA ATT           1414
Asn Phe Leu Asp Asn Lys Asn Asp Ile Lys Thr Asn Tyr Lys Glu Ile
                100                 105                 110

ACT TTT TCT ATG GCA GGC TCA TTT GAA GAT GAA ATA AAA GAT TTA AAA           1462
Thr Phe Ser Met Ala Gly Ser Phe Glu Asp Glu Ile Lys Asp Leu Lys
                115                 120                 125

GAA ATT GAT AAG ATG TTT GAT AAA ACC AAT CTA TCA AAT TCT ATT ATC           1510
Glu Ile Asp Lys Met Phe Asp Lys Thr Asn Leu Ser Asn Ser Ile Ile
            130                 135                 140

ACC TAT AAA AAT GTG GAA CCG ACA ACA ATT GGA TTT AAT AAA TCT TTA           1558
Thr Tyr Lys Asn Val Glu Pro Thr Thr Ile Gly Phe Asn Lys Ser Leu
145                 150                 155

ACA GAA GGT AAT ACG ATT AAT TCT GAT GCA ATG GCA CAG TTT AAA GAA           1606
Thr Glu Gly Asn Thr Ile Asn Ser Asp Ala Met Ala Gln Phe Lys Glu
160                 165                 170                 175

CAA TTT TTA GAT AGG GAT ATT AAG TTT GAT AGT TAT CTA GAT ACG CAT           1654
Gln Phe Leu Asp Arg Asp Ile Lys Phe Asp Ser Tyr Leu Asp Thr His
                180                 185                 190

TTA ACT GCT CAA CAA GTT TCC AGT AAA GAA AGA GTT ATT TTG AAG GTT           1702
Leu Thr Ala Gln Gln Val Ser Ser Lys Glu Arg Val Ile Leu Lys Val
                195                 200                 205

ACG GTT CCG AGT GGG AAA GGT TCT ACT ACT CCA ACA AAA GCA GGT GTC           1750
Thr Val Pro Ser Gly Lys Gly Ser Thr Thr Pro Thr Lys Ala Gly Val
            210                 215                 220

ATT TTA AAT AAT AGT GAA TAC AAA ATG CTC ATT GAT AAT GGG TAT ATG           1798
Ile Leu Asn Asn Ser Glu Tyr Lys Met Leu Ile Asp Asn Gly Tyr Met
            225                 230                 235

GTC CAT GTA GAT AAG GTA TCA AAA GTG GTG AAA AAA GGG GTG GAG TGC           1846
Val His Val Asp Lys Val Ser Lys Val Val Lys Lys Gly Val Glu Cys
240                 245                 250                 255

TTA CAA ATT GAA GGG ACT TTA AAA AAG AGT CTT GAC TTT AAA AAT GAT           1894
Leu Gln Ile Glu Gly Thr Leu Lys Lys Ser Leu Asp Phe Lys Asn Asp
                260                 265                 270

ATA AAT GCT GAA GCG CAT AGC TGG GGT ATG AAG AAT TAT GAA GAG TGG           1942
Ile Asn Ala Glu Ala His Ser Trp Gly Met Lys Asn Tyr Glu Glu Trp
                275                 280                 285

GCT AAA GAT TTA ACC GAT TCG CAA AGG GAA GCT TTA GAT GGG TAT GCT           1990
Ala Lys Asp Leu Thr Asp Ser Gln Arg Glu Ala Leu Asp Gly Tyr Ala
            290                 295                 300

AGG CAA GAT TAT AAA GAA ATC AAT AAT TAT TTA AGA AAT CAA GGC GGA           2038
```

```
Arg Gln Asp Tyr Lys Glu Ile Asn Asn Tyr Leu Arg Asn Gln Gly Gly
    305                 310                 315

AGT GGA AAT GAA AAA CTA GAT GCT CAA ATA AAA AAT ATT TCT GAT GCT    2086
Ser Gly Asn Glu Lys Leu Asp Ala Gln Ile Lys Asn Ile Ser Asp Ala
320                 325                 330                 335

TTA GGG AAG AAA CCA ATA CCG GAA AAT ATT ACT GTG TAT AGA TGG TGT    2134
Leu Gly Lys Lys Pro Ile Pro Glu Asn Ile Thr Val Tyr Arg Trp Cys
                340                 345                 350

GGC ATG CCG GAA TTT GGT TAT CAA ATT AGT GAT CCG TTA CCT TCT TTA    2182
Gly Met Pro Glu Phe Gly Tyr Gln Ile Ser Asp Pro Leu Pro Ser Leu
            355                 360                 365

AAA GAT TTT GAA GAA CAA TTT TTA AAT ACA ATC AAA GAA GAC AAA GGA    2230
Lys Asp Phe Glu Glu Gln Phe Leu Asn Thr Ile Lys Glu Asp Lys Gly
        370                 375                 380

TAT ATG AGT ACA AGC TTA TCG AGT GAA CGT CTT GCA GCT TTT GGA TCT    2278
Tyr Met Ser Thr Ser Leu Ser Ser Glu Arg Leu Ala Ala Phe Gly Ser
385                 390                 395

AGA AAA ATT ATA TTA CGA TTA CAA GTT CCG AAA GGA AGT ACG GGT GCG    2326
Arg Lys Ile Ile Leu Arg Leu Gln Val Pro Lys Gly Ser Thr Gly Ala
400                 405                 410                 415

TAT TTA AGT GCC ATT GGT GGA TTT GCA AGT GAA AAA GAG ATC CTA CTT    2374
Tyr Leu Ser Ala Ile Gly Gly Phe Ala Ser Glu Lys Glu Ile Leu Leu
                420                 425                 430

GAT AAA GAT AGT AAA TAT CAT ATT GAT AAA GTA ACA GAG GTA ATT ATT    2422
Asp Lys Asp Ser Lys Tyr His Ile Asp Lys Val Thr Glu Val Ile Ile
            435                 440                 445

AAA GGT GTT AAG CGA TAT GTA GTG GAT GCA ACA TTA TTA ACA AAT        2467
Lys Gly Val Lys Arg Tyr Val Val Asp Ala Thr Leu Leu Thr Asn
        450                 455                 460

TAAGGAGATG AAAAATATGA AGAAAAAGTT AGCAAGTGTT GTAACGTGTA CGTTATTAGC  2527
TCCTATGTTT TTGAATGGAA ATGTGAATGC TGTTTACGCA GACAGCAAAA CAAATCAAAT  2587
TTCTACAACA CAGAAAAATC AACAGAAAGA GATGGACCGA AAGGATTAC TTGGGTATTA   2647
TTTCAAGGA AAAGATTTTA GTAATCTTAC TATGTTTGCA CCGACACGTG ATAGTACTCT   2707
TATTTATGAT CAACAAACAG CAAATAAACT ATTAGATAAA AACAACAAG AATATCAGTC   2767
TATTCGTTGG ATTGGTTTGA TTCAGAGTAA AGAAACGGGA GATTTCACAT TTAACTTATC  2827
TGAGGATGAA CAGGCAATTA TAGAAATCAA TGGGAAAATT ATTTCTAATA AGGGAAAGA   2887
AAAGCAAGTT GTCCATTTAG AAAAAGGAAA ATTAGTTCCA ATCAAAATAG AGTATCAATC  2947
AGATACAAAA TTTAATATTG ACAGTAAAAC ATTTAAAGAA CTTAAATTAT TTAAAATAGA  3007
TAGTCAAAAC CAACCCCAGC AAGTCCAGCA AGATGAACTG AGAAATCCTG AATTTAACAA  3067
GAAAGAATCA CAGGAATTCT TAGCGAAACC ATCGAAAATA AATCTTTTCA CTCAAAAAAT  3127
GAAAAGGGAA ATTGATGAAG ACACGGATAC GGATGGGGAC TCTATTCCTG ACCTTTGGGA  3187
AGAAAATGGG TATACGATTC ACAATAGAAT CGCTGTAAAG TGGGACGATT CTCTAGCAAG  3247
TAAAGGGTAT ACGAAATTTG TTTCAAATCC ACTAGAAAGT CACACAGTTG GTGATCCTTA  3307
TACAGATTAT GAAAAGGCAG CAAGAGATCT AGATTTGTCA AATGCAAAGG AAACGTTTAA  3367
CCCATTGGTA GCTGCTTTTC CAAGTGTGAA TGTTAGTATG GAAAAGGTGA TATTATCACC  3427
AAATGAAAAT TTATCCAATA GTGTAGAGTC TCATTCATCC ACGAATTGGT CTTATACAAA  3487
TACAGAAGGT GCTTCTGTTG AAGCGGGGAT TGGACCAAAA GGTATTTCGT TCGGAGTTAG  3547
CGTAAACTAT CAACACTCTG AAACAGTTGC ACAAGAATGG GAACATCTA CAGGAAATAC   3607
TTCGCAATTC AATACGGCTT CAGCGGGATA TTTAAATGCA AATGTTCGAT ATAACAATGT  3667
AGGAACTGGT GCCATCTACG ATGTAAAACC TACAACAAGT TTTGTATTAA ATAACGATAC  3727
```

```
TATCGCAACT  ATTACGGCGA  AATCTAATTC  TACAGCCTTA  AATATATCTC  CTGGAGAAAG  3787
TTACCCGAAA  AAAGGACAAA  ATGGAATCGC  AATAACATCA  ATGGATGATT  TTAATTCCCA  3847
TCCGATTACA  TTAAATAAAA  AACAAGTAGA  TAATCTGCTA  AATAATAAAC  CTATGATGTT  3907
GGAAACAAAC  CAAACAGATG  GTGTTTATAA  GATAAAAGAT  ACACATGGAA  ATATAGTAAC  3967
TGGCGGAGAA  TGGAATGGTG  TCATACAACA  AATCAAGGCT  AAAACAGCGT  CTATTATTGT  4027
GGATGATGGG  GAACGTGTAG  CAGAAAAACG  TGTAGCGGCA  AAAGATTATG  AAAATCCAGA  4087
AGATAAAACA  CCGTCTTTAA  CTTTAAAAGA  TGCCCTGAAG  CTTTCATATC  CAGATGAAAT  4147
AAAAGAAATA  GAGGGATTAT  TATATTATAA  AAACAAACCG  ATATACGAAT  CGAGCGTTAT  4207
GACTTACTTA  GATGAAAATA  CAGCAAAAGA  AGTGACCAAA  CAATTAAATG  ATACCACTGG  4267
GAAATTTAAA  GATGTAAGTC  ATTTATATGA  TGTAAAACTG  ACTCCAAAAA  TGAATGTTAC  4327
AATCAAATTG  TCTATACTTT  ATGATAATGC  TGAGTCTAAT  GATAACTCAA  TTGGTAAATG  4387
GACAAACACA  ATATTGTTT   CAGGTGGAAA  TAACGGAAAA  AAACAATATT  CTTCTAATAA  4447
TCCGGATGCT  AATTTGACAT  TAAATACAGA  TGCTCAAGAA  AAATTAAATA  AAAATCGTGA  4507
CTATTATATA  AGTTTATATA  TGAAGTCAGA  AAAAAACACA  CAATGTGAGA  TTACTATAGA  4567
TGGGGAGATT  TATCCGATCA  CTACAAAAAC  AGTGAATGTG  AATAAAGACA  ATTACAAAAG  4627
ATTAGATATT  ATAGCTCATA  ATATAAAAAG  TAATCCAATT  TCTTCACTTC  ATATTAAAAC  4687
GAATGATGAA  ATAACTTTAT  TTTGGGATGA  TATTTCTATA  ACAGATGTAG  CATCAATAAA  4747
ACCGGAAAAT  TTAACAGATT  CAGAAATTAA  ACAGATTTAT  AGTAGGTATG  GTATTAAGTT  4807
AGAAGATGGA  ATCCTTATTG  ATAAAAAGG   TGGGATTCAT  TATGGTGAAT  TTATTAATGA  4867
AGCTAGTTTT  AATATTGAAC  CATTGCAAAA  TTATGTGACC  AAATATGAAG  TTACTTATAG  4927
TAGTGAGTTA  GGACCAAACG  TGAGTGACAC  ACTTGAAAGT  GATAAAATTT  ACAAGGATGG  4987
GACAATTAAA  TTTGATTTTA  CCAAATATAG  TAAAAATGAA  CAAGGATTAT  TTTATGACAG  5047
TGGATTAAAT  TGGGACTTTA  AAATTAATGC  TATTACTTAT  GATGGTAAAG  AGATGAATGT  5107
TTTTCATAGA  TATAATAAAT  AGTTATTATA  TCTATGAAGC  TGGTGCTAAA  GATAGTGTAA  5167
AAGTTAATAT  ACTGTAGGAT  TGTAATAAAA  GTAATGGAAT  TGATATCGTA  CTTTGGAGTG  5227
GGGGATACTT  TGTAAATAGT  TCTATCAGAA  ACATTAGACT  AAGAAAAGTT  ACTACCCCCA  5287
CTTGAAAATG  AAGATTCAAC  TGATTACAAA  CAACCTGTTA  AATATTATAA  GGTTTTAACA  5347
AAATATTAAA  CTCTTTATGT  TAATACTGTA  ATATAAAGAG  TTTAATTGTA  TTCAAATGAA  5407
GCTTTCCCAC  AAAATTAGAC  TGATTATCTA  ATGAAATAAT  CAGTCTAATT  TTGTAGAACA  5467
GGTCTGGTAT  TATTGTACGT  GGTCACTAAA  AGATATCTAA  TATTATTGGG  CAAGGCGTTC  5527
CATGATTGAA  TCCTCGAATG  TCTTGCCCTT  TCATTTATT   TAAGAAGGAT  TGTGGAGAAA  5587
TTATGGTTTA  GATAATGAAG  AAAGACTTCA  CTTCTAATTT  TTGATGTTAA  ATAAATCAAA  5647
ATTTGGCGAT  TCACATTGTT  TAATCCACTG  ATAAAACATA  CTGGAGTGTT  CTTAAAAAAT  5707
CAGCTTTTTT  CTTTATAAAA  TTTTGCTTAG  CGTACGAAAT  TCGTGTTTTG  TTGGTGGGAC  5767
CCCATGCCCA  TCAACTTAAG  AGTAAATTAG  TAATGAACTT  TCGTTCATCT  GGATTAAAAT  5827
AACCTCAAAT  TAGGACATGT  TTTTAAAAAT  AAGCAGACCA  ATAAGCCTA   GAATAGGTAT  5887
CATTTTTAAA  AATTATGCTG  CTTTCTTTTG  TTTTCCAAAT  CCATTATACT  CATAAGCAAC  5947
ACCCATAATG  TCAAAGACTG  TTTTTGTCTC  ATATCGATAA  GCTTGATATC  GAATTCCTGC  6007
AGCCCGGGGG  ATCCACTAGT  TCTAGAGCGG  CCGCCACCGC  GG                      6049
```

( 2 ) INFORMATION FOR SEQ ID NO:2:

( i ) SEQUENCE CHARACTERISTICS:
        ( A ) LENGTH: 462 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Lys Arg Met Glu Gly Lys Leu Phe Met Val Ser Lys Lys Leu Gln
 1               5                  10                  15
Val Val Thr Lys Thr Val Leu Leu Ser Thr Val Phe Ser Ile Ser Leu
            20                  25                  30
Leu Asn Asn Glu Val Ile Lys Ala Glu Gln Leu Asn Ile Asn Ser Gln
        35                  40                  45
Ser Lys Tyr Thr Asn Leu Gln Asn Leu Lys Ile Thr Asp Lys Val Glu
    50                  55                  60
Asp Phe Lys Glu Asp Lys Glu Lys Ala Lys Glu Trp Gly Lys Glu Lys
65                  70                  75                  80
Glu Lys Glu Trp Lys Leu Thr Ala Thr Glu Lys Gly Lys Met Asn Asn
                85                  90                  95
Phe Leu Asp Asn Lys Asn Asp Ile Lys Thr Asn Tyr Lys Glu Ile Thr
            100                 105                 110
Phe Ser Met Ala Gly Ser Phe Glu Asp Glu Ile Lys Asp Leu Lys Glu
        115                 120                 125
Ile Asp Lys Met Phe Asp Lys Thr Asn Leu Ser Asn Ser Ile Ile Thr
    130                 135                 140
Tyr Lys Asn Val Glu Pro Thr Thr Ile Gly Phe Asn Lys Ser Leu Thr
145                 150                 155                 160
Glu Gly Asn Thr Ile Asn Ser Asp Ala Met Ala Gln Phe Lys Glu Gln
                165                 170                 175
Phe Leu Asp Arg Asp Ile Lys Phe Asp Ser Tyr Leu Asp Thr His Leu
            180                 185                 190
Thr Ala Gln Gln Val Ser Ser Lys Glu Arg Val Ile Leu Lys Val Thr
        195                 200                 205
Val Pro Ser Gly Lys Gly Ser Thr Thr Pro Thr Lys Ala Gly Val Ile
    210                 215                 220
Leu Asn Asn Ser Glu Tyr Lys Met Leu Ile Asp Asn Gly Tyr Met Val
225                 230                 235                 240
His Val Asp Lys Val Ser Lys Val Val Lys Gly Val Glu Cys Leu
                245                 250                 255
Gln Ile Glu Gly Thr Leu Lys Lys Ser Leu Asp Phe Lys Asn Asp Ile
            260                 265                 270
Asn Ala Glu Ala His Ser Trp Gly Met Lys Asn Tyr Glu Glu Trp Ala
        275                 280                 285
Lys Asp Leu Thr Asp Ser Gln Arg Glu Ala Leu Asp Gly Tyr Ala Arg
    290                 295                 300
Gln Asp Tyr Lys Glu Ile Asn Asn Tyr Leu Arg Asn Gln Gly Gly Ser
305                 310                 315                 320
Gly Asn Glu Lys Leu Asp Ala Gln Ile Lys Asn Ile Ser Asp Ala Leu
                325                 330                 335
Gly Lys Lys Pro Ile Pro Glu Asn Ile Thr Val Tyr Arg Trp Cys Gly
            340                 345                 350
Met Pro Glu Phe Gly Tyr Gln Ile Ser Asp Pro Leu Pro Ser Leu Lys
        355                 360                 365
```

```
Asp  Phe  Glu  Glu  Gln  Phe  Leu  Asn  Thr  Ile  Lys  Glu  Asp  Lys  Gly  Tyr
     370                      375                      380

Met  Ser  Thr  Ser  Leu  Ser  Ser  Glu  Arg  Leu  Ala  Ala  Phe  Gly  Ser  Arg
385                      390                      395                      400

Lys  Ile  Ile  Leu  Arg  Leu  Gln  Val  Pro  Lys  Gly  Ser  Thr  Gly  Ala  Tyr
                    405                      410                      415

Leu  Ser  Ala  Ile  Gly  Gly  Phe  Ala  Ser  Glu  Lys  Glu  Ile  Leu  Leu  Asp
               420                      425                      430

Lys  Asp  Ser  Lys  Tyr  His  Ile  Asp  Lys  Val  Thr  Glu  Val  Ile  Ile  Lys
          435                      440                      445

Gly  Val  Lys  Arg  Tyr  Val  Val  Asp  Ala  Thr  Leu  Leu  Thr  Asn
     450                      455                      460
```

( 2 ) INFORMATION FOR SEQ ID NO:3:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..20
        ( D ) OTHER INFORMATION: /note= "Signal peptide for vacuolar
            targetting"

( x i ) SEQUENCE DESCRIPTION: SEQ ID NO:3:

```
Ser  Ser  Ser  Ser  Phe  Ala  Asp  Ser  Asn  Pro  Ile  Arg  Val  Thr  Asp  Arg
1                        5                        10                       15

Ala  Ala  Ser  Thr
               20
```

( 2 ) INFORMATION FOR SEQ ID NO:4:

( i ) SEQUENCE CHARACTERISTICS:
        ( A ) LENGTH: 2655 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Bacillus cereus
        ( B ) STRAIN: AB78
        ( C ) INDIVIDUAL ISOLATE: NRRL B- 21058

( i x ) FEATURE:
( A ) NAME/KEY: CDS
( B ) LOCATION: 1..2652
( D ) OTHER INFORMATION: /product="100 kDa protein VIP1A(a)"
/ note= "This sequence is identical to the portion of SEQ ID NO:1 between and including nucleotide 2475 to 5126."

( x i ) SEQUENCE DESCRIPTION: SEQ ID NO:4:

```
ATG AAA AAT ATG AAG AAA AAG TTA GCA AGT GTT GTA ACG TGT ACG TTA      48
Met Lys Asn Met Lys Lys Lys Leu Ala Ser Val Val Thr Cys Thr Leu
        465                 470                 475

TTA GCT CCT ATG TTT TTG AAT GGA AAT GTG AAT GCT GTT TAC GCA GAC      96
Leu Ala Pro Met Phe Leu Asn Gly Asn Val Asn Ala Val Tyr Ala Asp
    480                 485                 490
```

| | | | | | | | | | | | | | | | | |
|---|---|---|---|---|---|---|---|---|---|---|---|---|---|---|---|---|
| AGC | AAA | ACA | AAT | CAA | ATT | TCT | ACA | ACA | CAG | AAA | AAT | CAA | CAG | AAA | GAG | 144 |
| Ser | Lys | Thr | Asn | Gln | Ile | Ser | Thr | Thr | Gln | Lys | Asn | Gln | Gln | Lys | Glu | |
| 495 | | | | 500 | | | | | 505 | | | | | | 510 | |
| ATG | GAC | CGA | AAA | GGA | TTA | CTT | GGG | TAT | TAT | TTC | AAA | GGA | AAA | GAT | TTT | 192 |
| Met | Asp | Arg | Lys | Gly | Leu | Leu | Gly | Tyr | Tyr | Phe | Lys | Gly | Lys | Asp | Phe | |
| | | | | 515 | | | | 520 | | | | | 525 | | | |
| AGT | AAT | CTT | ACT | ATG | TTT | GCA | CCG | ACA | CGT | GAT | AGT | ACT | CTT | ATT | TAT | 240 |
| Ser | Asn | Leu | Thr | Met | Phe | Ala | Pro | Thr | Arg | Asp | Ser | Thr | Leu | Ile | Tyr | |
| | | | 530 | | | | | 535 | | | | | 540 | | | |
| GAT | CAA | CAA | ACA | GCA | AAT | AAA | CTA | TTA | GAT | AAA | AAA | CAA | CAA | GAA | TAT | 288 |
| Asp | Gln | Gln | Thr | Ala | Asn | Lys | Leu | Leu | Asp | Lys | Lys | Gln | Gln | Glu | Tyr | |
| | | 545 | | | | | 550 | | | | | 555 | | | | |
| CAG | TCT | ATT | CGT | TGG | ATT | GGT | TTG | ATT | CAG | AGT | AAA | GAA | ACG | GGA | GAT | 336 |
| Gln | Ser | Ile | Arg | Trp | Ile | Gly | Leu | Ile | Gln | Ser | Lys | Glu | Thr | Gly | Asp | |
| | 560 | | | | | 565 | | | | | 570 | | | | | |
| TTC | ACA | TTT | AAC | TTA | TCT | GAG | GAT | GAA | CAG | GCA | ATT | ATA | GAA | ATC | AAT | 384 |
| Phe | Thr | Phe | Asn | Leu | Ser | Glu | Asp | Glu | Gln | Ala | Ile | Ile | Glu | Ile | Asn | |
| 575 | | | | | 580 | | | | | 585 | | | | | 590 | |
| GGG | AAA | ATT | ATT | TCT | AAT | AAA | GGG | AAA | GAA | AAG | CAA | GTT | GTC | CAT | TTA | 432 |
| Gly | Lys | Ile | Ile | Ser | Asn | Lys | Gly | Lys | Glu | Lys | Gln | Val | Val | His | Leu | |
| | | | | 595 | | | | | 600 | | | | | 605 | | |
| GAA | AAA | GGA | AAA | TTA | GTT | CCA | ATC | AAA | ATA | GAG | TAT | CAA | TCA | GAT | ACA | 480 |
| Glu | Lys | Gly | Lys | Leu | Val | Pro | Ile | Lys | Ile | Glu | Tyr | Gln | Ser | Asp | Thr | |
| | | | 610 | | | | | 615 | | | | | 620 | | | |
| AAA | TTT | AAT | ATT | GAC | AGT | AAA | ACA | TTT | AAA | GAA | CTT | AAA | TTA | TTT | AAA | 528 |
| Lys | Phe | Asn | Ile | Asp | Ser | Lys | Thr | Phe | Lys | Glu | Leu | Lys | Leu | Phe | Lys | |
| | | | 625 | | | | | 630 | | | | | 635 | | | |
| ATA | GAT | AGT | CAA | AAC | CAA | CCC | CAG | CAA | GTC | CAG | CAA | GAT | GAA | CTG | AGA | 576 |
| Ile | Asp | Ser | Gln | Asn | Gln | Pro | Gln | Gln | Val | Gln | Gln | Asp | Glu | Leu | Arg | |
| | | 640 | | | | | 645 | | | | | 650 | | | | |
| AAT | CCT | GAA | TTT | AAC | AAG | AAA | GAA | TCA | CAG | GAA | TTC | TTA | GCG | AAA | CCA | 624 |
| Asn | Pro | Glu | Phe | Asn | Lys | Lys | Glu | Ser | Gln | Glu | Phe | Leu | Ala | Lys | Pro | |
| 655 | | | | | 660 | | | | | 665 | | | | | 670 | |
| TCG | AAA | ATA | AAT | CTT | TTC | ACT | CAA | AAA | ATG | AAA | AGG | GAA | ATT | GAT | GAA | 672 |
| Ser | Lys | Ile | Asn | Leu | Phe | Thr | Gln | Lys | Met | Lys | Arg | Glu | Ile | Asp | Glu | |
| | | | | 675 | | | | | 680 | | | | | 685 | | |
| GAC | ACG | GAT | ACG | GAT | GGG | GAC | TCT | ATT | CCT | GAC | CTT | TGG | GAA | GAA | AAT | 720 |
| Asp | Thr | Asp | Thr | Asp | Gly | Asp | Ser | Ile | Pro | Asp | Leu | Trp | Glu | Glu | Asn | |
| | | | 690 | | | | | 695 | | | | | 700 | | | |
| GGG | TAT | ACG | ATT | CAA | AAT | AGA | ATC | GCT | GTA | AAG | TGG | GAC | GAT | TCT | CTA | 768 |
| Gly | Tyr | Thr | Ile | Gln | Asn | Arg | Ile | Ala | Val | Lys | Trp | Asp | Asp | Ser | Leu | |
| | | 705 | | | | | 710 | | | | | 715 | | | | |
| GCA | AGT | AAA | GGG | TAT | ACG | AAA | TTT | GTT | TCA | AAT | CCA | CTA | GAA | AGT | CAC | 816 |
| Ala | Ser | Lys | Gly | Tyr | Thr | Lys | Phe | Val | Ser | Asn | Pro | Leu | Glu | Ser | His | |
| | 720 | | | | | 725 | | | | | 730 | | | | | |
| ACA | GTT | GGT | GAT | CCT | TAT | ACA | GAT | TAT | GAA | AAG | GCA | GCA | AGA | GAT | CTA | 864 |
| Thr | Val | Gly | Asp | Pro | Tyr | Thr | Asp | Tyr | Glu | Lys | Ala | Ala | Arg | Asp | Leu | |
| 735 | | | | | 740 | | | | | 745 | | | | | 750 | |
| GAT | TTG | TCA | AAT | GCA | AAG | GAA | ACG | TTT | AAC | CCA | TTG | GTA | GCT | GCT | TTT | 912 |
| Asp | Leu | Ser | Asn | Ala | Lys | Glu | Thr | Phe | Asn | Pro | Leu | Val | Ala | Ala | Phe | |
| | | | | 755 | | | | | 760 | | | | | 765 | | |
| CCA | AGT | GTG | AAT | GTT | AGT | ATG | GAA | AAG | GTG | ATA | TTA | TCA | CCA | AAT | GAA | 960 |
| Pro | Ser | Val | Asn | Val | Ser | Met | Glu | Lys | Val | Ile | Leu | Ser | Pro | Asn | Glu | |
| | | | 770 | | | | | 775 | | | | | 780 | | | |
| AAT | TTA | TCC | AAT | AGT | GTA | GAG | TCT | CAT | TCA | TCC | ACG | AAT | TGG | TCT | TAT | 1008 |
| Asn | Leu | Ser | Asn | Ser | Val | Glu | Ser | His | Ser | Ser | Thr | Asn | Trp | Ser | Tyr | |
| | | | 785 | | | | | 790 | | | | | 795 | | | |
| ACA | AAT | ACA | GAA | GGT | GCT | TCT | GTT | GAA | GCG | GGG | ATT | GGA | CCA | AAA | GGT | 1056 |
| Thr | Asn | Thr | Glu | Gly | Ala | Ser | Val | Glu | Ala | Gly | Ile | Gly | Pro | Lys | Gly | |
| | | 800 | | | | | 805 | | | | | 810 | | | | |

```
ATT TCG TTC GGA GTT AGC GTA AAC TAT CAA CAC TCT GAA ACA GTT GCA    1104
Ile Ser Phe Gly Val Ser Val Asn Tyr Gln His Ser Glu Thr Val Ala
815             820                 825                 830

CAA GAA TGG GGA ACA TCT ACA GGA AAT ACT TCG CAA TTC AAT ACG GCT    1152
Gln Glu Trp Gly Thr Ser Thr Gly Asn Thr Ser Gln Phe Asn Thr Ala
            835                 840                 845

TCA GCG GGA TAT TTA AAT GCA AAT GTT CGA TAT AAC AAT GTA GGA ACT    1200
Ser Ala Gly Tyr Leu Asn Ala Asn Val Arg Tyr Asn Asn Val Gly Thr
                850                 855                 860

GGT GCC ATC TAC GAT GTA AAA CCT ACA ACA AGT TTT GTA TTA AAT AAC    1248
Gly Ala Ile Tyr Asp Val Lys Pro Thr Thr Ser Phe Val Leu Asn Asn
            865                 870                 875

GAT ACT ATC GCA ACT ATT ACG GCG AAA TCT AAT TCT ACA GCC TTA AAT    1296
Asp Thr Ile Ala Thr Ile Thr Ala Lys Ser Asn Ser Thr Ala Leu Asn
880                 885                 890

ATA TCT CCT GGA GAA AGT TAC CCG AAA AAA GGA CAA AAT GGA ATC GCA    1344
Ile Ser Pro Gly Glu Ser Tyr Pro Lys Lys Gly Gln Asn Gly Ile Ala
895                 900                 905                 910

ATA ACA TCA ATG GAT GAT TTT AAT TCC CAT CCG ATT ACA TTA AAT AAA    1392
Ile Thr Ser Met Asp Asp Phe Asn Ser His Pro Ile Thr Leu Asn Lys
                915                 920                 925

AAA CAA GTA GAT AAT CTG CTA AAT AAT AAA CCT ATG ATG TTG GAA ACA    1440
Lys Gln Val Asp Asn Leu Leu Asn Asn Lys Pro Met Met Leu Glu Thr
            930                 935                 940

AAC CAA ACA GAT GGT GTT TAT AAG ATA AAA GAT ACA CAT GGA AAT ATA    1488
Asn Gln Thr Asp Gly Val Tyr Lys Ile Lys Asp Thr His Gly Asn Ile
            945                 950                 955

GTA ACT GGC GGA GAA TGG AAT GGT GTC ATA CAA CAA ATC AAG GCT AAA    1536
Val Thr Gly Gly Glu Trp Asn Gly Val Ile Gln Gln Ile Lys Ala Lys
        960                 965                 970

ACA GCG TCT ATT ATT GTG GAT GAT GGG GAA CGT GTA GCA GAA AAA CGT    1584
Thr Ala Ser Ile Ile Val Asp Asp Gly Glu Arg Val Ala Glu Lys Arg
975                 980                 985                 990

GTA GCG GCA AAA GAT TAT GAA AAT CCA GAA GAT AAA ACA CCG TCT TTA    1632
Val Ala Ala Lys Asp Tyr Glu Asn Pro Glu Asp Lys Thr Pro Ser Leu
                995                 1000                1005

ACT TTA AAA GAT GCC CTG AAG CTT TCA TAT CCA GAT GAA ATA AAA GAA    1680
Thr Leu Lys Asp Ala Leu Lys Leu Ser Tyr Pro Asp Glu Ile Lys Glu
            1010                1015                1020

ATA GAG GGA TTA TTA TAT TAT AAA AAC AAA CCG ATA TAC GAA TCG AGC    1728
Ile Glu Gly Leu Leu Tyr Tyr Lys Asn Lys Pro Ile Tyr Glu Ser Ser
        1025                1030                1035

GTT ATG ACT TAC TTA GAT GAA AAT ACA GCA AAA GAA GTG ACC AAA CAA    1776
Val Met Thr Tyr Leu Asp Glu Asn Thr Ala Lys Glu Val Thr Lys Gln
        1040                1045                1050

TTA AAT GAT ACC ACT GGG AAA TTT AAA GAT GTA AGT CAT TTA TAT GAT    1824
Leu Asn Asp Thr Thr Gly Lys Phe Lys Asp Val Ser His Leu Tyr Asp
1055                1060                1065                1070

GTA AAA CTG ACT CCA AAA ATG AAT GTT ACA ATC AAA TTG TCT ATA CTT    1872
Val Lys Leu Thr Pro Lys Met Asn Val Thr Ile Lys Leu Ser Ile Leu
                1075                1080                1085

TAT GAT AAT GCT GAG TCT AAT GAT AAC TCA ATT GGT AAA TGG ACA AAC    1920
Tyr Asp Asn Ala Glu Ser Asn Asp Asn Ser Ile Gly Lys Trp Thr Asn
            1090                1095                1100

ACA AAT ATT GTT TCA GGT GGA AAT AAC GGA AAA AAA CAA TAT TCT TCT    1968
Thr Asn Ile Val Ser Gly Gly Asn Asn Gly Lys Lys Gln Tyr Ser Ser
            1105                1110                1115

AAT AAT CCG GAT GCT AAT TTG ACA TTA AAT ACA GAT GCT CAA GAA AAA    2016
Asn Asn Pro Asp Ala Asn Leu Thr Leu Asn Thr Asp Ala Gln Glu Lys
        1120                1125                1130
```

| | | | | | | | | | | | | | | | | |
|---|---|---|---|---|---|---|---|---|---|---|---|---|---|---|---|---|
| TTA | AAT | AAA | AAT | CGT | GAC | TAT | TAT | ATA | AGT | TTA | TAT | ATG | AAG | TCA | GAA | 2064 |
| Leu | Asn | Lys | Asn | Arg | Asp | Tyr | Tyr | Ile | Ser | Leu | Tyr | Met | Lys | Ser | Glu | |
| 1135 | | | | 1140 | | | | | 1145 | | | | | | 1150 | |
| AAA | AAC | ACA | CAA | TGT | GAG | ATT | ACT | ATA | GAT | GGG | GAG | ATT | TAT | CCG | ATC | 2112 |
| Lys | Asn | Thr | Gln | Cys | Glu | Ile | Thr | Ile | Asp | Gly | Glu | Ile | Tyr | Pro | Ile | |
| | | | | 1155 | | | | | 1160 | | | | | | 1165 | |
| ACT | ACA | AAA | ACA | GTG | AAT | GTG | AAT | AAA | GAC | AAT | TAC | AAA | AGA | TTA | GAT | 2160 |
| Thr | Thr | Lys | Thr | Val | Asn | Val | Asn | Lys | Asp | Asn | Tyr | Lys | Arg | Leu | Asp | |
| | | | | 1170 | | | | | 1175 | | | | | | 1180 | |
| ATT | ATA | GCT | CAT | AAT | ATA | AAA | AGT | AAT | CCA | ATT | TCT | TCA | CTT | CAT | ATT | 2208 |
| Ile | Ile | Ala | His | Asn | Ile | Lys | Ser | Asn | Pro | Ile | Ser | Ser | Leu | His | Ile | |
| | | | | 1185 | | | | | 1190 | | | | | | 1195 | |
| AAA | ACG | AAT | GAT | GAA | ATA | ACT | TTA | TTT | TGG | GAT | GAT | ATT | TCT | ATA | ACA | 2256 |
| Lys | Thr | Asn | Asp | Glu | Ile | Thr | Leu | Phe | Trp | Asp | Asp | Ile | Ser | Ile | Thr | |
| | | | | 1200 | | | | | 1205 | | | | | | 1210 | |
| GAT | GTA | GCA | TCA | ATA | AAA | CCG | GAA | AAT | TTA | ACA | GAT | TCA | GAA | ATT | AAA | 2304 |
| Asp | Val | Ala | Ser | Ile | Lys | Pro | Glu | Asn | Leu | Thr | Asp | Ser | Glu | Ile | Lys | |
| 1215 | | | | 1220 | | | | | 1225 | | | | | | 1230 | |
| CAG | ATT | TAT | AGT | AGG | TAT | GGT | ATT | AAG | TTA | GAA | GAT | GGA | ATC | CTT | ATT | 2352 |
| Gln | Ile | Tyr | Ser | Arg | Tyr | Gly | Ile | Lys | Leu | Glu | Asp | Gly | Ile | Leu | Ile | |
| | | | | 1235 | | | | | 1240 | | | | | | 1245 | |
| GAT | AAA | AAA | GGT | GGG | ATT | CAT | TAT | GGT | GAA | TTT | ATT | AAT | GAA | GCT | AGT | 2400 |
| Asp | Lys | Lys | Gly | Gly | Ile | His | Tyr | Gly | Glu | Phe | Ile | Asn | Glu | Ala | Ser | |
| | | | | 1250 | | | | | 1255 | | | | | | 1260 | |
| TTT | AAT | ATT | GAA | CCA | TTG | CAA | AAT | TAT | GTG | ACC | AAA | TAT | GAA | GTT | ACT | 2448 |
| Phe | Asn | Ile | Glu | Pro | Leu | Gln | Asn | Tyr | Val | Thr | Lys | Tyr | Glu | Val | Thr | |
| | | | | 1265 | | | | | 1270 | | | | | | 1275 | |
| TAT | AGT | AGT | GAG | TTA | GGA | CCA | AAC | GTG | AGT | GAC | ACA | CTT | GAA | AGT | GAT | 2496 |
| Tyr | Ser | Ser | Glu | Leu | Gly | Pro | Asn | Val | Ser | Asp | Thr | Leu | Glu | Ser | Asp | |
| | | | | 1280 | | | | | 1285 | | | | | | 1290 | |
| AAA | ATT | TAC | AAG | GAT | GGG | ACA | ATT | AAA | TTT | GAT | TTT | ACC | AAA | TAT | AGT | 2544 |
| Lys | Ile | Tyr | Lys | Asp | Gly | Thr | Ile | Lys | Phe | Asp | Phe | Thr | Lys | Tyr | Ser | |
| 1295 | | | | 1300 | | | | | 1305 | | | | | | 1310 | |
| AAA | AAT | GAA | CAA | GGA | TTA | TTT | TAT | GAC | AGT | GGA | TTA | AAT | TGG | GAC | TTT | 2592 |
| Lys | Asn | Glu | Gln | Gly | Leu | Phe | Tyr | Asp | Ser | Gly | Leu | Asn | Trp | Asp | Phe | |
| | | | | 1315 | | | | | 1320 | | | | | | 1325 | |
| AAA | ATT | AAT | GCT | ATT | ACT | TAT | GAT | GGT | AAA | GAG | ATG | AAT | GTT | TTT | CAT | 2640 |
| Lys | Ile | Asn | Ala | Ile | Thr | Tyr | Asp | Gly | Lys | Glu | Met | Asn | Val | Phe | His | |
| | | | | 1330 | | | | | 1335 | | | | | | 1340 | |
| AGA | TAT | AAT | AAA | TAG | | | | | | | | | | | | 2655 |
| Arg | Tyr | Asn | Lys | | | | | | | | | | | | | |
| | | | | 1345 | | | | | | | | | | | | |

( 2 ) INFORMATION FOR SEQ ID NO:5:

( i ) SEQUENCE CHARACTERISTICS:
        ( A ) LENGTH: 884 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

| | | | | | | | | | | | | | | |
|---|---|---|---|---|---|---|---|---|---|---|---|---|---|---|
| Met | Lys | Asn | Met | Lys | Lys | Lys | Leu | Ala | Ser | Val | Val | Thr | Cys | Thr | Leu |
| 1 | | | | 5 | | | | | 10 | | | | | 15 | |
| Leu | Ala | Pro | Met | Phe | Leu | Asn | Gly | Asn | Val | Asn | Ala | Val | Tyr | Ala | Asp |
| | | | 20 | | | | | 25 | | | | | 30 | | |
| Ser | Lys | Thr | Asn | Gln | Ile | Ser | Thr | Thr | Gln | Lys | Asn | Gln | Gln | Lys | Glu |
| | | | 35 | | | | | 40 | | | | | 45 | | |
| Met | Asp | Arg | Lys | Gly | Leu | Leu | Gly | Tyr | Tyr | Phe | Lys | Gly | Lys | Asp | Phe |
| | 50 | | | | | 55 | | | | | 60 | | | | |

```
Ser  Asn  Leu  Thr  Met  Phe  Ala  Pro  Thr  Arg  Asp  Ser  Thr  Leu  Ile  Tyr
 65             70                  75                       80

Asp  Gln  Gln  Thr  Ala  Asn  Lys  Leu  Leu  Asp  Lys  Lys  Gln  Gln  Glu  Tyr
                85                       90                       95

Gln  Ser  Ile  Arg  Trp  Ile  Gly  Leu  Ile  Gln  Ser  Lys  Glu  Thr  Gly  Asp
               100                 105                      110

Phe  Thr  Phe  Asn  Leu  Ser  Glu  Asp  Glu  Gln  Ala  Ile  Ile  Glu  Ile  Asn
          115                      120                           125

Gly  Lys  Ile  Ile  Ser  Asn  Lys  Gly  Lys  Glu  Lys  Gln  Val  Val  His  Leu
     130                      135                      140

Glu  Lys  Gly  Lys  Leu  Val  Pro  Ile  Lys  Ile  Glu  Tyr  Gln  Ser  Asp  Thr
145                      150                      155                      160

Lys  Phe  Asn  Ile  Asp  Ser  Lys  Thr  Phe  Lys  Glu  Leu  Lys  Leu  Phe  Lys
                    165                      170                      175

Ile  Asp  Ser  Gln  Asn  Gln  Pro  Gln  Val  Gln  Gln  Asp  Glu  Leu  Arg
                    180                 185                      190

Asn  Pro  Glu  Phe  Asn  Lys  Lys  Glu  Ser  Gln  Glu  Phe  Leu  Ala  Lys  Pro
          195                      200                      205

Ser  Lys  Ile  Asn  Leu  Phe  Thr  Gln  Lys  Met  Lys  Arg  Glu  Ile  Asp  Glu
     210                      215                      220

Asp  Thr  Asp  Thr  Asp  Gly  Asp  Ser  Ile  Pro  Asp  Leu  Trp  Glu  Glu  Asn
225                      230                      235                      240

Gly  Tyr  Thr  Ile  Gln  Asn  Arg  Ile  Ala  Val  Lys  Trp  Asp  Asp  Ser  Leu
                    245                      250                      255

Ala  Ser  Lys  Gly  Tyr  Thr  Lys  Phe  Val  Ser  Asn  Pro  Leu  Glu  Ser  His
               260                      265                      270

Thr  Val  Gly  Asp  Pro  Tyr  Thr  Asp  Tyr  Glu  Lys  Ala  Ala  Arg  Asp  Leu
          275                      280                      285

Asp  Leu  Ser  Asn  Ala  Lys  Glu  Thr  Phe  Asn  Pro  Leu  Val  Ala  Ala  Phe
290                      295                      300

Pro  Ser  Val  Asn  Val  Ser  Met  Glu  Lys  Val  Ile  Leu  Ser  Pro  Asn  Glu
305                      310                      315                      320

Asn  Leu  Ser  Asn  Ser  Val  Glu  Ser  His  Ser  Ser  Thr  Asn  Trp  Ser  Tyr
                    325                      330                      335

Thr  Asn  Thr  Glu  Gly  Ala  Ser  Val  Glu  Ala  Gly  Ile  Gly  Pro  Lys  Gly
               340                      345                      350

Ile  Ser  Phe  Gly  Val  Ser  Val  Asn  Tyr  Gln  His  Ser  Glu  Thr  Val  Ala
          355                      360                      365

Gln  Glu  Trp  Gly  Thr  Ser  Thr  Gly  Asn  Thr  Ser  Gln  Phe  Asn  Thr  Ala
     370                      375                      380

Ser  Ala  Gly  Tyr  Leu  Asn  Ala  Asn  Val  Arg  Tyr  Asn  Asn  Val  Gly  Thr
385                      390                      395                      400

Gly  Ala  Ile  Tyr  Asp  Val  Lys  Pro  Thr  Thr  Ser  Phe  Val  Leu  Asn  Asn
                    405                      410                      415

Asp  Thr  Ile  Ala  Thr  Ile  Thr  Ala  Lys  Ser  Asn  Ser  Thr  Ala  Leu  Asn
               420                      425                      430

Ile  Ser  Pro  Gly  Glu  Ser  Tyr  Pro  Lys  Lys  Gly  Gln  Asn  Gly  Ile  Ala
          435                      440                      445

Ile  Thr  Ser  Met  Asp  Asp  Phe  Asn  Ser  His  Pro  Ile  Thr  Leu  Asn  Lys
     450                      455                      460

Lys  Gln  Val  Asp  Asn  Leu  Leu  Asn  Asn  Lys  Pro  Met  Met  Leu  Glu  Thr
465                      470                      475                      480

Asn  Gln  Thr  Asp  Gly  Val  Tyr  Lys  Ile  Lys  Asp  Thr  His  Gly  Asn  Ile
               485                      490                      495
```

```
Val  Thr  Gly  Gly  Glu  Trp  Asn  Gly  Val  Ile  Gln  Gln  Ile  Lys  Ala  Lys
               500                      505                      510

Thr  Ala  Ser  Ile  Ile  Val  Asp  Asp  Gly  Glu  Arg  Val  Ala  Glu  Lys  Arg
               515                      520                      525

Val  Ala  Ala  Lys  Asp  Tyr  Glu  Asn  Pro  Glu  Asp  Lys  Thr  Pro  Ser  Leu
          530                 535                      540

Thr  Leu  Lys  Asp  Ala  Leu  Lys  Leu  Ser  Tyr  Pro  Asp  Glu  Ile  Lys  Glu
545                      550                      555                      560

Ile  Glu  Gly  Leu  Leu  Tyr  Tyr  Lys  Asn  Lys  Pro  Ile  Tyr  Glu  Ser  Ser
                    565                      570                      575

Val  Met  Thr  Tyr  Leu  Asp  Glu  Asn  Thr  Ala  Lys  Glu  Val  Thr  Lys  Gln
               580                      585                      590

Leu  Asn  Asp  Thr  Thr  Gly  Lys  Phe  Lys  Asp  Val  Ser  His  Leu  Tyr  Asp
          595                      600                      605

Val  Lys  Leu  Thr  Pro  Lys  Met  Asn  Val  Thr  Ile  Lys  Leu  Ser  Ile  Leu
          610                      615                      620

Tyr  Asp  Asn  Ala  Glu  Ser  Asn  Asp  Asn  Ser  Ile  Gly  Lys  Trp  Thr  Asn
625                           630                      635                 640

Thr  Asn  Ile  Val  Ser  Gly  Gly  Asn  Asn  Gly  Lys  Lys  Gln  Tyr  Ser  Ser
                    645                      650                      655

Asn  Asn  Pro  Asp  Ala  Asn  Leu  Thr  Leu  Asn  Thr  Asp  Ala  Gln  Glu  Lys
               660                      665                      670

Leu  Asn  Lys  Asn  Arg  Asp  Tyr  Tyr  Ile  Ser  Leu  Tyr  Met  Lys  Ser  Glu
          675                      680                      685

Lys  Asn  Thr  Gln  Cys  Glu  Ile  Thr  Ile  Asp  Gly  Glu  Ile  Tyr  Pro  Ile
          690                      695                      700

Thr  Thr  Lys  Thr  Val  Asn  Val  Asn  Lys  Asp  Asn  Tyr  Lys  Arg  Leu  Asp
705                           710                      715                 720

Ile  Ile  Ala  His  Asn  Ile  Lys  Ser  Asn  Pro  Ile  Ser  Ser  Leu  His  Ile
                    725                      730                      735

Lys  Thr  Asn  Asp  Glu  Ile  Thr  Leu  Phe  Trp  Asp  Asp  Ile  Ser  Ile  Thr
               740                      745                      750

Asp  Val  Ala  Ser  Ile  Lys  Pro  Glu  Asn  Leu  Thr  Asp  Ser  Glu  Ile  Lys
          755                      760                      765

Gln  Ile  Tyr  Ser  Arg  Tyr  Gly  Ile  Lys  Leu  Glu  Asp  Gly  Ile  Leu  Ile
770                      775                      780

Asp  Lys  Lys  Gly  Gly  Ile  His  Tyr  Gly  Glu  Phe  Ile  Asn  Glu  Ala  Ser
785                      790                      795                      800

Phe  Asn  Ile  Glu  Pro  Leu  Gln  Asn  Tyr  Val  Thr  Lys  Tyr  Glu  Val  Thr
               805                      810                      815

Tyr  Ser  Ser  Glu  Leu  Gly  Pro  Asn  Val  Ser  Asp  Thr  Leu  Glu  Ser  Asp
               820                      825                      830

Lys  Ile  Tyr  Lys  Asp  Gly  Thr  Ile  Lys  Phe  Asp  Phe  Thr  Lys  Tyr  Ser
          835                      840                      845

Lys  Asn  Glu  Gln  Gly  Leu  Phe  Tyr  Asp  Ser  Gly  Leu  Asn  Trp  Asp  Phe
          850                      855                      860

Lys  Ile  Asn  Ala  Ile  Thr  Tyr  Asp  Gly  Lys  Glu  Met  Asn  Val  Phe  His
865                      870                      875                      880

Arg  Tyr  Asn  Lys
```

( 2 ) INFORMATION FOR SEQ ID NO:6:

( i ) SEQUENCE CHARACTERISTICS:

( A ) LENGTH: 2004 base pairs

-continued

```
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Bacillus cereus
        ( B ) STRAIN: AB78
        ( C

| | | | | | | | | | | | | | | | | |
|---|---|---|---|---|---|---|---|---|---|---|---|---|---|---|---|---|
| AAA | GGA | CAA | AAT | GGA | ATC | GCA | ATA | ACA | TCA | ATG | GAT | GAT | TTT | AAT | TCC | 720 |
| Lys | Gly | Gln | Asn | Gly | Ile | Ala | Ile | Thr | Ser | Met | Asp | Asp | Phe | Asn | Ser | |
| 1110 | | | | 1115 | | | | | 1120 | | | | | | | |
| CAT | CCG | ATT | ACA | TTA | AAT | AAA | AAA | CAA | GTA | GAT | AAT | CTG | CTA | AAT | AAT | 768 |
| His | Pro | Ile | Thr | Leu | Asn | Lys | Lys | Gln | Val | Asp | Asn | Leu | Leu | Asn | Asn | |
| 1125 | | | | | 1130 | | | | | 1135 | | | | | 1140 | |
| AAA | CCT | ATG | ATG | TTG | GAA | ACA | AAC | CAA | ACA | GAT | GGT | GTT | TAT | AAG | ATA | 816 |
| Lys | Pro | Met | Met | Leu | Glu | Thr | Asn | Gln | Thr | Asp | Gly | Val | Tyr | Lys | Ile | |
| | | | | 1145 | | | | | 1150 | | | | | 1155 | | |
| AAA | GAT | ACA | CAT | GGA | AAT | ATA | GTA | ACT | GGC | GGA | GAA | TGG | AAT | GGT | GTC | 864 |
| Lys | Asp | Thr | His | Gly | Asn | Ile | Val | Thr | Gly | Gly | Glu | Trp | Asn | Gly | Val | |
| | | | 1160 | | | | | 1165 | | | | | 1170 | | | |
| ATA | CAA | CAA | ATC | AAG | GCT | AAA | ACA | GCG | TCT | ATT | ATT | GTG | GAT | GAT | GGG | 912 |
| Ile | Gln | Gln | Ile | Lys | Ala | Lys | Thr | Ala | Ser | Ile | Ile | Val | Asp | Asp | Gly | |
| | | | 1175 | | | | | 1180 | | | | | 1185 | | | |
| GAA | CGT | GTA | GCA | GAA | AAA | CGT | GTA | GCG | GCA | AAA | GAT | TAT | GAA | AAT | CCA | 960 |
| Glu | Arg | Val | Ala | Glu | Lys | Arg | Val | Ala | Ala | Lys | Asp | Tyr | Glu | Asn | Pro | |
| | | | 1190 | | | | | 1195 | | | | | 1200 | | | |
| GAA | GAT | AAA | ACA | CCG | TCT | TTA | ACT | TTA | AAA | GAT | GCC | CTG | AAG | CTT | TCA | 1008 |
| Glu | Asp | Lys | Thr | Pro | Ser | Leu | Thr | Leu | Lys | Asp | Ala | Leu | Lys | Leu | Ser | |
| 1205 | | | | 1210 | | | | | 1215 | | | | | 1220 | | |
| TAT | CCA | GAT | GAA | ATA | AAA | GAA | ATA | GAG | GGA | TTA | TTA | TAT | TAT | AAA | AAC | 1056 |
| Tyr | Pro | Asp | Glu | Ile | Lys | Glu | Ile | Glu | Gly | Leu | Leu | Tyr | Tyr | Lys | Asn | |
| | | | | 1225 | | | | | 1230 | | | | | 1235 | | |
| AAA | CCG | ATA | TAC | GAA | TCG | AGC | GTT | ATG | ACT | TAC | TTA | GAT | GAA | AAT | ACA | 1104 |
| Lys | Pro | Ile | Tyr | Glu | Ser | Ser | Val | Met | Thr | Tyr | Leu | Asp | Glu | Asn | Thr | |
| | | | 1240 | | | | | 1245 | | | | | 1250 | | | |
| GCA | AAA | GAA | GTG | ACC | AAA | CAA | TTA | AAT | GAT | ACC | ACT | GGG | AAA | TTT | AAA | 1152 |
| Ala | Lys | Glu | Val | Thr | Lys | Gln | Leu | Asn | Asp | Thr | Thr | Gly | Lys | Phe | Lys | |
| | | 1255 | | | | | 1260 | | | | | 1265 | | | | |
| GAT | GTA | AGT | CAT | TTA | TAT | GAT | GTA | AAA | CTG | ACT | CCA | AAA | ATG | AAT | GTT | 1200 |
| Asp | Val | Ser | His | Leu | Tyr | Asp | Val | Lys | Leu | Thr | Pro | Lys | Met | Asn | Val | |
| | | | 1270 | | | | | 1275 | | | | | 1280 | | | |
| ACA | ATC | AAA | TTG | TCT | ATA | CTT | TAT | GAT | AAT | GCT | GAG | TCT | AAT | GAT | AAC | 1248 |
| Thr | Ile | Lys | Leu | Ser | Ile | Leu | Tyr | Asp | Asn | Ala | Glu | Ser | Asn | Asp | Asn | |
| 1285 | | | | | 1290 | | | | | 1295 | | | | | 1300 | |
| TCA | ATT | GGT | AAA | TGG | ACA | AAC | ACA | AAT | ATT | GTT | TCA | GGT | GGA | AAT | AAC | 1296 |
| Ser | Ile | Gly | Lys | Trp | Thr | Asn | Thr | Asn | Ile | Val | Ser | Gly | Gly | Asn | Asn | |
| | | | | 1305 | | | | | 1310 | | | | | 1315 | | |
| GGA | AAA | AAA | CAA | TAT | TCT | TCT | AAT | AAT | CCG | GAT | GCT | AAT | TTG | ACA | TTA | 1344 |
| Gly | Lys | Lys | Gln | Tyr | Ser | Ser | Asn | Asn | Pro | Asp | Ala | Asn | Leu | Thr | Leu | |
| | | | 1320 | | | | | 1325 | | | | | 1330 | | | |
| AAT | ACA | GAT | GCT | CAA | GAA | AAA | TTA | AAT | AAA | AAT | CGT | GAC | TAT | TAT | ATA | 1392 |
| Asn | Thr | Asp | Ala | Gln | Glu | Lys | Leu | Asn | Lys | Asn | Arg | Asp | Tyr | Tyr | Ile | |
| | | | 1335 | | | | | 1340 | | | | | 1345 | | | |
| AGT | TTA | TAT | ATG | AAG | TCA | GAA | AAA | AAC | ACA | CAA | TGT | GAG | ATT | ACT | ATA | 1440 |
| Ser | Leu | Tyr | Met | Lys | Ser | Glu | Lys | Asn | Thr | Gln | Cys | Glu | Ile | Thr | Ile | |
| | | | 1350 | | | | | 1355 | | | | | 1360 | | | |
| GAT | GGG | GAG | ATT | TAT | CCG | ATC | ACT | ACA | AAA | ACA | GTG | AAT | GTG | AAT | AAA | 1488 |
| Asp | Gly | Glu | Ile | Tyr | Pro | Ile | Thr | Thr | Lys | Thr | Val | Asn | Val | Asn | Lys | |
| 1365 | | | | | 1370 | | | | | 1375 | | | | | 1380 | |
| GAC | AAT | TAC | AAA | AGA | TTA | GAT | ATT | ATA | GCT | CAT | AAT | ATA | AAA | AGT | AAT | 1536 |
| Asp | Asn | Tyr | Lys | Arg | Leu | Asp | Ile | Ile | Ala | His | Asn | Ile | Lys | Ser | Asn | |
| | | | | 1385 | | | | | 1390 | | | | | 1395 | | |
| CCA | ATT | TCT | TCA | CTT | CAT | ATT | AAA | ACG | AAT | GAT | GAA | ATA | ACT | TTA | TTT | 1584 |
| Pro | Ile | Ser | Ser | Leu | His | Ile | Lys | Thr | Asn | Asp | Glu | Ile | Thr | Leu | Phe | |
| | | | | 1400 | | | | | 1405 | | | | | 1410 | | |
| TGG | GAT | GAT | ATT | TCT | ATA | ACA | GAT | GTA | GCA | TCA | ATA | AAA | CCG | GAA | AAT | 1632 |
| Trp | Asp | Asp | Ile | Ser | Ile | Thr | Asp | Val | Ala | Ser | Ile | Lys | Pro | Glu | Asn | |
| | | 1415 | | | | | 1420 | | | | | 1425 | | | | |

```
TTA  ACA  GAT  TCA  GAA  ATT  AAA  CAG  ATT  TAT  AGT  AGG  TAT  GGT  ATT  AAG      1680
Leu  Thr  Asp  Ser  Glu  Ile  Lys  Gln  Ile  Tyr  Ser  Arg  Tyr  Gly  Ile  Lys
     1430                    1435                    1440

TTA  GAA  GAT  GGA  ATC  CTT  ATT  GAT  AAA  AAA  GGT  GGG  ATT  CAT  TAT  GGT      1728
Leu  Glu  Asp  Gly  Ile  Leu  Ile  Asp  Lys  Lys  Gly  Gly  Ile  His  Tyr  Gly
1445                    1450                    1455                    1460

GAA  TTT  ATT  AAT  GAA  GCT  AGT  TTT  AAT  ATT  GAA  CCA  TTG  CCA  AAT  TAT      1776
Glu  Phe  Ile  Asn  Glu  Ala  Ser  Phe  Asn  Ile  Glu  Pro  Leu  Pro  Asn  Tyr
               1465                    1470                    1475

GTG  ACC  AAA  TAT  GAA  GTT  ACT  TAT  AGT  AGT  GAG  TTA  GGA  CCA  AAC  GTG      1824
Val  Thr  Lys  Tyr  Glu  Val  Thr  Tyr  Ser  Ser  Glu  Leu  Gly  Pro  Asn  Val
          1480                    1485                    1490

AGT  GAC  ACA  CTT  GAA  AGT  GAT  AAA  ATT  TAC  AAG  GAT  GGG  ACA  ATT  AAA      1872
Ser  Asp  Thr  Leu  Glu  Ser  Asp  Lys  Ile  Tyr  Lys  Asp  Gly  Thr  Ile  Lys
     1495                    1500                    1505

TTT  GAT  TTT  ACC  AAA  TAT  AGT  AAA  AAT  GAA  CAA  GGA  TTA  TTT  TAT  GAC      1920
Phe  Asp  Phe  Thr  Lys  Tyr  Ser  Lys  Asn  Glu  Gln  Gly  Leu  Phe  Tyr  Asp
1510                    1515                    1520

AGT  GGA  TTA  AAT  TGG  GAC  TTT  AAA  ATT  AAT  GCT  ATT  ACT  TAT  GAT  GGT      1968
Ser  Gly  Leu  Asn  Trp  Asp  Phe  Lys  Ile  Asn  Ala  Ile  Thr  Tyr  Asp  Gly
1525                    1530                    1535                    1540

AAA  GAG  ATG  AAT  GTT  TTT  CAT  AGA  TAT  AAT  AAA  TAG                          2004
Lys  Glu  Met  Asn  Val  Phe  His  Arg  Tyr  Asn  Lys
               1545                    1550
```

( 2 ) INFORMATION FOR SEQ ID NO:7:

( i ) SEQUENCE CHARACTERISTICS:
        ( A ) LENGTH: 667 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

```
Met  Lys  Arg  Glu  Ile  Asp  Glu  Asp  Thr  Asp  Thr  Asp  Gly  Asp  Ser  Ile
 1              5                        10                       15

Pro  Asp  Leu  Trp  Glu  Glu  Asn  Gly  Tyr  Thr  Ile  Gln  Asn  Arg  Ile  Ala
               20                       25                       30

Val  Lys  Trp  Asp  Asp  Ser  Leu  Ala  Ser  Lys  Gly  Tyr  Thr  Lys  Phe  Val
               35                       40                       45

Ser  Asn  Pro  Leu  Glu  Ser  His  Thr  Val  Gly  Asp  Pro  Tyr  Thr  Asp  Tyr
     50                       55                       60

Glu  Lys  Ala  Ala  Arg  Asp  Leu  Asp  Leu  Ser  Asn  Ala  Lys  Glu  Thr  Phe
 65                      70                       75                       80

Asn  Pro  Leu  Val  Ala  Ala  Phe  Pro  Ser  Val  Asn  Val  Ser  Met  Glu  Lys
                    85                       90                       95

Val  Ile  Leu  Ser  Pro  Asn  Glu  Asn  Leu  Ser  Asn  Ser  Val  Glu  Ser  His
                    100                      105                      110

Ser  Ser  Thr  Asn  Trp  Ser  Tyr  Thr  Asn  Thr  Glu  Gly  Ala  Ser  Val  Glu
               115                      120                      125

Ala  Gly  Ile  Gly  Pro  Lys  Gly  Ile  Ser  Phe  Gly  Val  Ser  Val  Asn  Tyr
          130                      135                      140

Gln  His  Ser  Glu  Thr  Val  Ala  Gln  Glu  Trp  Gly  Thr  Ser  Thr  Gly  Asn
145                      150                      155                      160

Thr  Ser  Gln  Phe  Asn  Thr  Ala  Ser  Ala  Gly  Tyr  Leu  Asn  Ala  Asn  Val
               165                      170                      175

Arg  Tyr  Asn  Asn  Val  Gly  Thr  Gly  Ala  Ile  Tyr  Asp  Val  Lys  Pro  Thr
               180                      185                      190
```

```
Thr  Ser  Phe  Val  Leu  Asn  Asn  Asp  Thr  Ile  Ala  Thr  Ile  Thr  Ala  Lys
          195                      200                      205

Ser  Asn  Ser  Thr  Ala  Leu  Asn  Ile  Ser  Pro  Gly  Glu  Ser  Tyr  Pro  Lys
          210                      215                      220

Lys  Gly  Gln  Asn  Gly  Ile  Ala  Ile  Thr  Ser  Met  Asp  Asp  Phe  Asn  Ser
225                      230                      235                      240

His  Pro  Ile  Thr  Leu  Asn  Lys  Lys  Gln  Val  Asp  Asn  Leu  Leu  Asn  Asn
               245                      250                           255

Lys  Pro  Met  Met  Leu  Glu  Thr  Asn  Gln  Thr  Asp  Gly  Val  Tyr  Lys  Ile
               260                      265                      270

Lys  Asp  Thr  His  Gly  Asn  Ile  Val  Thr  Gly  Gly  Glu  Trp  Asn  Gly  Val
          275                      280                      285

Ile  Gln  Gln  Ile  Lys  Ala  Lys  Thr  Ala  Ser  Ile  Ile  Val  Asp  Asp  Gly
     290                      295                 300

Glu  Arg  Val  Ala  Glu  Lys  Arg  Val  Ala  Lys  Asp  Tyr  Glu  Asn  Pro
305                      310                 315                      320

Glu  Asp  Lys  Thr  Pro  Ser  Leu  Thr  Leu  Lys  Asp  Ala  Leu  Lys  Leu  Ser
               325                      330                      335

Tyr  Pro  Asp  Glu  Ile  Lys  Glu  Ile  Glu  Gly  Leu  Leu  Tyr  Tyr  Lys  Asn
               340                      345                      350

Lys  Pro  Ile  Tyr  Glu  Ser  Ser  Val  Met  Thr  Tyr  Leu  Asp  Glu  Asn  Thr
               355                      360                      365

Ala  Lys  Glu  Val  Thr  Lys  Gln  Leu  Asn  Asp  Thr  Thr  Gly  Lys  Phe  Lys
     370                      375                      380

Asp  Val  Ser  His  Leu  Tyr  Asp  Val  Lys  Leu  Thr  Pro  Lys  Met  Asn  Val
385                      390                      395                      400

Thr  Ile  Lys  Leu  Ser  Ile  Leu  Tyr  Asp  Asn  Ala  Glu  Ser  Asn  Asp  Asn
                    405                      410                      415

Ser  Ile  Gly  Lys  Trp  Thr  Asn  Thr  Asn  Ile  Val  Ser  Gly  Asn  Asn
               420                      425                      430

Gly  Lys  Lys  Gln  Tyr  Ser  Ser  Asn  Asn  Pro  Asp  Ala  Asn  Leu  Thr  Leu
          435                      440                      445

Asn  Thr  Asp  Ala  Gln  Glu  Lys  Leu  Asn  Lys  Asn  Arg  Asp  Tyr  Tyr  Ile
     450                      455                      460

Ser  Leu  Tyr  Met  Lys  Ser  Glu  Lys  Asn  Thr  Gln  Cys  Glu  Ile  Thr  Ile
465                      470                      475                      480

Asp  Gly  Glu  Ile  Tyr  Pro  Ile  Thr  Thr  Lys  Thr  Val  Asn  Val  Asn  Lys
                    485                      490                      495

Asp  Asn  Tyr  Lys  Arg  Leu  Asp  Ile  Ile  Ala  His  Asn  Ile  Lys  Ser  Asn
               500                      505                      510

Pro  Ile  Ser  Ser  Leu  His  Ile  Lys  Thr  Asn  Asp  Glu  Ile  Thr  Leu  Phe
          515                      520                      525

Trp  Asp  Asp  Ile  Ser  Ile  Thr  Asp  Val  Ala  Ser  Ile  Lys  Pro  Glu  Asn
     530                      535                      540

Leu  Thr  Asp  Ser  Glu  Ile  Lys  Gln  Ile  Tyr  Ser  Arg  Tyr  Gly  Ile  Lys
545                      550                      555                      560

Leu  Glu  Asp  Gly  Ile  Leu  Ile  Asp  Lys  Lys  Gly  Gly  Ile  His  Tyr  Gly
               565                      570                      575

Glu  Phe  Ile  Asn  Glu  Ala  Ser  Phe  Asn  Ile  Glu  Pro  Leu  Pro  Asn  Tyr
               580                      585                      590

Val  Thr  Lys  Tyr  Glu  Val  Thr  Tyr  Ser  Ser  Glu  Leu  Gly  Pro  Asn  Val
          595                      600                      605

Ser  Asp  Thr  Leu  Glu  Ser  Asp  Lys  Ile  Tyr  Lys  Asp  Gly  Thr  Ile  Lys
```

```
                    610                         615                         620
Phe  Asp  Phe  Thr  Lys  Tyr  Ser  Lys  Asn  Glu  Gln  Gly  Leu  Phe  Tyr  Asp
625                      630                       635                      640

Ser  Gly  Leu  Asn  Trp  Asp  Phe  Lys  Ile  Asn  Ala  Ile  Thr  Tyr  Asp  Gly
                    645                       650                       655

Lys  Glu  Met  Asn  Val  Phe  His  Arg  Tyr  Asn  Lys
                    660                       665
```

( 2 ) INFORMATION FOR SEQ ID NO:8:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: N-terminal ( v i ) ORIGINAL SOURCE:
        ( A ) ORGANISM: Bacillus cereus
        ( B ) STRAIN: AB78
        ( C ) INDIVIDUAL ISOLATE: NRRL B- 21058

&nb ( v ) FRAGMENT TYPE: N-terminal ( v i ) ORIGINAL SOURCE:
    ( A ) ORGANISM: Bacillus thuringiensis
    ( B ) STRAIN: AB88

( i x ) FEATURE:
    ( A ) NAME/KEY: Peptide

Ala  Leu  Ser  Glu  Asn  Thr  Gly  Lys  Asp  Gly  Gly  Tyr  Ile  Val  Pro
       1                   5                        10                       15

( 2 ) INFORMATION FOR SEQ ID NO:14:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( v i ) ORIGINAL SOURCE:
        ( A ) ORGANISM: Bacillus thuringiensis

&

-continued ( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
( A ) NAME/KEY: misc_feature
( B ) LOCATION: 1..2652
( D ) OTHER INFORMATION: /note= "Maize optimized DNA sequence for 100 kd VIP1A(a) protein from AB78"

( x i ) SEQUENCE DESCRIPTION: SEQ ID NO:17:

ATGAAGAACA TGAAGAAGAA GCTGGCCAGC GTGGTGACCT GCACCCTGCT GGCCCCCATG 60

TTCCTGAACG GCAACGTGAA CGCCGTGTAC GCCGACAGCA AGACCAACCA GATCAGCACC 120

ACCCAGAAGA ACCAGCAGAA GGAGATGGAC CGCAAGGGCC TGCTGGGCTA CTACTTCAAG 180

GGCAAGGACT TCAGCAACCT GACCATGTTC GCCCCCACGC GTGACAGCAC CCTGATCTAC 240

GACCAGCAGA CCGCCAACAA GCTGCTGGAC AAGAAGCAGC AGGAGTACCA GAGCATCCGC 300

TGGATCGGCC TGATCCAGAG CAAGGAGACC GGCGACTTCA CCTTCAACCT GAGCGAGGAC 360

GAGCAGGCCA TCATCGAGAT CAACGGCAAG ATCATCAGCA ACAAGGGCAA GGAGAAGCAG 420

GTGGTGCACC TGGAGAAGGG CAAGCTGGTG CCCATCAAGA TCGAGTACCA GAGCGACACC 480

AAGTTCAACA TCGACAGCAA GACCTTCAAG GAGCTGAAGC TTTTCAAGAT CGACAGCCAG 540

AACCAGCCCC AGCAGGTGCA GCAGGACGAG CTGCGCAACC CCGAGTTCAA CAAGAAGGAG 600

AGCCAGGAGT TCCTGGCCAA GCCCAGCAAG ATCAACCTGT TCACCCAGCA GATGAAGCGC 660

GAGATCGACG AGGACACCGA CACCGACGGC GACAGCATCC CCGACCTGTG GGAGGAGAAC 720

GGCTACACCA TCCAGAACCG CATCGCCGTG AAGTGGGACG ACAGCCTGGC TAGCAAGGGC 780

TACACCAAGT TCGTGAGCAA CCCCCTGGAG AGCCACACCG TGGGCGACCC CTACACCGAC 840

TACGAGAAGG CCGCCCGCGA CCTGGACCTG AGCAACGCCA AGGAGACCTT CAACCCCCTG 900

GTGGCCGCCT TCCCCAGCGT GAACGTGAGC ATGGAGAAGG TGATCCTGAG CCCCAACGAG 960

AACCTGAGCA ACAGCGTGGA GAGCCACTCG AGCACCAACT GGAGCTACAC CAACACCGAG 1020

GGCGCCAGCG TGGAGGCCGG CATCGGTCCC AAGGGCATCA GCTTCGGCGT GAGCGTGAAC 1080

TACCAGCACA GCGAGACCGT GGCCCAGGAG TGGGGCACCA GCACCGGCAA CACCAGCCAG 1140

TTCAACACCG CCAGCGCCGG CTACCTGAAC GCCAACGTGC GCTACAACAA CGTGGGCACC 1200

GGCGCCATCT ACGACGTGAA GCCCACCACC AGCTTCGTGC TGAACAACGA CACCATCGCC 1260

ACCATCACCG CCAAGTCGAA TTCCACCGCC CTGAACATCA GCCCCGGCGA GAGCTACCCC 1320

AAGAAGGGCC AGAACGGCAT CGCCATCACC AGCATGGACG ACTTCAACAG CCACCCCATC 1380

ACCCTGAACA AGAAGCAGGT GGACAACCTG CTGAACAACA AGCCCATGAT GCTGGAGACC 1440

AACCAGACCG ACGGCGTCTA CAAGATCAAG GACACCCACG GCAACATCGT GACCGGCGGC 1500

GAGTGGAACG GCGTGATCCA GCAGATCAAG GCCAAGACCG CCAGCATCAT CGTCGACGAC 1560

GGCGAGCGCG TGGCCGAGAA GCGCGTGGCC GCCAAGGACT ACGAGAACCC CGAGGACAAG 1620

ACCCCCAGCC TGACCCTGAA GGACGCCCTG AAGCTGAGCT ACCCCGACGA GATCAAGGAG 1680

ATCGAGGGCC TGCTGTACTA CAAGAACAAG CCCATCTACG AGAGCAGCGT GATGACCTAT 1740

CTAGACGAGA ACACCGCCAA GGAGGTGACC AAGCAGCTGA ACGACACCAC CGGCAAGTTC 1800

AAGGACGTGA GCCACCTGTA CGACGTGAAG CTGACCCCCA AGATGAACGT GACCATCAAG 1860

| | | | | | | |
|---|---|---|---|---|---|---|
| CTGAGCATCC | TGTACGACAA | CGCCGAGAGC | AACGACAACA | GCATCGGCAA | GTGGACCAAC | 1920 |
| ACCAACATCG | TGAGCGGCGG | CAACAACGGC | AAGAAGCAGT | ACAGCAGCAA | CAACCCCGAC | 1980 |
| GCCAACCTGA | CCCTGAACAC | CGACGCCCAG | GAGAAGCTGA | ACAAGAACCG | CGACTACTAC | 2040 |
| ATCAGCCTGT | ACATGAAGAG | CGAGAAGAAC | ACCCAGTGCG | AGATCACCAT | CGACGGCGAG | 2100 |
| ATATACCCCA | TCACCACCAA | GACCGTGAAC | GTGAACAAGG | ACAACTACAA | GCGCCTGGAC | 2160 |
| ATCATCGCCC | ACAACATCAA | GAGCAACCCC | ATCAGCAGCC | TGCACATCAA | GACCAACGAC | 2220 |
| GAGATCACCC | TGTTCTGGGA | CGACATATCG | ATTACCGACG | TCGCCAGCAT | CAAGCCCGAG | 2280 |
| AACCTGACCG | ACAGCGAGAT | CAAGCAGATA | TACAGTCGCT | ACGGCATCAA | GCTGGAGGAC | 2340 |
| GGCATCCTGA | TCGACAAGAA | GGGCGGCATC | CACTACGGCG | AGTTCATCAA | CGAGGCCAGC | 2400 |
| TTCAACATCG | AGCCCCTGCA | GAACTACGTG | ACCAAGTACG | AGGTGACCTA | CAGCAGCGAG | 2460 |
| CTGGGCCCCA | ACGTGAGCGA | CACCCTGGAG | AGCGACAAGA | TTTACAAGGA | CGGCACCATC | 2520 |
| AAGTTCGACT | TCACCAAGTA | CAGCAAGAAC | GAGCAGGGCC | TGTTCTACGA | CAGCGGCCTG | 2580 |
| AACTGGGACT | TCAAGATCAA | CGCCATCACC | TACGACGGCA | AGGAGATGAA | CGTGTTCCAC | 2640 |
| CGCTACAACA | AGTAG | | | | | 2655 |

(2) INFORMATION FOR SEQ ID NO:18:

(i) SEQUENCE CHARACTERISTICS:
        (A) LENGTH: 2004 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: misc_feature
        (B) LOCATION: 1..2004
        (D) OTHER INFORMATION: /note= "Maize optimized DNA sequence for VIP1A(a) 80 kd protein from -continued

GTCGACGACG GCGAGCGCGT GGCCGAGAAG CGCGTGGCCG CCAAGGACTA CGAGAACCCC 960

GAGGACAAGA CCCCCAGCCT GACCCTGAAG GACGCCCTGA AGCTGAGCTA CCCCGACGAG 1020

ATCAAGGAGA TCGAGGGCCT GCTGTACTAC AAGAACAAGC CCATCTACGA GAGCAGCGTG 1080

ATGACCTATC TAGACGAGAA CACCGCCAAG GAGGTGACCA AGCAGCTGAA CGACACCACC 1140

GGCAAGTTCA AGGACGTGAG CCACCTGTAC GACGTGAAGC TGACCCCCAA GATGAACGTG 1200

ACCATCAAGC TGAGCATCCT GTACGACAAC GCCGAGAGCA ACGACAACAG CATCGGCAAG 1260

TGGACCAACA CCAACATCGT GAGCGGCGGC AACAACGGCA AGAAGCAGTA CAGCAGCAAC 1320

AACCCCGACG CCAACCTGAC CCTGAACACC GACGCCCAGG AGAAGCTGAA CAAGAACCGC 1380

GACTACTACA TCAGCCTGTA CATGAAGAGC GAGAAGAACA CCCAGTGCGA GATCACCATC 1440

GACGGCGAGA TATACCCCAT CACCACCAAG ACCGTGAACG TGAACAAGGA CAACTACAAG 1500

CGCCTGGACA TCATCGCCCA CAACATCAAG AGCAACCCCA TCAGCAGCCT GCACATCAAG 1560

ACCAACGACG AGATCACCCT GTTCTGGGAC GACATATCGA TTACCGACGT CGCCAGCATC 1620

AAGCCCGAGA ACCTGACCGA CAGCGAGATC AAGCAGATAT ACAGTCGCTA CGGCATCAAG 1680

CTGGAGGACG GCATCCTGAT CGACAAGAAG GGCGGCATCC ACTACGGCGA GTTCATCAAC 1740

GAGGCCAGCT TCAACATCGA GCCCCTGCAG AACTACGTGA CCAAGTACGA GGTGACCTAC 1800

AGCAGCGAGC TGGGCCCCAA CGTGAGCGAC ACCCTGGAGA GCGACAAGAT TTACAAGGAC 1860

GGCACCATCA AGTTCGACTT CACCAAGTAC AGCAAGAACG AGCAGGGCCT GTTCTACGAC 1920

AGCGGCCTGA ACTGGGACTT CAAGATCAAC GCCATCACCT ACGACGGCAA GGAGATGAAC 1980

GTGTTCCACC GCTACAACAA GTAG 2004

( 2 ) INFORMATION FOR SEQ ID NO:19:

( i ) SEQUENCE CHARACTERISTICS:
( A ) LENGTH: 4074 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: 1..1386
( D ) OTHER INFORMATION: /product="VIP2A(b) from Btt"

( i x ) FEATURE:
( A ) NAME/KEY: CDS
( B ) LOCATION: 1394..3895
( D ) OTHER INFORMATION: /product="VIP1A(b) from Btt"

( i x ) FEATURE:
( A ) NAME/KEY: misc_feature
( B ) LOCATION: 1..4074
( D ) OTHER INFORMATION: /note= "Cloned DNA sequence from Btt which contains the genes for both VIP1A(b) and VIP2A(b)"

( x i ) SEQUENCE DESCRIPTION: SEQ ID NO:19:

ATG CAA AGA ATG GAG GGA AAG TTG TTT GTG GTG TCA AAA ACA TTA CAA 48
Met Gln Arg Met Glu Gly Lys Leu Phe Val Val Ser Lys Thr Leu Gln
670 675 680

GTA GTT ACT AGA ACT GTA TTG CTT AGT ACA GTT TAC TCT ATA ACT TTA 96
Val Val Thr Arg Thr Val Leu Leu Ser Thr Val Tyr Ser Ile Thr Leu
685 690 695

TTA AAT AAT GTA GTG ATA AAA GCT GAC CAA TTA AAT ATA AAT TCT CAA 144
Leu Asn Asn Val Val Ile Lys Ala Asp Gln Leu Asn Ile Asn Ser Gln
700 705 710 715

```
AGT  AAA  TAT  ACT  AAC  TTG  CAA  AAT  CTA  AAA  ATC  CCT  GAT  AAT  GCA  GAG        192
Ser  Lys  Tyr  Thr  Asn  Leu  Gln  Asn  Leu  Lys  Ile  Pro  Asp  Asn  Ala  Glu
               720                      725                      730

GAT  TTT  AAA  GAA  GAT  AAG  GGG  AAA  GCG  AAA  GAA  TGG  GGG  AAA  GAG  AAA        240
Asp  Phe  Lys  Glu  Asp  Lys  Gly  Lys  Ala  Lys  Glu  Trp  Gly  Lys  Glu  Lys
               735                      740                      745

GGG  GAA  GAG  TGG  AGG  CCT  CCT  GCT  ACT  GAG  AAA  GGA  GAA  ATG  AAT  AAT        288
Gly  Glu  Glu  Trp  Arg  Pro  Pro  Ala  Thr  Glu  Lys  Gly  Glu  Met  Asn  Asn
               750                      755                      760

TTT  TTA  GAT  AAT  AAA  AAT  GAT  ATA  AAG  ACC  AAT  TAT  AAA  GAA  ATT  ACT        336
Phe  Leu  Asp  Asn  Lys  Asn  Asp  Ile  Lys  Thr  Asn  Tyr  Lys  Glu  Ile  Thr
          765                      770                      775

TTT  TCT  ATG  GCA  GGT  TCA  TGT  GAA  GAT  GAA  ATA  AAA  GAT  TTA  GAA  GAA        384
Phe  Ser  Met  Ala  Gly  Ser  Cys  Glu  Asp  Glu  Ile  Lys  Asp  Leu  Glu  Glu
780                      785                      790                      795

ATT  GAT  AAG  ATC  TTT  GAT  AAA  GCC  AAT  CTC  TCG  AGT  TCT  ATT  ATC  ACC        432
Ile  Asp  Lys  Ile  Phe  Asp  Lys  Ala  Asn  Leu  Ser  Ser  Ser  Ile  Ile  Thr
                         800                      805                      810

TAT  AAA  AAT  GTG  GAA  CCA  GCA  ACA  ATT  GGA  TTT  AAT  AAA  TCT  TTA  ACA        480
Tyr  Lys  Asn  Val  Glu  Pro  Ala  Thr  Ile  Gly  Phe  Asn  Lys  Ser  Leu  Thr
               815                      820                      825

GAA  GGT  AAT  ACG  ATT  AAT  TCT  GAT  GCA  ATG  GCA  CAG  TTT  AAA  GAA  CAA        528
Glu  Gly  Asn  Thr  Ile  Asn  Ser  Asp  Ala  Met  Ala  Gln  Phe  Lys  Glu  Gln
               830                      835                      840

TTT  TTA  GGT  AAG  GAT  ATG  AAG  TTT  GAT  AGT  TAT  CTA  GAT  ACT  CAT  TTA        576
Phe  Leu  Gly  Lys  Asp  Met  Lys  Phe  Asp  Ser  Tyr  Leu  Asp  Thr  His  Leu
          845                      850                      855

ACT  GCT  CAA  CAA  GTT  TCC  AGT  AAA  AAA  AGA  GTT  ATT  TTG  AAG  GTT  ACG        624
Thr  Ala  Gln  Gln  Val  Ser  Ser  Lys  Lys  Arg  Val  Ile  Leu  Lys  Val  Thr
860                      865                      870                      875

GTT  CCG  AGT  GGG  AAA  GGT  TCT  ACT  ACT  CCA  ACA  AAA  GCA  GGT  GTC  ATT        672
Val  Pro  Ser  Gly  Lys  Gly  Ser  Thr  Thr  Pro  Thr  Lys  Ala  Gly  Val  Ile
                    880                      885                      890

TTA  AAC  AAT  AAT  GAA  TAC  AAA  ATG  CTC  ATT  GAT  AAT  GGG  TAT  GTG  CTC        720
Leu  Asn  Asn  Asn  Glu  Tyr  Lys  Met  Leu  Ile  Asp  Asn  Gly  Tyr  Val  Leu
               895                      900                      905

CAT  GTA  GAT  AAG  GTA  TCA  AAA  GTA  GTA  AAA  AAA  GGG  ATG  GAG  TGC  TTA        768
His  Val  Asp  Lys  Val  Ser  Lys  Val  Val  Lys  Lys  Gly  Met  Glu  Cys  Leu
          910                      915                      920

CAA  GTT  GAA  GGG  ACT  TTA  AAA  AAG  AGT  CTC  GAC  TTT  AAA  AAT  GAT  ATA        816
Gln  Val  Glu  Gly  Thr  Leu  Lys  Lys  Ser  Leu  Asp  Phe  Lys  Asn  Asp  Ile
     925                      930                      935

AAT  GCT  GAA  GCG  CAT  AGC  TGG  GGG  ATG  AAA  ATT  TAT  GAA  GAC  TGG  GCT        864
Asn  Ala  Glu  Ala  His  Ser  Trp  Gly  Met  Lys  Ile  Tyr  Glu  Asp  Trp  Ala
940                      945                      950                      955

AAA  AAT  TTA  ACC  GCT  TCG  CAA  AGG  GAA  GCT  TTA  GAT  GGG  TAT  GCT  AGG        912
Lys  Asn  Leu  Thr  Ala  Ser  Gln  Arg  Glu  Ala  Leu  Asp  Gly  Tyr  Ala  Arg
                    960                      965                      970

CAA  GAT  TAT  AAA  GAA  ATC  AAT  AAT  TAT  TTG  CGC  AAT  CAA  GGC  GGG  AGT        960
Gln  Asp  Tyr  Lys  Glu  Ile  Asn  Asn  Tyr  Leu  Arg  Asn  Gln  Gly  Gly  Ser
               975                      980                      985

GGA  AAT  GAA  AAG  CTG  GAT  GCC  CAA  TTA  AAA  AAT  ATT  TCT  GAT  GCT  TTA       1008
Gly  Asn  Glu  Lys  Leu  Asp  Ala  Gln  Leu  Lys  Asn  Ile  Ser  Asp  Ala  Leu
          990                      995                      1000

GGG  AAG  AAA  CCC  ATA  CCA  GAA  AAT  ATT  ACC  GTG  TAT  AGA  TGG  TGT  GGC       1056
Gly  Lys  Lys  Pro  Ile  Pro  Glu  Asn  Ile  Thr  Val  Tyr  Arg  Trp  Cys  Gly
     1005                     1010                     1015

ATG  CCG  GAA  TTT  GGT  TAT  CAA  ATT  AGT  GAT  CCG  TTA  CCT  TCT  TTA  AAA       1104
Met  Pro  Glu  Phe  Gly  Tyr  Gln  Ile  Ser  Asp  Pro  Leu  Pro  Ser  Leu  Lys
1020                     1025                     1030                     1035
```

```
GAT TTT GAA GAA CAA TTT TTA AAT ACA ATT AAA GAA GAC AAA GGG TAT    1152
Asp Phe Glu Glu Gln Phe Leu Asn Thr Ile Lys Glu Asp Lys Gly Tyr
            1040                1045                1050

ATG AGT ACA AGC TTA TCG AGT GAA CGT CTT GCA GCT TTT GGA TCT AGA    1200
Met Ser Thr Ser Leu Ser Ser Glu Arg Leu Ala Ala Phe Gly Ser Arg
        1055                1060                1065

AAA ATT ATA TTA CGC TTA CAA GTT CCG AAA GGA AGT ACG GGG GCG TAT    1248
Lys Ile Ile Leu Arg Leu Gln Val Pro Lys Gly Ser Thr Gly Ala Tyr
        1070                1075                1080

TTA AGT GCC ATT GGT GGA TTT GCA AGT GAA AAA GAG ATC CTA CTT GAT    1296
Leu Ser Ala Ile Gly Gly Phe Ala Ser Glu Lys Glu Ile Leu Leu Asp
        1085                1090                1095

AAA GAT AGT AAA TAT CAT ATT GAT AAA GCA ACA GAG GTA ATC ATT AAA    1344
Lys Asp Ser Lys Tyr His Ile Asp Lys Ala Thr Glu Val Ile Ile Lys
1100                1105                1110                1115

GGT GTT AAG CGA TAT GTA GTG GAT GCA ACA TTA TTA ACA AAT              1386
Gly Val Lys Arg Tyr Val Val Asp Ala Thr Leu Leu Thr Asn
        1120                1125

TAAGGAG ATG AAA AAT ATG AAG AAA AAG TTA GCA AGT GTT GTA ACC TGT    1435
        Met Lys Asn Met Lys Lys Lys Leu Ala Ser Val Val Thr Cys
        1           5               10

ATG TTA TTA GCT CCT ATG TTT TTG AAT GGA AAT GTG AAT GCT GTT AAC    1483
Met Leu Leu Ala Pro Met Phe Leu Asn Gly Asn Val Asn Ala Val Asn
15              20              25              30

GCG GAT AGT AAA ATA AAT CAG ATT TCT ACA ACG CAG GAA AAC CAA CAG    1531
Ala Asp Ser Lys Ile Asn Gln Ile Ser Thr Thr Gln Glu Asn Gln Gln
                35              40              45

AAA GAG ATG GAC CGA AAG GGA TTA TTG GGA TAT TAT TTC AAA GGA AAA    1579
Lys Glu Met Asp Arg Lys Gly Leu Leu Gly Tyr Tyr Phe Lys Gly Lys
            50              55              60

GAT TTT AAT AAT CTT ACT ATG TTT GCA CCG ACA CGT GAT AAT ACC CTT    1627
Asp Phe Asn Asn Leu Thr Met Phe Ala Pro Thr Arg Asp Asn Thr Leu
        65              70              75

ATG TAT GAC CAA CAA ACA GCG AAT GCA TTA TTA GAT AAA AAA CAA CAA    1675
Met Tyr Asp Gln Gln Thr Ala Asn Ala Leu Leu Asp Lys Lys Gln Gln
        80              85              90

GAA TAT CAG TCC ATT CGT TGG ATT GGT TTG ATT CAG CGT AAA GAA ACG    1723
Glu Tyr Gln Ser Ile Arg Trp Ile Gly Leu Ile Gln Arg Lys Glu Thr
95              100             105             110

GGC GAT TTC ACA TTT AAC TTA TCA AAG GAT GAA CAG GCA ATT ATA GAA    1771
Gly Asp Phe Thr Phe Asn Leu Ser Lys Asp Glu Gln Ala Ile Ile Glu
                115             120             125

ATC GAT GGG AAA ATC ATT TCT AAT AAA GGG AAA GAA AAG CAA GTT GTC    1819
Ile Asp Gly Lys Ile Ile Ser Asn Lys Gly Lys Glu Lys Gln Val Val
            130             135             140

CAT TTA GAA AAA GAA AAA TTA GTT CCA ATC AAA ATA GAG TAT CAA TCA    1867
His Leu Glu Lys Glu Lys Leu Val Pro Ile Lys Ile Glu Tyr Gln Ser
        145             150             155

GAT ACG AAA TTT AAT ATT GAT AGT AAA ACA TTT AAA GAA CTT AAA TTA    1915
Asp Thr Lys Phe Asn Ile Asp Ser Lys Thr Phe Lys Glu Leu Lys Leu
160             165             170

TTT AAA ATA GAT AGT CAA AAC CAA TCT CAA CAA GTT CAA CTG AGA AAC    1963
Phe Lys Ile Asp Ser Gln Asn Gln Ser Gln Gln Val Gln Leu Arg Asn
175             180             185             190

CCT GAA TTT AAC AAA AAA GAA TCA CAG GAA TTT TTA GCA AAA GCA TCA    2011
Pro Glu Phe Asn Lys Lys Glu Ser Gln Glu Phe Leu Ala Lys Ala Ser
                195             200             205

AAA ACA AAC CTT TTT AAG CAA AAA ATG AAA AGA GAT ATT GAT GAA GAT    2059
Lys Thr Asn Leu Phe Lys Gln Lys Met Lys Arg Asp Ile Asp Glu Asp
            210             215             220
```

| | | | | | | | | | | | | | | | |
|---|---|---|---|---|---|---|---|---|---|---|---|---|---|---|---|
| ACG | GAT | ACA | GAT | GGA | GAC | TCC | ATT | CCT | GAT | CTT | TGG | GAA | GAA | AAT | GGG |
| Thr | Asp | Thr | Asp | Gly | Asp | Ser | Ile | Pro | Asp | Leu | Trp | Glu | Glu | Asn | Gly |
| | | 225 | | | | 230 | | | | 235 | | | | | |

2107

| TAC | ACG | ATT | CAA | AAT | AAA | GTT | GCT | GTC | AAA | TGG | GAT | GAT | TCG | CTA | GCA |
|---|---|---|---|---|---|---|---|---|---|---|---|---|---|---|---|
| Tyr | Thr | Ile | Gln | Asn | Lys | Val | Ala | Val | Lys | Trp | Asp | Asp | Ser | Leu | Ala |
| | 240 | | | | 245 | | | | | 250 | | | | | |

2155

| AGT | AAG | GGA | TAT | ACA | AAA | TTT | GTT | TCG | AAT | CCA | TTA | GAC | AGC | CAC | ACA |
|---|---|---|---|---|---|---|---|---|---|---|---|---|---|---|---|
| Ser | Lys | Gly | Tyr | Thr | Lys | Phe | Val | Ser | Asn | Pro | Leu | Asp | Ser | His | Thr |
| 255 | | | | | 260 | | | | | 265 | | | | | 270 |

2203

| GTT | GGC | GAT | CCC | TAT | ACT | GAT | TAT | GAA | AAG | GCC | GCA | AGG | GAT | TTA | GAT |
|---|---|---|---|---|---|---|---|---|---|---|---|---|---|---|---|
| Val | Gly | Asp | Pro | Tyr | Thr | Asp | Tyr | Glu | Lys | Ala | Ala | Arg | Asp | Leu | Asp |
| | | | | 275 | | | | | 280 | | | | | 285 | |

2251

| TTA | TCA | AAT | GCA | AAG | GAA | ACG | TTC | AAC | CCA | TTG | GTA | GCT | GCT | TTT | CCA |
|---|---|---|---|---|---|---|---|---|---|---|---|---|---|---|---|
| Leu | Ser | Asn | Ala | Lys | Glu | Thr | Phe | Asn | Pro | Leu | Val | Ala | Ala | Phe | Pro |
| | | | 290 | | | | | 295 | | | | | 300 | | |

2299

| AGT | GTG | AAT | GTT | AGT | ATG | GAA | AAG | GTG | ATA | TTA | TCA | CCA | AAT | GAA | AAT |
|---|---|---|---|---|---|---|---|---|---|---|---|---|---|---|---|
| Ser | Val | Asn | Val | Ser | Met | Glu | Lys | Val | Ile | Leu | Ser | Pro | Asn | Glu | Asn |
| | | 305 | | | | | 310 | | | | | 315 | | | |

2347

| TTA | TCC | AAT | AGT | GTA | GAG | TCT | CAT | TCA | TCC | ACG | AAT | TGG | TCT | TAT | ACG |
|---|---|---|---|---|---|---|---|---|---|---|---|---|---|---|---|
| Leu | Ser | Asn | Ser | Val | Glu | Ser | His | Ser | Ser | Thr | Asn | Trp | Ser | Tyr | Thr |
| 320 | | | | | 325 | | | | | 330 | | | | | |

2395

| AAT | ACA | GAA | GGA | GCT | TCC | ATT | GAA | GCT | GGT | GGC | GGT | CCA | TTA | GGC | CTT |
|---|---|---|---|---|---|---|---|---|---|---|---|---|---|---|---|
| Asn | Thr | Glu | Gly | Ala | Ser | Ile | Glu | Ala | Gly | Gly | Gly | Pro | Leu | Gly | Leu |
| 335 | | | | | 340 | | | | | 345 | | | | | 350 |

2443

| TCT | TTT | GGC | GTG | AGT | GTT | ACT | TAT | CAA | CAC | TCT | GAA | ACA | GTT | GCA | CAA |
|---|---|---|---|---|---|---|---|---|---|---|---|---|---|---|---|
| Ser | Phe | Gly | Val | Ser | Val | Thr | Tyr | Gln | His | Ser | Glu | Thr | Val | Ala | Gln |
| | | | | 355 | | | | | 360 | | | | | 365 | |

2491

| GAA | TGG | GGA | ACA | TCT | ACA | GGA | AAT | ACT | TCA | CAA | TTC | AAT | ACG | GCT | TCA |
|---|---|---|---|---|---|---|---|---|---|---|---|---|---|---|---|
| Glu | Trp | Gly | Thr | Ser | Thr | Gly | Asn | Thr | Ser | Gln | Phe | Asn | Thr | Ala | Ser |
| | | | 370 | | | | | 375 | | | | | 380 | | |

2539

| GCG | GGA | TAT | TTA | AAT | GCA | AAT | GTT | CGG | TAT | AAC | AAT | GTA | GGG | ACT | GGT |
|---|---|---|---|---|---|---|---|---|---|---|---|---|---|---|---|
| Ala | Gly | Tyr | Leu | Asn | Ala | Asn | Val | Arg | Tyr | Asn | Asn | Val | Gly | Thr | Gly |
| | | 385 | | | | | 390 | | | | | 395 | | | |

2587

| GCC | ATC | TAT | GAT | GTA | AAA | CCT | ACA | ACA | AGT | TTT | GTA | TTA | AAT | AAC | AAT |
|---|---|---|---|---|---|---|---|---|---|---|---|---|---|---|---|
| Ala | Ile | Tyr | Asp | Val | Lys | Pro | Thr | Thr | Ser | Phe | Val | Leu | Asn | Asn | Asn |
| 400 | | | | | 405 | | | | | 410 | | | | | |

2635

| ACC | ATC | GCA | ACG | ATT | ACA | GCA | AAA | TCA | AAT | TCA | ACA | GCT | TTA | CGT | ATA |
|---|---|---|---|---|---|---|---|---|---|---|---|---|---|---|---|
| Thr | Ile | Ala | Thr | Ile | Thr | Ala | Lys | Ser | Asn | Ser | Thr | Ala | Leu | Arg | Ile |
| 415 | | | | | 420 | | | | | 425 | | | | | 430 |

2683

| TCT | CCG | GGG | GAT | AGT | TAT | CCA | GAA | ATA | GGA | GAA | AAC | GCT | ATT | GCG | ATT |
|---|---|---|---|---|---|---|---|---|---|---|---|---|---|---|---|
| Ser | Pro | Gly | Asp | Ser | Tyr | Pro | Glu | Ile | Gly | Glu | Asn | Ala | Ile | Ala | Ile |
| | | | | 435 | | | | | 440 | | | | | 445 | |

2731

| ACA | TCT | ATG | GAT | GAT | TTT | AAT | TCT | CAT | CCA | ATT | ACA | TTA | AAT | AAA | CAA |
|---|---|---|---|---|---|---|---|---|---|---|---|---|---|---|---|
| Thr | Ser | Met | Asp | Asp | Phe | Asn | Ser | His | Pro | Ile | Thr | Leu | Asn | Lys | Gln |
| | | | 450 | | | | | 455 | | | | | 460 | | |

2779

| CAG | GTA | AAT | CAA | TTG | ATA | AAT | AAT | AAG | CCA | ATT | ATG | CTA | GAG | ACA | GAC |
|---|---|---|---|---|---|---|---|---|---|---|---|---|---|---|---|
| Gln | Val | Asn | Gln | Leu | Ile | Asn | Asn | Lys | Pro | Ile | Met | Leu | Glu | Thr | Asp |
| | | 465 | | | | | 470 | | | | | 475 | | | |

2827

| CAA | ACA | GAT | GGT | GTT | TAT | AAA | ATA | AGA | GAT | ACA | CAT | GGA | AAT | ATT | GTA |
|---|---|---|---|---|---|---|---|---|---|---|---|---|---|---|---|
| Gln | Thr | Asp | Gly | Val | Tyr | Lys | Ile | Arg | Asp | Thr | His | Gly | Asn | Ile | Val |
| | 480 | | | | 485 | | | | | 490 | | | | | |

2875

| ACT | GGT | GGA | GAA | TGG | AAT | GGT | GTA | ACA | CAA | CAA | ATT | AAA | GCA | AAA | ACA |
|---|---|---|---|---|---|---|---|---|---|---|---|---|---|---|---|
| Thr | Gly | Gly | Glu | Trp | Asn | Gly | Val | Thr | Gln | Gln | Ile | Lys | Ala | Lys | Thr |
| 495 | | | | | 500 | | | | | 505 | | | | | 510 |

2923

| GCG | TCT | ATT | ATT | GTG | GAT | GAC | GGG | AAA | CAG | GTA | GCA | GAA | AAA | CGT | GTG |
|---|---|---|---|---|---|---|---|---|---|---|---|---|---|---|---|
| Ala | Ser | Ile | Ile | Val | Asp | Asp | Gly | Lys | Gln | Val | Ala | Glu | Lys | Arg | Val |
| | | | | 515 | | | | | 520 | | | | | 525 | |

2971

| GCG | GCA | AAA | GAT | TAT | GGT | CAT | CCA | GAA | GAT | AAA | ACA | CCA | CCT | TTA | ACT |
|---|---|---|---|---|---|---|---|---|---|---|---|---|---|---|---|
| Ala | Ala | Lys | Asp | Tyr | Gly | His | Pro | Glu | Asp | Lys | Thr | Pro | Pro | Leu | Thr |
| | | | | 530 | | | | | 535 | | | | | 540 | |

3019

| | | | | | | | | | | | | | | | | |
|---|---|---|---|---|---|---|---|---|---|---|---|---|---|---|---|---|
| TTA | AAA | GAT | ACC | CTG | AAG | CTT | TCA | TAC | CCA | GAT | GAA | ATA | AAA | GAA | ACT | 3067 |
| Leu | Lys | Asp | Thr | Leu | Lys | Leu | Ser | Tyr | Pro | Asp | Glu | Ile | Lys | Glu | Thr | |
| | | | 545 | | | | 550 | | | | | 555 | | | | |
| AAT | GGA | TTG | TTG | TAC | TAT | GAT | GAC | AAA | CCA | ATC | TAT | GAA | TCG | AGT | GTC | 3115 |
| Asn | Gly | Leu | Leu | Tyr | Tyr | Asp | Asp | Lys | Pro | Ile | Tyr | Glu | Ser | Ser | Val | |
| 560 | | | | | | 565 | | | | | 570 | | | | | |
| ATG | ACT | TAT | CTG | GAT | GAA | AAT | ACG | GCA | AAA | GAA | GTC | AAA | AAA | CAA | ATA | 3163 |
| Met | Thr | Tyr | Leu | Asp | Glu | Asn | Thr | Ala | Lys | Glu | Val | Lys | Lys | Gln | Ile | |
| 575 | | | | | 580 | | | | | 585 | | | | | 590 | |
| AAT | GAT | ACA | ACC | GGA | AAA | TTT | AAG | GAT | GTA | AAT | CAC | TTA | TAT | GAT | GTA | 3211 |
| Asn | Asp | Thr | Thr | Gly | Lys | Phe | Lys | Asp | Val | Asn | His | Leu | Tyr | Asp | Val | |
| | | | | 595 | | | | | 600 | | | | | 605 | | |
| AAA | CTG | ACT | CCA | AAA | ATG | AAT | TTT | ACG | ATT | AAA | ATG | GCT | TCC | TTG | TAT | 3259 |
| Lys | Leu | Thr | Pro | Lys | Met | Asn | Phe | Thr | Ile | Lys | Met | Ala | Ser | Leu | Tyr | |
| | | | 610 | | | | 615 | | | | | 620 | | | | |
| GAT | GGG | GCT | GAA | AAT | AAT | CAT | AAC | TCT | TTA | GGA | ACC | TGG | TAT | TTA | ACA | 3307 |
| Asp | Gly | Ala | Glu | Asn | Asn | His | Asn | Ser | Leu | Gly | Thr | Trp | Tyr | Leu | Thr | |
| | | 625 | | | | | 630 | | | | | 635 | | | | |
| TAT | AAT | GTT | GCT | GGT | GGA | AAT | ACT | GGG | AAG | AGA | CAA | TAT | CGT | TCA | GCT | 3355 |
| Tyr | Asn | Val | Ala | Gly | Gly | Asn | Thr | Gly | Lys | Arg | Gln | Tyr | Arg | Ser | Ala | |
| 640 | | | | | 645 | | | | | 650 | | | | | | |
| CAT | TCT | TGT | GCA | CAT | GTA | GCT | CTA | TCT | TCA | GAA | GCG | AAA | AAG | AAA | CTA | 3403 |
| His | Ser | Cys | Ala | His | Val | Ala | Leu | Ser | Ser | Glu | Ala | Lys | Lys | Lys | Leu | |
| 655 | | | | 660 | | | | | 665 | | | | | 670 | | |
| AAT | CAA | AAT | GCG | AAT | TAC | TAT | CTT | AGC | ATG | TAT | ATG | AAG | GCT | GAT | TCT | 3451 |
| Asn | Gln | Asn | Ala | Asn | Tyr | Tyr | Leu | Ser | Met | Tyr | Met | Lys | Ala | Asp | Ser | |
| | | | | 675 | | | | | 680 | | | | | 685 | | |
| ACT | ACG | GAA | CCT | ACA | ATA | GAA | GTA | GCT | GGG | GAA | AAA | TCT | GCA | ATA | ACA | 3499 |
| Thr | Thr | Glu | Pro | Thr | Ile | Glu | Val | Ala | Gly | Glu | Lys | Ser | Ala | Ile | Thr | |
| | | | 690 | | | | | 695 | | | | | 700 | | | |
| AGT | AAA | AAA | GTA | AAA | TTA | AAT | AAT | CAA | AAT | TAT | CAA | AGA | GTT | GAT | ATT | 3547 |
| Ser | Lys | Lys | Val | Lys | Leu | Asn | Asn | Gln | Asn | Tyr | Gln | Arg | Val | Asp | Ile | |
| | | 705 | | | | | 710 | | | | | 715 | | | | |
| TTA | GTG | AAA | AAT | TCT | GAA | AGA | AAT | CCA | ATG | GAT | AAA | ATA | TAT | ATA | AGA | 3595 |
| Leu | Val | Lys | Asn | Ser | Glu | Arg | Asn | Pro | Met | Asp | Lys | Ile | Tyr | Ile | Arg | |
| | 720 | | | | | 725 | | | | | 730 | | | | | |
| GGA | AAT | GGC | ACG | ACA | AAT | GTT | TAT | GGG | GAT | GAT | GTT | ACT | ATC | CCA | GAG | 3643 |
| Gly | Asn | Gly | Thr | Thr | Asn | Val | Tyr | Gly | Asp | Asp | Val | Thr | Ile | Pro | Glu | |
| 735 | | | | | 740 | | | | | 745 | | | | | 750 | |
| GTA | TCA | GCT | ATA | AAT | CCG | GCT | AGT | CTA | TCA | GAT | GAA | GAA | ATT | CAA | GAA | 3691 |
| Val | Ser | Ala | Ile | Asn | Pro | Ala | Ser | Leu | Ser | Asp | Glu | Glu | Ile | Gln | Glu | |
| | | | | 755 | | | | | 760 | | | | | 765 | | |
| ATA | TTT | AAA | GAC | TCA | ACT | ATT | GAA | TAT | GGA | AAT | CCT | AGT | TTC | GTT | GCT | 3739 |
| Ile | Phe | Lys | Asp | Ser | Thr | Ile | Glu | Tyr | Gly | Asn | Pro | Ser | Phe | Val | Ala | |
| | | | 770 | | | | | 775 | | | | | 780 | | | |
| GAT | GCC | GTA | ACA | TTT | AAA | AAT | ATA | AAA | CCT | TTA | CAA | AAT | TAT | GTA | AAG | 3787 |
| Asp | Ala | Val | Thr | Phe | Lys | Asn | Ile | Lys | Pro | Leu | Gln | Asn | Tyr | Val | Lys | |
| | | 785 | | | | | 790 | | | | | 795 | | | | |
| GAA | TAT | GAA | ATA | TAT | CAT | AAA | TCT | CAT | CGA | TAT | GAA | AAG | AAA | ACG | GTC | 3835 |
| Glu | Tyr | Glu | Ile | Tyr | His | Lys | Ser | His | Arg | Tyr | Glu | Lys | Lys | Thr | Val | |
| | 800 | | | | | 805 | | | | | 810 | | | | | |
| TTT | GAT | ATC | ATG | GGT | GTT | CAT | TAT | GAG | TAT | AGT | ATA | GCT | AGG | GAA | CAA | 3883 |
| Phe | Asp | Ile | Met | Gly | Val | His | Tyr | Glu | Tyr | Ser | Ile | Ala | Arg | Glu | Gln | |
| 815 | | | | 820 | | | | | 825 | | | | | 830 | | |

| | | | | | | |
|---|---|---|---|---|---|---|
| AAG | AAA | GCC | GCA | TAATTTTAAA AATAAACTC GTTAGAGTTT ATTTAGCATG | | 3935 |
| Lys | Lys | Ala | Ala | | | |
| GTATTTTTAA | GAATAATCAA | TATGTTGAAC | CGTTTGTAGC | TGTTTTGGAA | GGGAATTTCA | 3995 |
| TTTTATTTGG | TCTCTTAAGT | TGATGGGCAT | GGGATATGTT | CAGCATCCAA | GCGTTTNGGG | 4055 |
| GGTTANAAAA | TCCAATTTT | | | | | 4074 |

( 2 ) INFORMATION FOR SEQ ID NO:20:

( i ) SEQUENCE CHARACTERISTICS:
        ( A ) LENGTH: 462 amino acids
        ( B ) TYPE: amino acid
        ( D ) TOPOLOGY: linear ( i i ) MOLECULE TYPE: protein ( x i ) SEQUENCE DESCRIPTION: SEQ ID NO:20:

```
Met Gln Arg Met Glu Gly Lys Leu Phe Val Val Ser Lys Thr Leu Gln
 1               5                  10                 15
Val Val Thr Arg Thr Val Leu Leu Ser Thr Val Tyr Ser Ile Thr Leu
            20                  25                 30
Leu Asn Asn Val Val Ile Lys Ala Asp Gln Leu Asn Ile Asn Ser Gln
                35                  40                 45
Ser Lys Tyr Thr Asn Leu Gln Asn Leu Lys Ile Pro Asp Asn Ala Glu
        50                  55                 60
Asp Phe Lys Glu Asp Lys Gly Lys Ala Lys Glu Trp Gly Lys Glu Lys
65                  70                 75                     80
Gly Glu Glu Trp Arg Pro Pro Ala Thr Glu Lys Gly Glu Met Asn Asn
                85                  90                 95
Phe Leu Asp Asn Lys Asn Asp Ile Lys Thr Asn Tyr Lys Glu Ile Thr
                100                 105                110
Phe Ser Met Ala Gly Ser Cys Glu Asp Glu Ile Lys Asp Leu Glu Glu
            115                 120                125
Ile Asp Lys Ile Phe Asp Lys Ala Asn Leu Ser Ser Ser Ile Ile Thr
        130                 135                140
Tyr Lys Asn Val Glu Pro Ala Thr Ile Gly Phe Asn Lys Ser Leu Thr
145                 150                155                    160
Glu Gly Asn Thr Ile Asn Ser Asp Ala Met Ala Gln Phe Lys Glu Gln
                165                 170                175
Phe Leu Gly Lys Asp Met Lys Phe Asp Ser Tyr Leu Asp Thr His Leu
            180                 185                190
Thr Ala Gln Gln Val Ser Ser Lys Lys Arg Val Ile Leu Lys Val Thr
        195                 200                205
Val Pro Ser Gly Lys Gly Ser Thr Thr Pro Thr Lys Ala Gly Val Ile
    210                 215                220
Leu Asn Asn Asn Glu Tyr Lys Met Leu Ile Asp Asn Gly Tyr Val Leu
225                 230                 235                   240
His Val Asp Lys Val Ser Lys Val Val Lys Lys Gly Met Glu Cys Leu
                245                 250                255
Gln Val Glu Gly Thr Leu Lys Lys Ser Leu Asp Phe Lys Asn Asp Ile
            260                 265                270
Asn Ala Glu Ala His Ser Trp Gly Met Lys Ile Tyr Glu Asp Trp Ala
        275                 280                285
Lys Asn Leu Thr Ala Ser Gln Arg Glu Ala Leu Asp Gly Tyr Ala Arg
    290                 295                300
Gln Asp Tyr Lys Glu Ile Asn Asn Tyr Leu Arg Asn Gln Gly Gly Ser
305                 310                315                    320
Gly Asn Glu Lys Leu Asp Ala Gln Leu Lys Asn Ile Ser Asp Ala Leu
                325                 330                335
Gly Lys Lys Pro Ile Pro Glu Asn Ile Thr Val Tyr Arg Trp Cys Gly
            340                 345                350
Met Pro Glu Phe Gly Tyr Gln Ile Ser Asp Pro Leu Pro Ser Leu Lys
```

|     |     |     |     | 355 |     |     |     |     | 360 |     |     |     |     | 365 |     |     |     |
| --- | --- | --- | --- | --- | --- | --- | --- | --- | --- | --- | --- | --- | --- | --- | --- | --- | --- |
| Asp | Phe 370 | Glu | Glu | Gln | Phe | Leu 375 | Asn | Thr | Ile | Lys | Glu 380 | Asp | Lys | Gly | Tyr |
| Met 385 | Ser | Thr | Ser | Leu | Ser 390 | Ser | Glu | Arg | Leu | Ala 395 | Ala | Phe | Gly | Ser | Arg 400 |
| Lys | Ile | Ile | Leu | Arg 405 | Leu | Gln | Val | Pro | Lys 410 | Gly | Ser | Thr | Gly | Ala 415 | Tyr |
| Leu | Ser | Ala | Ile 420 | Gly | Gly | Phe | Ala | Ser 425 | Glu | Lys | Glu | Ile | Leu 430 | Leu | Asp |
| Lys | Asp | Ser 435 | Lys | Tyr | His | Ile | Asp 440 | Lys | Ala | Thr | Glu | Val 445 | Ile | Ile | Lys |
| Gly | Val 450 | Lys | Arg | Tyr | Val | Val 455 | Asp | Ala | Thr | Leu | Leu 460 | Thr | Asn |

( 2 ) INFORMATION FOR SEQ ID NO:21:

( i ) SEQUENCE CHARACTERISTICS:
        ( A ) LENGTH: 834 amino acids
        ( B ) TYPE: amino acid
        ( D ) TOPOLOGY: linear ( i i ) MOLECULE TYPE: protein ( x i ) SEQUENCE DESCRIPTION: SEQ ID NO:21:

| Met 1 | Lys | Asn | Met | Lys 5 | Lys | Lys | Leu | Ala | Ser 10 | Val | Val | Thr | Cys | Met 15 | Leu |
| --- | --- | --- | --- | --- | --- | --- | --- | --- | --- | --- | --- | --- | --- | --- | --- |
| Leu | Ala | Pro | Met 20 | Phe | Leu | Asn | Gly | Asn 25 | Val | Asn | Ala | Val | Asn 30 | Ala | Asp |
| Ser | Lys | Ile 35 | Asn | Gln | Ile | Ser | Thr 40 | Thr | Gln | Glu | Asn | Gln 45 | Gln | Lys | Glu |
| Met | Asp 50 | Arg | Lys | Gly | Leu | Leu 55 | Gly | Tyr | Tyr | Phe | Lys 60 | Gly | Lys | Asp | Phe |
| Asn 65 | Asn | Leu | Thr | Met | Phe 70 | Ala | Pro | Thr | Arg | Asp 75 | Asn | Thr | Leu | Met | Tyr 80 |
| Asp | Gln | Gln | Thr | Ala 85 | Asn | Ala | Leu | Leu | Asp 90 | Lys | Lys | Gln | Gln | Glu 95 | Tyr |
| Gln | Ser | Ile | Arg 100 | Trp | Ile | Gly | Leu | Ile 105 | Gln | Arg | Lys | Glu | Thr 110 | Gly | Asp |
| Phe | Thr | Phe 115 | Asn | Leu | Ser | Lys | Asp 120 | Glu | Gln | Ala | Ile | Ile 125 | Glu | Ile | Asp |
| Gly | Lys 130 | Ile | Ile | Ser | Asn | Lys 135 | Gly | Lys | Glu | Lys | Gln 140 | Val | Val | His | Leu |
| Glu | Lys 145 | Glu | Lys | Leu | Val | Pro 150 | Ile | Lys | Ile | Glu | Tyr 155 | Gln | Ser | Asp | Thr 160 |
| Lys | Phe | Asn | Ile | Asp 165 | Ser | Lys | Thr | Phe | Lys 170 | Glu | Leu | Lys | Leu | Phe 175 | Lys |
| Ile | Asp | Ser | Gln 180 | Asn | Gln | Ser | Gln | Gln 185 | Val | Gln | Leu | Arg | Asn 190 | Pro | Glu |
| Phe | Asn | Lys 195 | Lys | Glu | Ser | Gln | Glu 200 | Phe | Leu | Ala | Lys | Ala 205 | Ser | Lys | Thr |
| Asn | Leu 210 | Phe | Lys | Gln | Lys | Met 215 | Lys | Arg | Asp | Ile | Asp 220 | Glu | Asp | Thr | Asp |
| Thr 225 | Asp | Gly | Asp | Ser | Ile 230 | Pro | Asp | Leu | Trp | Glu 235 | Glu | Asn | Gly | Tyr | Thr 240 |
| Ile | Gln | Asn | Lys | Val 245 | Ala | Val | Lys | Trp | Asp 250 | Asp | Ser | Leu | Ala | Ser 255 | Lys |

-continued

| | | | | | | | | | | | | | | |
|---|---|---|---|---|---|---|---|---|---|---|---|---|---|---|
| Gly | Tyr | Thr | Lys 260 | Phe | Val | Ser | Asn 265 | Pro | Leu | Asp | Ser | His | Thr 270 | Val | Gly |
| Asp | Pro | Tyr 275 | Thr | Asp | Tyr | Glu 280 | Lys | Ala | Ala | Arg | Asp 285 | Leu | Asp | Leu | Ser |
| Asn | Ala 290 | Lys | Glu | Thr | Phe | Asn 295 | Pro | Leu | Val | Ala | Ala 300 | Phe | Pro | Ser | Val |
| Asn 305 | Val | Ser | Met | Glu 310 | Lys | Val | Ile | Leu | Ser 315 | Pro | Asn | Glu | Asn | Leu | Ser 320 |
| Asn | Ser | Val | Glu | Ser 325 | His | Ser | Ser | Thr | Asn 330 | Trp | Ser | Tyr | Thr | Asn 335 | Thr |
| Glu | Gly | Ala | Ser 340 | Ile | Glu | Ala | Gly 345 | Gly | Pro | Leu | Gly 350 | Leu | Ser | Phe |
| Gly | Val | Ser 355 | Val | Thr | Tyr | Gln 360 | His | Ser | Glu | Thr | Val 365 | Ala | Gln | Glu | Trp |
| Gly | Thr 370 | Ser | Thr | Gly | Asn | Thr 375 | Ser | Gln | Phe | Asn | Thr 380 | Ala | Ser | Ala | Gly |
| Tyr 385 | Leu | Asn | Ala | Asn | Val 390 | Arg | Tyr | Asn | Asn | Val 395 | Gly | Thr | Gly | Ala | Ile 400 |
| Tyr | Asp | Val | Lys | Pro 405 | Thr | Thr | Ser | Phe | Val 410 | Leu | Asn | Asn | Asn | Thr 415 | Ile |
| Ala | Thr | Ile | Thr 420 | Ala | Lys | Ser | Asn | Ser 425 | Thr | Ala | Leu | Arg | Ile 430 | Ser | Pro |
| Gly | Asp | Ser 435 | Tyr | Pro | Glu | Ile | Gly 440 | Glu | Asn | Ala | Ile | Ala 445 | Ile | Thr | Ser |
| Met | Asp 450 | Asp | Phe | Asn | Ser | His 455 | Pro | Ile | Thr | Leu | Asn 460 | Lys | Gln | Gln | Val |
| Asn 465 | Gln | Leu | Ile | Asn | Asn 470 | Lys | Pro | Ile | Met | Leu 475 | Glu | Thr | Asp | Gln | Thr 480 |
| Asp | Gly | Val | Tyr | Lys 485 | Ile | Arg | Asp | Thr | His 490 | Gly | Asn | Ile | Val | Thr 495 | Gly |
| Gly | Glu | Trp | Asn 500 | Gly | Val | Thr | Gln 505 | Gln | Ile | Lys | Ala | Lys 510 | Thr | Ala | Ser |
| Ile | Ile | Val | Asp 515 | Asp | Gly | Lys | Gln 520 | Val | Ala | Glu | Lys | Arg 525 | Val | Ala | Ala |
| Lys | Asp 530 | Tyr | Gly | His | Pro | Glu 535 | Asp | Lys | Thr | Pro | Pro 540 | Leu | Thr | Leu | Lys |
| Asp 545 | Thr | Leu | Lys | Leu | Ser 550 | Tyr | Pro | Asp | Glu | Ile 555 | Lys | Glu | Thr | Asn | Gly 560 |
| Leu | Leu | Tyr | Tyr | Asp 565 | Asp | Lys | Pro | Ile | Tyr 570 | Glu | Ser | Ser | Val | Met 575 | Thr |
| Tyr | Leu | Asp | Glu 580 | Asn | Thr | Ala | Lys | Glu 585 | Val | Lys | Lys | Gln | Ile 590 | Asn | Asp |
| Thr | Thr | Gly 595 | Lys | Phe | Lys | Asp | Val 600 | Asn | His | Leu | Tyr | Asp 605 | Val | Lys | Leu |
| Thr | Pro 610 | Lys | Met | Asn | Phe | Thr 615 | Ile | Lys | Met | Ala | Ser 620 | Leu | Tyr | Asp | Gly |
| Ala 625 | Glu | Asn | Asn | His | Asn 630 | Ser | Leu | Gly | Thr | Trp 635 | Tyr | Leu | Thr | Tyr | Asn 640 |
| Val | Ala | Gly | Gly | Asn 645 | Thr | Gly | Lys | Arg | Gln 650 | Tyr | Arg | Ser | Ala | His 655 | Ser |
| Cys | Ala | His | Val 660 | Ala | Leu | Ser | Ser | Glu 665 | Ala | Lys | Lys | Lys | Leu 670 | Asn | Gln |
| Asn | Ala | Asn | Tyr 675 | Tyr | Leu | Ser | Met 680 | Tyr | Met | Lys | Ala | Asp 685 | Ser | Thr | Thr |

| Glu | Pro | Thr | Ile | Glu | Val | Ala | Gly | Glu | Lys | Ser | Ala | Ile | Thr | Ser | Lys |
|---|---|---|---|---|---|---|---|---|---|---|---|---|---|---|---|
|  | 690 |  |  |  | 695 |  |  |  |  |  | 700 |  |  |  |  |

| Lys | Val | Lys | Leu | Asn | Asn | Gln | Asn | Tyr | Gln | Arg | Val | Asp | Ile | Leu | Val |
|---|---|---|---|---|---|---|---|---|---|---|---|---|---|---|---|
| 705 |  |  |  |  | 710 |  |  |  |  | 715 |  |  |  |  | 720 |

| Lys | Asn | Ser | Glu | Arg | Asn | Pro | Met | Asp | Lys | Ile | Tyr | Ile | Arg | Gly | Asn |
|---|---|---|---|---|---|---|---|---|---|---|---|---|---|---|---|
|  |  |  |  | 725 |  |  |  |  | 730 |  |  |  |  | 735 |  |

| Gly | Thr | Thr | Asn | Val | Tyr | Gly | Asp | Asp | Val | Thr | Ile | Pro | Glu | Val | Ser |
|---|---|---|---|---|---|---|---|---|---|---|---|---|---|---|---|
|  |  |  | 740 |  |  |  |  | 745 |  |  |  |  | 750 |  |  |

| Ala | Ile | Asn | Pro | Ala | Ser | Leu | Ser | Asp | Glu | Glu | Ile | Gln | Glu | Ile | Phe |
|---|---|---|---|---|---|---|---|---|---|---|---|---|---|---|---|
|  |  | 755 |  |  |  |  | 760 |  |  |  |  | 765 |  |  |  |

| Lys | Asp | Ser | Thr | Ile | Glu | Tyr | Gly | Asn | Pro | Ser | Phe | Val | Ala | Asp | Ala |
|---|---|---|---|---|---|---|---|---|---|---|---|---|---|---|---|
|  | 770 |  |  |  |  | 775 |  |  |  |  | 780 |  |  |  |  |

| Val | Thr | Phe | Lys | Asn | Ile | Lys | Pro | Leu | Gln | Asn | Tyr | Val | Lys | Glu | Tyr |
|---|---|---|---|---|---|---|---|---|---|---|---|---|---|---|---|
| 785 |  |  |  |  | 790 |  |  |  |  | 795 |  |  |  |  | 800 |

| Glu | Ile | Tyr | His | Lys | Ser | His | Arg | Tyr | Glu | Lys | Lys | Thr | Val | Phe | Asp |
|---|---|---|---|---|---|---|---|---|---|---|---|---|---|---|---|
|  |  |  |  | 805 |  |  |  |  | 810 |  |  |  |  | 815 |  |

| Ile | Met | Gly | Val | His | Tyr | Glu | Tyr | Ser | Ile | Ala | Arg | Glu | Gln | Lys | Lys |
|---|---|---|---|---|---|---|---|---|---|---|---|---|---|---|---|
|  |  |  | 820 |  |  |  |  | 825 |  |  |  |  | 830 |  |  |

| Ala | Ala |
|---|---|

( 2 ) INFORMATION FOR SEQ ID NO:22:

( i ) SEQUENCE CHARACTERISTICS:
        ( A ) LENGTH: 4041 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..4038
        ( D ) OTHER INFORMATION: /product="VIP1A(a)/VIP2A(a) fusion product"

( x i ) SEQUENCE DESCRIPTION: SEQ ID NO:22:

ATG AAA AGA ATG GAG GGA AAG TTG TTT ATG GTG TCA AAA AAA TTA CAA 48
Met Lys Arg Met Glu Gly Lys Leu Phe Met Val Ser Lys Lys Leu Gln
835 840 845 850

GTA GTT ACT AAA ACT GTA TTG CTT AGT ACA GTT TTC TCT ATA TCT TTA 96
Val Val Thr Lys Thr Val Leu Leu Ser Thr Val Phe Ser Ile Ser Leu
855 860 865

TTA AAT AAT GAA GTG ATA AAA GCT GAA CAA TTA AAT ATA AAT TCT CAA 144
Leu Asn Asn Glu Val Ile Lys Ala Glu Gln Leu Asn Ile Asn Ser Gln
870 875 880

AGT AAA TAT ACT AAC TTG CAA AAT CTA AAA ATC ACT GAC AAG GTA GAG 192
Ser Lys Tyr Thr Asn Leu Gln Asn Leu Lys Ile Thr Asp Lys Val Glu
885 890 895

GAT TTT AAA GAA GAT AAG GAA AAA GCG AAA GAA TGG GGG AAA GAA AAA 240
Asp Phe Lys Glu Asp Lys Glu Lys Ala Lys Glu Trp Gly Lys Glu Lys
900 905 910

GAA AAA GAG TGG AAA CTA ACT GCT ACT GAA AAA GGA AAA ATG AAT AAT 288
Glu Lys Glu Trp Lys Leu Thr Ala Thr Glu Lys Gly Lys Met Asn Asn
915 920 925 930

TTT TTA GAT AAT AAA AAT GAT ATA AAG ACA AAT TAT AAA GAA ATT ACT 336
Phe Leu Asp Asn Lys Asn Asp Ile Lys Thr Asn Tyr Lys Glu Ile Thr
935 940 945

TTT TCT ATG GCA GGC TCA TTT GAA GAT GAA ATA AAA GAT TTA AAA GAA 384
Phe Ser Met Ala Gly Ser Phe Glu Asp Glu Ile Lys Asp Leu Lys Glu
950 955 960

```
ATT GAT AAG ATG TTT GAT AAA ACC AAT CTA TCA AAT TCT ATT ATC ACC        432
Ile Asp Lys Met Phe Asp Lys Thr Asn Leu Ser Asn Ser Ile Ile Thr
    965                 970                 975

TAT AAA AAT GTG GAA CCG ACA ACA ATT GGA TTT AAT AAA TCT TTA ACA        480
Tyr Lys Asn Val Glu Pro Thr Thr Ile Gly Phe Asn Lys Ser Leu Thr
    980                 985                 990

GAA GGT AAT ACG ATT AAT TCT GAT GCA ATG GCA CAG TTT AAA GAA CAA        528
Glu Gly Asn Thr Ile Asn Ser Asp Ala Met Ala Gln Phe Lys Glu Gln
995                 1000                1005                1010

TTT TTA GAT AGG GAT ATT AAG TTT GAT AGT TAT CTA GAT ACG CAT TTA        576
Phe Leu Asp Arg Asp Ile Lys Phe Asp Ser Tyr Leu Asp Thr His Leu
                1015                1020                1025

ACT GCT CAA CAA GTT TCC AGT AAA GAA AGA GTT ATT TTG AAG GTT ACG        624
Thr Ala Gln Gln Val Ser Ser Lys Glu Arg Val Ile Leu Lys Val Thr
                1030                1035                1040

GTT CCG AGT GGG AAA GGT TCT ACT ACT CCA ACA AAA GCA GGT GTC ATT        672
Val Pro Ser Gly Lys Gly Ser Thr Thr Pro Thr Lys Ala Gly Val Ile
                1045                1050                1055

TTA AAT AAT AGT GAA TAC AAA ATG CTC ATT GAT AAT GGG TAT ATG GTC        720
Leu Asn Asn Ser Glu Tyr Lys Met Leu Ile Asp Asn Gly Tyr Met Val
                1060                1065                1070

CAT GTA GAT AAG GTA TCA AAA GTG GTG AAA AAA GGG GTG GAG TGC TTA        768
His Val Asp Lys Val Ser Lys Val Val Lys Lys Gly Val Glu Cys Leu
1075                1080                1085                1090

CAA ATT GAA GGG ACT TTA AAA AAG AGT CTT GAC TTT AAA AAT GAT ATA        816
Gln Ile Glu Gly Thr Leu Lys Lys Ser Leu Asp Phe Lys Asn Asp Ile
                1095                1100                1105

AAT GCT GAA GCG CAT AGC TGG GGT ATG AAG AAT TAT GAA GAG TGG GCT        864
Asn Ala Glu Ala His Ser Trp Gly Met Lys Asn Tyr Glu Glu Trp Ala
                1110                1115                1120

AAA GAT TTA ACC GAT TCG CAA AGG GAA GCT TTA GAT GGG TAT GCT AGG        912
Lys Asp Leu Thr Asp Ser Gln Arg Glu Ala Leu Asp Gly Tyr Ala Arg
                1125                1130                1135

CAA GAT TAT AAA GAA ATC AAT AAT TAT TTA AGA AAT CAA GGC GGA AGT        960
Gln Asp Tyr Lys Glu Ile Asn Asn Tyr Leu Arg Asn Gln Gly Gly Ser
    1140                1145                1150

GGA AAT GAA AAA CTA GAT GCT CAA ATA AAA AAT ATT TCT GAT GCT TTA       1008
Gly Asn Glu Lys Leu Asp Ala Gln Ile Lys Asn Ile Ser Asp Ala Leu
1155                1160                1165                1170

GGG AAG AAA CCA ATA CCG GAA AAT ATT ACT GTG TAT AGA TGG TGT GGC       1056
Gly Lys Lys Pro Ile Pro Glu Asn Ile Thr Val Tyr Arg Trp Cys Gly
                1175                1180                1185

ATG CCG GAA TTT GGT TAT CAA ATT AGT GAT CCG TTA CCT TCT TTA AAA       1104
Met Pro Glu Phe Gly Tyr Gln Ile Ser Asp Pro Leu Pro Ser Leu Lys
                1190                1195                1200

GAT TTT GAA GAA CAA TTT TTA AAT ACA ATC AAA GAA GAC AAA GGA TAT       1152
Asp Phe Glu Glu Gln Phe Leu Asn Thr Ile Lys Glu Asp Lys Gly Tyr
                1205                1210                1215

ATG AGT ACA AGC TTA TCG AGT GAA CGT CTT GCA GCT TTT GGA TCT AGA       1200
Met Ser Thr Ser Leu Ser Ser Glu Arg Leu Ala Ala Phe Gly Ser Arg
    1220                1225                1230

AAA ATT ATA TTA CGA TTA CAA GTT CCG AAA GGA AGT ACG GGT GCG TAT       1248
Lys Ile Ile Leu Arg Leu Gln Val Pro Lys Gly Ser Thr Gly Ala Tyr
1235                1240                1245                1250

TTA AGT GCC ATT GGT GGA TTT GCA AGT GAA AAA GAG ATC CTA CTT GAT       1296
Leu Ser Ala Ile Gly Gly Phe Ala Ser Glu Lys Glu Ile Leu Leu Asp
                1255                1260                1265

AAA GAT AGT AAA TAT CAT ATT GAT AAA GTA ACA GAG GTA ATT ATT AAA       1344
Lys Asp Ser Lys Tyr His Ile Asp Lys Val Thr Glu Val Ile Ile Lys
                1270                1275                1280
```

```
GGT GTT AAG CGA TAT GTA GTG GAT GCA ACA TTA TTA ACA AAT ATG AAA    1392
Gly Val Lys Arg Tyr Val Val Asp Ala Thr Leu Leu Thr Asn Met Lys
1285                1290                1295

AAT ATG AAG AAA AAG TTA GCA AGT GTT GTA ACG TGT ACG TTA TTA GCT    1440
Asn Met Lys Lys Lys Leu Ala Ser Val Val Thr Cys Thr Leu Leu Ala
    1300                1305                1310

CCT ATG TTT TTG AAT GGA AAT GTG AAT GCT GTT TAC GCA GAC AGC AAA    1488
Pro Met Phe Leu Asn Gly Asn Val Asn Ala Val Tyr Ala Asp Ser Lys
1315                1320                1325                1330

ACA AAT CAA ATT TCT ACA ACA CAG AAA AAT CAA CAG AAA GAG ATG GAC    1536
Thr Asn Gln Ile Ser Thr Thr Gln Lys Asn Gln Gln Lys Glu Met Asp
        1335                1340                1345

CGA AAA GGA TTA CTT GGG TAT TAT TTC AAA GGA AAA GAT TTT AGT AAT    1584
Arg Lys Gly Leu Leu Gly Tyr Tyr Phe Lys Gly Lys Asp Phe Ser Asn
            1350                1355                1360

CTT ACT ATG TTT GCA CCG ACA CGT GAT AGT ACT CTT ATT TAT GAT CAA    1632
Leu Thr Met Phe Ala Pro Thr Arg Asp Ser Thr Leu Ile Tyr Asp Gln
                1365                1370                1375

CAA ACA GCA AAT AAA CTA TTA GAT AAA AAA CAA CAA GAA TAT CAG TCT    1680
Gln Thr Ala Asn Lys Leu Leu Asp Lys Lys Gln Gln Glu Tyr Gln Ser
1380                1385                1390

ATT CGT TGG ATT GGT TTG ATT CAG AGT AAA GAA ACG GGA GAT TTC ACA    1728
Ile Arg Trp Ile Gly Leu Ile Gln Ser Lys Glu Thr Gly Asp Phe Thr
1395                1400                1405                1410

TTT AAC TTA TCT GAG GAT GAA CAG GCA ATT ATA GAA ATC AAT GGG AAA    1776
Phe Asn Leu Ser Glu Asp Glu Gln Ala Ile Ile Glu Ile Asn Gly Lys
                1415                1420                1425

ATT ATT TCT AAT AAA GGG AAA GAA AAG CAA GTT GTC CAT TTA GAA AAA    1824
Ile Ile Ser Asn Lys Gly Lys Glu Lys Gln Val Val His Leu Glu Lys
            1430                1435                1440

GGA AAA TTA GTT CCA ATC AAA ATA GAG TAT CAA TCA GAT ACA AAA TTT    1872
Gly Lys Leu Val Pro Ile Lys Ile Glu Tyr Gln Ser Asp Thr Lys Phe
        1445                1450                1455

AAT ATT GAC AGT AAA ACA TTT AAA GAA CTT AAA TTA TTT AAA ATA GAT    1920
Asn Ile Asp Ser Lys Thr Phe Lys Glu Leu Lys Leu Phe Lys Ile Asp
    1460                1465                1470

AGT CAA AAC CAA CCC CAG CAA GTC CAG CAA GAT GAA CTG AGA AAT CCT    1968
Ser Gln Asn Gln Pro Gln Gln Val Gln Gln Asp Glu Leu Arg Asn Pro
1475                1480                1485                1490

GAA TTT AAC AAG AAA GAA TCA CAG GAA TTC TTA GCG AAA CCA TCG AAA    2016
Glu Phe Asn Lys Lys Glu Ser Gln Glu Phe Leu Ala Lys Pro Ser Lys
                1495                1500                1505

ATA AAT CTT TTC ACT CAA AAA ATG AAA AGG GAA ATT GAT GAA GAC ACG    2064
Ile Asn Leu Phe Thr Gln Lys Met Lys Arg Glu Ile Asp Glu Asp Thr
            1510                1515                1520

GAT ACG GAT GGG GAC TCT ATT CCT GAC CTT TGG GAA GAA AAT GGG TAT    2112
Asp Thr Asp Gly Asp Ser Ile Pro Asp Leu Trp Glu Glu Asn Gly Tyr
        1525                1530                1535

ACG ATT CAA AAT AGA ATC GCT GTA AAG TGG GAC GAT TCT CTA GCA AGT    2160
Thr Ile Gln Asn Arg Ile Ala Val Lys Trp Asp Asp Ser Leu Ala Ser
    1540                1545                1550

AAA GGG TAT ACG AAA TTT GTT TCA AAT CCA CTA GAA AGT CAC ACA GTT    2208
Lys Gly Tyr Thr Lys Phe Val Ser Asn Pro Leu Glu Ser His Thr Val
1555                1560                1565                1570

GGT GAT CCT TAT ACA GAT TAT GAA AAG GCA GCA AGA GAT CTA GAT TTG    2256
Gly Asp Pro Tyr Thr Asp Tyr Glu Lys Ala Ala Arg Asp Leu Asp Leu
                1575                1580                1585

TCA AAT GCA AAG GAA ACG TTT AAC CCA TTG GTA GCT GCT TTT CCA AGT    2304
Ser Asn Ala Lys Glu Thr Phe Asn Pro Leu Val Ala Ala Phe Pro Ser
            1590                1595                1600
```

```
GTG AAT GTT AGT ATG GAA AAG GTG ATA TTA TCA CCA AAT GAA AAT TTA     2352
Val Asn Val Ser Met Glu Lys Val Ile Leu Ser Pro Asn Glu Asn Leu
         1605                1610                1615

TCC AAT AGT GTA GAG TCT CAT TCA TCC ACG AAT TGG TCT TAT ACA AAT     2400
Ser Asn Ser Val Glu Ser His Ser Ser Thr Asn Trp Ser Tyr Thr Asn
1620                1625                1630

ACA GAA GGT GCT TCT GTT GAA GCG GGG ATT GGA CCA AAA GGT ATT TCG     2448
Thr Glu Gly Ala Ser Val Glu Ala Gly Ile Gly Pro Lys Gly Ile Ser
1635                1640                1645                1650

TTC GGA GTT AGC GTA AAC TAT CAA CAC TCT GAA ACA GTT GCA CAA GAA     2496
Phe Gly Val Ser Val Asn Tyr Gln His Ser Glu Thr Val Ala Gln Glu
             1655                1660                1665

TGG GGA ACA TCT ACA GGA AAT ACT TCG CAA TTC AAT ACG GCT TCA GCG     2544
Trp Gly Thr Ser Thr Gly Asn Thr Ser Gln Phe Asn Thr Ala Ser Ala
         1670                1675                1680

GGA TAT TTA AAT GCA AAT GTT CGA TAT AAC AAT GTA GGA ACT GGT GCC     2592
Gly Tyr Leu Asn Ala Asn Val Arg Tyr Asn Asn Val Gly Thr Gly Ala
         1685                1690                1695

ATC TAC GAT GTA AAA CCT ACA ACA AGT TTT GTA TTA AAT AAC GAT ACT     2640
Ile Tyr Asp Val Lys Pro Thr Thr Ser Phe Val Leu Asn Asn Asp Thr
         1700                1705                1710

ATC GCA ACT ATT ACG GCG AAA TCT AAT TCT ACA GCC TTA AAT ATA TCT     2688
Ile Ala Thr Ile Thr Ala Lys Ser Asn Ser Thr Ala Leu Asn Ile Ser
1715                1720                1725                1730

CCT GGA GAA AGT TAC CCG AAA AAA GGA CAA AAT GGA ATC GCA ATA ACA     2736
Pro Gly Glu Ser Tyr Pro Lys Lys Gly Gln Asn Gly Ile Ala Ile Thr
             1735                1740                1745

TCA ATG GAT GAT TTT AAT TCC CAT CCG ATT ACA TTA AAT AAA AAA CAA     2784
Ser Met Asp Asp Phe Asn Ser His Pro Ile Thr Leu Asn Lys Lys Gln
         1750                1755                1760

GTA GAT AAT CTG CTA AAT AAT AAA CCT ATG ATG TTG GAA ACA AAC CAA     2832
Val Asp Asn Leu Leu Asn Asn Lys Pro Met Met Leu Glu Thr Asn Gln
         1765                1770                1775

ACA GAT GGT GTT TAT AAG ATA AAA GAT ACA CAT GGA AAT ATA GTA ACT     2880
Thr Asp Gly Val Tyr Lys Ile Lys Asp Thr His Gly Asn Ile Val Thr
         1780                1785                1790

GGC GGA GAA TGG AAT GGT GTC ATA CAA CAA ATC AAG GCT AAA ACA GCG     2928
Gly Gly Glu Trp Asn Gly Val Ile Gln Gln Ile Lys Ala Lys Thr Ala
1795                1800                1805                1810

TCT ATT ATT GTG GAT GAT GGG GAA CGT GTA GCA GAA AAA CGT GTA GCG     2976
Ser Ile Ile Val Asp Asp Gly Glu Arg Val Ala Glu Lys Arg Val Ala
             1815                1820                1825

GCA AAA GAT TAT GAA AAT CCA GAA GAT AAA ACA CCG TCT TTA ACT TTA     3024
Ala Lys Asp Tyr Glu Asn Pro Glu Asp Lys Thr Pro Ser Leu Thr Leu
         1830                1835                1840

AAA GAT GCC CTG AAG CTT TCA TAT CCA GAT GAA ATA AAA GAA ATA GAG     3072
Lys Asp Ala Leu Lys Leu Ser Tyr Pro Asp Glu Ile Lys Glu Ile Glu
         1845                1850                1855

GGA TTA TTA TAT TAT AAA AAC AAA CCG ATA TAC GAA TCG AGC GTT ATG     3120
Gly Leu Leu Tyr Tyr Lys Asn Lys Pro Ile Tyr Glu Ser Ser Val Met
1860                1865                1870

ACT TAC TTA GAT GAA AAT ACA GCA AAA GAA GTG ACC AAA CAA TTA AAT     3168
Thr Tyr Leu Asp Glu Asn Thr Ala Lys Glu Val Thr Lys Gln Leu Asn
1875                1880                1885                1890

GAT ACC ACT GGG AAA TTT AAA GAT GTA AGT CAT TTA TAT GAT GTA AAA     3216
Asp Thr Thr Gly Lys Phe Lys Asp Val Ser His Leu Tyr Asp Val Lys
             1895                1900                1905

CTG ACT CCA AAA ATG AAT GTT ACA ATC AAA TTG TCT ATA CTT TAT GAT     3264
Leu Thr Pro Lys Met Asn Val Thr Ile Lys Leu Ser Ile Leu Tyr Asp
         1910                1915                1920
```

| | | | | | | | | | | | | | | | |
|---|---|---|---|---|---|---|---|---|---|---|---|---|---|---|---|
| AAT | GCT | GAG | TCT | AAT | GAT | AAC | TCA | ATT | GGT | AAA | TGG | ACA | AAC | ACA | AAT | 3312 |
| Asn | Ala | Glu | Ser | Asn | Asp | Asn | Ser | Ile | Gly | Lys | Trp | Thr | Asn | Thr | Asn | |
| | | | 1925 | | | | 1930 | | | | | 1935 | | | | |
| ATT | GTT | TCA | GGT | GGA | AAT | AAC | GGA | AAA | AAA | CAA | TAT | TCT | TCT | AAT | AAT | 3360 |
| Ile | Val | Ser | Gly | Gly | Asn | Asn | Gly | Lys | Lys | Gln | Tyr | Ser | Ser | Asn | Asn | |
| | | | 1940 | | | | 1945 | | | | | 1950 | | | | |
| CCG | GAT | GCT | AAT | TTG | ACA | TTA | AAT | ACA | GAT | GCT | CAA | GAA | AAA | TTA | AAT | 3408 |
| Pro | Asp | Ala | Asn | Leu | Thr | Leu | Asn | Thr | Asp | Ala | Gln | Glu | Lys | Leu | Asn | |
| 1955 | | | | | 1960 | | | | | 1965 | | | | | 1970 | |
| AAA | AAT | CGT | GAC | TAT | TAT | ATA | AGT | TTA | TAT | ATG | AAG | TCA | GAA | AAA | AAC | 3456 |
| Lys | Asn | Arg | Asp | Tyr | Tyr | Ile | Ser | Leu | Tyr | Met | Lys | Ser | Glu | Lys | Asn | |
| | | | | 1975 | | | | 1980 | | | | | 1985 | | | |
| ACA | CAA | TGT | GAG | ATT | ACT | ATA | GAT | GGG | GAG | ATT | TAT | CCG | ATC | ACT | ACA | 3504 |
| Thr | Gln | Cys | Glu | Ile | Thr | Ile | Asp | Gly | Glu | Ile | Tyr | Pro | Ile | Thr | Thr | |
| | | | 1990 | | | | | 1995 | | | | | 2000 | | | |
| AAA | ACA | GTG | AAT | GTG | AAT | AAA | GAC | AAT | TAC | AAA | AGA | TTA | GAT | ATT | ATA | 3552 |
| Lys | Thr | Val | Asn | Val | Asn | Lys | Asp | Asn | Tyr | Lys | Arg | Leu | Asp | Ile | Ile | |
| | | | 2005 | | | | 2010 | | | | | 2015 | | | | |
| GCT | CAT | AAT | ATA | AAA | AGT | AAT | CCA | ATT | TCT | TCA | CTT | CAT | ATT | AAA | ACG | 3600 |
| Ala | His | Asn | Ile | Lys | Ser | Asn | Pro | Ile | Ser | Ser | Leu | His | Ile | Lys | Thr | |
| | | 2020 | | | | | 2025 | | | | | 2030 | | | | |
| AAT | GAT | GAA | ATA | ACT | TTA | TTT | TGG | GAT | GAT | ATT | TCT | ATA | ACA | GAT | GTA | 3648 |
| Asn | Asp | Glu | Ile | Thr | Leu | Phe | Trp | Asp | Asp | Ile | Ser | Ile | Thr | Asp | Val | |
| 2035 | | | | | 2040 | | | | | 2045 | | | | | 2050 | |
| GCA | TCA | ATA | AAA | CCG | GAA | AAT | TTA | ACA | GAT | TCA | GAA | ATT | AAA | CAG | ATT | 3696 |
| Ala | Ser | Ile | Lys | Pro | Glu | Asn | Leu | Thr | Asp | Ser | Glu | Ile | Lys | Gln | Ile | |
| | | | | 2055 | | | | | 2060 | | | | | 2065 | | |
| TAT | AGT | AGG | TAT | GGT | ATT | AAG | TTA | GAA | GAT | GGA | ATC | CTT | ATT | GAT | AAA | 3744 |
| Tyr | Ser | Arg | Tyr | Gly | Ile | Lys | Leu | Glu | Asp | Gly | Ile | Leu | Ile | Asp | Lys | |
| | | | 2070 | | | | | 2075 | | | | | 2080 | | | |
| AAA | GGT | GGG | ATT | CAT | TAT | GGT | GAA | TTT | ATT | AAT | GAA | GCT | AGT | TTT | AAT | 3792 |
| Lys | Gly | Gly | Ile | His | Tyr | Gly | Glu | Phe | Ile | Asn | Glu | Ala | Ser | Phe | Asn | |
| | | | 2085 | | | | | 2090 | | | | | 2095 | | | |
| ATT | GAA | CCA | TTG | CAA | AAT | TAT | GTG | ACC | AAA | TAT | GAA | GTT | ACT | TAT | AGT | 3840 |
| Ile | Glu | Pro | Leu | Gln | Asn | Tyr | Val | Thr | Lys | Tyr | Glu | Val | Thr | Tyr | Ser | |
| | | | 2100 | | | | | 2105 | | | | | 2110 | | | |
| AGT | GAG | TTA | GGA | CCA | AAC | GTG | AGT | GAC | ACA | CTT | GAA | AGT | GAT | AAA | ATT | 3888 |
| Ser | Glu | Leu | Gly | Pro | Asn | Val | Ser | Asp | Thr | Leu | Glu | Ser | Asp | Lys | Ile | |
| 2115 | | | | | 2120 | | | | | 2125 | | | | | 2130 | |
| TAC | AAG | GAT | GGG | ACA | ATT | AAA | TTT | GAT | TTT | ACC | AAA | TAT | AGT | AAA | AAT | 3936 |
| Tyr | Lys | Asp | Gly | Thr | Ile | Lys | Phe | Asp | Phe | Thr | Lys | Tyr | Ser | Lys | Asn | |
| | | | | 2135 | | | | 2140 | | | | | | 2145 | | |
| GAA | CAA | GGA | TTA | TTT | TAT | GAC | AGT | GGA | TTA | AAT | TGG | GAC | TTT | AAA | ATT | 3984 |
| Glu | Gln | Gly | Leu | Phe | Tyr | Asp | Ser | Gly | Leu | Asn | Trp | Asp | Phe | Lys | Ile | |
| | | | 2150 | | | | | 2155 | | | | | 2160 | | | |
| AAT | GCT | ATT | ACT | TAT | GAT | GGT | AAA | GAG | ATG | AAT | GTT | TTT | CAT | AGA | TAT | 4032 |
| Asn | Ala | Ile | Thr | Tyr | Asp | Gly | Lys | Glu | Met | Asn | Val | Phe | His | Arg | Tyr | |
| | | | 2165 | | | | | 2170 | | | | | 2175 | | | |
| AAT | AAA | TAG | | | | | | | | | | | | | | 4041 |
| Asn | Lys | | | | | | | | | | | | | | | |
| 2180 | | | | | | | | | | | | | | | | |

( 2 ) INFORMATION FOR SEQ ID NO:23:

( i ) SEQUENCE CHARACTERISTICS:
        ( A ) LENGTH: 1346 amino acids
        ( B ) TYPE: amino acid
        ( D ) TOPOLOGY: linear ( i i ) MOLECULE TYPE: protein ( x i ) SEQUENCE DESCRIPTION: SEQ ID NO:23:

| | | | | | | | | | | | | | | |
|---|---|---|---|---|---|---|---|---|---|---|---|---|---|---|
| Met | Lys | Arg | Met | Glu | Gly | Lys | Leu | Phe | Met | Val | Ser | Lys | Lys | Leu | Gln |
| 1 | | | | 5 | | | | | 10 | | | | | 15 | |
| Val | Val | Thr | Lys | Thr | Val | Leu | Leu | Ser | Thr | Val | Phe | Ser | Ile | Ser | Leu |
| | | | 20 | | | | | 25 | | | | | 30 | | |
| Leu | Asn | Asn | Glu | Val | Ile | Lys | Ala | Glu | Gln | Leu | Asn | Ile | Asn | Ser | Gln |
| | | | 35 | | | | 40 | | | | | 45 | | | |
| Ser | Lys | Tyr | Thr | Asn | Leu | Gln | Asn | Leu | Lys | Ile | Thr | Asp | Lys | Val | Glu |
| | 50 | | | | | 55 | | | | | 60 | | | | |
| Asp | Phe | Lys | Glu | Asp | Lys | Glu | Lys | Ala | Lys | Glu | Trp | Gly | Lys | Glu | Lys |
| 65 | | | | | 70 | | | | 75 | | | | | | 80 |
| Glu | Lys | Glu | Trp | Lys | Leu | Thr | Ala | Thr | Glu | Lys | Gly | Lys | Met | Asn | Asn |
| | | | | 85 | | | | | 90 | | | | | 95 | |
| Phe | Leu | Asp | Asn | Lys | Asn | Asp | Ile | Lys | Thr | Asn | Tyr | Lys | Glu | Ile | Thr |
| | | | 100 | | | | | 105 | | | | | 110 | | |
| Phe | Ser | Met | Ala | Gly | Ser | Phe | Glu | Asp | Glu | Ile | Lys | Asp | Leu | Lys | Glu |
| | | | 115 | | | | | 120 | | | | | 125 | | |
| Ile | Asp | Lys | Met | Phe | Asp | Lys | Thr | Asn | Leu | Ser | Asn | Ser | Ile | Ile | Thr |
| | | 130 | | | | 135 | | | | | 140 | | | | |
| Tyr | Lys | Asn | Val | Glu | Pro | Thr | Thr | Ile | Gly | Phe | Asn | Lys | Ser | Leu | Thr |
| 145 | | | | | 150 | | | | | 155 | | | | | 160 |
| Glu | Gly | Asn | Thr | Ile | Asn | Ser | Asp | Ala | Met | Ala | Gln | Phe | Lys | Glu | Gln |
| | | | | 165 | | | | | 170 | | | | | 175 | |
| Phe | Leu | Asp | Arg | Asp | Ile | Lys | Phe | Asp | Ser | Tyr | Leu | Asp | Thr | His | Leu |
| | | | 180 | | | | | 185 | | | | | 190 | | |
| Thr | Ala | Gln | Gln | Val | Ser | Ser | Lys | Glu | Arg | Val | Ile | Leu | Lys | Val | Thr |
| | | | 195 | | | | | 200 | | | | | 205 | | |
| Val | Pro | Ser | Gly | Lys | Gly | Ser | Thr | Thr | Pro | Thr | Lys | Ala | Gly | Val | Ile |
| | 210 | | | | | 215 | | | | | 220 | | | | |
| Leu | Asn | Asn | Ser | Glu | Tyr | Lys | Met | Leu | Ile | Asp | Asn | Gly | Tyr | Met | Val |
| 225 | | | | | 230 | | | | | 235 | | | | | 240 |
| His | Val | Asp | Lys | Val | Ser | Lys | Val | Val | Lys | Lys | Gly | Val | Glu | Cys | Leu |
| | | | | 245 | | | | | 250 | | | | | 255 | |
| Gln | Ile | Glu | Gly | Thr | Leu | Lys | Lys | Ser | Leu | Asp | Phe | Lys | Asn | Asp | Ile |
| | | | 260 | | | | | 265 | | | | | 270 | | |
| Asn | Ala | Glu | Ala | His | Ser | Trp | Gly | Met | Lys | Asn | Tyr | Glu | Glu | Trp | Ala |
| | | | 275 | | | | 280 | | | | | 285 | | | |
| Lys | Asp | Leu | Thr | Asp | Ser | Gln | Arg | Glu | Ala | Leu | Asp | Gly | Tyr | Ala | Arg |
| | 290 | | | | | 295 | | | | | 300 | | | | |
| Gln | Asp | Tyr | Lys | Glu | Ile | Asn | Asn | Tyr | Leu | Arg | Asn | Gln | Gly | Gly | Ser |
| 305 | | | | | 310 | | | | | 315 | | | | | 320 |
| Gly | Asn | Glu | Lys | Leu | Asp | Ala | Gln | Ile | Lys | Asn | Ile | Ser | Asp | Ala | Leu |
| | | | | 325 | | | | | 330 | | | | | 335 | |
| Gly | Lys | Lys | Pro | Ile | Pro | Glu | Asn | Ile | Thr | Val | Tyr | Arg | Trp | Cys | Gly |
| | | | 340 | | | | | 345 | | | | | 350 | | |
| Met | Pro | Glu | Phe | Gly | Tyr | Gln | Ile | Ser | Asp | Pro | Leu | Pro | Ser | Leu | Lys |
| | | 355 | | | | | 360 | | | | | 365 | | | |
| Asp | Phe | Glu | Glu | Gln | Phe | Leu | Asn | Thr | Ile | Lys | Glu | Asp | Lys | Gly | Tyr |
| | 370 | | | | | 375 | | | | | 380 | | | | |
| Met | Ser | Thr | Ser | Leu | Ser | Ser | Glu | Arg | Leu | Ala | Ala | Phe | Gly | Ser | Arg |
| 385 | | | | | 390 | | | | | 395 | | | | | 400 |
| Lys | Ile | Ile | Leu | Arg | Leu | Gln | Val | Pro | Lys | Gly | Ser | Thr | Gly | Ala | Tyr |
| | | | | 405 | | | | | 410 | | | | | 415 | |
| Leu | Ser | Ala | Ile | Gly | Gly | Phe | Ala | Ser | Glu | Lys | Glu | Ile | Leu | Leu | Asp |

-continued

|   |   |   |   | 420 |   |   |   |   | 425 |   |   |   |   | 430 |   |
|---|---|---|---|-----|---|---|---|---|-----|---|---|---|---|-----|---|

Lys Asp Ser Lys Tyr His Ile Asp Lys Val Thr Glu Val Ile Ile Lys
          435             440             445

Gly Val Lys Arg Tyr Val Val Asp Ala Thr Leu Leu Thr Asn Met Lys
    450             455             460

Asn Met Lys Lys Lys Leu Ala Ser Val Val Thr Cys Thr Leu Leu Ala
465             470             475             480

Pro Met Phe Leu Asn Gly Asn Val Asn Ala Val Tyr Ala Asp Ser Lys
              485             490             495

Thr Asn Gln Ile Ser Thr Thr Gln Lys Asn Gln Gln Lys Glu Met Asp
        500             505             510

Arg Lys Gly Leu Leu Gly Tyr Tyr Phe Lys Gly Lys Asp Phe Ser Asn
        515             520             525

Leu Thr Met Phe Ala Pro Thr Arg Asp Ser Thr Leu Ile Tyr Asp Gln
    530             535             540

Gln Thr Ala Asn Lys Leu Leu Asp Lys Lys Gln Gln Glu Tyr Gln Ser
545             550             555             560

Ile Arg Trp Ile Gly Leu Ile Gln Ser Lys Glu Thr Gly Asp Phe Thr
              565             570             575

Phe Asn Leu Ser Glu Asp Glu Gln Ala Ile Ile Glu Ile Asn Gly Lys
            580             585             590

Ile Ile Ser Asn Lys Gly Lys Glu Lys Gln Val Val His Leu Glu Lys
        595             600             605

Gly Lys Leu Val Pro Ile Lys Ile Glu Tyr Gln Ser Asp Thr Lys Phe
    610             615             620

Asn Ile Asp Ser Lys Thr Phe Lys Glu Leu Lys Leu Phe Lys Ile Asp
625             630             635             640

Ser Gln Asn Gln Pro Gln Gln Val Gln Gln Asp Glu Leu Arg Asn Pro
              645             650             655

Glu Phe Asn Lys Lys Glu Ser Gln Glu Phe Leu Ala Lys Pro Ser Lys
            660             665             670

Ile Asn Leu Phe Thr Gln Lys Met Lys Arg Glu Ile Asp Glu Asp Thr
        675             680             685

Asp Thr Asp Gly Asp Ser Ile Pro Asp Leu Trp Glu Glu Asn Gly Tyr
    690             695             700

Thr Ile Gln Asn Arg Ile Ala Val Lys Trp Asp Asp Ser Leu Ala Ser
705             710             715             720

Lys Gly Tyr Thr Lys Phe Val Ser Asn Pro Leu Glu Ser His Thr Val
              725             730             735

Gly Asp Pro Tyr Thr Asp Tyr Glu Lys Ala Ala Arg Asp Leu Asp Leu
            740             745             750

Ser Asn Ala Lys Glu Thr Phe Asn Pro Leu Val Ala Ala Phe Pro Ser
        755             760             765

Val Asn Val Ser Met Glu Lys Val Ile Leu Ser Pro Asn Glu Asn Leu
    770             775             780

Ser Asn Ser Val Glu Ser His Ser Ser Thr Asn Trp Ser Tyr Thr Asn
785             790             795             800

Thr Glu Gly Ala Ser Val Glu Ala Gly Ile Gly Pro Lys Gly Ile Ser
              805             810             815

Phe Gly Val Ser Val Asn Tyr Gln His Ser Glu Thr Val Ala Gln Glu
            820             825             830

Trp Gly Thr Ser Thr Gly Asn Thr Ser Gln Phe Asn Thr Ala Ser Ala
        835             840             845

-continued

| | | | | | | | | | | | | | |
|---|---|---|---|---|---|---|---|---|---|---|---|---|---|
| Gly | Tyr | Leu | Asn | Ala | Asn | Val | Arg | Tyr | Asn | Asn | Val | Gly | Thr | Gly | Ala |
| | 850 | | | | 855 | | | | 860 | | | | |
| Ile | Tyr | Asp | Val | Lys | Pro | Thr | Thr | Ser | Phe | Val | Leu | Asn | Asn | Asp | Thr |
| 865 | | | | | 870 | | | | 875 | | | | | 880 |
| Ile | Ala | Thr | Ile | Thr | Ala | Lys | Ser | Asn | Thr | Ala | Leu | Asn | Ile | Ser |
| | | | | 885 | | | | | 890 | | | | 895 |
| Pro | Gly | Glu | Ser | Tyr | Pro | Lys | Gly | Gln | Asn | Gly | Ile | Ala | Ile | Thr |
| | | | 900 | | | | 905 | | | | 910 | | |
| Ser | Met | Asp | Asp | Phe | Asn | Ser | His | Pro | Ile | Thr | Leu | Asn | Lys | Lys | Gln |
| | | 915 | | | | 920 | | | | 925 | | | | |
| Val | Asp | Asn | Leu | Leu | Asn | Asn | Lys | Pro | Met | Met | Leu | Glu | Thr | Asn | Gln |
| | 930 | | | | 935 | | | | 940 | | | | | |
| Thr | Asp | Gly | Val | Tyr | Lys | Ile | Lys | Asp | Thr | His | Gly | Asn | Ile | Val | Thr |
| 945 | | | | 950 | | | | 955 | | | | | 960 |
| Gly | Gly | Glu | Trp | Asn | Gly | Val | Ile | Gln | Gln | Ile | Lys | Ala | Lys | Thr | Ala |
| | | | | 965 | | | | 970 | | | | | 975 |
| Ser | Ile | Ile | Val | Asp | Asp | Gly | Glu | Arg | Val | Ala | Glu | Lys | Arg | Val | Ala |
| | | | 980 | | | | 985 | | | | 990 | | |
| Ala | Lys | Asp | Tyr | Glu | Asn | Pro | Glu | Asp | Lys | Thr | Pro | Ser | Leu | Thr | Leu |
| | | 995 | | | | 1000 | | | | 1005 | | | |
| Lys | Asp | Ala | Leu | Lys | Leu | Ser | Tyr | Pro | Asp | Glu | Ile | Lys | Glu | Ile | Glu |
| 1010 | | | | | 1015 | | | | 1020 | | | | | |
| Gly | Leu | Leu | Tyr | Tyr | Lys | Asn | Lys | Pro | Ile | Tyr | Glu | Ser | Ser | Val | Met |
| 1025 | | | | | 1030 | | | | 1035 | | | | 1040 |
| Thr | Tyr | Leu | Asp | Glu | Asn | Thr | Ala | Lys | Glu | Val | Thr | Lys | Gln | Leu | Asn |
| | | | 1045 | | | | 1050 | | | | 1055 | | |
| Asp | Thr | Thr | Gly | Lys | Phe | Lys | Asp | Val | Ser | His | Leu | Tyr | Asp | Val | Lys |
| | | | 1060 | | | | 1065 | | | | 1070 | | |
| Leu | Thr | Pro | Lys | Met | Asn | Val | Thr | Ile | Lys | Leu | Ser | Ile | Leu | Tyr | Asp |
| | | 1075 | | | | 1080 | | | | 1085 | | | |
| Asn | Ala | Glu | Ser | Asn | Asp | Asn | Ser | Ile | Gly | Lys | Trp | Thr | Asn | Thr | Asn |
| | 1090 | | | | 1095 | | | | 1100 | | | | |
| Ile | Val | Ser | Gly | Gly | Asn | Asn | Gly | Lys | Lys | Gln | Tyr | Ser | Ser | Asn | Asn |
| 1105 | | | | 1110 | | | | 1115 | | | | 1120 |
| Pro | Asp | Ala | Asn | Leu | Thr | Leu | Asn | Thr | Asp | Ala | Gln | Glu | Lys | Leu | Asn |
| | | | | 1125 | | | | 1130 | | | | 1135 | |
| Lys | Asn | Arg | Asp | Tyr | Tyr | Ile | Ser | Leu | Tyr | Met | Lys | Ser | Glu | Lys | Asn |
| | | | 1140 | | | | 1145 | | | | 1150 | | |
| Thr | Gln | Cys | Glu | Ile | Thr | Ile | Asp | Gly | Glu | Ile | Tyr | Pro | Ile | Thr | Thr |
| | | 1155 | | | | 1160 | | | | 1165 | | | |
| Lys | Thr | Val | Asn | Val | Asn | Lys | Asp | Asn | Tyr | Lys | Arg | Leu | Asp | Ile | Ile |
| | 1170 | | | | 1175 | | | | 1180 | | | | |
| Ala | His | Asn | Ile | Lys | Ser | Asn | Pro | Ile | Ser | Ser | Leu | His | Ile | Lys | Thr |
| 1185 | | | | | 1190 | | | | 1195 | | | | | 1200 |
| Asn | Asp | Glu | Ile | Thr | Leu | Phe | Trp | Asp | Asp | Ile | Ser | Ile | Thr | Asp | Val |
| | | | | 1205 | | | | 1210 | | | | | 1215 |
| Ala | Ser | Ile | Lys | Pro | Glu | Asn | Leu | Thr | Asp | Ser | Glu | Ile | Lys | Gln | Ile |
| | | | | 1220 | | | | 1225 | | | | 1230 | |
| Tyr | Ser | Arg | Tyr | Gly | Ile | Lys | Leu | Glu | Asp | Gly | Ile | Leu | Ile | Asp | Lys |
| | | | 1235 | | | | 1240 | | | | 1245 | | |
| Lys | Gly | Gly | Ile | His | Tyr | Gly | Glu | Phe | Ile | Asn | Glu | Ala | Ser | Phe | Asn |
| | | | 1250 | | | | 1255 | | | | 1260 | | |
| Ile | Glu | Pro | Leu | Gln | Asn | Tyr | Val | Thr | Lys | Tyr | Glu | Val | Thr | Tyr | Ser |
| 1265 | | | | | 1270 | | | | 1275 | | | | | 1280 |

```
Ser Glu Leu Gly Pro Asn Val Ser Asp Thr Leu Glu Ser Asp Lys Ile
                1285                1290                1295

Tyr Lys Asp Gly Thr Ile Lys Phe Asp Phe Thr Lys Tyr Ser Lys Asn
            1300                1305                1310

Glu Gln Gly Leu Phe Tyr Asp Ser Gly Leu Asn Trp Asp Phe Lys Ile
        1315                1320                1325

Asn Ala Ile Thr Tyr Asp Gly Lys Glu Met Asn Val Phe His Arg Tyr
    1330                1335                1340

Asn Lys
1345
```

( 2 ) INFORMATION FOR SEQ ID NO:24:

( i ) SEQUENCE CHARACTERISTICS:
( A ) LENGTH: 1399 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: misc_feature
( B ) LOCATION: 1..1386
( D ) OTHER INFORMATION: /note= "Maize optimized DNA sequence for VIP2A(a) protein from AB78"

( x i ) SEQUENCE DESCRIPTION: SEQ ID NO:24:

```
ATGAAGCGCA TGGAGGGCAA GCTGTTCATG GTGAGCAAGA AGCTCCAGGT GGTGACCAAG   60
ACCGTGCTGC TGAGCACCGT GTTCAGCATC AGCCTGCTGA ACAACGAGGT GATCAAGGCC  120
GAGCAGCTGA ACATCAACAG CCAGAGCAAG TACACCAACC TCCAGAACCT GAAGATCACC  180
GACAAGGTGG AGGACTTCAA GGAGGACAAG GAGAAGGCCA AGGAGTGGGG CAAGGAGAAG  240
GAGAAGGAGT GGAAGCTTAC CGCCACCGAG AAGGGCAAGA TGAACAACTT CCTGGACAAC  300
AAGAACGACA TCAAGACCAA CTACAAGGAG ATCACCTTCA GCATGGCCGG CAGCTTCGAG  360
GACGAGATCA AGGACCTGAA GGAGATCGAC AAGATGTTCG ACAAGACCAA CCTGAGCAAC  420
AGCATCATCA CCTACAAGAA CGTGGAGCCC ACCACCATCG GCTTCAACAA GAGCCTGACC  480
GAGGGCAACA CCATCAACAG CGACGCCATG GCCCAGTTCA AGGAGCAGTT CCTGGACCGC  540
GACATCAAGT TCGACAGCTA CCTGGACACC CACCTGACCG CCCAGCAGGT GAGCAGCAAG  600
GAGCGCGTGA TCCTGAAGGT GACCGTCCCC AGCGGCAAGG GCAGCACCAC CCCCACCAAG  660
GCCGGCGTGA TCCTGAACAA CAGCGAGTAC AAGATGCTGA TCGACAACGG CTACATGGTG  720
CACGTGGACA AGGTGAGCAA GGTGGTGAAG AAGGGCGTGG AGTGCCTCCA GATCGAGGGC  780
ACCCTGAAGA AGAGTCTAGA CTTCAAGAAC GACATCAACG CCGAGGCCCA CAGCTGGGGC  840
ATGAAGAACT ACGAGGAGTG GGCCAAGGAC CTGACCGACA GCCAGCGCGA GGCCCTGGAC  900
GGCTACGCCC GCCAGGACTA CAAGGAGATC AACAACTACC TGCGCAACCA GGGCGGCAGC  960
GGCAACGAGA AGCTGGACGC CCAGATCAAG AACATCAGCG ACGCCCTGGG CAAGAAGCCC 1020
ATCCCCGAGA ACATCACCGT GTACCGCTGG TGCGGCATGC CCGAGTTCGG CTACCAGATC 1080
AGCGACCCCC TGCCCAGCCT GAAGGACTTC GAGGAGCAGT TCCTGAACAC CATCAAGGAG 1140
GACAAGGGCT ACATGAGCAC CAGCCTGAGC AGCGAGCGCC TGGCCGCCTT CGGCAGCCGC 1200
AAGATCATCC TGCGCCTGCA GGTGCCCAAG GGCAGCACCG GCGCCTACCT GAGCGCCATC 1260
GGCGGCTTCG CCAGCGAGAA GGAGATCCTG CTGGACAAGG ACAGCAAGTA CCACATCGAC 1320
AAGGTGACCG AGGTGATCAT CAAGGGCGTG AAGCGCTACG TGGTGGACGC CACCCTGCTG 1380

ACCAACTAGA TCTGAGCTC                                                                              1399

( 2 ) INFORMATION FOR SEQ ID NO:25:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..19
        ( D ) OTHER INFORMATION: /note= "Secretion signal peptide to
            secrete VIP2 out of a cell"

( x i ) SEQUENCE DESCRIPTION: SEQ ID NO:25:

Gly Trp Ser Trp Ile Phe Leu Phe Leu Leu Ser Gly Ala Ala Gly Val
1 5 10 15

His Cys Leu ( 2 ) INFORMATION FOR SEQ ID NO:26:

( i ) SEQUENCE CHARACTERISTICS:
( A ) LENGTH: 2655 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "Synthetic DNA"

( i i i ) HYPOTHETICAL: NO ( i x ) FEATURE:
( A ) NAME/KEY: misc_feature
( B ) LOCATION: 1..2655
( D ) OTHER INFORMATION: /note= "maize optimized DNA sequence encoding VIP1A(a)"

( x i ) SEQUENCE DESCRIPTION: SEQ ID NO:26:

ATGAAGAACA TGAAGAAGAA GCTGGCCAGC GTGGTGACCT GCACCCTGCT GGCCCCCATG 60

TTCCTGAACG GCAACGTGAA CGCCGTGTAC GCCGACAGCA AGACCAACCA GATCAGCACC 120

ACCCAGAAGA ACCAGCAGAA GGAGATGGAC CGCAAGGGCC TGCTGGGCTA CTACTTCAAG 180

GGCAAGGACT TCAGCAACCT GACCATGTTC GCCCCCACGC GTGACAGCAC CCTGATCTAC 240

GACCAGCAGA CCGCCAACAA GCTGCTGGAC AAGAAGCAGC AGGAGTACCA GAGCATCCGC 300

TGGATCGGCC TGATCCAGAG CAAGGAGACC GGCGACTTCA CCTTCAACCT GAGCGAGGAC 360

GAGCAGGCCA TCATCGAGAT CAACGGCAAG ATCATCAGCA ACAAGGGCAA GGAGAAGCAG 420

GTGGTGCACC TGGAGAAGGG CAAGCTGGTG CCCATCAAGA TCGAGTACCA GAGCGACACC 480

AAGTTCAACA TCGACAGCAA GACCTTCAAG GAGCTGAAGC TTTTCAAGAT CGACAGCCAG 540

AACCAGCCCC AGCAGGTGCA GCAGGACGAG CTGCGCAACC CCGAGTTCAA CAAGAAGGAG 600

AGCCAGGAGT TCCTGGCCAA GCCCAGCAAG ATCAACCTGT TCACCCAGCA GATGAAGCGC 660

GAGATCGACG AGGACACCGA CACCGACGGC GACAGCATCC CCGACCTGTG GGAGGAGAAC 720

GGCTACACCA TCCAGAACCG CATCGCCGTG AAGTGGGACG ACAGCCTGGC TAGCAAGGGC 780

TACACCAAGT TCGTGAGCAA CCCCCTGGAG AGCCACACCG TGGGCGACCC CTACACCGAC 840

TACGAGAAGG CCGCCCGCGA CCTGGACCTG AGCAACGCCA AGGAGACCTT CAACCCCCTG 900

GTGGCCGCCT TCCCCAGCGT GAACGTGAGC ATGGAGAAGG TGATCCTGAG CCCCAACGAG 960

| | | | | | | |
|---|---|---|---|---|---|---|
|AACCTGAGCA|ACAGCGTGGA|GAGCCACTCG|AGCACCAACT|GGAGCTACAC|CAACACCGAG|1020|
|GGCGCCAGCG|TGGAGGCCGG|CATCGGTCCC|AAGGGCATCA|GCTTCGGCGT|GAGCGTGAAC|1080|
|TACCAGCACA|GCGAGACCGT|GGCCCAGGAG|TGGGGCACCA|GCACCGGCAA|CACCAGCCAG|1140|
|TTCAACACCG|CCAGCGCCGG|CTACCTGAAC|GCCAACGTGC|GCTACAACAA|CGTGGGCACC|1200|
|GGCGCCATCT|ACGACGTGAA|GCCCACCACC|AGCTTCGTGC|TGAACAACGA|CACCATCGCC|1260|
|ACCATCACCG|CCAAGTCGAA|TTCCACCGCC|CTGAACATCA|GCCCCGGCGA|GAGCTACCCC|1320|
|AAGAAGGGCC|AGAACGGCAT|CGCCATCACC|AGCATGGACG|ACTTCAACAG|CCACCCCATC|1380|
|ACCCTGAACA|AGAAGCAGGT|GGACAACCTG|CTGAACAACA|AGCCCATGAT|GCTGGAGACC|1440|
|AACCAGACCG|ACGGCGTCTA|CAAGATCAAG|GACACCCACG|GCAACATCGT|GACGGGCGGC|1500|
|GAGTGGAACG|GCGTGATCCA|GCAGATCAAG|GCCAAGACCG|CCAGCATCAT|CGTCGACGAC|1560|
|GGCGAGCGCG|TGGCCGAGAA|GCGCGTGGCC|GCCAAGGACT|ACGAGAACCC|CGAGGACAAG|1620|
|ACCCCCAGCC|TGACCCTGAA|GGACGCCCTG|AAGCTGAGCT|ACCCCGACGA|GATCAAGGAG|1680|
|ATCGAGGGCT|TGCTGTACTA|CAAGAACAAG|CCCATCTACG|AGAGCAGCGT|GATGACCTAT|1740|
|CTAGACGAGA|ACACCGCCAA|GGAGGTGACC|AAGCAGCTGA|ACGACACCAC|CGGCAAGTTC|1800|
|AAGGACGTGA|GCCACCTGTA|CGACGTGAAG|CTGACCCCCA|AGATGAACGT|GACCATCAAG|1860|
|CTGAGCATCC|TGTACGACAA|CGCCGAGAGC|AACGACAACA|GCATCGGCAA|GTGGACCAAC|1920|
|ACCAACATCG|TGAGCGGCGG|CAACAACGGC|AAGAAGCAGT|ACAGCAGCAA|CAACCCCGAC|1980|
|GCCAACCTGA|CCCTGAACAC|CGACGCCCAG|GAGAAGCTGA|ACAAGAACCG|CGACTACTAC|2040|
|ATCAGCCTGT|ACATGAAGAG|CGAGAAGAAC|ACCCAGTGCG|AGATCACCAT|CGACGGCGAG|2100|
|ATATACCCCA|TCACCACCAA|GACCGTGAAC|GTGAACAAGG|ACAACTACAA|GCGCCTGGAC|2160|
|ATCATCGCCC|ACAACATCAA|GAGCAACCCC|ATCAGCAGCC|TGCACATCAA|GACCAACGAC|2220|
|GAGATCACCC|TGTTCTGGGA|CGACATATCG|ATTACCGACG|TCGCCAGCAT|CAAGCCCGAG|2280|
|AACCTGACCG|ACAGCGAGAT|CAAGCAGATA|TACAGTCGCT|ACGGCATCAA|GCTGGAGGAC|2340|
|GGCATCCTGA|TCGACAAGAA|AGGCGGCATC|CACTACGGCG|AGTTCATCAA|CGAGGCCAGC|2400|
|TTCAACATCG|AGCCCCTGCA|GAACTACGTG|ACCAAGTACG|AGGTGACCTA|CAGCAGCGAG|2460|
|CTGGGCCCCA|ACGTGAGCGA|CACCCTGGAG|AGCGACAAGA|TTTACAAGGA|CGGCACCATC|2520|
|AAGTTCGACT|TCACCAAGTA|CAGCAAGAAC|GAGCAGGGCC|TGTTCTACGA|CAGCGGCCTG|2580|
|AACTGGGACT|TCAAGATCAA|CGCCATCACC|TACGACGGCA|AGGAGATGAA|CGTGTTCCAC|2640|
|CGCTACAACA|AGTAG| | | | |2655|

( 2 ) INFORMATION FOR SEQ ID NO:27:

( i ) SEQUENCE CHARACTERISTICS:
        ( A ) LENGTH: 1389 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Synthetic DNA"

( i i i ) HYPOTHETICAL: NO ( i x ) FEATURE:
        ( A ) NAME/KEY: misc_feature
        ( B ) LOCATION: 1..1389
        ( D ) OTHER INFORMATION: /note= "maize optimized DNA
            sequence encoding VIP2A(a)"

( x i ) SEQUENCE DESCRIPT

| | | | | | | |
|---|---|---|---|---|---|---|
|ATGAAGCGCA|TGGAGGGCAA|GCTGTTCATG|GTGAGCAAGA|AGCTCCAGGT|GGTGACCAAG|60|
|ACCGTGCTGC|TGAGCACCGT|GTTCAGCATC|AGCCTGCTGA|CAACGAGGT|GATCAAGGCC|120|
|GAGCAGCTGA|ACATCAACAG|CCAGAGCAAG|TACACCAACC|TCCAGAACCT|GAAGATCACC|180|
|GACAAGGTGG|AGGACTTCAA|GGAGGACAAG|GAGAAGGCCA|AGGAGTGGGG|CAAGGAGAAG|240|
|GAGAAGGAGT|GGAAGCTTAC|CGCCACCGAG|AAGGGCAAGA|TGAACAACTT|CCTGGACAAC|300|
|AAGAACGACA|TCAAGACCAA|CTACAAGGAG|ATCACCTTCA|GCATAGCCGG|CAGCTTCGAG|360|
|GACGAGATCA|AGGACCTGAA|GGAGATCGAC|AAGATGTTCG|ACAAGACCAA|CCTGAGCAAC|420|
|AGCATCATCA|CCTACAAGAA|CGTGGAGCCC|ACCACCATCG|GCTTCAACAA|GAGCCTGACC|480|
|GAGGGCAACA|CCATCAACAG|CGACGCCATG|GCCCAGTTCA|AGGAGCAGTT|CCTGGACCGC|540|
|GACATCAAGT|TCGACAGCTA|CCTGGACACC|CACCTGACCG|CCCAGCAGGT|GAGCAGCAAG|600|
|GAGCGCGTGA|TCCTGAAGGT|GACCGTCCCC|AGCGGCAAGG|GCAGCACCAC|CCCCACCAAG|660|
|GCCGGCGTGA|TCCTGAACAA|CAGCGAGTAC|AAGATGCTGA|TCGACAACGG|CTACATGGTG|720|
|CACGTGGACA|AGGTGAGCAA|GGTGGTGAAG|AAGGGCGTGG|AGTGCCTCCA|GATCGAGGGC|780|
|ACCCTGAAGA|AGAGTCTAGA|CTTCAAGAAC|GACATCAACG|CCGAGGCCCA|CAGCTGGGGC|840|
|ATGAAGAACT|ACGAGGAGTG|GGCCAAGGAC|CTGACCGACA|GCCAGCGCGA|GGCCCTGGAC|900|
|GGCTACGCCC|GCCAGGACTA|CAAGGAGATC|AACAACTACC|TGCGCAACCA|GGGCGGCAGC|960|
|GGCAACGAGA|AGCTGGACGC|CCAGATCAAG|AACATCAGCG|ACGCCCTGGG|CAAGAAGCCC|1020|
|ATCCCCGAGA|ACATCACCGT|GTACCGCTGG|TGCGGCATGC|CCGAGTTCGG|CTACCAGATC|1080|
|AGCGACCCCC|TGCCCAGCCT|GAAGGACTTC|GAGGAGCAGT|TCCTGAACAC|CATCAAGGAG|1140|
|GACAAGGGCT|ACATGAGCAC|CAGCCTGAGC|AGCGAGCGCC|TGGCCGCCTT|CGGCAGCCGC|1200|
|AAGATCATCC|TGCGCCTGCA|GGTGCCCAAG|GGCAGCACTG|GTGCCTACCT|GAGCGCCATC|1260|
|GGCGGCTTCG|CCAGCGAGAA|GGAGATCCTG|CTGGATAAGG|ACAGCAAGTA|CCACATCGAC|1320|
|AAGGTGACCG|AGGTGATCAT|CAAGGGCGTG|AAGCGCTACG|TGGTGGACGC|CACCCTGCTG|1380|
|ACCAACTAG| | | | | |1389|

(2) INFORMATION FOR SEQ ID NO:28:

(i) SEQUENCE CHARACTERISTICS:
        (A) LENGTH: 2378 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (ix) FEATURE:
        (A) NAME/KEY: CDS
        (B) LOCATION: 9..2375
        (D) OTHER INFORMATION: /note= "Native DNA sequence
            encoding VIP3A(a) protein from AB88 as contained in
            pCIB7104"

(xi) SEQUENCE DESCRIPTION: SEQ ID NO:28:

```
AGATGAAC ATG AAC AAG AAT AAT ACT AAA TTA AGC ACA AGA GCC TTA CCA        50
         Met Asn Lys Asn Asn Thr Lys Leu Ser Thr Arg Ala Leu Pro
         1               5                  10

AGT TTT ATT GAT TAT TTT AAT GGC ATT TAT GGA TTT GCC ACT GGT ATC         98
Ser Phe Ile Asp Tyr Phe Asn Gly Ile Tyr Gly Phe Ala Thr Gly Ile
15              20                  25                  30

AAA GAC ATT ATG AAC ATG ATT TTT AAA ACG GAT ACA GGT GGT GAT CTA        146
```

```
           Lys   Asp   Ile   Met   Asn   Met   Ile   Phe   Lys   Thr   Asp   Thr   Gly   Gly   Asp   Leu
                             35                      40                            45

ACC   CTA   GAC   GAA   ATT   TTA   AAG   AAT   CAG   CAG   TTA   CTA   AAT   GAT   ATT   TCT                194
Thr   Leu   Asp   Glu   Ile   Leu   Lys   Asn   Gln   Gln   Leu   Leu   Asn   Asp   Ile   Ser
                  50                      55                            60

GGT   AAA   TTG   GAT   GGG   GTG   AAT   GGA   AGC   TTA   AAT   GAT   CTT   ATC   GCA   CAG                242
Gly   Lys   Leu   Asp   Gly   Val   Asn   Gly   Ser   Leu   Asn   Asp   Leu   Ile   Ala   Gln
            65                            70                            75

GGA   AAC   TTA   AAT   ACA   GAA   TTA   TCT   AAG   GAA   ATA   TTA   AAA   ATT   GCA   AAT                290
Gly   Asn   Leu   Asn   Thr   Glu   Leu   Ser   Lys   Glu   Ile   Leu   Lys   Ile   Ala   Asn
      80                            85                            90

GAA   CAA   AAT   CAA   GTT   TTA   AAT   GAT   GTT   AAT   AAC   AAA   CTC   GAT   GCG   ATA                338
Glu   Gln   Asn   Gln   Val   Leu   Asn   Asp   Val   Asn   Asn   Lys   Leu   Asp   Ala   Ile
95                      100                           105                           110

AAT   ACG   ATG   CTT   CGG   GTA   TAT   CTA   CCT   AAA   ATT   ACC   TCT   ATG   TTG   AGT                386
Asn   Thr   Met   Leu   Arg   Val   Tyr   Leu   Pro   Lys   Ile   Thr   Ser   Met   Leu   Ser
                        115                           120                           125

GAT   GTA   ATG   AAA   CAA   AAT   TAT   GCG   CTA   AGT   CTG   CAA   ATA   GAA   TAC   TTA                434
Asp   Val   Met   Lys   Gln   Asn   Tyr   Ala   Leu   Ser   Leu   Gln   Ile   Glu   Tyr   Leu
                  130                           135                           140

AGT   AAA   CAA   TTG   CAA   GAG   ATT   TCT   GAT   AAG   TTG   GAT   ATT   ATT   AAT   GTA                482
Ser   Lys   Gln   Leu   Gln   Glu   Ile   Ser   Asp   Lys   Leu   Asp   Ile   Ile   Asn   Val
            145                           150                           155

AAT   GTA   CTT   ATT   AAC   TCT   ACA   CTT   ACT   GAA   ATT   ACA   CCT   GCG   TAT   CAA                530
Asn   Val   Leu   Ile   Asn   Ser   Thr   Leu   Thr   Glu   Ile   Thr   Pro   Ala   Tyr   Gln
      160                           165                           170

AGG   ATT   AAA   TAT   GTG   AAC   GAA   AAA   TTT   GAG   GAA   TTA   ACT   TTT   GCT   ACA                578
Arg   Ile   Lys   Tyr   Val   Asn   Glu   Lys   Phe   Glu   Glu   Leu   Thr   Phe   Ala   Thr
175                     180                           185                           190

GAA   ACT   AGT   TCA   AAA   GTA   AAA   AAG   GAT   GGC   TCT   CCT   GCA   GAT   ATT   CTT                626
Glu   Thr   Ser   Ser   Lys   Val   Lys   Lys   Asp   Gly   Ser   Pro   Ala   Asp   Ile   Leu
                        195                           200                           205

GAT   GAG   TTA   ACT   GAG   TTA   ACT   GAA   CTA   GCG   AAA   AGT   GTA   ACA   AAA   AAT                674
Asp   Glu   Leu   Thr   Glu   Leu   Thr   Glu   Leu   Ala   Lys   Ser   Val   Thr   Lys   Asn
                  210                           215                           220

GAT   GTG   GAT   GGT   TTT   GAA   TTT   TAC   CTT   AAT   ACA   TTC   CAC   GAT   GTA   ATG                722
Asp   Val   Asp   Gly   Phe   Glu   Phe   Tyr   Leu   Asn   Thr   Phe   His   Asp   Val   Met
            225                           230                           235

GTA   GGA   AAT   AAT   TTA   TTC   GGG   CGT   TCA   GCT   TTA   AAA   ACT   GCA   TCG   GAA                770
Val   Gly   Asn   Asn   Leu   Phe   Gly   Arg   Ser   Ala   Leu   Lys   Thr   Ala   Ser   Glu
      240                           245                           250

TTA   ATT   ACT   AAA   GAA   AAT   GTG   AAA   ACA   AGT   GGC   AGT   GAG   GTC   GGA   AAT                818
Leu   Ile   Thr   Lys   Glu   Asn   Val   Lys   Thr   Ser   Gly   Ser   Glu   Val   Gly   Asn
255                     260                           265                           270

GTT   TAT   AAC   TTC   TTA   ATT   GTA   TTA   ACA   GCT   CTG   CAA   GCC   CAA   GCT   TTT                866
Val   Tyr   Asn   Phe   Leu   Ile   Val   Leu   Thr   Ala   Leu   Gln   Ala   Gln   Ala   Phe
                        275                           280                           285

CTT   ACT   TTA   ACA   ACA   TGC   CGA   AAA   TTA   TTA   GGC   TTA   GCA   GAT   ATT   GAT                914
Leu   Thr   Leu   Thr   Thr   Cys   Arg   Lys   Leu   Leu   Gly   Leu   Ala   Asp   Ile   Asp
                  290                           295                           300

TAT   ACT   TCT   ATT   ATG   AAT   GAA   CAT   TTA   AAT   AAG   GAA   AAA   GAG   GAA   TTT                962
Tyr   Thr   Ser   Ile   Met   Asn   Glu   His   Leu   Asn   Lys   Glu   Lys   Glu   Glu   Phe
            305                           310                           315

AGA   GTA   AAC   ATC   CTC   CCT   ACA   CTT   TCT   AAT   ACT   TTT   TCT   AAT   CCT   AAT                1010
Arg   Val   Asn   Ile   Leu   Pro   Thr   Leu   Ser   Asn   Thr   Phe   Ser   Asn   Pro   Asn
      320                           325                           330

TAT   GCA   AAA   GTT   AAA   GGA   AGT   GAT   GAA   GAT   GCA   AAG   ATG   ATT   GTG   GAA                1058
Tyr   Ala   Lys   Val   Lys   Gly   Ser   Asp   Glu   Asp   Ala   Lys   Met   Ile   Val   Glu
335                     340                           345                           350

GCT   AAA   CCA   GGA   CAT   GCA   TTG   ATT   GGG   TTT   GAA   ATT   AGT   AAT   GAT   TCA                1106
```

|     |     |     |     |     |     |     |     |     |     |     |     |     |     |     |      |
|-----|-----|-----|-----|-----|-----|-----|-----|-----|-----|-----|-----|-----|-----|-----|------|
| Ala | Lys | Pro | Gly | His | Ala | Leu | Ile | Gly | Phe | Glu | Ile | Ser | Asn | Asp | Ser  |
|     |     |     |     | 355 |     |     |     | 360 |     |     |     |     | 365 |     |      |
| ATT | ACA | GTA | TTA | AAA | GTA | TAT | GAG | GCT | AAG | CTA | AAA | CAA | AAT | TAT | CAA  | 1154 |
| Ile | Thr | Val | Leu | Lys | Val | Tyr | Glu | Ala | Lys | Leu | Lys | Gln | Asn | Tyr | Gln  |
|     |     |     | 370 |     |     |     | 375 |     |     |     |     | 380 |     |     |      |
| GTC | GAT | AAG | GAT | TCC | TTA | TCG | GAA | GTT | ATT | TAT | GGT | GAT | ATG | GAT | AAA  | 1202 |
| Val | Asp | Lys | Asp | Ser | Leu | Ser | Glu | Val | Ile | Tyr | Gly | Asp | Met | Asp | Lys  |
|     |     | 385 |     |     |     |     | 390 |     |     |     |     | 395 |     |     |      |
| TTA | TTG | TGC | CCA | GAT | CAA | TCT | GAA | CAA | ATC | TAT | TAT | ACA | AAT | AAC | ATA  | 1250 |
| Leu | Leu | Cys | Pro | Asp | Gln | Ser | Glu | Gln | Ile | Tyr | Tyr | Thr | Asn | Asn | Ile  |
|     | 400 |     |     |     |     | 405 |     |     |     |     | 410 |     |     |     |      |
| GTA | TTT | CCA | AAT | GAA | TAT | GTA | ATT | ACT | AAA | ATT | GAT | TTC | ACT | AAA | AAA  | 1298 |
| Val | Phe | Pro | Asn | Glu | Tyr | Val | Ile | Thr | Lys | Ile | Asp | Phe | Thr | Lys | Lys  |
| 415 |     |     |     |     | 420 |     |     |     | 425 |     |     |     |     | 430 |      |
| ATG | AAA | ACT | TTA | AGA | TAT | GAG | GTA | ACA | GCG | AAT | TTT | TAT | GAT | TCT | TCT  | 1346 |
| Met | Lys | Thr | Leu | Arg | Tyr | Glu | Val | Thr | Ala | Asn | Phe | Tyr | Asp | Ser | Ser  |
|     |     |     |     | 435 |     |     |     | 440 |     |     |     |     | 445 |     |      |
| ACA | GGA | GAA | ATT | GAC | TTA | AAT | AAG | AAA | AAA | GTA | GAA | TCA | AGT | GAA | GCG  | 1394 |
| Thr | Gly | Glu | Ile | Asp | Leu | Asn | Lys | Lys | Lys | Val | Glu | Ser | Ser | Glu | Ala  |
|     |     |     | 450 |     |     |     | 455 |     |     |     | 460 |     |     |     |      |
| GAG | TAT | AGA | ACG | TTA | AGT | GCT | AAT | GAT | GAT | GGG | GTG | TAT | ATG | CCG | TTA  | 1442 |
| Glu | Tyr | Arg | Thr | Leu | Ser | Ala | Asn | Asp | Asp | Gly | Val | Tyr | Met | Pro | Leu  |
|     |     | 465 |     |     |     |     | 470 |     |     |     |     | 475 |     |     |      |
| GGT | GTC | ATC | AGT | GAA | ACA | TTT | TTG | ACT | CCG | ATT | AAT | GGG | TTT | GGC | CTC  | 1490 |
| Gly | Val | Ile | Ser | Glu | Thr | Phe | Leu | Thr | Pro | Ile | Asn | Gly | Phe | Gly | Leu  |
|     | 480 |     |     |     |     | 485 |     |     |     |     | 490 |     |     |     |      |
| CAA | GCT | GAT | GAA | AAT | TCA | AGA | TTA | ATT | ACT | TTA | ACA | TGT | AAA | TCA | TAT  | 1538 |
| Gln | Ala | Asp | Glu | Asn | Ser | Arg | Leu | Ile | Thr | Leu | Thr | Cys | Lys | Ser | Tyr  |
| 495 |     |     |     |     | 500 |     |     |     | 505 |     |     |     |     | 510 |      |
| TTA | AGA | GAA | CTA | CTG | CTA | GCA | ACA | GAC | TTA | AGC | AAT | AAA | GAA | ACT | AAA  | 1586 |
| Leu | Arg | Glu | Leu | Leu | Leu | Ala | Thr | Asp | Leu | Ser | Asn | Lys | Glu | Thr | Lys  |
|     |     |     |     | 515 |     |     |     | 520 |     |     |     |     | 525 |     |      |
| TTG | ATC | GTC | CCG | CCA | AGT | GGT | TTT | ATT | AGC | AAT | ATT | GTA | GAG | AAC | GGG  | 1634 |
| Leu | Ile | Val | Pro | Pro | Ser | Gly | Phe | Ile | Ser | Asn | Ile | Val | Glu | Asn | Gly  |
|     |     |     | 530 |     |     |     | 535 |     |     |     | 540 |     |     |     |      |
| TCC | ATA | GAA | GAG | GAC | AAT | TTA | GAG | CCG | TGG | AAA | GCA | AAT | AAT | AAG | AAT  | 1682 |
| Ser | Ile | Glu | Glu | Asp | Asn | Leu | Glu | Pro | Trp | Lys | Ala | Asn | Asn | Lys | Asn  |
|     |     | 545 |     |     |     |     | 550 |     |     |     |     | 555 |     |     |      |
| GCG | TAT | GTA | GAT | CAT | ACA | GGC | GGA | GTG | AAT | GGA | ACT | AAA | GCT | TTA | TAT  | 1730 |
| Ala | Tyr | Val | Asp | His | Thr | Gly | Gly | Val | Asn | Gly | Thr | Lys | Ala | Leu | Tyr  |
|     | 560 |     |     |     |     | 565 |     |     |     |     | 570 |     |     |     |      |
| GTT | CAT | AAG | GAC | GGA | GGA | ATT | TCA | CAA | TTT | ATT | GGA | GAT | AAG | TTA | AAA  | 1778 |
| Val | His | Lys | Asp | Gly | Gly | Ile | Ser | Gln | Phe | Ile | Gly | Asp | Lys | Leu | Lys  |
| 575 |     |     |     |     | 580 |     |     |     | 585 |     |     |     |     | 590 |      |
| CCG | AAA | ACT | GAG | TAT | GTA | ATC | CAA | TAT | ACT | GTT | AAA | GGA | AAA | CCT | TCT  | 1826 |
| Pro | Lys | Thr | Glu | Tyr | Val | Ile | Gln | Tyr | Thr | Val | Lys | Gly | Lys | Pro | Ser  |
|     |     |     |     | 595 |     |     |     | 600 |     |     |     |     | 605 |     |      |
| ATT | CAT | TTA | AAA | GAT | GAA | AAT | ACT | GGA | TAT | ATT | CAT | TAT | GAA | GAT | ACA  | 1874 |
| Ile | His | Leu | Lys | Asp | Glu | Asn | Thr | Gly | Tyr | Ile | His | Tyr | Glu | Asp | Thr  |
|     |     |     | 610 |     |     |     | 615 |     |     |     | 620 |     |     |     |      |
| AAT | AAT | AAT | TTA | GAA | GAT | TAT | CAA | ACT | ATT | AAT | AAA | CGT | TTT | ACT | ACA  | 1922 |
| Asn | Asn | Asn | Leu | Glu | Asp | Tyr | Gln | Thr | Ile | Asn | Lys | Arg | Phe | Thr | Thr  |
|     |     | 625 |     |     |     |     | 630 |     |     |     |     | 635 |     |     |      |
| GGA | ACT | GAT | TTA | AAG | GGA | GTG | TAT | TTA | ATT | TTA | AAA | AGT | CAA | AAT | GGA  | 1970 |
| Gly | Thr | Asp | Leu | Lys | Gly | Val | Tyr | Leu | Ile | Leu | Lys | Ser | Gln | Asn | Gly  |
|     |     | 640 |     |     |     |     | 645 |     |     |     |     | 650 |     |     |      |
| GAT | GAA | GCT | TGG | GGA | GAT | AAC | TTT | ATT | ATT | TTG | GAA | ATT | AGT | CCT | TCT  | 2018 |
| Asp | Glu | Ala | Trp | Gly | Asp | Asn | Phe | Ile | Ile | Leu | Glu | Ile | Ser | Pro | Ser  |
| 655 |     |     |     |     | 660 |     |     |     | 665 |     |     |     |     | 670 |      |
| GAA | AAG | TTA | TTA | AGT | CCA | GAA | TTA | ATT | AAT | ACA | AAT | AAT | TGG | ACG | AGT  | 2066 |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| Glu | Lys | Leu | Leu | Ser | Pro | Glu | Leu | Ile | Asn | Thr | Asn | Asn | Trp | Thr | Ser |      |
|     |     |     |     | 675 |     |     |     | 680 |     |     |     |     |     | 685 |     |      |
| ACG | GGA | TCA | ACT | AAT | ATT | AGC | GGT | AAT | ACA | CTC | ACT | CTT | TAT | CAG | GGA | 2114 |
| Thr | Gly | Ser | Thr | Asn | Ile | Ser | Gly | Asn | Thr | Leu | Thr | Leu | Tyr | Gln | Gly |      |
|     |     |     | 690 |     |     |     | 695 |     |     |     |     |     | 700 |     |     |      |
| GGA | CGA | GGG | ATT | CTA | AAA | CAA | AAC | CTT | CAA | TTA | GAT | AGT | TTT | TCA | ACT | 2162 |
| Gly | Arg | Gly | Ile | Leu | Lys | Gln | Asn | Leu | Gln | Leu | Asp | Ser | Phe | Ser | Thr |      |
|     |     | 705 |     |     |     |     | 710 |     |     |     |     | 715 |     |     |     |      |
| TAT | AGA | GTG | TAT | TTT | TCT | GTG | TCC | GGA | GAT | GCT | AAT | GTA | AGG | ATT | AGA | 2210 |
| Tyr | Arg | Val | Tyr | Phe | Ser | Val | Ser | Gly | Asp | Ala | Asn | Val | Arg | Ile | Arg |      |
|     | 720 |     |     |     |     | 725 |     |     |     |     | 730 |     |     |     |     |      |
| AAT | TCT | AGG | GAA | GTG | TTA | TTT | GAA | AAA | AGA | TAT | ATG | AGC | GGT | GCT | AAA | 2258 |
| Asn | Ser | Arg | Glu | Val | Leu | Phe | Glu | Lys | Arg | Tyr | Met | Ser | Gly | Ala | Lys |      |
| 735 |     |     |     |     | 740 |     |     |     |     | 745 |     |     |     |     | 750 |      |
| GAT | GTT | TCT | GAA | ATG | TTC | ACT | ACA | AAA | TTT | GAG | AAA | GAT | AAC | TTT | TAT | 2306 |
| Asp | Val | Ser | Glu | Met | Phe | Thr | Thr | Lys | Phe | Glu | Lys | Asp | Asn | Phe | Tyr |      |
|     |     |     |     | 755 |     |     |     |     | 760 |     |     |     |     | 765 |     |      |
| ATA | GAG | CTT | TCT | CAA | GGG | AAT | AAT | TTA | TAT | GGT | GGT | CCT | ATT | GTA | CAT | 2354 |
| Ile | Glu | Leu | Ser | Gln | Gly | Asn | Asn | Leu | Tyr | Gly | Gly | Pro | Ile | Val | His |      |
|     |     |     | 770 |     |     |     |     | 775 |     |     |     |     | 780 |     |     |      |
| TTT | TAC | GAT | GTC | TCT | ATT | AAG | TAA |     |     |     |     |     |     |     |     | 2378 |
| Phe | Tyr | Asp | Val | Ser | Ile | Lys |     |     |     |     |     |     |     |     |     |      |
|     |     | 785 |     |     |     |     |     |     |     |     |     |     |     |     |     |      |

(2) INFORMATION FOR SEQ ID NO:29:

(i) SEQUENCE CHARACTERISTICS:
        (A) LENGTH: 789 amino acids
        (B) TYPE: amino acid
        (D) TOPOLOGY: linear (ii) MOLECULE TYPE: protein (xi) SEQUENCE DESCRIPTION: SEQ ID NO:29:

|     |     |     |     |     |     |     |     |     |     |     |     |     |     |     |
|-----|-----|-----|-----|-----|-----|-----|-----|-----|-----|-----|-----|-----|-----|-----|
| Met | Asn | Lys | Asn | Asn | Thr | Lys | Leu | Ser | Thr | Arg | Ala | Leu | Pro | Ser | Phe |
| 1   |     |     |     | 5   |     |     |     |     | 10  |     |     |     |     | 15  |
| Ile | Asp | Tyr | Phe | Asn | Gly | Ile | Tyr | Gly | Phe | Ala | Thr | Gly | Ile | Lys | Asp |
|     |     |     | 20  |     |     |     | 25  |     |     |     |     | 30  |     |     |     |
| Ile | Met | Asn | Met | Ile | Phe | Lys | Thr | Asp | Thr | Gly | Gly | Asp | Leu | Thr | Leu |
|     |     | 35  |     |     |     |     | 40  |     |     |     |     | 45  |     |     |     |
| Asp | Glu | Ile | Leu | Lys | Asn | Gln | Leu | Leu | Asn | Asp | Ile | Ser | Gly | Lys |
|     | 50  |     |     |     |     | 55  |     |     |     |     | 60  |     |     |     |
| Leu | Asp | Gly | Val | Asn | Gly | Ser | Leu | Asn | Asp | Leu | Ile | Ala | Gln | Gly | Asn |
| 65  |     |     |     |     | 70  |     |     |     |     | 75  |     |     |     |     | 80  |
| Leu | Asn | Thr | Glu | Leu | Ser | Lys | Glu | Ile | Leu | Lys | Ile | Ala | Asn | Glu | Gln |
|     |     |     |     | 85  |     |     |     |     | 90  |     |     |     |     | 95  |     |
| Asn | Gln | Val | Leu | Asn | Asp | Val | Asn | Asn | Lys | Leu | Asp | Ala | Ile | Asn | Thr |
|     |     |     | 100 |     |     |     |     | 105 |     |     |     |     | 110 |     |     |
| Met | Leu | Arg | Val | Tyr | Leu | Pro | Lys | Ile | Thr | Ser | Met | Leu | Ser | Asp | Val |
|     |     | 115 |     |     |     |     | 120 |     |     |     |     | 125 |     |     |     |
| Met | Lys | Gln | Asn | Tyr | Ala | Leu | Ser | Leu | Gln | Ile | Glu | Tyr | Leu | Ser | Lys |
|     | 130 |     |     |     |     | 135 |     |     |     |     | 140 |     |     |     |     |
| Gln | Leu | Gln | Glu | Ile | Ser | Asp | Lys | Leu | Asp | Ile | Ile | Asn | Val | Asn | Val |
| 145 |     |     |     |     | 150 |     |     |     |     | 155 |     |     |     |     | 160 |
| Leu | Ile | Asn | Ser | Thr | Leu | Thr | Glu | Ile | Thr | Pro | Ala | Tyr | Gln | Arg | Ile |
|     |     |     |     | 165 |     |     |     |     | 170 |     |     |     |     | 175 |     |
| Lys | Tyr | Val | Asn | Glu | Lys | Phe | Glu | Glu | Leu | Thr | Phe | Ala | Thr | Glu | Thr |
|     |     |     | 180 |     |     |     |     | 185 |     |     |     |     | 190 |     |     |
| Ser | Ser | Lys | Val | Lys | Lys | Asp | Gly | Ser | Pro | Ala | Asp | Ile | Leu | Asp | Glu |

-continued

```
                    195                      200                        205

Leu   Thr   Glu   Leu   Thr   Glu   Leu   Ala   Lys   Ser   Val   Thr   Lys   Asn   Asp   Val
      210                     215                     220

Asp   Gly   Phe   Glu   Phe   Tyr   Leu   Asn   Thr   Phe   His   Asp   Val   Met   Val   Gly
225                           230                     235                                 240

Asn   Asn   Leu   Phe   Gly   Arg   Ser   Ala   Leu   Lys   Thr   Ala   Ser   Glu   Leu   Ile
                        245                     250                           255

Thr   Lys   Glu   Asn   Val   Lys   Thr   Ser   Gly   Ser   Glu   Val   Gly   Asn   Val   Tyr
                  260                     265                           270

Asn   Phe   Leu   Ile   Val   Leu   Thr   Ala   Leu   Gln   Ala   Gln   Ala   Phe   Leu   Thr
                  275                     280                     285

Leu   Thr   Thr   Cys   Arg   Lys   Leu   Leu   Gly   Leu   Ala   Asp   Ile   Asp   Tyr   Thr
      290                     295                           300

Ser   Ile   Met   Asn   Glu   His   Leu   Asn   Lys   Glu   Lys   Glu   Glu   Phe   Arg   Val
305                           310                     315                                 320

Asn   Ile   Leu   Pro   Thr   Leu   Ser   Asn   Thr   Phe   Ser   Asn   Pro   Asn   Tyr   Ala
                        325                     330                           335

Lys   Val   Lys   Gly   Ser   Asp   Glu   Asp   Ala   Lys   Met   Ile   Val   Glu   Ala   Lys
                  340                     345                           350

Pro   Gly   His   Ala   Leu   Ile   Gly   Phe   Glu   Ile   Ser   Asn   Asp   Ser   Ile   Thr
            355                     360                           365

Val   Leu   Lys   Val   Tyr   Glu   Ala   Lys   Leu   Lys   Gln   Asn   Tyr   Gln   Val   Asp
      370                     375                           380

Lys   Asp   Ser   Leu   Ser   Glu   Val   Ile   Tyr   Gly   Asp   Met   Asp   Lys   Leu   Leu
385                           390                     395                                 400

Cys   Pro   Asp   Gln   Ser   Glu   Gln   Ile   Tyr   Tyr   Thr   Asn   Asn   Ile   Val   Phe
                        405                     410                           415

Pro   Asn   Glu   Tyr   Val   Ile   Thr   Lys   Ile   Asp   Phe   Thr   Lys   Met   Lys
                  420                     425                           430

Thr   Leu   Arg   Tyr   Glu   Val   Thr   Ala   Asn   Phe   Tyr   Asp   Ser   Ser   Thr   Gly
            435                     440                           445

Glu   Ile   Asp   Leu   Asn   Lys   Lys   Val   Glu   Ser   Ser   Glu   Ala   Glu   Tyr
            450                     455                           460

Arg   Thr   Leu   Ser   Ala   Asn   Asp   Asp   Gly   Val   Tyr   Met   Pro   Leu   Gly   Val
465                           470                     475                                 480

Ile   Ser   Glu   Thr   Phe   Leu   Thr   Pro   Ile   Asn   Gly   Phe   Gly   Leu   Gln   Ala
                        485                     490                           495

Asp   Glu   Asn   Ser   Arg   Leu   Ile   Thr   Leu   Thr   Cys   Lys   Ser   Tyr   Leu   Arg
                  500                     505                           510

Glu   Leu   Leu   Leu   Ala   Thr   Asp   Leu   Ser   Asn   Lys   Glu   Thr   Lys   Leu   Ile
            515                     520                           525

Val   Pro   Pro   Ser   Gly   Phe   Ile   Ser   Asn   Ile   Val   Glu   Asn   Gly   Ser   Ile
      530                     535                           540

Glu   Glu   Asp   Asn   Leu   Glu   Pro   Trp   Lys   Ala   Asn   Asn   Lys   Asn   Ala   Tyr
545                           550                     555                                 560

Val   Asp   His   Thr   Gly   Gly   Val   Asn   Gly   Thr   Lys   Ala   Leu   Tyr   Val   His
                        565                     570                           575

Lys   Asp   Gly   Gly   Ile   Ser   Gln   Phe   Ile   Gly   Asp   Lys   Leu   Lys   Pro   Lys
                  580                     585                           590

Thr   Glu   Tyr   Val   Ile   Gln   Tyr   Thr   Val   Lys   Gly   Lys   Pro   Ser   Ile   His
                  595                     600                           605

Leu   Lys   Asp   Glu   Asn   Thr   Gly   Tyr   Ile   His   Tyr   Glu   Asp   Thr   Asn   Asn
      610                     615                           620
```

| Asn<br>625 | Leu | Glu | Asp | Tyr | Gln<br>630 | Thr | Ile | Asn | Lys<br>635 | Arg | Phe | Thr | Thr | Gly | Thr<br>640 |
|---|---|---|---|---|---|---|---|---|---|---|---|---|---|---|---|
| Asp | Leu | Lys | Gly | Val<br>645 | Tyr | Leu | Ile | Leu | Lys<br>650 | Ser | Gln | Asn | Gly | Asp<br>655 | Glu |
| Ala | Trp | Gly | Asp<br>660 | Asn | Phe | Ile | Ile | Leu<br>665 | Glu | Ile | Ser | Pro | Ser<br>670 | Glu | Lys |
| Leu | Leu | Ser<br>675 | Pro | Glu | Leu | Ile | Asn<br>680 | Thr | Asn | Asn | Trp | Thr<br>685 | Ser | Thr | Gly |
| Ser | Thr<br>690 | Asn | Ile | Ser | Gly | Asn<br>695 | Thr | Leu | Thr | Leu | Tyr<br>700 | Gln | Gly | Gly | Arg |
| Gly<br>705 | Ile | Leu | Lys | Gln | Asn<br>710 | Leu | Gln | Leu | Asp<br>715 | Ser | Phe | Ser | Thr | Tyr | Arg<br>720 |
| Val | Tyr | Phe | Ser | Val<br>725 | Ser | Gly | Asp | Ala | Asn<br>730 | Val | Arg | Ile | Arg | Asn<br>735 | Ser |
| Arg | Glu | Val | Leu<br>740 | Phe | Glu | Lys | Arg | Tyr<br>745 | Met | Ser | Gly | Ala | Lys<br>750 | Asp | Val |
| Ser | Glu | Met<br>755 | Phe | Thr | Thr | Lys | Phe<br>760 | Glu | Lys | Asp | Asn | Phe<br>765 | Tyr | Ile | Glu |
| Leu | Ser | Gln<br>770 | Gly | Asn | Asn | Leu<br>775 | Tyr | Gly | Gly | Pro | Ile<br>780 | Val | His | Phe | Tyr |
| Asp<br>785 | Val | Ser | Ile | Lys | | | | | | | | | | | |

( 2 ) INFORMATION FOR SEQ ID NO:30:

( i ) SEQUENCE CHARACTERISTICS:
        ( A ) LENGTH: 2403 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Synthetic DNA"

( i i i ) HYPOTHETICAL: NO ( i x ) FEATURE:
        ( A ) NAME/KEY: misc_feature
        ( B ) LOCATION: 11..2389
        ( D ) OTHER INFORMATION: /note= "maize optimized DNA
            sequence encoding VIP3A(a)"

-continued

GATCACCAAG GAGAACGTGA AGACCAGCGG CAGCGAGGTG GGCAACGTGT ACAACTTCCT 840

GATCGTGCTG ACCGCCCTGC AGGCCCAGGC CTTCCTGACC CTGACCACCT GTCGCAAGCT 900

GCTGGGCCTG GCCGACATCG ACTACACCAG CATCATGAAC GAGCACTTGA ACAAGGAGAA 960

GGAGGAGTTC CGCGTGAACA TCCTGCCGAC CCTGAGCAAC ACCTTCAGCA ACCCGAACTA 1020

CGCCAAGGTG AAGGGCAGCG ACGAGGACGC CAAGATGATC GTGGAGGCTA AGCCGGGCCA 1080

CGCGTTGATC GGCTTCGAGA TCAGCAACGA CAGCATCACC GTGCTGAAGG TGTACGAGGC 1140

CAAGCTGAAG CAGAACTACC AGGTGGACAA GGACAGCTTG AGCGAGGTGA TCTACGGCGA 1200

CATGGACAAG CTGCTGTGTC CGGACCAGAG CGAGCAAATC TACTACACCA ACAACATCGT 1260

GTTCCCGAAC GAGTACGTGA TCACCAAGAT CGACTTCACC AAGAAGATGA AGACCCTGCG 1320

CTACGAGGTG ACCGCCAACT TCTACGACAG CAGCACCGGC GAGATCGACC TGAACAAGAA 1380

GAAGGTGGAG AGCAGCGAGG CCGAGTACCG CACCCTGAGC GCGAACGACG ACGGCGTCTA 1440

CATGCCACTG GGCGTGATCA GCGAGACCTT CCTGACCCCG ATCAACGGCT TTGGCCTGCA 1500

GGCCGACGAG AACAGCCGCC TGATCACCCT GACCTGTAAG AGCTACCTGC GCGAGCTGCT 1560

GCTAGCCACC GACCTGAGCA ACAAGGAGAC CAAGCTGATC GTGCCACCGA GCGGCTTCAT 1620

CAGCAACATC GTGGAGAACG GCAGCATCGA GGAGGACAAC CTGGAGCCGT GGAAGGCCAA 1680

CAACAAGAAC GCCTACGTGG ACCACACCGG CGGCGTGAAC GGCACCAAGG CCCTGTACGT 1740

GCACAAGGAC GGCGGCATCA GCCAGTTCAT CGGCGACAAG CTGAAGCCGA AGACCGAGTA 1800

CGTGATCCAG TACACCGTGA AGGGCAAGCC ATCGATTCAC CTGAAGGACG AGAACACCGG 1860

CTACATCCAC TACGAGGACA CCAACAACAA CCTGGAGGAC TACCAGACCA TCAACAAGCG 1920

CTTCACCACC GGCACCGACC TGAAGGGCGT GTACCTGATC CTGAAGAGCC AGAACGGCGA 1980

CGAGGCCTGG GGCGACAACT TCATCATCCT GGAGATCAGC CCGAGCGAGA AGCTGCTGAG 2040

CCCGGAGCTG ATCAACACCA ACAACTGGAC CAGCACCGGC AGCACCAACA TCAGCGGCAA 2100

CACCCTGACC CTGTACCAGG GCGGCCGCGG CATCCTGAAG CAGAACCTGC AGCTGGACAG 2160

CTTCAGCACC TACCGCGTGT ACTTCAGCGT GAGCGGCGAC GCCAACGTGC GCATCCGCAA 2220

CAGCCGCGAG GTGCTGTTCG AGAAGAGGTA CATGAGCGGC GCCAAGGACG TGAGCGAGAT 2280

GTTCACCACC AAGTTCGAGA AGGACAACTT CTACATCGAG CTGAGCCAGG GCAACAACCT 2340

GTACGGCGGC CCGATCGTGC ACTTCTACGA CGTGAGCATC AAGTTAACGT AGAGCTCAGA 2400

TCT 2403

( 2 ) INFORMATION FOR SEQ ID NO:31:

( i ) SEQUENCE CHARACTERISTICS:
( A ) LENGTH: 2612 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i x ) FEATURE:
( A ) NAME/KEY: CDS
( B ) LOCATION: 118..2484
( D ) OTHER INFORMATION: /note= "Native DNA sequence encoding VIP3A(b) from AB424"

( x i ) SEQUENCE DESCRIPTION: SEQ ID NO:31:

ATTGAAATTG ATAAAAAGTT ATGAGTGTTT AATAATCAGT AATTACCAAT AAAGAATTAA 60

```
GAATACAAGT TTACAAGAAA TAAGTGTTAC AAAAAATAGC TGAAAAGGAA GATGAAC                                         117

ATG AAC AAG AAT AAT ACT AAA TTA AGC ACA AGA GCC TTA CCA AGT TTT                                       165
Met Asn Lys Asn Asn Thr Lys Leu Ser Thr Arg Ala Leu Pro Ser Phe
790             795             800             805

ATT GAT TAT TTC AAT GGC ATT TAT GGA TTT GCC ACT GGT ATC AAA GAC                                       213
Ile Asp Tyr Phe Asn Gly Ile Tyr Gly Phe Ala Thr Gly Ile Lys Asp
                810             815             820

ATT ATG AAC ATG ATT TTT AAA ACG GAT ACA GGT GGT GAT CTA ACC CTA                                       261
Ile Met Asn Met Ile Phe Lys Thr Asp Thr Gly Gly Asp Leu Thr Leu
            825             830             835

GAC GAA ATT TTA AAG AAT CAG CAG CTA CTA AAT GAT ATT TCT GGT AAA                                       309
Asp Glu Ile Leu Lys Asn Gln Gln Leu Leu Asn Asp Ile Ser Gly Lys
        840             845             850

TTG GAT GGG GTG AAT GGA AGC TTA AAT GAT CTT ATC GCA CAG GGA AAC                                       357
Leu Asp Gly Val Asn Gly Ser Leu Asn Asp Leu Ile Ala Gln Gly Asn
855             860             865

TTA AAT ACA GAA TTA TCT AAG GAA ATA TTA AAA ATT GCA AAT GAA CAA                                       405
Leu Asn Thr Glu Leu Ser Lys Glu Ile Leu Lys Ile Ala Asn Glu Gln
870             875             880             885

AAT CAA GTT TTA AAT GAT GTT AAT AAC AAA CTC GAT GCG ATA AAT ACG                                       453
Asn Gln Val Leu Asn Asp Val Asn Asn Lys Leu Asp Ala Ile Asn Thr
            890             895             900

ATG CTT CGG GTA TAT CTA CCT AAA ATT ACC TCT ATG TTG AGT GAT GTA                                       501
Met Leu Arg Val Tyr Leu Pro Lys Ile Thr Ser Met Leu Ser Asp Val
        905             910             915

ATG AAA CAA AAT TAT GCG CTA AGT CTG CAA ATA GAA TAC TTA AGT AAA                                       549
Met Lys Gln Asn Tyr Ala Leu Ser Leu Gln Ile Glu Tyr Leu Ser Lys
920             925             930

CAA TTG CAA GAG ATT TCT GAT AAG TTG GAT ATT ATT AAT GTA AAT GTA                                       597
Gln Leu Gln Glu Ile Ser Asp Lys Leu Asp Ile Ile Asn Val Asn Val
935             940             945

CTT ATT AAC TCT ACA CTT ACT GAA ATT ACA CCT GCG TAT CAA AGG ATT                                       645
Leu Ile Asn Ser Thr Leu Thr Glu Ile Thr Pro Ala Tyr Gln Arg Ile
950             955             960             965

AAA TAT GTG AAC GAA AAA TTT GAG GAA TTA ACT TTT GCT ACA GAA ACT                                       693
Lys Tyr Val Asn Glu Lys Phe Glu Glu Leu Thr Phe Ala Thr Glu Thr
            970             975             980

AGT TCA AAA GTA AAA AAG GAT GGC TCT CCT GCA GAT ATT CGT GAT GAG                                       741
Ser Ser Lys Val Lys Lys Asp Gly Ser Pro Ala Asp Ile Arg Asp Glu
        985             990             995

TTA ACT GAG TTA ACT GAA CTA GCG AAA AGT GTA ACA AAA AAT GAT GTG                                       789
Leu Thr Glu Leu Thr Glu Leu Ala Lys Ser Val Thr Lys Asn Asp Val
1000            1005            1010

GAT GGT TTT GAA TTT TAC CTT AAT ACA TTC CAC GAT GTA ATG GTA GGA                                       837
Asp Gly Phe Glu Phe Tyr Leu Asn Thr Phe His Asp Val Met Val Gly
1015            1020            1025

AAT AAT TTA TTC GGG CGT TCA GCT TTA AAA ACT GCA TCG GAA TTA ATT                                       885
Asn Asn Leu Phe Gly Arg Ser Ala Leu Lys Thr Ala Ser Glu Leu Ile
1030            1035            1040            1045

ACT AAA GAA AAT GTG AAA ACA AGT GGC AGT GAG GTC GGA AAT GTT TAT                                       933
Thr Lys Glu Asn Val Lys Thr Ser Gly Ser Glu Val Gly Asn Val Tyr
            1050            1055            1060

AAC TTC CTA ATT GTA TTA ACA GCT CTG CAA GCA AAA GCT TTT CTT ACT                                       981
Asn Phe Leu Ile Val Leu Thr Ala Leu Gln Ala Lys Ala Phe Leu Thr
        1065            1070            1075

TTA ACA CCA TGC CGA AAA TTA TTA GGC TTA GCA GAT ATT GAT TAT ACT                                       1029
Leu Thr Pro Cys Arg Lys Leu Leu Gly Leu Ala Asp Ile Asp Tyr Thr
1080            1085            1090

TCT ATT ATG AAT GAA CAT TTA AAT AAG GAA AAA GAG GAA TTT AGA GTA                                       1077
Ser Ile Met Asn Glu His Leu Asn Lys Glu Lys Glu Glu Phe Arg Val
```

```
                  1095                          1100                          1105
AAC  ATC  CTC  CCT  ACA  CTT  TCT  AAT  ACT  TTT  TCT  AAT  CCT  AAT  TAT  GCA    1125
Asn  Ile  Leu  Pro  Thr  Leu  Ser  Asn  Thr  Phe  Ser  Asn  Pro  Asn  Tyr  Ala
1110                     1115                     1120                     1125

AAA  GTT  AAA  GGA  AGT  GAT  GAA  GAT  GCA  AAG  ATG  ATT  GTG  GAA  GCT  AAA    1173
Lys  Val  Lys  Gly  Ser  Asp  Glu  Asp  Ala  Lys  Met  Ile  Val  Glu  Ala  Lys
                         1130                     1135                     1140

CCA  GGA  CAT  GCA  TTG  ATT  GGG  TTT  GAA  ATT  AGT  AAT  GAT  TCA  ATT  ACA    1221
Pro  Gly  His  Ala  Leu  Ile  Gly  Phe  Glu  Ile  Ser  Asn  Asp  Ser  Ile  Thr
               1145                     1150                     1155

GTA  TTA  AAA  GTA  TAT  GAG  GCT  AAG  CTA  AAA  CAA  AAT  TAT  CAA  GTC  GAT    1269
Val  Leu  Lys  Val  Tyr  Glu  Ala  Lys  Leu  Lys  Gln  Asn  Tyr  Gln  Val  Asp
               1160                     1165                     1170

AAG  GAT  TCC  TTA  TCG  GAA  GTT  ATT  TAT  GGC  GAT  ATG  GAT  AAA  TTA  TTG    1317
Lys  Asp  Ser  Leu  Ser  Glu  Val  Ile  Tyr  Gly  Asp  Met  Asp  Lys  Leu  Leu
               1175                     1180                     1185

TGC  CCA  GAT  CAA  TCT  GGA  CAA  ATC  TAT  TAT  ACA  AAT  AAC  ATA  GTA  TTT    1365
Cys  Pro  Asp  Gln  Ser  Gly  Gln  Ile  Tyr  Tyr  Thr  Asn  Asn  Ile  Val  Phe
1190                     1195                     1200                     1205

CCA  AAT  GAA  TAT  GTA  ATT  ACT  AAA  ATT  GAT  TTC  ACT  AAA  AAA  ATG  AAA    1413
Pro  Asn  Glu  Tyr  Val  Ile  Thr  Lys  Ile  Asp  Phe  Thr  Lys  Lys  Met  Lys
                         1210                     1215                     1220

ACT  TTA  AGA  TAT  GAG  GTA  ACA  GCG  AAT  TTT  TAT  GAT  TCT  TCT  ACA  GGA    1461
Thr  Leu  Arg  Tyr  Glu  Val  Thr  Ala  Asn  Phe  Tyr  Asp  Ser  Ser  Thr  Gly
               1225                     1230                     1235

GAA  ATT  GAC  TTA  AAT  AAG  AAA  AAA  GTA  GAA  TCA  AGT  GAA  GCG  GAG  TAT    1509
Glu  Ile  Asp  Leu  Asn  Lys  Lys  Lys  Val  Glu  Ser  Ser  Glu  Ala  Glu  Tyr
               1240                     1245                     1250

AGA  ACG  TTA  AGT  GCT  AAT  GAT  GAT  GGG  GTG  TAT  ATG  CCG  TTA  GGT  GTC    1557
Arg  Thr  Leu  Ser  Ala  Asn  Asp  Asp  Gly  Val  Tyr  Met  Pro  Leu  Gly  Val
1255                     1260                     1265

ATC  AGT  GAA  ACA  TTT  TTG  ACT  CCG  ATT  AAT  GGG  TTT  GGC  CTC  CAA  GCT    1605
Ile  Ser  Glu  Thr  Phe  Leu  Thr  Pro  Ile  Asn  Gly  Phe  Gly  Leu  Gln  Ala
1270                     1275                     1280                     1285

GAT  GAA  AAT  TCA  AGA  TTA  ATT  ACT  TTA  ACA  TGT  AAA  TCA  TAT  TTA  AGA    1653
Asp  Glu  Asn  Ser  Arg  Leu  Ile  Thr  Leu  Thr  Cys  Lys  Ser  Tyr  Leu  Arg
               1290                     1295                     1300

GAA  CTA  CTG  CTA  GCA  ACA  GAC  TTA  AGC  AAT  AAA  GAA  ACT  AAA  TTG  ATC    1701
Glu  Leu  Leu  Leu  Ala  Thr  Asp  Leu  Ser  Asn  Lys  Glu  Thr  Lys  Leu  Ile
               1305                     1310                     1315

GTC  CCG  CCA  AGT  GGT  TTT  ATT  AGC  AAT  ATT  GTA  GAG  AAC  GGG  TCC  ATA    1749
Val  Pro  Pro  Ser  Gly  Phe  Ile  Ser  Asn  Ile  Val  Glu  Asn  Gly  Ser  Ile
               1320                     1325                     1330

GAA  GAG  GAC  AAT  TTA  GAG  CCG  TGG  AAA  GCA  AAT  AAT  AAG  AAT  GCG  TAT    1797
Glu  Glu  Asp  Asn  Leu  Glu  Pro  Trp  Lys  Ala  Asn  Asn  Lys  Asn  Ala  Tyr
               1335                     1340                     1345

GTA  GAT  CAT  ACA  GGC  GGA  GTG  AAT  GGA  ACT  AAA  GCT  TTA  TAT  GTT  CAT    1845
Val  Asp  His  Thr  Gly  Gly  Val  Asn  Gly  Thr  Lys  Ala  Leu  Tyr  Val  His
1350                     1355                     1360                     1365

AAG  GAC  GGA  GGA  ATT  TCA  CAA  TTT  ATT  GGA  GAT  AAG  TTA  AAA  CCG  AAA    1893
Lys  Asp  Gly  Gly  Ile  Ser  Gln  Phe  Ile  Gly  Asp  Lys  Leu  Lys  Pro  Lys
               1370                     1375                     1380

ACT  GAG  TAT  GTA  ATC  CAA  TAT  ACT  GTT  AAA  GGA  AAA  CCT  TCT  ATT  CAT    1941
Thr  Glu  Tyr  Val  Ile  Gln  Tyr  Thr  Val  Lys  Gly  Lys  Pro  Ser  Ile  His
               1385                     1390                     1395

TTA  AAA  GAT  GAA  AAT  ACT  GGA  TAT  ATT  CAT  TAT  GAA  GAT  ACA  AAT  AAT    1989
Leu  Lys  Asp  Glu  Asn  Thr  Gly  Tyr  Ile  His  Tyr  Glu  Asp  Thr  Asn  Asn
               1400                     1405                     1410

AAT  TTA  GAA  GAT  TAT  CAA  ACT  ATT  AAT  AAA  CGT  TTT  ACT  ACA  GGA  ACT    2037
Asn  Leu  Glu  Asp  Tyr  Gln  Thr  Ile  Asn  Lys  Arg  Phe  Thr  Thr  Gly  Thr
```

-continued

```
                 1415                           1420                              1425
GAT  TTA  AAG  GGA  GTG  TAT  TTA  ATT  TTA  AAA  AGT  CAA  AAT  GGA  GAT  GAA         2085
Asp  Leu  Lys  Gly  Val  Tyr  Leu  Ile  Leu  Lys  Ser  Gln  Asn  Gly  Asp  Glu
1430                     1435                     1440                     1445

GCT  TGG  GGA  GAT  AAC  TTT  ATT  ATT  TTG  GAA  ATT  AGT  CCT  TCT  GAA  AAG         2133
Ala  Trp  Gly  Asp  Asn  Phe  Ile  Ile  Leu  Glu  Ile  Ser  Pro  Ser  Glu  Lys
                         1450                     1455                     1460

TTA  TTA  AGT  CCA  GAA  TTA  ATT  AAT  ACA  AAT  AAT  TGG  ACG  AGT  ACG  GGA         2181
Leu  Leu  Ser  Pro  Glu  Leu  Ile  Asn  Thr  Asn  Asn  Trp  Thr  Ser  Thr  Gly
               1465                     1470                     1475

TCA  ACT  AAT  ATT  AGC  GGT  AAT  ACA  CTC  ACT  CTT  TAT  CAG  GGA  GGA  CGA         2229
Ser  Thr  Asn  Ile  Ser  Gly  Asn  Thr  Leu  Thr  Leu  Tyr  Gln  Gly  Gly  Arg
          1480                     1485                     1490

GGG  ATT  CTA  AAA  CAA  AAC  CTT  CAA  TTA  GAT  AGT  TTT  TCA  ACT  TAT  AGA         2277
Gly  Ile  Leu  Lys  Gln  Asn  Leu  Gln  Leu  Asp  Ser  Phe  Ser  Thr  Tyr  Arg
1495                     1500                     1505

GTG  TAT  TTC  TCT  GTG  TCC  GGA  GAT  GCT  AAT  GTA  AGG  ATT  AGA  AAT  TCT         2325
Val  Tyr  Phe  Ser  Val  Ser  Gly  Asp  Ala  Asn  Val  Arg  Ile  Arg  Asn  Ser
1510                     1515                     1520                     1525

AGG  GAA  GTG  TTA  TTT  GAA  AAA  AGA  TAT  ATG  AGC  GGT  GCT  AAA  GAT  GTT         2373
Arg  Glu  Val  Leu  Phe  Glu  Lys  Arg  Tyr  Met  Ser  Gly  Ala  Lys  Asp  Val
                         1530                     1535                     1540

TCT  GAA  ATG  TTC  ACT  ACA  AAA  TTT  GAG  AAA  GAT  AAC  TTC  TAT  ATA  GAG         2421
Ser  Glu  Met  Phe  Thr  Thr  Lys  Phe  Glu  Lys  Asp  Asn  Phe  Tyr  Ile  Glu
               1545                     1550                     1555

CTT  TCT  CAA  GGG  AAT  AAT  TTA  TAT  GGT  GGT  CCT  ATT  GTA  CAT  TTT  TAC         2469
Leu  Ser  Gln  Gly  Asn  Asn  Leu  Tyr  Gly  Gly  Pro  Ile  Val  His  Phe  Tyr
          1560                     1565                     1570

GAT  GTC  TCT  ATT  AAG  TAAGATCGGG  ATCTAATATT  AACAGTTTTT  AGAAGCTAAT                 2524
Asp  Val  Ser  Ile  Lys
               1575

TCTTGTATAA  TGTCCTTGAT  TATGGAAAAA  CACAATTTTG  TTTGCTAAGA  TGTATATATA                 2584

GCTCACTCAT  TAAAAGGCAA  TCAAGCTT                                                       2612
```

( 2 ) INFORMATION FOR SEQ ID NO:32:

( i ) SEQUENCE CHARACTERISTICS:
        ( A ) LENGTH: 789 amino acids
        ( B ) TYPE: amino acid
        ( D ) TOPOLOGY: linear ( i i ) MOLECULE TYPE: protein ( x i ) SEQUENCE DESCRIPTION: SEQ ID NO:32:

```
Met  Asn  Lys  Asn  Asn  Thr  Lys  Leu  Ser  Thr  Arg  Ala  Leu  Pro  Ser  Phe
 1                    5                      10                      15

Ile  Asp  Tyr  Phe  Asn  Gly  Ile  Tyr  Gly  Phe  Ala  Thr  Gly  Ile  Lys  Asp
                20                      25                      30

Ile  Met  Asn  Met  Ile  Phe  Lys  Thr  Asp  Thr  Gly  Gly  Asp  Leu  Thr  Leu
          35                      40                      45

Asp  Glu  Ile  Leu  Lys  Asn  Gln  Gln  Leu  Leu  Asn  Asp  Ile  Ser  Gly  Lys
     50                      55                      60

Leu  Asp  Gly  Val  Asn  Gly  Ser  Leu  Asn  Asp  Leu  Ile  Ala  Gln  Gly  Asn
 65                      70                      75                      80

Leu  Asn  Thr  Glu  Leu  Ser  Lys  Glu  Ile  Leu  Lys  Ile  Ala  Asn  Glu  Gln
                    85                      90                      95

Asn  Gln  Val  Leu  Asn  Asp  Val  Asn  Asn  Lys  Leu  Asp  Ala  Ile  Asn  Thr
               100                     105                     110

Met  Leu  Arg  Val  Tyr  Leu  Pro  Lys  Ile  Thr  Ser  Met  Leu  Ser  Asp  Val
```

-continued

```
                115                       120                       125
Met Lys Gln Asn Tyr Ala Leu Ser Leu Gln Ile Tyr Leu Ser Lys
    130                     135                     140
Gln Leu Gln Glu Ile Ser Asp Lys Leu Asp Ile Ile Asn Val Asn Val
145                     150                     155                 160
Leu Ile Asn Ser Thr Leu Thr Glu Ile Thr Pro Ala Tyr Gln Arg Ile
                165                     170                     175
Lys Tyr Val Asn Glu Lys Phe Glu Glu Leu Thr Phe Ala Thr Glu Thr
                180                     185                     190
Ser Ser Lys Val Lys Lys Asp Gly Ser Pro Ala Asp Ile Arg Asp Glu
            195                     200                     205
Leu Thr Glu Leu Thr Glu Leu Ala Lys Ser Val Thr Lys Asn Asp Val
    210                     215                     220
Asp Gly Phe Glu Phe Tyr Leu Asn Thr Phe His Asp Val Met Val Gly
225                     230                     235                 240
Asn Asn Leu Phe Gly Arg Ser Ala Leu Lys Thr Ala Ser Glu Leu Ile
                245                     250                     255
Thr Lys Glu Asn Val Lys Thr Ser Gly Ser Glu Val Gly Asn Val Tyr
                260                     265                     270
Asn Phe Leu Ile Val Leu Thr Ala Leu Gln Ala Lys Ala Phe Leu Thr
                275                     280                     285
Leu Thr Pro Cys Arg Lys Leu Leu Gly Leu Ala Asp Ile Asp Tyr Thr
    290                     295                     300
Ser Ile Met Asn Glu His Leu Asn Lys Glu Lys Glu Glu Phe Arg Val
305                     310                     315                 320
Asn Ile Leu Pro Thr Leu Ser Asn Thr Phe Ser Asn Pro Asn Tyr Ala
                325                     330                     335
Lys Val Lys Gly Ser Asp Glu Asp Ala Lys Met Ile Val Glu Ala Lys
                340                     345                     350
Pro Gly His Ala Leu Ile Gly Phe Glu Ile Ser Asn Asp Ser Ile Thr
            355                     360                     365
Val Leu Lys Val Tyr Glu Ala Lys Leu Lys Gln Asn Tyr Gln Val Asp
    370                     375                     380
Lys Asp Ser Leu Ser Glu Val Ile Tyr Gly Asp Met Asp Lys Leu Leu
385                     390                     395                 400
Cys Pro Asp Gln Ser Gly Gln Ile Tyr Tyr Thr Asn Asn Ile Val Phe
                405                     410                     415
Pro Asn Glu Tyr Val Ile Thr Lys Ile Asp Phe Thr Lys Lys Met Lys
                420                     425                     430
Thr Leu Arg Tyr Glu Val Thr Ala Asn Phe Tyr Asp Ser Ser Thr Gly
                435                     440                     445
Glu Ile Asp Leu Asn Lys Lys Lys Val Glu Ser Ser Glu Ala Glu Tyr
    450                     455                     460
Arg Thr Leu Ser Ala Asn Asp Asp Gly Val Tyr Met Pro Leu Gly Val
465                     470                     475                 480
Ile Ser Glu Thr Phe Leu Thr Pro Ile Asn Gly Phe Gly Leu Gln Ala
                485                     490                     495
Asp Glu Asn Ser Arg Leu Ile Thr Leu Thr Cys Lys Ser Tyr Leu Arg
            500                     505                     510
Glu Leu Leu Leu Ala Thr Asp Leu Ser Asn Lys Glu Thr Lys Leu Ile
    515                     520                     525
Val Pro Pro Ser Gly Phe Ile Ser Asn Ile Val Glu Asn Gly Ser Ile
    530                     535                     540
```

| Glu<br>545 | Glu | Asp | Asn | Leu | Glu<br>550 | Pro | Trp | Lys | Ala | Asn<br>555 | Asn | Lys | Asn | Ala | Tyr<br>560 |
|---|---|---|---|---|---|---|---|---|---|---|---|---|---|---|---|
| Val | Asp | His | Thr | Gly<br>565 | Gly | Val | Asn | Gly | Thr<br>570 | Lys | Ala | Leu | Tyr | Val<br>575 | His |
| Lys | Asp | Gly | Gly<br>580 | Ile | Ser | Gln | Phe | Ile<br>585 | Gly | Asp | Lys | Leu | Lys<br>590 | Pro | Lys |
| Thr | Glu | Tyr<br>595 | Val | Ile | Gln | Tyr | Thr<br>600 | Val | Lys | Gly | Lys | Pro<br>605 | Ser | Ile | His |
| Leu | Lys<br>610 | Asp | Glu | Asn | Thr | Gly<br>615 | Tyr | Ile | His | Tyr | Glu<br>620 | Asp | Thr | Asn | Asn |
| Asn<br>625 | Leu | Glu | Asp | Tyr | Gln<br>630 | Thr | Ile | Asn | Lys | Arg<br>635 | Phe | Thr | Thr | Gly | Thr<br>640 |
| Asp | Leu | Lys | Gly | Val<br>645 | Tyr | Leu | Ile | Leu | Lys<br>650 | Ser | Gln | Asn | Gly | Asp<br>655 | Glu |
| Ala | Trp | Gly | Asp<br>660 | Asn | Phe | Ile | Ile | Leu<br>665 | Glu | Ile | Ser | Pro | Ser<br>670 | Glu | Lys |
| Leu | Leu | Ser<br>675 | Pro | Glu | Leu | Ile | Asn<br>680 | Thr | Asn | Asn | Trp | Thr<br>685 | Ser | Thr | Gly |
| Ser | Thr<br>690 | Asn | Ile | Ser | Gly | Asn<br>695 | Thr | Leu | Thr | Leu | Tyr<br>700 | Gln | Gly | Gly | Arg |
| Gly<br>705 | Ile | Leu | Lys | Gln | Asn<br>710 | Leu | Gln | Leu | Asp | Ser<br>715 | Phe | Ser | Thr | Tyr | Arg<br>720 |
| Val | Tyr | Phe | Ser | Val<br>725 | Ser | Gly | Asp | Ala | Asn<br>730 | Val | Arg | Ile | Arg | Asn<br>735 | Ser |
| Arg | Glu | Val | Leu<br>740 | Phe | Glu | Lys | Arg | Tyr<br>745 | Met | Ser | Gly | Ala | Lys<br>750 | Asp | Val |
| Ser | Glu | Met<br>755 | Phe | Thr | Thr | Lys | Phe<br>760 | Glu | Lys | Asp | Asn | Phe<br>765 | Tyr | Ile | Glu |
| Leu | Ser<br>770 | Gln | Gly | Asn | Asn | Leu<br>775 | Tyr | Gly | Gly | Pro | Ile<br>780 | Val | His | Phe | Tyr |
| Asp<br>785 | Val | Ser | Ile | Lys | | | | | | | | | | | |

( 2 ) INFORMATION FOR SEQ ID NO:33:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "forward primer used to make
            pCIB5526"

( i i i ) HYPOTHETICAL: NO ( x i ) SEQUENCE DESCRIPTION: SEQ ID NO:33:

GGATCCACCA TGAAGACCAA CCAGATCAGC 30

( 2 ) INFORMATION FOR SEQ ID NO:34:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "reverse primer used to make
            pCIB5526"

5,888,801

153                                                                         154
-continued (  i i i  ) HYPOTHETICAL: NO (  x i  ) SEQUENCE DESCRIPTION: SEQ ID NO:34:

AAGCTTCAGC TCCTT                                                                                    15

( 2 ) INFORMATION FOR SEQ ID NO:35:

( i ) SEQUENCE CHARACTERISTICS:
       ( A ) LENGTH: 2576 base pairs
       ( B ) TYPE: nucleic acid
       ( C ) STRANDEDNESS: single
       ( D ) TOPOLOGY: linear ( i i ) MOLECULE TYPE: other nucleic acid
       ( A ) DESCRIPTION: /desc = "Synthetic DNA"

( i i i ) HYPOTHETICAL: NO ( i x ) FEATURE:
       ( A ) NAME/KEY: CDS
       ( B ) LOCATION: 9..2564
       ( D ) OTHER INFORMATION: /note= "Maize optimized sequence
             encoding VIP1A(a) with the Bacillus secretion signal
             removed as contained in pCIB5526"

( x i ) SEQUENCE DESCRIPTION: SEQ ID NO:35:

| GATCCACC | ATG | AAG | ACC | AAC | CAG | ATC | AGC | ACC | ACC | CAG | AAG | AAC | CAG | CAG | 50 |
| | Met | Lys | Thr | Asn | Gln | Ile | Ser | Thr | Thr | Gln | Lys | Asn | Gln | Gln | |
| | | | | 825 | | | | 830 | | | | | | 835 | |

| AAG | GAG | ATG | GAC | CGC | AAG | GGC | CTG | CTG | GGC | TAC | TAC | TTC | AAG | GGC | AAG | 98 |
| Lys | Glu | Met | Asp | Arg | Lys | Gly | Leu | Leu | Gly | Tyr | Tyr | Phe | Lys | Gly | Lys | |
| | | | | 840 | | | | | 845 | | | | | 850 | | |

| GAC | TTC | AGC | AAC | CTG | ACC | ATG | TTC | GCC | CCC | ACG | CGT | GAC | AGC | ACC | CTG | 146 |
| Asp | Phe | Ser | Asn | Leu | Thr | Met | Phe | Ala | Pro | Thr | Arg | Asp | Ser | Thr | Leu | |
| | | | 855 | | | | | 860 | | | | | 865 | | | |

| ATC | TAC | GAC | CAG | CAG | ACC | GCC | AAC | AAG | CTG | CTG | GAC | AAG | AAG | CAG | CAG | 194 |
| Ile | Tyr | Asp | Gln | Gln | Thr | Ala | Asn | Lys | Leu | Leu | Asp | Lys | Lys | Gln | Gln | |
| | | 870 | | | | | 875 | | | | | 880 | | | | |

| GAG | TAC | CAG | AGC | ATC | CGC | TGG | ATC | GGC | CTG | ATC | CAG | AGC | AAG | GAG | ACC | 242 |
| Glu | Tyr | Gln | Ser | Ile | Arg | Trp | Ile | Gly | Leu | Ile | Gln | Ser | Lys | Glu | Thr | |
| | | 885 | | | | 890 | | | | | 895 | | | | | |

| GGC | GAC | TTC | ACC | TTC | AAC | CTG | AGC | GAG | GAC | GAG | CAG | GCC | ATC | ATC | GAG | 290 |
| Gly | Asp | Phe | Thr | Phe | Asn | Leu | Ser | Glu | Asp | Glu | Gln | Ala | Ile | Ile | Glu | |
| 900 | | | | | 905 | | | | | 910 | | | | | 915 | |

| ATC | AAC | GGC | AAG | ATC | ATC | AGC | AAC | AAG | GGC | AAG | GAG | AAG | CAG | GTG | GTG | 338 |
| Ile | Asn | Gly | Lys | Ile | Ile | Ser | Asn | Lys | Gly | Lys | Glu | Lys | Gln | Val | Val | |
| | | | | 920 | | | | | 925 | | | | | 930 | | |

| CAC | CTG | GAG | AAG | GGC | AAG | CTG | GTG | CCC | ATC | AAG | ATC | GAG | TAC | CAG | AGC | 386 |
| His | Leu | Glu | Lys | Gly | Lys | Leu | Val | Pro | Ile | Lys | Ile | Glu | Tyr | Gln | Ser | |
| | | | 935 | | | | | 940 | | | | | 945 | | | |

| GAC | ACC | AAG | TTC | AAC | ATC | GAC | AGC | AAG | ACC | TTC | AAG | GAG | CTG | AAG | CTT | 434 |
| Asp | Thr | Lys | Phe | Asn | Ile | Asp | Ser | Lys | Thr | Phe | Lys | Glu | Leu | Lys | Leu | |
| | | 950 | | | | | 955 | | | | | 960 | | | | |

| TTC | AAG | ATC | GAC | AGC | CAG | AAC | CAG | CCC | CAG | CAG | GTG | CAG | CAG | GAC | GAG | 482 |
| Phe | Lys | Ile | Asp | Ser | Gln | Asn | Gln | Pro | Gln | Gln | Val | Gln | Gln | Asp | Glu | |
| | 965 | | | | | 970 | | | | | 975 | | | | | |

| CTG | CGC | AAC | CCC | GAG | TTC | AAC | AAG | AAG | GAG | AGC | CAG | GAG | TTC | CTG | GCC | 530 |
| Leu | Arg | Asn | Pro | Glu | Phe | Asn | Lys | Lys | Glu | Ser | Gln | Glu | Phe | Leu | Ala | |
| 980 | | | | | 985 | | | | | 990 | | | | | 995 | |

| AAG | CCC | AGC | AAG | ATC | AAC | CTG | TTC | ACC | CAG | CAG | ATG | AAG | CGC | GAG | ATC | 578 |
| Lys | Pro | Ser | Lys | Ile | Asn | Leu | Phe | Thr | Gln | Gln | Met | Lys | Arg | Glu | Ile | |
| | | | | 1000 | | | | 1005 | | | | | 1010 | | | |

| GAC | GAG | GAC | ACC | GAC | ACC | GAC | GGC | GAC | AGC | ATC | CCC | GAC | CTG | TGG | GAG | 626 |
| Asp | Glu | Asp | Thr | Asp | Thr | Asp | Gly | Asp | Ser | Ile | Pro | Asp | Leu | Trp | Glu | |
| | | | 1015 | | | | 1020 | | | | | 1025 | | | | |

```
GAG AAC GGC TAC ACC ATC CAG AAC CGC ATC GCC GTG AAG TGG GAC GAC         674
Glu Asn Gly Tyr Thr Ile Gln Asn Arg Ile Ala Val Lys Trp Asp Asp
            1030                1035                1040

AGC CTG GCT AGC AAG GGC TAC ACC AAG TTC GTG AGC AAC CCC CTG GAG         722
Ser Leu Ala Ser Lys Gly Tyr Thr Lys Phe Val Ser Asn Pro Leu Glu
            1045                1050                1055

AGC CAC ACC GTG GGC GAC CCC TAC ACC GAC TAC GAG AAG GCC GCC CGC         770
Ser His Thr Val Gly Asp Pro Tyr Thr Asp Tyr Glu Lys Ala Ala Arg
1060                1065                1070                1075

GAC CTG GAC CTG AGC AAC GCC AAG GAG ACC TTC AAC CCC CTG GTG GCC         818
Asp Leu Asp Leu Ser Asn Ala Lys Glu Thr Phe Asn Pro Leu Val Ala
            1080                1085                1090

GCC TTC CCC AGC GTG AAC GTG AGC ATG GAG AAG GTG ATC CTG AGC CCC         866
Ala Phe Pro Ser Val Asn Val Ser Met Glu Lys Val Ile Leu Ser Pro
            1095                1100                1105

AAC GAG AAC CTG AGC AAC AGC GTG GAG AGC CAC TCG AGC ACC AAC TGG         914
Asn Glu Asn Leu Ser Asn Ser Val Glu Ser His Ser Ser Thr Asn Trp
            1110                1115                1120

AGC TAC ACC AAC ACC GAG GGC GCC AGC GTG GAG GCC GGC ATC GGT CCC         962
Ser Tyr Thr Asn Thr Glu Gly Ala Ser Val Glu Ala Gly Ile Gly Pro
            1125                1130                1135

AAG GGC ATC AGC TTC GGC GTG AGC GTG AAC TAC CAG CAC AGC GAG ACC        1010
Lys Gly Ile Ser Phe Gly Val Ser Val Asn Tyr Gln His Ser Glu Thr
1140                1145                1150                1155

GTG GCC CAG GAG TGG GGC ACC AGC ACC GGC AAC ACC AGC CAG TTC AAC        1058
Val Ala Gln Glu Trp Gly Thr Ser Thr Gly Asn Thr Ser Gln Phe Asn
            1160                1165                1170

ACC GCC AGC GCC GGC TAC CTG AAC GCC AAC GTG CGC TAC AAC AAC GTG        1106
Thr Ala Ser Ala Gly Tyr Leu Asn Ala Asn Val Arg Tyr Asn Asn Val
            1175                1180                1185

GGC ACC GGC GCC ATC TAC GAC GTG AAG CCC ACC ACC AGC TTC GTG CTG        1154
Gly Thr Gly Ala Ile Tyr Asp Val Lys Pro Thr Thr Ser Phe Val Leu
            1190                1195                1200

AAC AAC GAC ACC ATC GCC ACC ATC ACC GCC AAG TCG AAT TCC ACC GCC        1202
Asn Asn Asp Thr Ile Ala Thr Ile Thr Ala Lys Ser Asn Ser Thr Ala
            1205                1210                1215

CTG AAC ATC AGC CCC GGC GAG AGC TAC CCC AAG AAG GGC CAG AAC GGC        1250
Leu Asn Ile Ser Pro Gly Glu Ser Tyr Pro Lys Lys Gly Gln Asn Gly
1220                1225                1230                1235

ATC GCC ATC ACC AGC ATG GAC GAC TTC AAC AGC CAC CCC ATC ACC CTG        1298
Ile Ala Ile Thr Ser Met Asp Asp Phe Asn Ser His Pro Ile Thr Leu
            1240                1245                1250

AAC AAG AAG CAG GTG GAC AAC CTG CTG AAC AAC AAG CCC ATG ATG CTG        1346
Asn Lys Lys Gln Val Asp Asn Leu Leu Asn Asn Lys Pro Met Met Leu
            1255                1260                1265

GAG ACC AAC CAG ACC GAC GGC GTC TAC AAG ATC AAG GAC ACC CAC GGC        1394
Glu Thr Asn Gln Thr Asp Gly Val Tyr Lys Ile Lys Asp Thr His Gly
            1270                1275                1280

AAC ATC GTG ACG GGC GGC GAG TGG AAC GGC GTG ATC CAG CAG ATC AAG        1442
Asn Ile Val Thr Gly Gly Glu Trp Asn Gly Val Ile Gln Gln Ile Lys
            1285                1290                1295

GCC AAG ACC GCC AGC ATC ATC GTC GAC GAC GGC GAG CGC GTG GCC GAG        1490
Ala Lys Thr Ala Ser Ile Ile Val Asp Asp Gly Glu Arg Val Ala Glu
1300                1305                1310                1315

AAG CGC GTG GCC GCC AAG GAC TAC GAG AAC CCC GAG GAC AAG ACC CCC        1538
Lys Arg Val Ala Ala Lys Asp Tyr Glu Asn Pro Glu Asp Lys Thr Pro
            1320                1325                1330

AGC CTG ACC CTG AAG GAC GCC AAG CTG AGC TAC CCC GAC GAG ATC            1586
Ser Leu Thr Leu Lys Asp Ala Lys Leu Ser Tyr Pro Asp Glu Ile
            1335                1340                1345
```

```
AAG GAG ATC GAG GGC TTG CTG TAC TAC AAG AAC AAG CCC ATC TAC GAG        1634
Lys Glu Ile Glu Gly Leu Leu Tyr Tyr Lys Asn Lys Pro Ile Tyr Glu
            1350                1355                1360

AGC AGC GTG ATG ACC TAT CTA GAC GAG AAC ACC GCC AAG GAG GTG ACC        1682
Ser Ser Val Met Thr Tyr Leu Asp Glu Asn Thr Ala Lys Glu Val Thr
        1365                1370                1375

AAG CAG CTG AAC GAC ACC ACC GGC AAG TTC AAG GAC GTG AGC CAC CTG        1730
Lys Gln Leu Asn Asp Thr Thr Gly Lys Phe Lys Asp Val Ser His Leu
1380                1385                1390                1395

TAC GAC GTG AAG CTG ACC CCC AAG ATG AAC GTG ACC ATC AAG CTG AGC        1778
Tyr Asp Val Lys Leu Thr Pro Lys Met Asn Val Thr Ile Lys Leu Ser
                1400                1405                1410

ATC CTG TAC GAC AAC GCC GAG AGC AAC GAC AAC AGC ATC GGC AAG TGG        1826
Ile Leu Tyr Asp Asn Ala Glu Ser Asn Asp Asn Ser Ile Gly Lys Trp
            1415                1420                1425

ACC AAC ACC AAC ATC GTG AGC GGC GGC AAC AAC GGC AAG AAG CAG TAC        1874
Thr Asn Thr Asn Ile Val Ser Gly Gly Asn Asn Gly Lys Lys Gln Tyr
        1430                1435                1440

AGC AGC AAC AAC CCC GAC GCC AAC CTG ACC CTG AAC ACC GAC GCC CAG        1922
Ser Ser Asn Asn Pro Asp Ala Asn Leu Thr Leu Asn Thr Asp Ala Gln
    1445                1450                1455

GAG AAG CTG AAC AAG AAC CGC GAC TAC TAC ATC AGC CTG TAC ATG AAG        1970
Glu Lys Leu Asn Lys Asn Arg Asp Tyr Tyr Ile Ser Leu Tyr Met Lys
1460                1465                1470                1475

AGC GAG AAG AAC ACC CAG TGC GAG ATC ACC ATC GAC GGC GAG ATA TAC        2018
Ser Glu Lys Asn Thr Gln Cys Glu Ile Thr Ile Asp Gly Glu Ile Tyr
                1480                1485                1490

CCC ATC ACC ACC AAG ACC GTG AAC GTG AAC AAG GAC AAC TAC AAG CGC        2066
Pro Ile Thr Thr Lys Thr Val Asn Val Asn Lys Asp Asn Tyr Lys Arg
            1495                1500                1505

CTG GAC ATC ATC GCC CAC AAC ATC AAG AGC AAC CCC ATC AGC AGC CTG        2114
Leu Asp Ile Ile Ala His Asn Ile Lys Ser Asn Pro Ile Ser Ser Leu
        1510                1515                1520

CAC ATC AAG ACC AAC GAC GAG ATC ACC CTG TTC TGG GAC GAC ATA TCG        2162
His Ile Lys Thr Asn Asp Glu Ile Thr Leu Phe Trp Asp Asp Ile Ser
    1525                1530                1535

ATT ACC GAC GTC GCC AGC ATC AAG CCC GAG AAC CTG ACC GAC AGC GAG        2210
Ile Thr Asp Val Ala Ser Ile Lys Pro Glu Asn Leu Thr Asp Ser Glu
1540                1545                1550                1555

ATC AAG CAG ATA TAC AGT CGC TAC GGC ATC AAG CTG GAG GAC GGC ATC        2258
Ile Lys Gln Ile Tyr Ser Arg Tyr Gly Ile Lys Leu Glu Asp Gly Ile
                1560                1565                1570

CTG ATC GAC AAG AAA GGC GGC ATC CAC TAC GGC GAG TTC ATC AAC GAG        2306
Leu Ile Asp Lys Lys Gly Gly Ile His Tyr Gly Glu Phe Ile Asn Glu
            1575                1580                1585

GCC AGC TTC AAC ATC GAG CCC CTG CAG AAC TAC GTG ACC AAG TAC GAG        2354
Ala Ser Phe Asn Ile Glu Pro Leu Gln Asn Tyr Val Thr Lys Tyr Glu
        1590                1595                1600

GTG ACC TAC AGC AGC GAG CTG GGC CCC AAC GTG AGC GAC ACC CTG GAG        2402
Val Thr Tyr Ser Ser Glu Leu Gly Pro Asn Val Ser Asp Thr Leu Glu
    1605                1610                1615

AGC GAC AAG ATT TAC AAG GAC GGC ACC ATC AAG TTC GAC TTC ACC AAG        2450
Ser Asp Lys Ile Tyr Lys Asp Gly Thr Ile Lys Phe Asp Phe Thr Lys
1620                1625                1630                1635

TAC AGC AAG AAC GAG CAG GGC CTG TTC TAC GAC AGC GGC CTG AAC TGG        2498
Tyr Ser Lys Asn Glu Gln Gly Leu Phe Tyr Asp Ser Gly Leu Asn Trp
                1640                1645                1650

GAC TTC AAG ATC AAC GCC ATC ACC TAC GAC GGC AAG GAG ATG AAC GTG        2546
Asp Phe Lys Ile Asn Ala Ile Thr Tyr Asp Gly Lys Glu Met Asn Val
            1655                1660                1665
```

```
TTC CAC CGC TAC AAC AAG TAGATCTGAG CT                                    2576
Phe His Arg Tyr Asn Lys
        1670
```

( 2 ) INFORMATION FOR SEQ ID NO:36:

( i ) SEQUENCE CHARACTERISTICS:
        ( A ) LENGTH: 852 amino acids
        ( B ) TYPE: amino acid
        ( D ) TOPOLOGY: linear ( i i ) MOLECULE TYPE: protein ( x i ) SEQUENCE DESCRIPTION: SEQ ID NO:36:

```
Met Lys Thr Asn Gln Ile Ser Thr Thr Gln Lys Asn Gln Gln Lys Glu
 1               5                  10                  15

Met Asp Arg Lys Gly Leu Leu Gly Tyr Tyr Phe Lys Gly Lys Asp Phe
             20                  25                  30

Ser Asn Leu Thr Met Phe Ala Pro Thr Arg Asp Ser Thr Leu Ile Tyr
         35                  40                  45

Asp Gln Gln Thr Ala Asn Lys Leu Leu Asp Lys Lys Gln Gln Glu Tyr
     50                  55                  60

Gln Ser Ile Arg Trp Ile Gly Leu Ile Gln Ser Lys Glu Thr Gly Asp
 65                  70                  75                  80

Phe Thr Phe Asn Leu Ser Glu Asp Glu Gln Ala Ile Ile Glu Ile Asn
                 85                  90                  95

Gly Lys Ile Ile Ser Asn Lys Gly Lys Glu Lys Gln Val Val His Leu
            100                 105                 110

Glu Lys Gly Lys Leu Val Pro Ile Lys Ile Glu Tyr Gln Ser Asp Thr
            115                 120                 125

Lys Phe Asn Ile Asp Ser Lys Thr Phe Lys Glu Leu Lys Leu Phe Lys
130                 135                 140

Ile Asp Ser Gln Asn Gln Pro Gln Gln Val Gln Gln Asp Glu Leu Arg
145                 150                 155                 160

Asn Pro Glu Phe Asn Lys Lys Glu Ser Gln Glu Phe Leu Ala Lys Pro
                165                 170                 175

Ser Lys Ile Asn Leu Phe Thr Gln Gln Met Lys Arg Glu Ile Asp Glu
                180                 185                 190

Asp Thr Asp Thr Asp Gly Asp Ser Ile Pro Asp Leu Trp Glu Glu Asn
            195                 200                 205

Gly Tyr Thr Ile Gln Asn Arg Ile Ala Val Lys Trp Asp Asp Ser Leu
        210                 215                 220

Ala Ser Lys Gly Tyr Thr Lys Phe Val Ser Asn Pro Leu Glu Ser His
225                 230                 235                 240

Thr Val Gly Asp Pro Tyr Thr Asp Tyr Glu Lys Ala Ala Arg Asp Leu
                245                 250                 255

Asp Leu Ser Asn Ala Lys Glu Thr Phe Asn Pro Leu Val Ala Ala Phe
            260                 265                 270

Pro Ser Val Asn Val Ser Met Glu Lys Val Ile Leu Ser Pro Asn Glu
            275                 280                 285

Asn Leu Ser Asn Ser Val Glu Ser His Ser Ser Thr Asn Trp Ser Tyr
        290                 295                 300

Thr Asn Thr Glu Gly Ala Ser Val Glu Ala Gly Ile Gly Pro Lys Gly
305                 310                 315                 320

Ile Ser Phe Gly Val Ser Val Asn Tyr Gln His Ser Glu Thr Val Ala
                325                 330                 335
```

-continued

| | | | | | | | | | | | | | | |
|---|---|---|---|---|---|---|---|---|---|---|---|---|---|---|
| Gln | Glu | Trp | Gly<br>340 | Thr | Ser | Thr | Gly<br>345 | Asn | Thr | Ser | Gln | Phe<br>350 | Asn | Thr | Ala |
| Ser | Ala | Gly<br>355 | Tyr | Leu | Asn | Ala | Asn<br>360 | Val | Arg | Tyr | Asn<br>365 | Asn | Val | Gly | Thr |
| Gly | Ala<br>370 | Ile | Tyr | Asp | Val | Lys<br>375 | Pro | Thr | Thr | Ser | Phe<br>380 | Val | Leu | Asn | Asn |
| Asp<br>385 | Thr | Ile | Ala | Thr | Ile<br>390 | Thr | Ala | Lys | Ser | Asn<br>395 | Ser | Thr | Ala | Leu | Asn<br>400 |
| Ile | Ser | Pro | Gly | Glu<br>405 | Ser | Tyr | Pro | Lys | Lys<br>410 | Gly | Gln | Asn | Gly | Ile<br>415 | Ala |
| Ile | Thr | Ser | Met<br>420 | Asp | Asp | Phe | Asn | Ser<br>425 | His | Pro | Ile | Thr | Leu<br>430 | Asn | Lys |
| Lys | Gln | Val<br>435 | Asp | Asn | Leu | Leu | Asn<br>440 | Asn | Lys | Pro | Met | Met<br>445 | Leu | Glu | Thr |
| Asn | Gln<br>450 | Thr | Asp | Gly | Val | Tyr<br>455 | Lys | Ile | Lys | Asp | Thr<br>460 | His | Gly | Asn | Ile |
| Val<br>465 | Thr | Gly | Gly | Glu | Trp<br>470 | Asn | Gly | Val | Ile | Gln<br>475 | Gln | Ile | Lys | Ala | Lys<br>480 |
| Thr | Ala | Ser | Ile | Ile<br>485 | Val | Asp | Asp | Gly | Glu<br>490 | Arg | Val | Ala | Glu | Lys<br>495 | Arg |
| Val | Ala | Ala | Lys | Asp<br>500 | Tyr | Glu | Asn | Pro | Glu<br>505 | Asp | Lys | Thr | Pro<br>510 | Ser | Leu |
| Thr | Leu | Lys<br>515 | Asp | Ala | Leu | Lys | Leu<br>520 | Ser | Tyr | Pro | Asp | Glu<br>525 | Ile | Lys | Glu |
| Ile | Glu<br>530 | Gly | Leu | Leu | Tyr | Tyr<br>535 | Lys | Asn | Lys | Pro | Ile<br>540 | Tyr | Glu | Ser | Ser |
| Val<br>545 | Met | Thr | Tyr | Leu | Asp<br>550 | Glu | Asn | Thr | Ala | Lys<br>555 | Glu | Val | Thr | Lys | Gln<br>560 |
| Leu | Asn | Asp | Thr | Thr<br>565 | Gly | Lys | Phe | Lys | Asp<br>570 | Val | Ser | His | Leu | Tyr<br>575 | Asp |
| Val | Lys | Leu | Thr<br>580 | Pro | Lys | Met | Asn | Val<br>585 | Thr | Ile | Lys | Leu | Ser<br>590 | Ile | Leu |
| Tyr | Asp | Asn<br>595 | Ala | Glu | Ser | Asn | Asp<br>600 | Asn | Ser | Ile | Gly | Lys<br>605 | Trp | Thr | Asn |
| Thr | Asn | Ile<br>610 | Val | Ser | Gly | Gly<br>615 | Asn | Asn | Gly | Lys | Lys<br>620 | Gln | Tyr | Ser | Ser |
| Asn<br>625 | Asn | Pro | Asp | Ala | Asn<br>630 | Leu | Thr | Leu | Asn | Thr<br>635 | Asp | Ala | Gln | Glu | Lys<br>640 |
| Leu | Asn | Lys | Asn | Arg<br>645 | Asp | Tyr | Tyr | Ile | Ser<br>650 | Leu | Tyr | Met | Lys | Ser<br>655 | Glu |
| Lys | Asn | Thr | Gln<br>660 | Cys | Glu | Ile | Thr | Ile<br>665 | Asp | Gly | Glu | Ile | Tyr<br>670 | Pro | Ile |
| Thr | Thr | Lys<br>675 | Thr | Val | Asn | Val | Asn<br>680 | Lys | Asp | Asn | Tyr | Lys<br>685 | Arg | Leu | Asp |
| Ile | Ile | Ala<br>690 | His | Asn | Ile | Lys<br>695 | Ser | Asn | Pro | Ile | Ser<br>700 | Ser | Leu | His | Ile |
| Lys<br>705 | Thr | Asn | Asp | Glu | Ile<br>710 | Thr | Leu | Phe | Trp | Asp<br>715 | Asp | Ile | Ser | Ile | Thr<br>720 |
| Asp | Val | Ala | Ser | Ile<br>725 | Lys | Pro | Glu | Asn | Leu<br>730 | Thr | Asp | Ser | Glu | Ile<br>735 | Lys |
| Gln | Ile | Tyr | Ser<br>740 | Arg | Tyr | Gly | Ile | Lys<br>745 | Leu | Glu | Asp | Gly | Ile<br>750 | Leu | Ile |
| Asp | Lys | Lys<br>755 | Gly | Gly | Ile | His | Tyr<br>760 | Gly | Glu | Phe | Ile | Asn<br>765 | Glu | Ala | Ser |

```
Phe Asn Ile Glu Pro Leu Gln Asn Tyr Val Thr Lys Tyr Glu Val Thr
    770                     775                 780

Tyr Ser Ser Glu Leu Gly Pro Asn Val Ser Asp Thr Leu Glu Ser Asp
785                 790                 795                     800

Lys Ile Tyr Lys Asp Gly Thr Ile Lys Phe Asp Phe Thr Lys Tyr Ser
                805                 810                 815

Lys Asn Glu Gln Gly Leu Phe Tyr Asp Ser Gly Leu Asn Trp Asp Phe
            820                 825                 830

Lys Ile Asn Ala Ile Thr Tyr Asp Gly Lys Glu Met Asn Val Phe His
        835                 840                 845

Arg Tyr Asn Lys
    850
```

( 2 ) INFORMATION FOR SEQ ID NO:37:

( i ) SEQUENCE CHARACTERISTICS:
( A ) LENGTH: 32 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "forward primer used to make pCIB5527"

( i i i ) HYPOTHETICAL: NO ( x i ) SEQUENCE DESCRIPTION: SEQ ID NO:37:

```
GGATCCACCA TGCTGCAGAA CCTGAAGATC AC                                32
```

( 2 ) INFORMATION FOR SEQ ID NO:38:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "reverse primer used to make pCIB5527"

( i i i ) HYPOTHETICAL: NO ( x i ) SEQUENCE DESCRIPTION: SEQ ID NO:38:

```
AAGCTTCCAC TCCTTCTC                                                18
```

( 2 ) INFORMATION FOR SEQ ID NO:39:

( i ) SEQUENCE CHARACTERISTICS:
( A ) LENGTH: 1241 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "Synthetic DNA"

( i i i ) HYPOTHETICAL: NO ( i x ) FEATURE:
( A ) NAME/KEY: CDS
( B ) LOCATION: 9..1238
( D ) OTHER INFORMATION: /note= "Maize optimized DNA sequence encoding VIP2A(a) with the Bacillus secretion signal removed as contained in pCIB5527"

( x i ) SEQUENCE DESCRIPTION: SEQ ID NO:39:

| | | | | | | | | | | | | | | | | |
|---|---|---|---|---|---|---|---|---|---|---|---|---|---|---|---|---|
| GATCCACC | ATG | CTG | CAG | AAC | CTG | AAG | ATC | ACC | GAC | AAG | GTG | GAG | GAC | TTC | | 50 |
| | Met | Leu | Gln | Asn | Leu | Lys | Ile | Thr | Asp | Lys | Val | Glu | Asp | Phe | | |
| | | | 855 | | | | 860 | | | | | 865 | | | | |
| AAG | GAG | GAC | AAG | GAG | AAG | GCC | AAG | GAG | TGG | GGC | AAG | GAG | AAG | GAG | AAG | 98 |
| Lys | Glu | Asp | Lys | Glu | Lys | Ala | Lys | Glu | Trp | Gly | Lys | Glu | Lys | Glu | Lys | |
| | | | 870 | | | | 875 | | | | | 880 | | | | |
| GAG | TGG | AAG | CTT | ACC | GCC | ACC | GAG | AAG | GGC | AAG | ATG | AAC | AAC | TTC | CTG | 146 |
| Glu | Trp | Lys | Leu | Thr | Ala | Thr | Glu | Lys | Gly | Lys | Met | Asn | Asn | Phe | Leu | |
| | | 885 | | | | | 890 | | | | | 895 | | | | |
| GAC | AAC | AAG | AAC | GAC | ATC | AAG | ACC | AAC | TAC | AAG | GAG | ATC | ACC | TTC | AGC | 194 |
| Asp | Asn | Lys | Asn | Asp | Ile | Lys | Thr | Asn | Tyr | Lys | Glu | Ile | Thr | Phe | Ser | |
| | | 900 | | | | | 905 | | | | | 910 | | | | |
| ATA | GCC | GGC | AGC | TTC | GAG | GAC | GAG | ATC | AAG | GAC | CTG | AAG | GAG | ATC | GAC | 242 |
| Ile | Ala | Gly | Ser | Phe | Glu | Asp | Glu | Ile | Lys | Asp | Leu | Lys | Glu | Ile | Asp | |
| 915 | | | | | 920 | | | | | 925 | | | | | 930 | |
| AAG | ATG | TTC | GAC | AAG | ACC | AAC | CTG | AGC | AAC | AGC | ATC | ATC | ACC | TAC | AAG | 290 |
| Lys | Met | Phe | Asp | Lys | Thr | Asn | Leu | Ser | Asn | Ser | Ile | Ile | Thr | Tyr | Lys | |
| | | | | 935 | | | | | 940 | | | | | 945 | | |
| AAC | GTG | GAG | CCC | ACC | ACC | ATC | GGC | TTC | AAC | AAG | AGC | CTG | ACC | GAG | GGC | 338 |
| Asn | Val | Glu | Pro | Thr | Thr | Ile | Gly | Phe | Asn | Lys | Ser | Leu | Thr | Glu | Gly | |
| | | | 950 | | | | | 955 | | | | | 960 | | | |
| AAC | ACC | ATC | AAC | AGC | GAC | GCC | ATG | GCC | CAG | TTC | AAG | GAG | CAG | TTC | CTG | 386 |
| Asn | Thr | Ile | Asn | Ser | Asp | Ala | Met | Ala | Gln | Phe | Lys | Glu | Gln | Phe | Leu | |
| | | 965 | | | | | 970 | | | | | 975 | | | | |
| GAC | CGC | GAC | ATC | AAG | TTC | GAC | AGC | TAC | CTG | GAC | ACC | CAC | CTG | ACC | GCC | 434 |
| Asp | Arg | Asp | Ile | Lys | Phe | Asp | Ser | Tyr | Leu | Asp | Thr | His | Leu | Thr | Ala | |
| | 980 | | | | | 985 | | | | | 990 | | | | | |
| CAG | CAG | GTG | AGC | AGC | AAG | GAG | CGC | GTG | ATC | CTG | AAG | GTG | ACC | GTC | CCC | 482 |
| Gln | Gln | Val | Ser | Ser | Lys | Glu | Arg | Val | Ile | Leu | Lys | Val | Thr | Val | Pro | |
| 995 | | | | | 1000 | | | | | 1005 | | | | | 1010 | |
| AGC | GGC | AAG | GGC | AGC | ACC | ACC | CCC | ACC | AAG | GCC | GGC | GTG | ATC | CTG | AAC | 530 |
| Ser | Gly | Lys | Gly | Ser | Thr | Thr | Pro | Thr | Lys | Ala | Gly | Val | Ile | Leu | Asn | |
| | | | | 1015 | | | | | 1020 | | | | | 1025 | | |
| AAC | AGC | GAG | TAC | AAG | ATG | CTG | ATC | GAC | AAC | GGC | TAC | ATG | GTG | CAC | GTG | 578 |
| Asn | Ser | Glu | Tyr | Lys | Met | Leu | Ile | Asp | Asn | Gly | Tyr | Met | Val | His | Val | |
| | | | | 1030 | | | | | 1035 | | | | | 1040 | | |
| GAC | AAG | GTG | AGC | AAG | GTG | GTG | AAG | AAG | GGC | GTG | GAG | TGC | CTC | CAG | ATC | 626 |
| Asp | Lys | Val | Ser | Lys | Val | Val | Lys | Lys | Gly | Val | Glu | Cys | Leu | Gln | Ile | |
| | | | 1045 | | | | | 1050 | | | | | 1055 | | | |
| GAG | GGC | ACC | CTG | AAG | AAG | AGT | CTA | GAC | TTC | AAG | AAC | GAC | ATC | AAC | GCC | 674 |
| Glu | Gly | Thr | Leu | Lys | Lys | Ser | Leu | Asp | Phe | Lys | Asn | Asp | Ile | Asn | Ala | |
| | 1060 | | | | | 1065 | | | | | 1070 | | | | | |
| GAG | GCC | CAC | AGC | TGG | GGC | ATG | AAG | AAC | TAC | GAG | GAG | TGG | GCC | AAG | GAC | 722 |
| Glu | Ala | His | Ser | Trp | Gly | Met | Lys | Asn | Tyr | Glu | Glu | Trp | Ala | Lys | Asp | |
| 1075 | | | | 1080 | | | | | 1085 | | | | | 1090 | | |
| CTG | ACC | GAC | AGC | CAG | CGC | GAG | GCC | CTG | GAC | GGC | TAC | GCC | CGC | CAG | GAC | 770 |
| Leu | Thr | Asp | Ser | Gln | Arg | Glu | Ala | Leu | Asp | Gly | Tyr | Ala | Arg | Gln | Asp | |
| | | | | 1095 | | | | | 1100 | | | | | 1105 | | |
| TAC | AAG | GAG | ATC | AAC | AAC | TAC | CTG | CGC | AAC | CAG | GGC | GGC | AGC | GGC | AAC | 818 |
| Tyr | Lys | Glu | Ile | Asn | Asn | Tyr | Leu | Arg | Asn | Gln | Gly | Gly | Ser | Gly | Asn | |
| | | | | 1110 | | | | | 1115 | | | | | 1120 | | |
| GAG | AAG | CTG | GAC | GCC | CAG | ATC | AAG | AAC | ATC | AGC | GAC | GCC | CTG | GGC | AAG | 866 |
| Glu | Lys | Leu | Asp | Ala | Gln | Ile | Lys | Asn | Ile | Ser | Asp | Ala | Leu | Gly | Lys | |
| | | | 1125 | | | | | 1130 | | | | | 1135 | | | |
| AAG | CCC | ATC | CCC | GAG | AAC | ATC | ACC | GTG | TAC | CGC | TGG | TGC | GGC | ATG | CCC | 914 |
| Lys | Pro | Ile | Pro | Glu | Asn | Ile | Thr | Val | Tyr | Arg | Trp | Cys | Gly | Met | Pro | |
| | | | 1140 | | | | | 1145 | | | | | 1150 | | | |
| GAG | TTC | GGC | TAC | CAG | ATC | AGC | GAC | CCC | CTG | CCC | AGC | CTG | AAG | GAC | TTC | 962 |
| Glu | Phe | Gly | Tyr | Gln | Ile | Ser | Asp | Pro | Leu | Pro | Ser | Leu | Lys | Asp | Phe | |
| 1155 | | | | | 1160 | | | | | 1165 | | | | | 1170 | |

-continued

| | | | | | | | | | | | | | | | | |
|---|---|---|---|---|---|---|---|---|---|---|---|---|---|---|---|---|
| GAG | GAG | CAG | TTC | CTG | AAC | ACC | ATC | AAG | GAG | GAC | AAG | GGC | TAC | ATG | AGC | 1010 |
| Glu | Glu | Gln | Phe | Leu | Asn | Thr | Ile | Lys | Glu | Asp | Lys | Gly | Tyr | Met | Ser | |
| | | | | 1175 | | | | 1180 | | | | | 1185 | | | |
| ACC | AGC | CTG | AGC | AGC | GAG | CGC | CTG | GCC | GCC | TTC | GGC | AGC | CGC | AAG | ATC | 1058 |
| Thr | Ser | Leu | Ser | Ser | Glu | Arg | Leu | Ala | Ala | Phe | Gly | Ser | Arg | Lys | Ile | |
| | | | 1190 | | | | | 1195 | | | | | 1200 | | | |
| ATC | CTG | CGC | CTG | CAG | GTG | CCC | AAG | GGC | AGC | ACT | GGT | GCC | TAC | CTG | AGC | 1106 |
| Ile | Leu | Arg | Leu | Gln | Val | Pro | Lys | Gly | Ser | Thr | Gly | Ala | Tyr | Leu | Ser | |
| | | 1205 | | | | | 1210 | | | | | 1215 | | | | |
| GCC | ATC | GGC | GGC | TTC | GCC | AGC | GAG | AAG | GAG | ATC | CTG | CTG | GAT | AAG | GAC | 1154 |
| Ala | Ile | Gly | Gly | Phe | Ala | Ser | Glu | Lys | Glu | Ile | Leu | Leu | Asp | Lys | Asp | |
| | 1220 | | | | | 1225 | | | | | 1230 | | | | | |
| AGC | AAG | TAC | CAC | ATC | GAC | AAG | GTG | ACC | GAG | GTG | ATC | ATC | AAG | GGC | GTG | 1202 |
| Ser | Lys | Tyr | His | Ile | Asp | Lys | Val | Thr | Glu | Val | Ile | Ile | Lys | Gly | Val | |
| 1235 | | | | 1240 | | | | | 1245 | | | | | 1250 | | |
| AAG | CGC | TAC | GTG | GTG | GAC | GCC | ACC | CTG | CTG | ACC | AAC | TAG | | | | 1241 |
| Lys | Arg | Tyr | Val | Val | Asp | Ala | Thr | Leu | Leu | Thr | Asn | | | | | |
| | | | | 1255 | | | | | 1260 | | | | | | | |

( 2 ) INFORMATION FOR SEQ ID NO:40:

( i ) SEQUENCE CHARACTERISTICS:
        ( A ) LENGTH: 410 amino acids
        ( B ) TYPE: amino acid
        ( D ) TOPOLOGY: linear ( i i ) MOLECULE TYPE: protein ( x i ) SEQUENCE DESCRIPTION: SEQ ID NO:40:

| | | | | | | | | | | | | | | |
|---|---|---|---|---|---|---|---|---|---|---|---|---|---|---|
| Met | Leu | Gln | Asn | Leu | Lys | Ile | Thr | Asp | Lys | Val | Glu | Asp | Phe | Lys | Glu |
| 1 | | | | 5 | | | | | 10 | | | | | 15 | |
| Asp | Lys | Glu | Lys | Ala | Lys | Glu | Trp | Gly | Lys | Glu | Lys | Glu | Lys | Glu | Trp |
| | | | 20 | | | | | 25 | | | | | 30 | | |
| Lys | Leu | Thr | Ala | Thr | Glu | Lys | Gly | Lys | Met | Asn | Asn | Phe | Leu | Asp | Asn |
| | | | 35 | | | | | 40 | | | | | 45 | | |
| Lys | Asn | Asp | Ile | Lys | Thr | Asn | Tyr | Lys | Glu | Ile | Thr | Phe | Ser | Ile | Ala |
| | | 50 | | | | | 55 | | | | | 60 | | | |
| Gly | Ser | Phe | Glu | Asp | Glu | Ile | Lys | Asp | Leu | Lys | Glu | Ile | Asp | Lys | Met |
| 65 | | | | | 70 | | | | | 75 | | | | | 80 |
| Phe | Asp | Lys | Thr | Asn | Leu | Ser | Asn | Ser | Ile | Ile | Thr | Tyr | Lys | Asn | Val |
| | | | | 85 | | | | | 90 | | | | | 95 | |
| Glu | Pro | Thr | Thr | Ile | Gly | Phe | Asn | Lys | Ser | Leu | Thr | Glu | Gly | Asn | Thr |
| | | | 100 | | | | | 105 | | | | | 110 | | |
| Ile | Asn | Ser | Asp | Ala | Met | Ala | Gln | Phe | Lys | Glu | Gln | Phe | Leu | Asp | Arg |
| | | 115 | | | | | 120 | | | | | 125 | | | |
| Asp | Ile | Lys | Phe | Asp | Ser | Tyr | Leu | Asp | Thr | His | Leu | Thr | Ala | Gln | Gln |
| | 130 | | | | | 135 | | | | | 140 | | | | |
| Val | Ser | Ser | Lys | Glu | Arg | Val | Ile | Leu | Lys | Val | Thr | Val | Pro | Ser | Gly |
| 145 | | | | | 150 | | | | | 155 | | | | | 160 |
| Lys | Gly | Ser | Thr | Thr | Pro | Thr | Lys | Ala | Gly | Val | Ile | Leu | Asn | Asn | Ser |
| | | | | 165 | | | | | 170 | | | | | 175 | |
| Glu | Tyr | Lys | Met | Leu | Ile | Asp | Asn | Gly | Tyr | Met | Val | His | Val | Asp | Lys |
| | | | | 180 | | | | | 185 | | | | | 190 | |
| Val | Ser | Lys | Val | Val | Lys | Lys | Gly | Val | Glu | Cys | Leu | Gln | Ile | Glu | Gly |
| | | 195 | | | | | 200 | | | | | 205 | | | |
| Thr | Leu | Lys | Lys | Ser | Leu | Asp | Phe | Lys | Asn | Asp | Ile | Asn | Ala | Glu | Ala |
| | 210 | | | | | 215 | | | | | 220 | | | | |
| His | Ser | Trp | Gly | Met | Lys | Asn | Tyr | Glu | Glu | Trp | Ala | Lys | Asp | Leu | Thr |
| 225 | | | | | 230 | | | | | 235 | | | | | 240 |

-continued

```
Asp Ser Gln Arg Glu Ala Leu Asp Gly Tyr Ala Arg Gln Asp Tyr Lys
                245                 250                 255

Glu Ile Asn Asn Tyr Leu Arg Asn Gln Gly Gly Ser Gly Asn Glu Lys
            260                 265                 270

Leu Asp Ala Gln Ile Lys Asn Ile Ser Asp Ala Leu Gly Lys Lys Pro
        275                 280                 285

Ile Pro Glu Asn Ile Thr Val Tyr Arg Trp Cys Gly Met Pro Glu Phe
    290                 295                 300

Gly Tyr Gln Ile Ser Asp Pro Leu Pro Ser Leu Lys Asp Phe Glu Glu
305                 310                 315                 320

Gln Phe Leu Asn Thr Ile Lys Glu Asp Lys Gly Tyr Met Ser Thr Ser
                325                 330                 335

Leu Ser Ser Glu Arg Leu Ala Ala Phe Gly Ser Arg Lys Ile Ile Leu
            340                 345                 350

Arg Leu Gln Val Pro Lys Gly Ser Thr Gly Ala Tyr Leu Ser Ala Ile
        355                 360                 365

Gly Gly Phe Ala Ser Glu Lys Glu Ile Leu Leu Asp Lys Asp Ser Lys
    370                 375                 380

Tyr His Ile Asp Lys Val Thr Glu Val Ile Ile Lys Gly Val Lys Arg
385                 390                 395                 400

Tyr Val Val Asp Ala Thr Leu Leu Thr Asn
                405                 410
```

( 2 ) INFORMATION FOR SEQ ID NO:41:

( i ) SEQUENCE CHARACTERISTICS:
( A ) LENGTH: 72 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "oligonucleotide encoding eukaryotic secretion signal used to construct pCIB5527"

( i i i ) HYPOTHETICAL: NO ( x i ) SEQUENCE DESCRIPTION: SEQ ID NO:41:

```
GGATCCACCA TGGGCTGGAG CTGGATCTTC CTGTTCCTGC TGAGCGGCGC CGCGGGCGTG     60

CACTGCCTGC AG                                                         72
```

( 2 ) INFORMATION FOR SEQ ID NO:42:

( i ) SEQUENCE CHARACTERISTICS:
( A ) LENGTH: 1241 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "Synthetic DNA"

( i i i ) HYPOTHETICAL: NO ( i x ) FEATURE:
( A ) NAME/KEY: CDS
( B ) LOCATION: 9..1238
( D ) OTHER INFORMATION: /note= "Maize optimized DNA sequence encoding VIP2A(a) with the Bacillus secretion signal removed and the eukaryotic secretion signal inserted as contained in pCIB5528"

( x i ) SEQUENCE DESCRIPTION: SEQ ID NO:42:

```
GATCCACC ATG CTG CAG AAC CTG AAG ATC ACC GAC AAG GTG GAG GAC TTC     50
```

|  |  |  |  |  |  |  |  |  |  |  |  |  |  |  |  |
|---|---|---|---|---|---|---|---|---|---|---|---|---|---|---|---|
|  | Met | Leu | Gln | Asn | Leu | Lys | Ile | Thr | Asp | Lys | Val | Glu | Asp | Phe |  |
|  |  |  |  |  | 415 |  |  |  |  | 420 |  |  |  |  |  |

| AAG | GAG | GAC | AAG | GAG | AAG | GCC | AAG | GAG | TGG | GGC | AAG | GAG | AAG | GAG | AAG | 98 |
|---|---|---|---|---|---|---|---|---|---|---|---|---|---|---|---|---|
| Lys | Glu | Asp | Lys | Glu | Lys | Ala | Lys | Glu | Trp | Gly | Lys | Glu | Lys | Glu | Lys |  |
| 425 |  |  |  | 430 |  |  |  |  | 435 |  |  |  |  |  | 440 |  |

| GAG | TGG | AAG | CTT | ACC | GCC | ACC | GAG | AAG | GGC | AAG | ATG | AAC | AAC | TTC | CTG | 146 |
|---|---|---|---|---|---|---|---|---|---|---|---|---|---|---|---|---|
| Glu | Trp | Lys | Leu | Thr | Ala | Thr | Glu | Lys | Gly | Lys | Met | Asn | Asn | Phe | Leu |  |
|  |  |  |  | 445 |  |  |  |  | 450 |  |  |  |  | 455 |  |  |

| GAC | AAC | AAG | AAC | GAC | ATC | AAG | ACC | AAC | TAC | AAG | GAG | ATC | ACC | TTC | AGC | 194 |
|---|---|---|---|---|---|---|---|---|---|---|---|---|---|---|---|---|
| Asp | Asn | Lys | Asn | Asp | Ile | Lys | Thr | Asn | Tyr | Lys | Glu | Ile | Thr | Phe | Ser |  |
|  |  |  | 460 |  |  |  |  | 465 |  |  |  |  | 470 |  |  |  |

| ATA | GCC | GGC | AGC | TTC | GAG | GAC | GAG | ATC | AAG | GAC | CTG | AAG | GAG | ATC | GAC | 242 |
|---|---|---|---|---|---|---|---|---|---|---|---|---|---|---|---|---|
| Ile | Ala | Gly | Ser | Phe | Glu | Asp | Glu | Ile | Lys | Asp | Leu | Lys | Glu | Ile | Asp |  |
|  |  | 475 |  |  |  |  | 480 |  |  |  |  | 485 |  |  |  |  |

| AAG | ATG | TTC | GAC | AAG | ACC | AAC | CTG | AGC | AAC | AGC | ATC | ATC | ACC | TAC | AAG | 290 |
|---|---|---|---|---|---|---|---|---|---|---|---|---|---|---|---|---|
| Lys | Met | Phe | Asp | Lys | Thr | Asn | Leu | Ser | Asn | Ser | Ile | Ile | Thr | Tyr | Lys |  |
|  | 490 |  |  |  |  | 495 |  |  |  |  | 500 |  |  |  |  |  |

| AAC | GTG | GAG | CCC | ACC | ACC | ATC | GGC | TTC | AAC | AAG | AGC | CTG | ACC | GAG | GGC | 338 |
|---|---|---|---|---|---|---|---|---|---|---|---|---|---|---|---|---|
| Asn | Val | Glu | Pro | Thr | Thr | Ile | Gly | Phe | Asn | Lys | Ser | Leu | Thr | Glu | Gly |  |
| 505 |  |  |  |  | 510 |  |  |  |  | 515 |  |  |  |  | 520 |  |

| AAC | ACC | ATC | AAC | AGC | GAC | GCC | ATG | GCC | CAG | TTC | AAG | GAG | CAG | TTC | CTG | 386 |
|---|---|---|---|---|---|---|---|---|---|---|---|---|---|---|---|---|
| Asn | Thr | Ile | Asn | Ser | Asp | Ala | Met | Ala | Gln | Phe | Lys | Glu | Gln | Phe | Leu |  |
|  |  |  |  | 525 |  |  |  |  | 530 |  |  |  |  | 535 |  |  |

| GAC | CGC | GAC | ATC | AAG | TTC | GAC | AGC | TAC | CTG | GAC | ACC | CAC | CTG | ACC | GCC | 434 |
|---|---|---|---|---|---|---|---|---|---|---|---|---|---|---|---|---|
| Asp | Arg | Asp | Ile | Lys | Phe | Asp | Ser | Tyr | Leu | Asp | Thr | His | Leu | Thr | Ala |  |
|  |  |  | 540 |  |  |  |  | 545 |  |  |  |  | 550 |  |  |  |

| CAG | CAG | GTG | AGC | AGC | AAG | GAG | CGC | GTG | ATC | CTG | AAG | GTG | ACC | GTC | CCC | 482 |
|---|---|---|---|---|---|---|---|---|---|---|---|---|---|---|---|---|
| Gln | Gln | Val | Ser | Ser | Lys | Glu | Arg | Val | Ile | Leu | Lys | Val | Thr | Val | Pro |  |
|  |  | 555 |  |  |  |  | 560 |  |  |  |  | 565 |  |  |  |  |

| AGC | GGC | AAG | GGC | AGC | ACC | ACC | CCC | ACC | AAG | GCC | GGC | GTG | ATC | CTG | AAC | 530 |
|---|---|---|---|---|---|---|---|---|---|---|---|---|---|---|---|---|
| Ser | Gly | Lys | Gly | Ser | Thr | Thr | Pro | Thr | Lys | Ala | Gly | Val | Ile | Leu | Asn |  |
|  | 570 |  |  |  |  | 575 |  |  |  |  | 580 |  |  |  |  |  |

| AAC | AGC | GAG | TAC | AAG | ATG | CTG | ATC | GAC | AAC | GGC | TAC | ATG | GTG | CAC | GTG | 578 |
|---|---|---|---|---|---|---|---|---|---|---|---|---|---|---|---|---|
| Asn | Ser | Glu | Tyr | Lys | Met | Leu | Ile | Asp | Asn | Gly | Tyr | Met | Val | His | Val |  |
| 585 |  |  |  |  | 590 |  |  |  |  | 595 |  |  |  |  | 600 |  |

| GAC | AAG | GTG | AGC | AAG | GTG | GTG | AAG | AAG | GGC | GTG | GAG | TGC | CTC | CAG | ATC | 626 |
|---|---|---|---|---|---|---|---|---|---|---|---|---|---|---|---|---|
| Asp | Lys | Val | Ser | Lys | Val | Val | Lys | Lys | Gly | Val | Glu | Cys | Leu | Gln | Ile |  |
|  |  |  |  | 605 |  |  |  |  | 610 |  |  |  |  | 615 |  |  |

| GAG | GGC | ACC | CTG | AAG | AAG | AGT | CTA | GAC | TTC | AAG | AAC | GAC | ATC | AAC | GCC | 674 |
|---|---|---|---|---|---|---|---|---|---|---|---|---|---|---|---|---|
| Glu | Gly | Thr | Leu | Lys | Lys | Ser | Leu | Asp | Phe | Lys | Asn | Asp | Ile | Asn | Ala |  |
|  |  |  | 620 |  |  |  |  | 625 |  |  |  |  | 630 |  |  |  |

| GAG | GCC | CAC | AGC | TGG | GGC | ATG | AAG | AAC | TAC | GAG | GAG | TGG | GCC | AAG | GAC | 722 |
|---|---|---|---|---|---|---|---|---|---|---|---|---|---|---|---|---|
| Glu | Ala | His | Ser | Trp | Gly | Met | Lys | Asn | Tyr | Glu | Glu | Trp | Ala | Lys | Asp |  |
|  |  | 635 |  |  |  |  | 640 |  |  |  |  | 645 |  |  |  |  |

| CTG | ACC | GAC | AGC | CAG | CGC | GAG | GCC | CTG | GAC | GGC | TAC | GCC | CGC | CAG | GAC | 770 |
|---|---|---|---|---|---|---|---|---|---|---|---|---|---|---|---|---|
| Leu | Thr | Asp | Ser | Gln | Arg | Glu | Ala | Leu | Asp | Gly | Tyr | Ala | Arg | Gln | Asp |  |
| 650 |  |  |  |  | 655 |  |  |  |  | 660 |  |  |  |  |  |  |

| TAC | AAG | GAG | ATC | AAC | AAC | TAC | CTG | CGC | AAC | CAG | GGC | GGC | AGC | GGC | AAC | 818 |
|---|---|---|---|---|---|---|---|---|---|---|---|---|---|---|---|---|
| Tyr | Lys | Glu | Ile | Asn | Asn | Tyr | Leu | Arg | Asn | Gln | Gly | Gly | Ser | Gly | Asn |  |
| 665 |  |  |  |  | 670 |  |  |  |  | 675 |  |  |  |  | 680 |  |

| GAG | AAG | CTG | GAC | GCC | CAG | ATC | AAG | AAC | ATC | AGC | GAC | GCC | CTG | GGC | AAG | 866 |
|---|---|---|---|---|---|---|---|---|---|---|---|---|---|---|---|---|
| Glu | Lys | Leu | Asp | Ala | Gln | Ile | Lys | Asn | Ile | Ser | Asp | Ala | Leu | Gly | Lys |  |
|  |  |  |  | 685 |  |  |  |  | 690 |  |  |  |  | 695 |  |  |

| AAG | CCC | ATC | CCC | GAG | AAC | ATC | ACC | GTG | TAC | CGC | TGG | TGC | GGC | ATG | CCC | 914 |
|---|---|---|---|---|---|---|---|---|---|---|---|---|---|---|---|---|
| Lys | Pro | Ile | Pro | Glu | Asn | Ile | Thr | Val | Tyr | Arg | Trp | Cys | Gly | Met | Pro |  |
|  |  |  | 700 |  |  |  |  | 705 |  |  |  |  | 710 |  |  |  |

| GAG | TTC | GGC | TAC | CAG | ATC | AGC | GAC | CCC | CTG | CCC | AGC | CTG | AAG | GAC | TTC | 962 |
|---|---|---|---|---|---|---|---|---|---|---|---|---|---|---|---|---|
| Glu | Phe | Gly | Tyr | Gln | Ile | Ser | Asp | Pro | Leu | Pro | Ser | Leu | Lys | Asp | Phe |  |
|  |  | 715 |  |  |  |  | 720 |  |  |  |  | 725 |  |  |  |  |

| GAG | GAG | CAG | TTC | CTG | AAC | ACC | ATC | AAG | GAG | GAC | AAG | GGC | TAC | ATG | AGC | 1010 |

|  |  |  |  |  |  |  |  |  |  |  |  |  |  |  |  |
|---|---|---|---|---|---|---|---|---|---|---|---|---|---|---|---|
| Glu | Glu | Gln | Phe | Leu | Asn | Thr | Ile | Lys | Glu | Asp | Lys | Gly | Tyr | Met | Ser |
|  | 730 |  |  |  | 735 |  |  |  | 740 |  |  |  |  |  |  |

| ACC | AGC | CTG | AGC | AGC | GAG | CGC | CTG | GCC | GCC | TTC | GGC | AGC | CGC | AAG | ATC | 1058 |
|---|---|---|---|---|---|---|---|---|---|---|---|---|---|---|---|---|
| Thr | Ser | Leu | Ser | Ser | Glu | Arg | Leu | Ala | Ala | Phe | Gly | Ser | Arg | Lys | Ile |  |
| 745 |  |  |  |  | 750 |  |  |  | 755 |  |  |  |  |  | 760 |  |

| ATC | CTG | CGC | CTG | CAG | GTG | CCC | AAG | GGC | AGC | ACT | GGT | GCC | TAC | CTG | AGC | 1106 |
|---|---|---|---|---|---|---|---|---|---|---|---|---|---|---|---|---|
| Ile | Leu | Arg | Leu | Gln | Val | Pro | Lys | Gly | Ser | Thr | Gly | Ala | Tyr | Leu | Ser |  |
|  |  |  |  | 765 |  |  |  |  | 770 |  |  |  |  | 775 |  |  |

| GCC | ATC | GGC | GGC | TTC | GCC | AGC | GAG | AAG | GAG | ATC | CTG | CTG | GAT | AAG | GAC | 1154 |
|---|---|---|---|---|---|---|---|---|---|---|---|---|---|---|---|---|
| Ala | Ile | Gly | Gly | Phe | Ala | Ser | Glu | Lys | Glu | Ile | Leu | Leu | Asp | Lys | Asp |  |
|  |  |  | 780 |  |  |  |  | 785 |  |  |  |  | 790 |  |  |  |

| AGC | AAG | TAC | CAC | ATC | GAC | AAG | GTG | ACC | GAG | GTG | ATC | ATC | AAG | GGC | GTG | 1202 |
|---|---|---|---|---|---|---|---|---|---|---|---|---|---|---|---|---|
| Ser | Lys | Tyr | His | Ile | Asp | Lys | Val | Thr | Glu | Val | Ile | Ile | Lys | Gly | Val |  |
|  |  | 795 |  |  |  |  | 800 |  |  |  |  | 805 |  |  |  |  |

| AAG | CGC | TAC | GTG | GTG | GAC | GCC | ACC | CTG | CTG | ACC | AAC | TAG |  |  |  | 1241 |
|---|---|---|---|---|---|---|---|---|---|---|---|---|---|---|---|---|
| Lys | Arg | Tyr | Val | Val | Asp | Ala | Thr | Leu | Leu | Thr | Asn |  |  |  |  |  |
| 810 |  |  |  |  | 815 |  |  |  |  | 820 |  |  |  |  |  |  |

(2) INFORMATION FOR SEQ ID NO:43:

(i) SEQUENCE CHARACTERISTICS:
        (A) LENGTH: 410 amino acids
        (B) TYPE: amino acid
        (D) TOPOLOGY: linear (ii) MOLECULE TYPE: protein (xi) SEQUENCE DESCRIPTION: SEQ ID NO:43:

| Met | Leu | Gln | Asn | Leu | Lys | Ile | Thr | Asp | Lys | Val | Glu | Asp | Phe | Lys | Glu |
|---|---|---|---|---|---|---|---|---|---|---|---|---|---|---|---|
| 1 |  |  |  | 5 |  |  |  |  | 10 |  |  |  |  | 15 |  |

| Asp | Lys | Glu | Lys | Ala | Lys | Glu | Trp | Gly | Lys | Glu | Lys | Glu | Lys | Glu | Trp |
|---|---|---|---|---|---|---|---|---|---|---|---|---|---|---|---|
|  |  |  | 20 |  |  |  |  | 25 |  |  |  |  | 30 |  |  |

| Lys | Leu | Thr | Ala | Thr | Glu | Lys | Gly | Lys | Met | Asn | Asn | Phe | Leu | Asp | Asn |
|---|---|---|---|---|---|---|---|---|---|---|---|---|---|---|---|
|  |  |  | 35 |  |  |  |  | 40 |  |  |  |  | 45 |  |  |

| Lys | Asn | Asp | Ile | Lys | Thr | Asn | Tyr | Lys | Glu | Ile | Thr | Phe | Ser | Ile | Ala |
|---|---|---|---|---|---|---|---|---|---|---|---|---|---|---|---|
|  | 50 |  |  |  |  | 55 |  |  |  |  | 60 |  |  |  |  |

| Gly | Ser | Phe | Glu | Asp | Glu | Ile | Lys | Asp | Leu | Lys | Glu | Ile | Asp | Lys | Met |
|---|---|---|---|---|---|---|---|---|---|---|---|---|---|---|---|
| 65 |  |  |  |  | 70 |  |  |  |  | 75 |  |  |  |  | 80 |

| Phe | Asp | Lys | Thr | Asn | Leu | Ser | Asn | Ser | Ile | Ile | Thr | Tyr | Lys | Asn | Val |
|---|---|---|---|---|---|---|---|---|---|---|---|---|---|---|---|
|  |  |  |  | 85 |  |  |  |  | 90 |  |  |  |  | 95 |  |

| Glu | Pro | Thr | Thr | Ile | Gly | Phe | Asn | Lys | Ser | Leu | Thr | Gly | Asn | Thr |
|---|---|---|---|---|---|---|---|---|---|---|---|---|---|---|
|  |  |  | 100 |  |  |  |  | 105 |  |  |  |  | 110 |  |

| Ile | Asn | Ser | Asp | Ala | Met | Ala | Gln | Phe | Lys | Glu | Gln | Phe | Leu | Asp | Arg |
|---|---|---|---|---|---|---|---|---|---|---|---|---|---|---|---|
|  |  |  | 115 |  |  |  |  | 120 |  |  |  |  | 125 |  |  |

| Asp | Ile | Lys | Phe | Asp | Ser | Tyr | Leu | Asp | Thr | His | Leu | Thr | Ala | Gln | Gln |
|---|---|---|---|---|---|---|---|---|---|---|---|---|---|---|---|
|  | 130 |  |  |  |  | 135 |  |  |  |  | 140 |  |  |  |  |

| Val | Ser | Ser | Lys | Glu | Arg | Val | Ile | Leu | Lys | Val | Thr | Val | Pro | Ser | Gly |
|---|---|---|---|---|---|---|---|---|---|---|---|---|---|---|---|
| 145 |  |  |  |  | 150 |  |  |  |  | 155 |  |  |  |  | 160 |

| Lys | Gly | Ser | Thr | Thr | Pro | Thr | Lys | Ala | Gly | Val | Ile | Leu | Asn | Asn | Ser |
|---|---|---|---|---|---|---|---|---|---|---|---|---|---|---|---|
|  |  |  |  | 165 |  |  |  |  | 170 |  |  |  |  | 175 |  |

| Glu | Tyr | Lys | Met | Leu | Ile | Asp | Asn | Gly | Tyr | Met | Val | His | Val | Asp | Lys |
|---|---|---|---|---|---|---|---|---|---|---|---|---|---|---|---|
|  |  |  | 180 |  |  |  |  | 185 |  |  |  |  | 190 |  |  |

| Val | Ser | Lys | Val | Val | Lys | Lys | Gly | Val | Glu | Cys | Leu | Gln | Ile | Glu | Gly |
|---|---|---|---|---|---|---|---|---|---|---|---|---|---|---|---|
|  |  | 195 |  |  |  |  | 200 |  |  |  |  | 205 |  |  |  |

| Thr | Leu | Lys | Lys | Ser | Leu | Asp | Phe | Lys | Asn | Asp | Ile | Asn | Ala | Glu | Ala |
|---|---|---|---|---|---|---|---|---|---|---|---|---|---|---|---|
|  | 210 |  |  |  |  | 215 |  |  |  |  | 220 |  |  |  |  |

| His | Ser | Trp | Gly | Met | Lys | Asn | Tyr | Glu | Glu | Trp | Ala | Lys | Asp | Leu | Thr |
|---|---|---|---|---|---|---|---|---|---|---|---|---|---|---|---|
| 225 |  |  |  |  | 230 |  |  |  |  | 235 |  |  |  |  | 240 |

-continued

```
Asp  Ser  Gln  Arg  Glu  Ala  Leu  Asp  Gly  Tyr  Ala  Arg  Gln  Asp  Tyr  Lys
               245                 250                      255

Glu  Ile  Asn  Asn  Tyr  Leu  Arg  Asn  Gln  Gly  Gly  Ser  Gly  Asn  Glu  Lys
               260                 265                 270

Leu  Asp  Ala  Gln  Ile  Lys  Asn  Ile  Ser  Asp  Ala  Leu  Gly  Lys  Lys  Pro
               275                 280                 285

Ile  Pro  Glu  Asn  Ile  Thr  Val  Tyr  Arg  Trp  Cys  Gly  Met  Pro  Glu  Phe
     290                      295                 300

Gly  Tyr  Gln  Ile  Ser  Asp  Pro  Leu  Pro  Ser  Leu  Lys  Asp  Phe  Glu  Glu
305                      310                      315                      320

Gln  Phe  Leu  Asn  Thr  Ile  Lys  Glu  Asp  Lys  Gly  Tyr  Met  Ser  Thr  Ser
               325                 330                      335

Leu  Ser  Ser  Glu  Arg  Leu  Ala  Ala  Phe  Gly  Ser  Arg  Lys  Ile  Ile  Leu
          340                      345                      350

Arg  Leu  Gln  Val  Pro  Lys  Gly  Ser  Thr  Gly  Ala  Tyr  Leu  Ser  Ala  Ile
          355                      360                 365

Gly  Gly  Phe  Ala  Ser  Glu  Lys  Glu  Ile  Leu  Leu  Asp  Lys  Asp  Ser  Lys
     370                      375                 380

Tyr  His  Ile  Asp  Lys  Val  Thr  Glu  Val  Ile  Ile  Lys  Gly  Val  Lys  Arg
385                      390                      395                      400

Tyr  Val  Val  Asp  Ala  Thr  Leu  Leu  Thr  Asn
                    405                      410
```

( 2 ) INFORMATION FOR SEQ ID NO:44:

( i ) SEQUENCE CHARACTERISTICS:
  ( A ) LENGTH: 86 base pairs
  ( B ) TYPE: nucleic acid
  ( C ) STRANDEDNESS: single
  ( D ) TOPOLOGY: linear ( i i ) MOLECULE TYPE: other nucleic acid
  ( A ) DESCRIPTION: /desc = "oligonucleotide encoding
   vacuolar targetting peptide used to construct pCIB5533"

( i i i ) HYPOTHETICAL: NO ( x i ) SEQUENCE DESCRIPTION: SEQ ID NO:44:

```
CCGCGGGCGT  GCACTGCCTC  AGCAGCAGCA  GCTTCGCCGA  CAGCAACCCC  ATCCGCGTGA    60

CCGACCGCGC  CGCCAGCACC  CTGCAG                                            86
```

( 2 ) INFORMATION FOR SEQ ID NO:45:

( i ) SEQUENCE CHARACTERISTICS:
  ( A ) LENGTH: 1358 base pairs
  ( B ) TYPE: nucleic acid
  ( C ) STRANDEDNESS: single
  ( D ) TOPOLOGY: linear ( i i ) MOLECULE TYPE: other nucleic acid
  ( A ) DESCRIPTION: /desc = "Synthetic DNA"

( i i i ) HYPOTHETICAL: NO ( i x ) FEATURE:
  ( A ) NAME/KEY: CDS
  ( B ) LOCATION: 9..1355
  ( D ) OTHER INFORMATION: /note= "Maize optimized VIP2A(a)
   with the Bacillus secretion signal removed and the vacuolar targetting signal inserted as contained in pCIB5533"

( x i ) SEQUENCE DESCRIPTION: SEQ ID NO:45:

```
GATCCACC ATG GGC TGG AGC TGG ATC TTC CTG TTC CTG CTG AGC GGC GCC    50
         Met Gly Trp Ser Trp Ile Phe Leu Phe Leu Leu Ser Gly Ala
```

-continued

```
                                    415                              420
GCG  GGC  GTG  CAC  TGC  CTC  AGC  AGC  AGC  AGC  TTC  GCC  GAC  AGC  AAC  CCC       98
Ala  Gly  Val  His  Cys  Leu  Ser  Ser  Ser  Ser  Phe  Ala  Asp  Ser  Asn  Pro
425                 430                      435                           440

ATC  CGC  GTG  ACC  GAC  CGC  GCC  GCC  AGC  ACC  CTG  CAG  AAC  CTG  AAG  ATC      146
Ile  Arg  Val  Thr  Asp  Arg  Ala  Ala  Ser  Thr  Leu  Gln  Asn  Leu  Lys  Ile
                    445                      450                           455

ACC  GAC  AAG  GTG  GAG  GAC  TTC  AAG  GAG  GAC  AAG  GAG  AAG  GCC  AAG  GAG      194
Thr  Asp  Lys  Val  Glu  Asp  Phe  Lys  Glu  Asp  Lys  Glu  Lys  Ala  Lys  Glu
               460                           465                 470

TGG  GGC  AAG  GAG  AAG  GAG  AAG  GAG  TGG  AAG  CTT  ACC  GCC  ACC  GAG  AAG      242
Trp  Gly  Lys  Glu  Lys  Glu  Lys  Glu  Trp  Lys  Leu  Thr  Ala  Thr  Glu  Lys
               475                      480                 485

GGC  AAG  ATG  AAC  AAC  TTC  CTG  GAC  AAC  AAG  AAC  GAC  ATC  AAG  ACC  AAC      290
Gly  Lys  Met  Asn  Asn  Phe  Leu  Asp  Asn  Lys  Asn  Asp  Ile  Lys  Thr  Asn
               490                 495                      500

TAC  AAG  GAG  ATC  ACC  TTC  AGC  ATA  GCC  GGC  AGC  TTC  GAG  GAC  GAG  ATC      338
Tyr  Lys  Glu  Ile  Thr  Phe  Ser  Ile  Ala  Gly  Ser  Phe  Glu  Asp  Glu  Ile
505                           510                      515                 520

AAG  GAC  CTG  AAG  GAG  ATC  GAC  AAG  ATG  TTC  GAC  AAG  ACC  AAC  CTG  AGC      386
Lys  Asp  Leu  Lys  Glu  Ile  Asp  Lys  Met  Phe  Asp  Lys  Thr  Asn  Leu  Ser
                         525                      530                 535

AAC  AGC  ATC  ATC  ACC  TAC  AAG  AAC  GTG  GAG  CCC  ACC  ACC  ATC  GGC  TTC      434
Asn  Ser  Ile  Ile  Thr  Tyr  Lys  Asn  Val  Glu  Pro  Thr  Thr  Ile  Gly  Phe
               540                      545                      550

AAC  AAG  AGC  CTG  ACC  GAG  GGC  AAC  ACC  ATC  AAC  AGC  GAC  GCC  ATG  GCC      482
Asn  Lys  Ser  Leu  Thr  Glu  Gly  Asn  Thr  Ile  Asn  Ser  Asp  Ala  Met  Ala
          555                           560                 565

CAG  TTC  AAG  GAG  CAG  TTC  CTG  GAC  CGC  GAC  ATC  AAG  TTC  GAC  AGC  TAC      530
Gln  Phe  Lys  Glu  Gln  Phe  Leu  Asp  Arg  Asp  Ile  Lys  Phe  Asp  Ser  Tyr
570                           575                      580

CTG  GAC  ACC  CAC  CTG  ACC  GCC  CAG  CAG  GTG  AGC  AGC  AAG  GAG  CGC  GTG      578
Leu  Asp  Thr  His  Leu  Thr  Ala  Gln  Gln  Val  Ser  Ser  Lys  Glu  Arg  Val
585                      590                      595                      600

ATC  CTG  AAG  GTG  ACC  GTC  CCC  AGC  GGC  AAG  GGC  AGC  ACC  ACC  CCC  ACC      626
Ile  Leu  Lys  Val  Thr  Val  Pro  Ser  Gly  Lys  Gly  Ser  Thr  Thr  Pro  Thr
                    605                      610                      615

AAG  GCC  GGC  GTG  ATC  CTG  AAC  AAC  AGC  GAG  TAC  AAG  ATG  CTG  ATC  GAC      674
Lys  Ala  Gly  Val  Ile  Leu  Asn  Asn  Ser  Glu  Tyr  Lys  Met  Leu  Ile  Asp
                    620                      625                      630

AAC  GGC  TAC  ATG  GTG  CAC  GTG  GAC  AAG  GTG  AGC  AAG  GTG  GTG  AAG  AAG      722
Asn  Gly  Tyr  Met  Val  His  Val  Asp  Lys  Val  Ser  Lys  Val  Val  Lys  Lys
          635                      640                      645

GGC  GTG  GAG  TGC  CTC  CAG  ATC  GAG  GGC  ACC  CTG  AAG  AAG  AGT  CTA  GAC      770
Gly  Val  Glu  Cys  Leu  Gln  Ile  Glu  Gly  Thr  Leu  Lys  Lys  Ser  Leu  Asp
650                           655                      660

TTC  AAG  AAC  GAC  ATC  AAC  GCC  GAG  GCC  CAC  AGC  TGG  GGC  ATG  AAG  AAC      818
Phe  Lys  Asn  Asp  Ile  Asn  Ala  Glu  Ala  His  Ser  Trp  Gly  Met  Lys  Asn
665                      670                      675                      680

TAC  GAG  GAG  TGG  GCC  AAG  GAC  CTG  ACC  GAC  AGC  CAG  CGC  GAG  GCC  CTG      866
Tyr  Glu  Glu  Trp  Ala  Lys  Asp  Leu  Thr  Asp  Ser  Gln  Arg  Glu  Ala  Leu
                    685                      690                      695

GAC  GGC  TAC  GCC  CGC  CAG  GAC  TAC  AAG  GAG  ATC  AAC  AAC  TAC  CTG  CGC      914
Asp  Gly  Tyr  Ala  Arg  Gln  Asp  Tyr  Lys  Glu  Ile  Asn  Asn  Tyr  Leu  Arg
               700                      705                      710

AAC  CAG  GGC  GGC  AGC  GGC  AAC  GAG  AAG  CTG  GAC  GCC  CAG  ATC  AAG  AAC      962
Asn  Gln  Gly  Gly  Ser  Gly  Asn  Glu  Lys  Leu  Asp  Ala  Gln  Ile  Lys  Asn
               715                      720                      725

ATC  AGC  GAC  GCC  CTG  GGC  AAG  AAG  CCC  ATC  CCC  GAG  AAC  ATC  ACC  GTG     1010
Ile  Ser  Asp  Ala  Leu  Gly  Lys  Lys  Pro  Ile  Pro  Glu  Asn  Ile  Thr  Val
```

|     |     |     |     | 730 |     |     |     |     | 735 |     |     |     |     | 740 |     |      |
|-----|-----|-----|-----|-----|-----|-----|-----|-----|-----|-----|-----|-----|-----|-----|-----|------|
| TAC | CGC | TGG | TGC | GGC | ATG | CCC | GAG | TTC | GGC | TAC | CAG | ATC | AGC | GAC | CCC | 1058 |
| Tyr | Arg | Trp | Cys | Gly | Met | Pro | Glu | Phe | Gly | Tyr | Gln | Ile | Ser | Asp | Pro |      |
| 745 |     |     |     | 750 |     |     |     |     | 755 |     |     |     |     |     | 760 |      |
| CTG | CCC | AGC | CTG | AAG | GAC | TTC | GAG | GAG | CAG | TTC | CTG | AAC | ACC | ATC | AAG | 1106 |
| Leu | Pro | Ser | Leu | Lys | Asp | Phe | Glu | Glu | Gln | Phe | Leu | Asn | Thr | Ile | Lys |      |
|     |     |     |     | 765 |     |     |     |     | 770 |     |     |     |     | 775 |     |      |
| GAG | GAC | AAG | GGC | TAC | ATG | AGC | ACC | AGC | CTG | AGC | AGC | GAG | CGC | CTG | GCC | 1154 |
| Glu | Asp | Lys | Gly | Tyr | Met | Ser | Thr | Ser | Leu | Ser | Ser | Glu | Arg | Leu | Ala |      |
|     |     |     | 780 |     |     |     |     | 785 |     |     |     |     | 790 |     |     |      |
| GCC | TTC | GGC | AGC | CGC | AAG | ATC | ATC | CTG | CGC | CTG | CAG | GTG | CCC | AAG | GGC | 1202 |
| Ala | Phe | Gly | Ser | Arg | Lys | Ile | Ile | Leu | Arg | Leu | Gln | Val | Pro | Lys | Gly |      |
|     |     | 795 |     |     |     | 800 |     |     |     |     |     | 805 |     |     |     |      |
| AGC | ACT | GGT | GCC | TAC | CTG | AGC | GCC | ATC | GGC | GGC | TTC | GCC | AGC | GAG | AAG | 1250 |
| Ser | Thr | Gly | Ala | Tyr | Leu | Ser | Ala | Ile | Gly | Gly | Phe | Ala | Ser | Glu | Lys |      |
|     | 810 |     |     |     |     | 815 |     |     |     |     | 820 |     |     |     |     |      |
| GAG | ATC | CTG | CTG | GAT | AAG | GAC | AGC | AAG | TAC | CAC | ATC | GAC | AAG | GTG | ACC | 1298 |
| Glu | Ile | Leu | Leu | Asp | Lys | Asp | Ser | Lys | Tyr | His | Ile | Asp | Lys | Val | Thr |      |
| 825 |     |     |     |     | 830 |     |     |     |     | 835 |     |     |     |     | 840 |      |
| GAG | GTG | ATC | ATC | AAG | GGC | GTG | AAG | CGC | TAC | GTG | GTG | GAC | GCC | ACC | CTG | 1346 |
| Glu | Val | Ile | Ile | Lys | Gly | Val | Lys | Arg | Tyr | Val | Val | Asp | Ala | Thr | Leu |      |
|     |     |     |     | 845 |     |     |     |     | 850 |     |     |     |     | 855 |     |      |
| CTG | ACC | AAC | TAG |     |     |     |     |     |     |     |     |     |     |     |     | 1358 |
| Leu | Thr | Asn |     |     |     |     |     |     |     |     |     |     |     |     |     |      |

( 2 ) INFORMATION FOR SEQ ID NO:46:

( i ) SEQUENCE CHARACTERISTICS:
        ( A ) LENGTH: 449 amino acids
        ( B ) TYPE: amino acid
        ( D ) TOPOLOGY: linear ( i i ) MOLECULE TYPE: protein ( x i ) SEQUENCE DESCRIPTION: SEQ ID NO:46:

| Met | Gly | Trp | Ser | Trp | Ile | Phe | Leu | Phe | Leu | Leu | Ser | Gly | Ala | Ala | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Val | His | Cys | Leu | Ser | Ser | Ser | Ser | Phe | Ala | Asp | Ser | Asn | Pro | Ile | Arg |
|     |     |     | 20  |     |     |     |     | 25  |     |     |     |     | 30  |     |     |
| Val | Thr | Asp | Arg | Ala | Ala | Ser | Thr | Leu | Gln | Asn | Leu | Lys | Ile | Thr | Asp |
|     |     | 35  |     |     |     |     | 40  |     |     |     |     | 45  |     |     |     |
| Lys | Val | Glu | Asp | Phe | Lys | Glu | Asp | Lys | Glu | Lys | Ala | Lys | Glu | Trp | Gly |
|     | 50  |     |     |     |     | 55  |     |     |     |     | 60  |     |     |     |     |
| Lys | Glu | Lys | Glu | Lys | Glu | Trp | Lys | Leu | Thr | Ala | Thr | Glu | Lys | Gly | Lys |
| 65  |     |     |     |     | 70  |     |     |     |     | 75  |     |     |     |     | 80  |
| Met | Asn | Asn | Phe | Leu | Asp | Asn | Lys | Asn | Asp | Ile | Lys | Thr | Asn | Tyr | Lys |
|     |     |     |     | 85  |     |     |     |     | 90  |     |     |     |     | 95  |     |
| Glu | Ile | Thr | Phe | Ser | Ile | Ala | Gly | Ser | Phe | Glu | Asp | Glu | Ile | Lys | Asp |
|     |     |     | 100 |     |     |     |     | 105 |     |     |     |     | 110 |     |     |
| Leu | Lys | Glu | Ile | Asp | Lys | Met | Phe | Asp | Lys | Thr | Asn | Leu | Ser | Asn | Ser |
|     |     | 115 |     |     |     |     | 120 |     |     |     |     | 125 |     |     |     |
| Ile | Ile | Thr | Tyr | Lys | Asn | Val | Glu | Pro | Thr | Thr | Ile | Gly | Phe | Asn | Lys |
|     | 130 |     |     |     |     | 135 |     |     |     |     | 140 |     |     |     |     |
| Ser | Leu | Thr | Glu | Gly | Asn | Thr | Ile | Asn | Ser | Asp | Ala | Met | Ala | Gln | Phe |
| 145 |     |     |     |     | 150 |     |     |     |     | 155 |     |     |     |     | 160 |
| Lys | Glu | Gln | Phe | Leu | Asp | Arg | Asp | Ile | Lys | Phe | Asp | Ser | Tyr | Leu | Asp |
|     |     |     |     | 165 |     |     |     |     | 170 |     |     |     |     | 175 |     |
| Thr | His | Leu | Thr | Ala | Gln | Gln | Val | Ser | Ser | Lys | Glu | Arg | Val | Ile | Leu |
|     |     |     | 180 |     |     |     |     | 185 |     |     |     |     | 190 |     |     |

| | | | | | | | | | | | | | | |
|---|---|---|---|---|---|---|---|---|---|---|---|---|---|---|
| Lys | Val | Thr<br>195 | Val | Pro | Ser | Gly | Lys<br>200 | Gly | Ser | Thr | Thr<br>205 | Pro | Thr | Lys | Ala |
| Gly | Val<br>210 | Ile | Leu | Asn | Asn | Ser<br>215 | Glu | Tyr | Lys | Met | Leu<br>220 | Ile | Asp | Asn | Gly |
| Tyr<br>225 | Met | Val | His | Val | Asp<br>230 | Lys | Val | Ser | Lys | Val<br>235 | Val | Lys | Lys | Gly | Val<br>240 |
| Glu | Cys | Leu | Gln | Ile<br>245 | Glu | Gly | Thr | Leu | Lys<br>250 | Lys | Ser | Leu | Asp | Phe<br>255 | Lys |
| Asn | Asp | Ile | Asn<br>260 | Ala | Glu | Ala | His | Ser<br>265 | Trp | Gly | Met | Lys | Asn<br>270 | Tyr | Glu |
| Glu | Trp | Ala<br>275 | Lys | Asp | Leu | Thr | Asp<br>280 | Ser | Gln | Arg | Glu | Ala<br>285 | Leu | Asp | Gly |
| Tyr | Ala<br>290 | Arg | Gln | Asp | Tyr | Lys<br>295 | Glu | Ile | Asn | Asn | Tyr<br>300 | Leu | Arg | Asn | Gln |
| Gly<br>305 | Gly | Ser | Gly | Asn | Glu<br>310 | Lys | Leu | Asp | Ala | Gln<br>315 | Ile | Lys | Asn | Ile | Ser<br>320 |
| Asp | Ala | Leu | Gly | Lys<br>325 | Lys | Pro | Ile | Pro | Glu<br>330 | Asn | Ile | Thr | Val | Tyr<br>335 | Arg |
| Trp | Cys | Gly | Met<br>340 | Pro | Glu | Phe | Gly | Tyr<br>345 | Gln | Ile | Ser | Asp | Pro<br>350 | Leu | Pro |
| Ser | Leu | Lys<br>355 | Asp | Phe | Glu | Glu | Gln<br>360 | Phe | Leu | Asn | Thr | Ile<br>365 | Lys | Glu | Asp |
| Lys | Gly<br>370 | Tyr | Met | Ser | Thr | Ser<br>375 | Leu | Ser | Ser | Glu | Arg<br>380 | Leu | Ala | Ala | Phe |
| Gly | Ser | Arg | Lys | Ile | Ile<br>390 | Leu | Arg | Leu | Gln | Val<br>395 | Pro | Lys | Gly | Ser | Thr<br>400 |
| Gly<br>385 | | | | | | | | | | | | | | | |
| Gly | Ala | Tyr | Leu | Ser<br>405 | Ala | Ile | Gly | Gly | Phe<br>410 | Ala | Ser | Glu | Lys | Glu<br>415 | Ile |
| Leu | Leu | Asp | Lys<br>420 | Asp | Ser | Lys | Tyr | His<br>425 | Ile | Asp | Lys | Val | Thr<br>430 | Glu | Val |
| Ile | Ile | Lys<br>435 | Gly | Val | Lys | Arg | Tyr<br>440 | Val | Val | Asp | Ala | Thr<br>445 | Leu | Leu | Thr |
| Asn | | | | | | | | | | | | | | | |

(2) INFORMATION FOR SEQ ID NO:47:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (iii) HYPOTHETICAL: NO (ix) FEATURE:
        (A) NAME/KEY: Peptide
        (B) LOCATION: 1..16
        (D) OTHER INFORMATION: /note= "linker peptide for fusion
            of VIP1A(a) and VIP2A(a) used to construct pCIB5533"

(xi) SEQUENCE DESCRIPTION: SEQ ID NO:47:

| | | | | | | | | | | | | | | | |
|---|---|---|---|---|---|---|---|---|---|---|---|---|---|---|---|
| Pro<br>1 | Ser | Thr | Pro | Pro<br>5 | Thr | Pro | Ser | Pro | Ser<br>10 | Thr | Pro | Pro | Thr | Pro<br>15 | Ser |

(2) INFORMATION FOR SEQ ID NO:48:

(i) SEQUENCE CHARACTERISTICS:
        (A) LENGTH: 66 base pairs ( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "DNA encoding linker peptide used to construct pCIB5533"

( i i i ) HYPOTHETICAL: NO ( x i ) SEQUENCE DESCRIPTION: SEQ ID NO:48:

```
CCCGGGCCTT  CTACTCCCCC  AACTCCCTCT  CCTAGCACGC  CTCCGACACC  TAGCGATATC       60
GGATCC                                                                       66
```

( 2 ) INFORMATION FOR SEQ ID NO:49:

( i ) SEQUENCE CHARACTERISTICS:
( A ) LENGTH: 4031 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "Synthetic DNA"

( i i i ) HYPOTHETICAL: NO ( i x ) FEATURE:
( A ) NAME/KEY: CDS
( B ) LOCATION: 6..4019
( D ) OTHER INFORMATION: /note= "Maize optimized DNA sequence encoding a VIP2A(a) - VIP1A(a) fusion protein as contained in pCIB5531"

( x i ) SEQUENCE DESCRIPTION: SEQ ID NO:49:

```
GATCC  ATG  AAG  CGC  ATG  GAG  GGC  AAG  CTG  TTC  ATG  GTG  AGC  AAG  AAG         47
       Met  Lys  Arg  Met  Glu  Gly  Lys  Leu  Phe  Met  Val  Ser  Lys  Lys
       450                      455                      460

CTC  CAG  GTG  GTG  ACC  AAG  ACC  GTG  CTG  CTG  AGC  ACC  GTG  TTC  AGC  ATC      95
Leu  Gln  Val  Val  Thr  Lys  Thr  Val  Leu  Leu  Ser  Thr  Val  Phe  Ser  Ile
465                      470                      475

AGC  CTG  CTG  AAC  AAC  GAG  GTG  ATC  AAG  GCC  GAG  CAG  CTG  AAC  ATC  AAC     143
Ser  Leu  Leu  Asn  Asn  Glu  Val  Ile  Lys  Ala  Glu  Gln  Leu  Asn  Ile  Asn
480                      485                      490                      495

AGC  CAG  AGC  AAG  TAC  ACC  AAC  CTC  CAG  AAC  CTG  AAG  ATC  ACC  GAC  AAG     191
Ser  Gln  Ser  Lys  Tyr  Thr  Asn  Leu  Gln  Asn  Leu  Lys  Ile  Thr  Asp  Lys
                         500                      505                      510

GTG  GAG  GAC  TTC  AAG  GAG  GAC  AAG  GAG  AAG  GCC  AAG  GAG  TGG  GGC  AAG     239
Val  Glu  Asp  Phe  Lys  Glu  Asp  Lys  Glu  Lys  Ala  Lys  Glu  Trp  Gly  Lys
                    515                      520                      525

GAG  AAG  GAG  AAG  GAG  TGG  AAG  CTT  ACC  GCC  ACC  GAG  AAG  GGC  AAG  ATG     287
Glu  Lys  Glu  Lys  Glu  Trp  Lys  Leu  Thr  Ala  Thr  Glu  Lys  Gly  Lys  Met
               530                      535                      540

AAC  AAC  TTC  CTG  GAC  AAC  AAG  AAC  GAC  ATC  AAG  ACC  AAC  TAC  AAG  GAG     335
Asn  Asn  Phe  Leu  Asp  Asn  Lys  Asn  Asp  Ile  Lys  Thr  Asn  Tyr  Lys  Glu
          545                      550                      555

ATC  ACC  TTC  AGC  ATA  GCC  GGC  AGC  TTC  GAG  GAC  GAG  ATC  AAG  GAC  CTG     383
Ile  Thr  Phe  Ser  Ile  Ala  Gly  Ser  Phe  Glu  Asp  Glu  Ile  Lys  Asp  Leu
560                      565                      570                      575

AAG  GAG  ATC  GAC  AAG  ATG  TTC  GAC  AAG  ACC  AAC  CTG  AGC  AAC  AGC  ATC     431
Lys  Glu  Ile  Asp  Lys  Met  Phe  Asp  Lys  Thr  Asn  Leu  Ser  Asn  Ser  Ile
                    580                      585                      590

ATC  ACC  TAC  AAG  AAC  GTG  GAG  CCC  ACC  ACC  ATC  GGC  TTC  AAC  AAG  AGC     479
Ile  Thr  Tyr  Lys  Asn  Val  Glu  Pro  Thr  Thr  Ile  Gly  Phe  Asn  Lys  Ser
               595                      600                      605

CTG  ACC  GAG  GGC  AAC  ACC  ATC  AAC  AGC  GAC  GCC  ATG  GCC  CAG  TTC  AAG     527
```

|  |  |  |  |  |  |  |  |  |  |  |  |  |  |  |  |  |
|---|---|---|---|---|---|---|---|---|---|---|---|---|---|---|---|---|
| Leu | Thr | Glu | Gly | Asn | Thr | Ile | Asn | Ser | Asp | Ala | Met | Ala | Gln | Phe | Lys |  |
|  |  |  | 610 |  |  |  | 615 |  |  |  |  | 620 |  |  |  |  |
| GAG | CAG | TTC | CTG | GAC | CGC | GAC | ATC | AAG | TTC | GAC | AGC | TAC | CTG | GAC | ACC | 575 |
| Glu | Gln | Phe | Leu | Asp | Arg | Asp | Ile | Lys | Phe | Asp | Ser | Tyr | Leu | Asp | Thr |  |
|  | 625 |  |  |  | 630 |  |  |  |  | 635 |  |  |  |  |  |  |
| CAC | CTG | ACC | GCC | CAG | CAG | GTG | AGC | AGC | AAG | GAG | CGC | GTG | ATC | CTG | AAG | 623 |
| His | Leu | Thr | Ala | Gln | Gln | Val | Ser | Ser | Lys | Glu | Arg | Val | Ile | Leu | Lys |  |
| 640 |  |  |  |  | 645 |  |  |  |  | 650 |  |  |  |  | 655 |  |
| GTG | ACC | GTC | CCC | AGC | GGC | AAG | GGC | AGC | ACC | ACC | CCC | ACC | AAG | GCC | GGC | 671 |
| Val | Thr | Val | Pro | Ser | Gly | Lys | Gly | Ser | Thr | Thr | Pro | Thr | Lys | Ala | Gly |  |
|  |  |  |  | 660 |  |  |  |  | 665 |  |  |  |  | 670 |  |  |
| GTG | ATC | CTG | AAC | AAC | AGC | GAG | TAC | AAG | ATG | CTG | ATC | GAC | AAC | GGC | TAC | 719 |
| Val | Ile | Leu | Asn | Asn | Ser | Glu | Tyr | Lys | Met | Leu | Ile | Asp | Asn | Gly | Tyr |  |
|  |  |  |  | 675 |  |  |  |  | 680 |  |  |  |  | 685 |  |  |
| ATG | GTG | CAC | GTG | GAC | AAG | GTG | AGC | AAG | GTG | GTG | AAG | AAG | GGC | GTG | GAG | 767 |
| Met | Val | His | Val | Asp | Lys | Val | Ser | Lys | Val | Val | Lys | Lys | Gly | Val | Glu |  |
|  |  | 690 |  |  |  |  | 695 |  |  |  |  | 700 |  |  |  |  |
| TGC | CTC | CAG | ATC | GAG | GGC | ACC | CTG | AAG | AAG | AGT | CTA | GAC | TTC | AAG | AAC | 815 |
| Cys | Leu | Gln | Ile | Glu | Gly | Thr | Leu | Lys | Lys | Ser | Leu | Asp | Phe | Lys | Asn |  |
|  | 705 |  |  |  |  | 710 |  |  |  |  | 715 |  |  |  |  |  |
| GAC | ATC | AAC | GCC | GAG | GCC | CAC | AGC | TGG | GGC | ATG | AAG | AAC | TAC | GAG | GAG | 863 |
| Asp | Ile | Asn | Ala | Glu | Ala | His | Ser | Trp | Gly | Met | Lys | Asn | Tyr | Glu | Glu |  |
| 720 |  |  |  |  | 725 |  |  |  |  | 730 |  |  |  |  | 735 |  |
| TGG | GCC | AAG | GAC | CTG | ACC | GAC | AGC | CAG | CGC | GAG | GCC | CTG | GAC | GGC | TAC | 911 |
| Trp | Ala | Lys | Asp | Leu | Thr | Asp | Ser | Gln | Arg | Glu | Ala | Leu | Asp | Gly | Tyr |  |
|  |  |  |  | 740 |  |  |  |  | 745 |  |  |  |  | 750 |  |  |
| GCC | CGC | CAG | GAC | TAC | AAG | GAG | ATC | AAC | AAC | TAC | CTG | CGC | AAC | CAG | GGC | 959 |
| Ala | Arg | Gln | Asp | Tyr | Lys | Glu | Ile | Asn | Asn | Tyr | Leu | Arg | Asn | Gln | Gly |  |
|  |  |  | 755 |  |  |  |  | 760 |  |  |  |  | 765 |  |  |  |
| GGC | AGC | GGC | AAC | GAG | AAG | CTG | GAC | GCC | CAG | ATC | AAG | AAC | ATC | AGC | GAC | 1007 |
| Gly | Ser | Gly | Asn | Glu | Lys | Leu | Asp | Ala | Gln | Ile | Lys | Asn | Ile | Ser | Asp |  |
|  |  | 770 |  |  |  |  | 775 |  |  |  |  | 780 |  |  |  |  |
| GCC | CTG | GGC | AAG | AAG | CCC | ATC | CCC | GAG | AAC | ATC | ACC | GTG | TAC | CGC | TGG | 1055 |
| Ala | Leu | Gly | Lys | Lys | Pro | Ile | Pro | Glu | Asn | Ile | Thr | Val | Tyr | Arg | Trp |  |
|  | 785 |  |  |  |  | 790 |  |  |  |  | 795 |  |  |  |  |  |
| TGC | GGC | ATG | CCC | GAG | TTC | GGC | TAC | CAG | ATC | AGC | GAC | CCC | CTG | CCC | AGC | 1103 |
| Cys | Gly | Met | Pro | Glu | Phe | Gly | Tyr | Gln | Ile | Ser | Asp | Pro | Leu | Pro | Ser |  |
| 800 |  |  |  |  | 805 |  |  |  |  | 810 |  |  |  |  | 815 |  |
| CTG | AAG | GAC | TTC | GAG | GAG | CAG | TTC | CTG | AAC | ACC | ATC | AAG | GAG | GAC | AAG | 1151 |
| Leu | Lys | Asp | Phe | Glu | Glu | Gln | Phe | Leu | Asn | Thr | Ile | Lys | Glu | Asp | Lys |  |
|  |  |  |  | 820 |  |  |  |  | 825 |  |  |  |  | 830 |  |  |
| GGC | TAC | ATG | AGC | ACC | AGC | CTG | AGC | AGC | GAG | CGC | CTG | GCC | GCC | TTC | GGC | 1199 |
| Gly | Tyr | Met | Ser | Thr | Ser | Leu | Ser | Ser | Glu | Arg | Leu | Ala | Ala | Phe | Gly |  |
|  |  |  | 835 |  |  |  |  | 840 |  |  |  |  | 845 |  |  |  |
| AGC | CGC | AAG | ATC | ATC | CTG | CGC | CTG | CAG | GTG | CCC | AAG | GGC | AGC | ACT | GGT | 1247 |
| Ser | Arg | Lys | Ile | Ile | Leu | Arg | Leu | Gln | Val | Pro | Lys | Gly | Ser | Thr | Gly |  |
|  |  | 850 |  |  |  |  | 855 |  |  |  |  | 860 |  |  |  |  |
| GCC | TAC | CTG | AGC | GCC | ATC | GGC | GGC | TTC | GCC | AGC | GAG | AAG | GAG | ATC | CTG | 1295 |
| Ala | Tyr | Leu | Ser | Ala | Ile | Gly | Gly | Phe | Ala | Ser | Glu | Lys | Glu | Ile | Leu |  |
|  | 865 |  |  |  |  | 870 |  |  |  |  | 875 |  |  |  |  |  |
| CTG | GAT | AAG | GAC | AGC | AAG | TAC | CAC | ATC | GAC | AAG | GTG | ACC | GAG | GTG | ATC | 1343 |
| Leu | Asp | Lys | Asp | Ser | Lys | Tyr | His | Ile | Asp | Lys | Val | Thr | Glu | Val | Ile |  |
| 880 |  |  |  |  | 885 |  |  |  |  | 890 |  |  |  |  | 895 |  |
| ATC | AAG | GGC | GTG | AAG | CGC | TAC | GTG | GTG | GAC | GCC | ACC | CTG | CTG | ACC | AAC | 1391 |
| Ile | Lys | Gly | Val | Lys | Arg | Tyr | Val | Val | Asp | Ala | Thr | Leu | Leu | Thr | Asn |  |
|  |  |  |  | 900 |  |  |  |  | 905 |  |  |  |  | 910 |  |  |
| TCC | CGG | GGG | CCT | TCT | ACT | CCC | CCA | ACT | CCC | TCT | CCT | AGC | ACG | CCT | CCG | 1439 |
| Ser | Arg | Gly | Pro | Ser | Thr | Pro | Pro | Thr | Pro | Ser | Pro | Ser | Thr | Pro | Pro |  |
|  |  |  | 915 |  |  |  | 920 |  |  |  |  | 925 |  |  |  |  |
| ACA | CCT | AGC | GAT | ATC | GGA | TCC | ACC | ATG | AAG | ACC | AAC | CAG | ATC | AGC | ACC | 1487 |

|     |     |     |     |     |     |     |     |     |     |     |     |     |     |     |      |
|-----|-----|-----|-----|-----|-----|-----|-----|-----|-----|-----|-----|-----|-----|-----|------|
| Thr | Pro | Ser | Asp | Ile | Gly | Ser | Thr | Met | Lys | Thr | Asn | Gln | Ile | Ser | Thr  |
|     |     |     | 930 |     |     |     | 935 |     |     |     |     | 940 |     |     |      |

| ACC | CAG | AAG | AAC | CAG | CAG | AAG | GAG | ATG | GAC | CGC | AAG | GGC | CTG | CTG | GGC | 1535 |
|-----|-----|-----|-----|-----|-----|-----|-----|-----|-----|-----|-----|-----|-----|-----|-----|------|
| Thr | Gln | Lys | Asn | Gln | Gln | Lys | Glu | Met | Asp | Arg | Lys | Gly | Leu | Leu | Gly |      |
|     | 945 |     |     |     | 950 |     |     |     |     | 955 |     |     |     |     |     |      |

| TAC | TAC | TTC | AAG | GGC | AAG | GAC | TTC | AGC | AAC | CTG | ACC | ATG | TTC | GCC | CCC | 1583 |
|-----|-----|-----|-----|-----|-----|-----|-----|-----|-----|-----|-----|-----|-----|-----|-----|------|
| Tyr | Tyr | Phe | Lys | Gly | Lys | Asp | Phe | Ser | Asn | Leu | Thr | Met | Phe | Ala | Pro |      |
| 960 |     |     |     |     | 965 |     |     |     |     | 970 |     |     |     |     | 975 |      |

| ACG | CGT | GAC | AGC | ACC | CTG | ATC | TAC | GAC | CAG | CAG | ACC | GCC | AAC | AAG | CTG | 1631 |
|-----|-----|-----|-----|-----|-----|-----|-----|-----|-----|-----|-----|-----|-----|-----|-----|------|
| Thr | Arg | Asp | Ser | Thr | Leu | Ile | Tyr | Asp | Gln | Gln | Thr | Ala | Asn | Lys | Leu |      |
|     |     |     |     | 980 |     |     |     |     | 985 |     |     |     |     | 990 |     |      |

| CTG | GAC | AAG | AAG | CAG | CAG | GAG | TAC | CAG | AGC | ATC | CGC | TGG | ATC | GGC | CTG | 1679 |
|-----|-----|-----|-----|-----|-----|-----|-----|-----|-----|-----|-----|-----|-----|-----|-----|------|
| Leu | Asp | Lys | Lys | Gln | Gln | Glu | Tyr | Gln | Ser | Ile | Arg | Trp | Ile | Gly | Leu |      |
|     |     |     | 995 |     |     |     | 1000|     |     |     |     | 1005|     |     |     |      |

| ATC | CAG | AGC | AAG | GAG | ACC | GGC | GAC | TTC | ACC | TTC | AAC | CTG | AGC | GAG | GAC | 1727 |
|-----|-----|-----|-----|-----|-----|-----|-----|-----|-----|-----|-----|-----|-----|-----|-----|------|
| Ile | Gln | Ser | Lys | Glu | Thr | Gly | Asp | Phe | Thr | Phe | Asn | Leu | Ser | Glu | Asp |      |
|     |     |     | 1010|     |     |     | 1015|     |     |     |     | 1020|     |     |     |      |

| GAG | CAG | GCC | ATC | ATC | GAG | ATC | AAC | GGC | AAG | ATC | ATC | AGC | AAC | AAG | GGC | 1775 |
|-----|-----|-----|-----|-----|-----|-----|-----|-----|-----|-----|-----|-----|-----|-----|-----|------|
| Glu | Gln | Ala | Ile | Ile | Glu | Ile | Asn | Gly | Lys | Ile | Ile | Ser | Asn | Lys | Gly |      |
|     |     |     | 1025|     |     |     | 1030|     |     |     |     | 1035|     |     |     |      |

| AAG | GAG | AAG | CAG | GTG | GTG | CAC | CTG | GAG | AAG | GGC | AAG | CTG | GTG | CCC | ATC | 1823 |
|-----|-----|-----|-----|-----|-----|-----|-----|-----|-----|-----|-----|-----|-----|-----|-----|------|
| Lys | Glu | Lys | Gln | Val | Val | His | Leu | Glu | Lys | Gly | Lys | Leu | Val | Pro | Ile |      |
| 1040|     |     |     |     | 1045|     |     |     |     | 1050|     |     |     |     | 1055|      |

| AAG | ATC | GAG | TAC | CAG | AGC | GAC | ACC | AAG | TTC | AAC | ATC | GAC | AGC | AAG | ACC | 1871 |
|-----|-----|-----|-----|-----|-----|-----|-----|-----|-----|-----|-----|-----|-----|-----|-----|------|
| Lys | Ile | Glu | Tyr | Gln | Ser | Asp | Thr | Lys | Phe | Asn | Ile | Asp | Ser | Lys | Thr |      |
|     |     |     |     | 1060|     |     |     |     | 1065|     |     |     |     | 1070|     |      |

| TTC | AAG | GAG | CTG | AAG | CTT | TTC | AAG | ATC | GAC | AGC | CAG | AAC | CAG | CCC | CAG | 1919 |
|-----|-----|-----|-----|-----|-----|-----|-----|-----|-----|-----|-----|-----|-----|-----|-----|------|
| Phe | Lys | Glu | Leu | Lys | Leu | Phe | Lys | Ile | Asp | Ser | Gln | Asn | Gln | Pro | Gln |      |
|     |     |     |     | 1075|     |     |     |     | 1080|     |     |     |     | 1085|     |      |

| CAG | GTG | CAG | CAG | GAC | GAG | CTG | CGC | AAC | CCC | GAG | TTC | AAC | AAG | AAG | GAG | 1967 |
|-----|-----|-----|-----|-----|-----|-----|-----|-----|-----|-----|-----|-----|-----|-----|-----|------|
| Gln | Val | Gln | Gln | Asp | Glu | Leu | Arg | Asn | Pro | Glu | Phe | Asn | Lys | Lys | Glu |      |
|     |     |     | 1090|     |     |     |     | 1095|     |     |     |     | 1100|     |     |      |

| AGC | CAG | GAG | TTC | CTG | GCC | AAG | CCC | AGC | AAG | ATC | AAC | CTG | TTC | ACC | CAG | 2015 |
|-----|-----|-----|-----|-----|-----|-----|-----|-----|-----|-----|-----|-----|-----|-----|-----|------|
| Ser | Gln | Glu | Phe | Leu | Ala | Lys | Pro | Ser | Lys | Ile | Asn | Leu | Phe | Thr | Gln |      |
|     | 1105|     |     |     |     | 1110|     |     |     |     | 1115|     |     |     |     |      |

| CAG | ATG | AAG | CGC | GAG | ATC | GAC | GAG | GAC | ACC | GAC | ACC | GAC | GGC | GAC | AGC | 2063 |
|-----|-----|-----|-----|-----|-----|-----|-----|-----|-----|-----|-----|-----|-----|-----|-----|------|
| Gln | Met | Lys | Arg | Glu | Ile | Asp | Glu | Asp | Thr | Asp | Thr | Asp | Gly | Asp | Ser |      |
| 1120|     |     |     |     | 1125|     |     |     |     | 1130|     |     |     |     | 1135|      |

| ATC | CCC | GAC | CTG | TGG | GAG | GAG | AAC | GGC | TAC | ACC | ATC | CAG | AAC | CGC | ATC | 2111 |
|-----|-----|-----|-----|-----|-----|-----|-----|-----|-----|-----|-----|-----|-----|-----|-----|------|
| Ile | Pro | Asp | Leu | Trp | Glu | Glu | Asn | Gly | Tyr | Thr | Ile | Gln | Asn | Arg | Ile |      |
|     |     |     |     | 1140|     |     |     |     | 1145|     |     |     |     | 1150|     |      |

| GCC | GTG | AAG | TGG | GAC | GAC | AGC | CTG | GCT | AGC | AAG | GGC | TAC | ACC | AAG | TTC | 2159 |
|-----|-----|-----|-----|-----|-----|-----|-----|-----|-----|-----|-----|-----|-----|-----|-----|------|
| Ala | Val | Lys | Trp | Asp | Asp | Ser | Leu | Ala | Ser | Lys | Gly | Tyr | Thr | Lys | Phe |      |
|     |     |     |     | 1155|     |     |     |     | 1160|     |     |     |     | 1165|     |      |

| GTG | AGC | AAC | CCC | CTG | GAG | AGC | CAC | ACC | GTG | GGC | GAC | CCC | TAC | ACC | GAC | 2207 |
|-----|-----|-----|-----|-----|-----|-----|-----|-----|-----|-----|-----|-----|-----|-----|-----|------|
| Val | Ser | Asn | Pro | Leu | Glu | Ser | His | Thr | Val | Gly | Asp | Pro | Tyr | Thr | Asp |      |
|     |     | 1170|     |     |     |     | 1175|     |     |     |     | 1180|     |     |     |      |

| TAC | GAG | AAG | GCC | GCC | CGC | GAC | CTG | GAC | CTG | AGC | AAC | GCC | AAG | GAG | ACC | 2255 |
|-----|-----|-----|-----|-----|-----|-----|-----|-----|-----|-----|-----|-----|-----|-----|-----|------|
| Tyr | Glu | Lys | Ala | Ala | Arg | Asp | Leu | Asp | Leu | Ser | Asn | Ala | Lys | Glu | Thr |      |
|     |     | 1185|     |     |     |     | 1190|     |     |     |     | 1195|     |     |     |      |

| TTC | AAC | CCC | CTG | GTG | GCC | GCC | TTC | CCC | AGC | GTG | AAC | GTG | AGC | ATG | GAG | 2303 |
|-----|-----|-----|-----|-----|-----|-----|-----|-----|-----|-----|-----|-----|-----|-----|-----|------|
| Phe | Asn | Pro | Leu | Val | Ala | Ala | Phe | Pro | Ser | Val | Asn | Val | Ser | Met | Glu |      |
| 1200|     |     |     |     | 1205|     |     |     |     | 1210|     |     |     |     | 1215|      |

| AAG | GTG | ATC | CTG | AGC | CCC | AAC | GAG | AAC | CTG | AGC | AAC | AGC | GTG | GAG | AGC | 2351 |
|-----|-----|-----|-----|-----|-----|-----|-----|-----|-----|-----|-----|-----|-----|-----|-----|------|
| Lys | Val | Ile | Leu | Ser | Pro | Asn | Glu | Asn | Leu | Ser | Asn | Ser | Val | Glu | Ser |      |
|     |     |     |     | 1220|     |     |     |     | 1225|     |     |     |     | 1230|     |      |

| CAC | TCG | AGC | ACC | AAC | TGG | AGC | TAC | ACC | AAC | ACC | GAG | GGC | GCC | AGC | GTG | 2399 |
|-----|-----|-----|-----|-----|-----|-----|-----|-----|-----|-----|-----|-----|-----|-----|-----|------|
| His | Ser | Ser | Thr | Asn | Trp | Ser | Tyr | Thr | Asn | Thr | Glu | Gly | Ala | Ser | Val |      |
|     |     |     |     | 1235|     |     |     |     | 1240|     |     |     |     | 1245|     |      |

| GAG | GCC | GGC | ATC | GGT | CCC | AAG | GGC | ATC | AGC | TTC | GGC | GTG | AGC | GTG | AAC | 2447 |
|-----|-----|-----|-----|-----|-----|-----|-----|-----|-----|-----|-----|-----|-----|-----|-----|------|

```
          Glu Ala Gly Ile Gly Pro Lys Gly Ile Ser Phe Gly Val Ser Val Asn
                       1250                1255                1260

TAC CAG CAC AGC GAG ACC GTG GCC CAG GAG TGG GGC ACC AGC ACC GGC              2495
Tyr Gln His Ser Glu Thr Val Ala Gln Glu Trp Gly Thr Ser Thr Gly
    1265                1270                1275

AAC ACC AGC CAG TTC AAC ACC GCC AGC GCC GGC TAC CTG AAC GCC AAC              2543
Asn Thr Ser Gln Phe Asn Thr Ala Ser Ala Gly Tyr Leu Asn Ala Asn
1280                1285                1290                1295

GTG CGC TAC AAC AAC GTG GGC ACC GGC GCC ATC TAC GAC GTG AAG CCC              2591
Val Arg Tyr Asn Asn Val Gly Thr Gly Ala Ile Tyr Asp Val Lys Pro
                1300                1305                1310

ACC ACC AGC TTC GTG CTG AAC AAC GAC ACC ATC GCC ACC ATC ACC GCC              2639
Thr Thr Ser Phe Val Leu Asn Asn Asp Thr Ile Ala Thr Ile Thr Ala
            1315                1320                1325

AAG TCG AAT TCC ACC GCC CTG AAC ATC AGC CCC GGC GAG AGC TAC CCC              2687
Lys Ser Asn Ser Thr Ala Leu Asn Ile Ser Pro Gly Glu Ser Tyr Pro
        1330                1335                1340

AAG AAG GGC CAG AAC GGC ATC GCC ATC ACC AGC ATG GAC GAC TTC AAC              2735
Lys Lys Gly Gln Asn Gly Ile Ala Ile Thr Ser Met Asp Asp Phe Asn
    1345                1350                1355

AGC CAC CCC ATC ACC CTG AAC AAG AAG CAG GTG GAC AAC CTG CTG AAC              2783
Ser His Pro Ile Thr Leu Asn Lys Lys Gln Val Asp Asn Leu Leu Asn
1360                1365                1370                1375

AAC AAG CCC ATG ATG CTG GAG ACC AAC CAG ACC GAC GGC GTC TAC AAG              2831
Asn Lys Pro Met Met Leu Glu Thr Asn Gln Thr Asp Gly Val Tyr Lys
                1380                1385                1390

ATC AAG GAC ACC CAC GGC AAC ATC GTG ACG GGC GGC GAG TGG AAC GGC              2879
Ile Lys Asp Thr His Gly Asn Ile Val Thr Gly Gly Glu Trp Asn Gly
            1395                1400                1405

GTG ATC CAG CAG ATC AAG GCC AAG ACC GCC AGC ATC ATC GTC GAC GAC              2927
Val Ile Gln Gln Ile Lys Ala Lys Thr Ala Ser Ile Ile Val Asp Asp
        1410                1415                1420

GGC GAG CGC GTG GCC GAG AAG CGC GTG GCC GCC AAG GAC TAC GAG AAC              2975
Gly Glu Arg Val Ala Glu Lys Arg Val Ala Ala Lys Asp Tyr Glu Asn
    1425                1430                1435

CCC GAG GAC AAG ACC CCC AGC CTG ACC CTG AAG GAC GCC CTG AAG CTG              3023
Pro Glu Asp Lys Thr Pro Ser Leu Thr Leu Lys Asp Ala Leu Lys Leu
1440                1445                1450                1455

AGC TAC CCC GAC GAG ATC AAG GAG ATC GAG GGC TTG CTG TAC TAC AAG              3071
Ser Tyr Pro Asp Glu Ile Lys Glu Ile Glu Gly Leu Leu Tyr Tyr Lys
                1460                1465                1470

AAC AAG CCC ATC TAC GAG AGC AGC GTG ATG ACC TAT CTA GAC GAG AAC              3119
Asn Lys Pro Ile Tyr Glu Ser Ser Val Met Thr Tyr Leu Asp Glu Asn
            1475                1480                1485

ACC GCC AAG GAG GTG ACC AAG CAG CTG AAC GAC ACC ACC GGC AAG TTC              3167
Thr Ala Lys Glu Val Thr Lys Gln Leu Asn Asp Thr Thr Gly Lys Phe
        1490                1495                1500

AAG GAC GTG AGC CAC CTG TAC GAC GTG AAG CTG ACC CCC AAG ATG AAC              3215
Lys Asp Val Ser His Leu Tyr Asp Val Lys Leu Thr Pro Lys Met Asn
    1505                1510                1515

GTG ACC ATC AAG CTG AGC ATC CTG TAC GAC AAC GCC GAG AGC AAC GAC              3263
Val Thr Ile Lys Leu Ser Ile Leu Tyr Asp Asn Ala Glu Ser Asn Asp
1520                1525                1530                1535

AAC AGC ATC GGC AAG TGG ACC AAC ACC AAC ATC GTG AGC GGC GGC AAC              3311
Asn Ser Ile Gly Lys Trp Thr Asn Thr Asn Ile Val Ser Gly Gly Asn
                1540                1545                1550

AAC GGC AAG AAG CAG TAC AGC AGC AAC AAC CCC GAC GCC AAC CTG ACC              3359
Asn Gly Lys Lys Gln Tyr Ser Ser Asn Asn Pro Asp Ala Asn Leu Thr
            1555                1560                1565

CTG AAC ACC GAC GCC CAG GAG AAG CTG AAC AAG AAC CGC GAC TAC TAC              3407
```

| | | | | | | | | | | | | | | | | |
|---|---|---|---|---|---|---|---|---|---|---|---|---|---|---|---|---|
| Leu | Asn | Thr | Asp | Ala | Gln | Glu | Lys | Leu | Asn | Lys | Asn | Arg | Asp | Tyr | Tyr | |
| | | | 1570 | | | | 1575 | | | | 1580 | | | | | |
| ATC | AGC | CTG | TAC | ATG | AAG | AGC | GAG | AAG | AAC | ACC | CAG | TGC | GAG | ATC | ACC | 3455 |
| Ile | Ser | Leu | Tyr | Met | Lys | Ser | Glu | Lys | Asn | Thr | Gln | Cys | Glu | Ile | Thr | |
| | | 1585 | | | | 1590 | | | | | 1595 | | | | | |
| ATC | GAC | GGC | GAG | ATA | TAC | CCC | ATC | ACC | ACC | AAG | ACC | GTG | AAC | GTG | AAC | 3503 |
| Ile | Asp | Gly | Glu | Ile | Tyr | Pro | Ile | Thr | Thr | Lys | Thr | Val | Asn | Val | Asn | |
| 1600 | | | | | 1605 | | | | | 1610 | | | | | 1615 | |
| AAG | GAC | AAC | TAC | AAG | CGC | CTG | GAC | ATC | ATC | GCC | CAC | AAC | ATC | AAG | AGC | 3551 |
| Lys | Asp | Asn | Tyr | Lys | Arg | Leu | Asp | Ile | Ile | Ala | His | Asn | Ile | Lys | Ser | |
| | | | | 1620 | | | | | 1625 | | | | | 1630 | | |
| AAC | CCC | ATC | AGC | AGC | CTG | CAC | ATC | AAG | ACC | AAC | GAC | GAG | ATC | ACC | CTG | 3599 |
| Asn | Pro | Ile | Ser | Ser | Leu | His | Ile | Lys | Thr | Asn | Asp | Glu | Ile | Thr | Leu | |
| | | | | 1635 | | | | 1640 | | | | | 1645 | | | |
| TTC | TGG | GAC | GAC | ATA | TCG | ATT | ACC | GAC | GTC | GCC | AGC | ATC | AAG | CCC | GAG | 3647 |
| Phe | Trp | Asp | Asp | Ile | Ser | Ile | Thr | Asp | Val | Ala | Ser | Ile | Lys | Pro | Glu | |
| | | | 1650 | | | | | 1655 | | | | | 1660 | | | |
| AAC | CTG | ACC | GAC | AGC | GAG | ATC | AAG | CAG | ATA | TAC | AGT | CGC | TAC | GGC | ATC | 3695 |
| Asn | Leu | Thr | Asp | Ser | Glu | Ile | Lys | Gln | Ile | Tyr | Ser | Arg | Tyr | Gly | Ile | |
| | | 1665 | | | | 1670 | | | | | 1675 | | | | | |
| AAG | CTG | GAG | GAC | GGC | ATC | CTG | ATC | GAC | AAG | AAA | GGC | GGC | ATC | CAC | TAC | 3743 |
| Lys | Leu | Glu | Asp | Gly | Ile | Leu | Ile | Asp | Lys | Lys | Gly | Gly | Ile | His | Tyr | |
| 1680 | | | | | 1685 | | | | | 1690 | | | | | 1695 | |
| GGC | GAG | TTC | ATC | AAC | GAG | GCC | AGC | TTC | AAC | ATC | GAG | CCC | CTG | CAG | AAC | 3791 |
| Gly | Glu | Phe | Ile | Asn | Glu | Ala | Ser | Phe | Asn | Ile | Glu | Pro | Leu | Gln | Asn | |
| | | | | 1700 | | | | | 1705 | | | | | 1710 | | |
| TAC | GTG | ACC | AAG | TAC | GAG | GTG | ACC | TAC | AGC | AGC | GAG | CTG | GGC | CCC | AAC | 3839 |
| Tyr | Val | Thr | Lys | Tyr | Glu | Val | Thr | Tyr | Ser | Ser | Glu | Leu | Gly | Pro | Asn | |
| | | | 1715 | | | | | 1720 | | | | | 1725 | | | |
| GTG | AGC | GAC | ACC | CTG | GAG | AGC | GAC | AAG | ATT | TAC | AAG | GAC | GGC | ACC | ATC | 3887 |
| Val | Ser | Asp | Thr | Leu | Glu | Ser | Asp | Lys | Ile | Tyr | Lys | Asp | Gly | Thr | Ile | |
| | | | 1730 | | | | | 1735 | | | | | 1740 | | | |
| AAG | TTC | GAC | TTC | ACC | AAG | TAC | AGC | AAG | AAC | GAG | CAG | GGC | CTG | TTC | TAC | 3935 |
| Lys | Phe | Asp | Phe | Thr | Lys | Tyr | Ser | Lys | Asn | Glu | Gln | Gly | Leu | Phe | Tyr | |
| | | 1745 | | | | | 1750 | | | | | 1755 | | | | |
| GAC | AGC | GGC | CTG | AAC | TGG | GAC | TTC | AAG | ATC | AAC | GCC | ATC | ACC | TAC | GAC | 3983 |
| Asp | Ser | Gly | Leu | Asn | Trp | Asp | Phe | Lys | Ile | Asn | Ala | Ile | Thr | Tyr | Asp | |
| 1760 | | | | | 1765 | | | | | 1770 | | | | | 1775 | |
| GGC | AAG | GAG | ATG | AAC | GTG | TTC | CAC | CGC | TAC | AAC | AAG | TAGATCTGAG | | | | 4029 |
| Gly | Lys | Glu | Met | Asn | Val | Phe | His | Arg | Tyr | Asn | Lys | | | | | |
| | | | | 1780 | | | | | 1785 | | | | | | | |
| CT | | | | | | | | | | | | | | | | 4031 |

( 2 ) INFORMATION FOR SEQ ID NO:50:

( i ) SEQUENCE CHARACTERISTICS:
    ( A ) LENGTH: 1338 amino acids
    ( B ) TYPE: amino acid
    ( D ) TOPOLOGY: linear ( i i ) MOLECULE TYPE: protein ( x i ) SEQUENCE DESCRIPTION: SEQ ID NO:50:

| | | | | | | | | | | | | | | | |
|---|---|---|---|---|---|---|---|---|---|---|---|---|---|---|---|
| Met | Lys | Arg | Met | Glu | Gly | Lys | Leu | Phe | Met | Val | Ser | Lys | Lys | Leu | Gln |
| 1 | | | | 5 | | | | | 10 | | | | | 15 | |
| Val | Val | Thr | Lys | Thr | Val | Leu | Leu | Ser | Thr | Val | Phe | Ser | Ile | Ser | Leu |
| | | | 20 | | | | | 25 | | | | | 30 | | |
| Leu | Asn | Asn | Glu | Val | Ile | Lys | Ala | Glu | Gln | Leu | Asn | Ile | Asn | Ser | Gln |
| | | | 35 | | | | | 40 | | | | | 45 | | |
| Ser | Lys | Tyr | Thr | Asn | Leu | Gln | Asn | Leu | Lys | Ile | Thr | Asp | Lys | Val | Glu |
| | 50 | | | | | 55 | | | | | 60 | | | | |

```
Asp  Phe  Lys  Glu  Asp  Lys  Glu  Lys  Ala  Lys  Glu  Trp  Gly  Lys  Glu  Lys
 65                      70                       75                        80

Glu  Lys  Glu  Trp  Lys  Leu  Thr  Ala  Thr  Glu  Lys  Gly  Lys  Met  Asn  Asn
                     85                       90                        95

Phe  Leu  Asp  Asn  Lys  Asn  Asp  Ile  Lys  Thr  Asn  Tyr  Lys  Glu  Ile  Thr
               100                      105                      110

Phe  Ser  Ile  Ala  Gly  Ser  Phe  Glu  Asp  Glu  Ile  Lys  Asp  Leu  Lys  Glu
               115                      120                      125

Ile  Asp  Lys  Met  Phe  Asp  Lys  Thr  Asn  Leu  Ser  Asn  Ser  Ile  Ile  Thr
      130                      135                      140

Tyr  Lys  Asn  Val  Glu  Pro  Thr  Thr  Ile  Gly  Phe  Asn  Lys  Ser  Leu  Thr
 145                     150                      155                       160

Glu  Gly  Asn  Thr  Ile  Asn  Ser  Asp  Ala  Met  Ala  Gln  Phe  Lys  Glu  Gln
               165                      170                      175

Phe  Leu  Asp  Arg  Asp  Ile  Lys  Phe  Asp  Ser  Tyr  Leu  Asp  Thr  His  Leu
               180                      185                      190

Thr  Ala  Gln  Gln  Val  Ser  Ser  Lys  Glu  Arg  Val  Ile  Leu  Lys  Val  Thr
               195                      200                      205

Val  Pro  Ser  Gly  Lys  Gly  Ser  Thr  Thr  Pro  Thr  Lys  Ala  Gly  Val  Ile
 210                     215                      220

Leu  Asn  Asn  Ser  Glu  Tyr  Lys  Met  Leu  Ile  Asp  Asn  Gly  Tyr  Met  Val
 225                     230                      235                       240

His  Val  Asp  Lys  Val  Ser  Lys  Val  Val  Lys  Lys  Gly  Val  Glu  Cys  Leu
               245                      250                      255

Gln  Ile  Glu  Gly  Thr  Leu  Lys  Lys  Ser  Leu  Asp  Phe  Lys  Asn  Asp  Ile
               260                      265                      270

Asn  Ala  Glu  Ala  His  Ser  Trp  Gly  Met  Lys  Asn  Tyr  Glu  Glu  Trp  Ala
               275                      280                      285

Lys  Asp  Leu  Thr  Asp  Ser  Gln  Arg  Glu  Ala  Leu  Asp  Gly  Tyr  Ala  Arg
      290                      295                      300

Gln  Asp  Tyr  Lys  Glu  Ile  Asn  Asn  Tyr  Leu  Arg  Asn  Gln  Gly  Gly  Ser
 305                     310                      315                       320

Gly  Asn  Glu  Lys  Leu  Asp  Ala  Gln  Ile  Lys  Asn  Ile  Ser  Asp  Ala  Leu
               325                      330                      335

Gly  Lys  Lys  Pro  Ile  Pro  Glu  Asn  Ile  Thr  Val  Tyr  Arg  Trp  Cys  Gly
               340                      345                      350

Met  Pro  Glu  Phe  Gly  Tyr  Gln  Ile  Ser  Asp  Pro  Leu  Pro  Ser  Leu  Lys
               355                      360                      365

Asp  Phe  Glu  Glu  Gln  Phe  Leu  Asn  Thr  Ile  Lys  Glu  Asp  Lys  Gly  Tyr
      370                      375                      380

Met  Ser  Thr  Ser  Leu  Ser  Ser  Glu  Arg  Leu  Ala  Ala  Phe  Gly  Ser  Arg
 385                     390                      395                       400

Lys  Ile  Ile  Leu  Arg  Leu  Gln  Val  Pro  Lys  Gly  Ser  Thr  Gly  Ala  Tyr
               405                      410                      415

Leu  Ser  Ala  Ile  Gly  Gly  Phe  Ala  Ser  Glu  Lys  Glu  Ile  Leu  Leu  Asp
               420                      425                      430

Lys  Asp  Ser  Lys  Tyr  His  Ile  Asp  Lys  Val  Thr  Glu  Val  Ile  Ile  Lys
               435                      440                      445

Gly  Val  Lys  Arg  Tyr  Val  Val  Asp  Ala  Thr  Leu  Leu  Thr  Asn  Ser  Arg
 450                     455                      460

Gly  Pro  Ser  Thr  Pro  Pro  Thr  Pro  Ser  Pro  Ser  Thr  Pro  Pro  Thr  Pro
 465                     470                      475                       480

Ser  Asp  Ile  Gly  Ser  Thr  Met  Lys  Thr  Asn  Gln  Ile  Ser  Thr  Thr  Gln
```

|                |                |                |                |     485        |                |                |                |     490        |                |                |                |     495        |                |                |
|---|---|---|---|---|---|---|---|---|---|---|---|---|---|---|
| Lys | Asn | Gln | Gln | Lys | Glu | Met | Asp | Arg | Lys | Gly | Leu | Leu | Tyr | Tyr |
| | | | 500 | | | | 505 | | | | | 510 | | |
| Phe | Lys | Gly | Lys | Asp | Phe | Ser | Asn | Leu | Thr | Met | Phe | Ala | Pro | Thr | Arg |
| | | 515 | | | | 520 | | | | | 525 | | | |
| Asp | Ser | Thr | Leu | Ile | Tyr | Asp | Gln | Gln | Thr | Ala | Asn | Lys | Leu | Leu | Asp |
| | 530 | | | | | 535 | | | | | 540 | | | | |
| Lys | Lys | Gln | Gln | Glu | Tyr | Gln | Ser | Ile | Arg | Trp | Ile | Gly | Leu | Ile | Gln |
| 545 | | | | | 550 | | | | | 555 | | | | | 560 |
| Ser | Lys | Glu | Thr | Gly | Asp | Phe | Thr | Phe | Asn | Leu | Ser | Glu | Asp | Glu | Gln |
| | | | | 565 | | | | 570 | | | | | 575 | | |
| Ala | Ile | Ile | Glu | Ile | Asn | Gly | Lys | Ile | Ile | Ser | Asn | Lys | Gly | Lys | Glu |
| | | | 580 | | | | 585 | | | | | 590 | | | |
| Lys | Gln | Val | Val | His | Leu | Glu | Lys | Gly | Lys | Leu | Val | Pro | Ile | Lys | Ile |
| | | | 595 | | | | 600 | | | | | 605 | | | |
| Glu | Tyr | Gln | Ser | Asp | Thr | Lys | Phe | Asn | Ile | Asp | Ser | Lys | Thr | Phe | Lys |
| | 610 | | | | | 615 | | | | | 620 | | | | |
| Glu | Leu | Lys | Leu | Phe | Lys | Ile | Asp | Ser | Gln | Asn | Gln | Pro | Gln | Gln | Val |
| 625 | | | | | 630 | | | | | 635 | | | | | 640 |
| Gln | Gln | Asp | Glu | Leu | Arg | Asn | Pro | Glu | Phe | Asn | Lys | Lys | Glu | Ser | Gln |
| | | | | 645 | | | | 650 | | | | | 655 | | |
| Glu | Phe | Leu | Ala | Lys | Pro | Ser | Lys | Ile | Asn | Leu | Phe | Thr | Gln | Gln | Met |
| | | | 660 | | | | 665 | | | | | 670 | | | |
| Lys | Arg | Glu | Ile | Asp | Glu | Asp | Thr | Asp | Thr | Asp | Gly | Asp | Ser | Ile | Pro |
| | | 675 | | | | 680 | | | | | 685 | | | | |
| Asp | Leu | Trp | Glu | Glu | Asn | Gly | Tyr | Thr | Ile | Gln | Asn | Arg | Ile | Ala | Val |
| | 690 | | | | | 695 | | | | | 700 | | | | |
| Lys | Trp | Asp | Asp | Ser | Leu | Ala | Ser | Lys | Gly | Tyr | Thr | Lys | Phe | Val | Ser |
| 705 | | | | | 710 | | | | | 715 | | | | | 720 |
| Asn | Pro | Leu | Glu | Ser | His | Thr | Val | Gly | Asp | Pro | Tyr | Thr | Asp | Tyr | Glu |
| | | | | 725 | | | | 730 | | | | | 735 | | |
| Lys | Ala | Ala | Arg | Asp | Leu | Asp | Leu | Ser | Asn | Ala | Lys | Glu | Thr | Phe | Asn |
| | | | 740 | | | | 745 | | | | | 750 | | | |
| Pro | Leu | Val | Ala | Ala | Phe | Pro | Ser | Val | Asn | Val | Ser | Met | Glu | Lys | Val |
| | | 755 | | | | 760 | | | | | 765 | | | | |
| Ile | Leu | Ser | Pro | Asn | Glu | Asn | Leu | Ser | Asn | Ser | Val | Glu | Ser | His | Ser |
| | 770 | | | | | 775 | | | | | 780 | | | | |
| Ser | Thr | Asn | Trp | Ser | Tyr | Thr | Asn | Thr | Glu | Gly | Ala | Ser | Val | Glu | Ala |
| 785 | | | | | 790 | | | | | 795 | | | | | 800 |
| Gly | Ile | Gly | Pro | Lys | Gly | Ile | Ser | Phe | Gly | Val | Ser | Val | Asn | Tyr | Gln |
| | | | | 805 | | | | 810 | | | | | 815 | | |
| His | Ser | Glu | Thr | Val | Ala | Gln | Glu | Trp | Gly | Thr | Ser | Thr | Gly | Asn | Thr |
| | | | 820 | | | | 825 | | | | | 830 | | | |
| Ser | Gln | Phe | Asn | Thr | Ala | Ser | Ala | Gly | Tyr | Leu | Asn | Ala | Asn | Val | Arg |
| | | 835 | | | | 840 | | | | | 845 | | | | |
| Tyr | Asn | Asn | Val | Gly | Thr | Gly | Ala | Ile | Tyr | Asp | Val | Lys | Pro | Thr | Thr |
| | 850 | | | | | 855 | | | | | 860 | | | | |
| Ser | Phe | Val | Leu | Asn | Asn | Asp | Thr | Ile | Ala | Thr | Ile | Thr | Ala | Lys | Ser |
| 865 | | | | | 870 | | | | | 875 | | | | | 880 |
| Asn | Ser | Thr | Ala | Leu | Asn | Ile | Ser | Pro | Gly | Glu | Ser | Tyr | Pro | Lys | Lys |
| | | | | 885 | | | | 890 | | | | | 895 | | |
| Gly | Gln | Asn | Gly | Ile | Ala | Ile | Thr | Ser | Met | Asp | Asp | Phe | Asn | Ser | His |
| | | | 900 | | | | 905 | | | | | 910 | | | |

```
Pro  Ile  Thr  Leu  Asn  Lys  Lys  Gln  Val  Asp  Asn  Leu  Leu  Asn  Asn  Lys
          915                     920                    925

Pro  Met  Met  Leu  Glu  Thr  Asn  Gln  Thr  Asp  Gly  Val  Tyr  Lys  Ile  Lys
          930                     935                    940

Asp  Thr  His  Gly  Asn  Ile  Val  Thr  Gly  Gly  Glu  Trp  Asn  Gly  Val  Ile
945                      950                    955                         960

Gln  Gln  Ile  Lys  Ala  Lys  Thr  Ala  Ser  Ile  Ile  Val  Asp  Asp  Gly  Glu
               965                     970                         975

Arg  Val  Ala  Glu  Lys  Arg  Val  Ala  Ala  Lys  Asp  Tyr  Glu  Asn  Pro  Glu
               980                     985                         990

Asp  Lys  Thr  Pro  Ser  Leu  Thr  Leu  Lys  Asp  Ala  Leu  Lys  Leu  Ser  Tyr
               995                     1000                        1005

Pro  Asp  Glu  Ile  Lys  Glu  Ile  Glu  Gly  Leu  Leu  Tyr  Tyr  Lys  Asn  Lys
          1010                    1015                   1020

Pro  Ile  Tyr  Glu  Ser  Ser  Val  Met  Thr  Tyr  Leu  Asp  Glu  Asn  Thr  Ala
1025                     1030                    1035                       1040

Lys  Glu  Val  Thr  Lys  Gln  Leu  Asn  Asp  Thr  Thr  Gly  Lys  Phe  Lys  Asp
               1045                    1050                   1055

Val  Ser  His  Leu  Tyr  Asp  Val  Lys  Leu  Thr  Pro  Lys  Met  Asn  Val  Thr
               1060                    1065                        1070

Ile  Lys  Leu  Ser  Ile  Leu  Tyr  Asp  Asn  Ala  Glu  Ser  Asn  Asp  Asn  Ser
          1075                    1080                   1085

Ile  Gly  Lys  Trp  Thr  Asn  Thr  Asn  Ile  Val  Ser  Gly  Gly  Asn  Asn  Gly
          1090                    1095                   1100

Lys  Lys  Gln  Tyr  Ser  Ser  Asn  Asn  Pro  Asp  Ala  Asn  Leu  Thr  Leu  Asn
1105                     1110                    1115                       1120

Thr  Asp  Ala  Gln  Glu  Lys  Leu  Asn  Lys  Asn  Arg  Asp  Tyr  Tyr  Ile  Ser
               1125                    1130                        1135

Leu  Tyr  Met  Lys  Ser  Glu  Lys  Asn  Thr  Gln  Cys  Glu  Ile  Thr  Ile  Asp
               1140                    1145                        1150

Gly  Glu  Ile  Tyr  Pro  Ile  Thr  Thr  Lys  Thr  Val  Asn  Val  Asn  Lys  Asp
          1155                    1160                   1165

Asn  Tyr  Lys  Arg  Leu  Asp  Ile  Ile  Ala  His  Asn  Ile  Lys  Ser  Asn  Pro
          1170                    1175                   1180

Ile  Ser  Ser  Leu  His  Ile  Lys  Thr  Asn  Asp  Glu  Ile  Thr  Leu  Phe  Trp
1185                     1190                    1195                       1200

Asp  Asp  Ile  Ser  Ile  Thr  Asp  Val  Ala  Ser  Ile  Lys  Pro  Glu  Asn  Leu
               1205                    1210                        1215

Thr  Asp  Ser  Glu  Ile  Lys  Gln  Ile  Tyr  Ser  Arg  Tyr  Gly  Ile  Lys  Leu
               1220                    1225                        1230

Glu  Asp  Gly  Ile  Leu  Ile  Asp  Lys  Lys  Gly  Gly  Ile  His  Tyr  Gly  Glu
               1235                    1240                        1245

Phe  Ile  Asn  Glu  Ala  Ser  Phe  Asn  Ile  Glu  Pro  Leu  Gln  Asn  Tyr  Val
          1250                    1255                   1260

Thr  Lys  Tyr  Glu  Val  Thr  Tyr  Ser  Ser  Glu  Leu  Gly  Pro  Asn  Val  Ser
1265                     1270                    1275                       1280

Asp  Thr  Leu  Glu  Ser  Asp  Lys  Ile  Tyr  Lys  Asp  Gly  Thr  Ile  Lys  Phe
                    1285                   1290                        1295

Asp  Phe  Thr  Lys  Tyr  Ser  Lys  Asn  Glu  Gln  Gly  Leu  Phe  Tyr  Asp  Ser
               1300                    1305                        1310

Gly  Leu  Asn  Trp  Asp  Phe  Lys  Ile  Asn  Ala  Ile  Thr  Tyr  Asp  Gly  Lys
          1315                    1320                   1325

Glu  Met  Asn  Val  Phe  His  Arg  Tyr  Asn  Lys
```

| 1330 | 1335 |
|---|---|

What is claimed is:

1. A biologically pure culture of a *Bacillus thuringiensis* strain, which is selected from the group consisting of: NRRL B-21060, NRRL B-21224, NRRL B-21225, NRRL B-21226, NRRL B-21227, and NRRL B-21439.

2. A biologically pure culture of a Bacillus thuringiensis-strain according to claim 1, which is NRRL B-21060.

3. A biologically pure culture of a *Bacillus thuringiensis* strain according to claim 1, which is NRRL B-21224.

4. A biologically pure culture of a *Bacillus thuringiensis* strain according to claim 1, which is NRRL B-21225.

5. A biologically pure culture of a *Bacillus thuringiensis* strain according to claim 1, which is NRRL B-21226.

6. A biologically pure culture of a *Bacillus thuringiensis* strain according to claim 1, which is NRRL B-21227.

7. A biologically pure culture of a *Bacillus cereus* strain, which is NRRL B-21058.

8. A biologically pure culture of a Bacillus sp. strain, which is selected from the group consisting of: NRRL B-21228, NRRL B-21229, and NRRL B-21230.

9. A biologically pure culture of a Bacillus sp. strain according to claim 8, which is NRRL B-21228.

10. A biologically pure culture of a Bacillus sp. strain according to claim 8, which is NRRL B-21229.

11. A biologically pure culture of a Bacillus sp. strain according to claim 8, which is NRRL B-21230.

12. A biologically pure culture of a Bacillus strain according to claim 1, which is NRRL B-21439.

* * * * *